US009212168B2

(12) United States Patent
Long et al.

(10) Patent No.: US 9,212,168 B2
(45) Date of Patent: Dec. 15, 2015

(54) HEPATITIS C VIRUS INHIBITORS

(71) Applicants: Daniel D. Long, San Francisco, CA (US); Robert Murray McKinnell, Millbrae, CA (US); Lan Jiang, Foster City, CA (US); Mandy Loo, San Jose, CA (US); Kassandra Lepack, Calgary (CA); Lori Jean Van Orden, San Francisco, CA (US); Gavin Ogawa, San Francisco, CA (US)

(72) Inventors: Daniel D. Long, San Francisco, CA (US); Robert Murray McKinnell, Millbrae, CA (US); Lan Jiang, Foster City, CA (US); Mandy Loo, San Jose, CA (US); Kassandra Lepack, Calgary (CA); Lori Jean Van Orden, San Francisco, CA (US); Gavin Ogawa, San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 189 days.

(21) Appl. No.: 13/667,197

(22) Filed: Nov. 2, 2012

(65) Prior Publication Data

US 2013/0115194 A1 May 9, 2013

Related U.S. Application Data

(60) Provisional application No. 61/555,056, filed on Nov. 3, 2011, provisional application No. 61/600,089, filed on Feb. 17, 2012, provisional application No. 61/637,961, filed on Apr. 25, 2012.

(51) Int. Cl.

| | |
|---|---|
| ***C07D 405/14*** | (2006.01) |
| ***C07D 401/14*** | (2006.01) |
| ***C07D 413/14*** | (2006.01) |
| ***C07D 409/14*** | (2006.01) |
| ***C07D 491/113*** | (2006.01) |

(52) U.S. Cl.

CPC ............ *C07D 401/14* (2013.01); *C07D 405/14* (2013.01); *C07D 409/14* (2013.01); *C07D 413/14* (2013.01); *C07D 491/113* (2013.01)

(58) Field of Classification Search

CPC .................................................... C07D 405/14

See application file for complete search history.

(56) References Cited

U.S. PATENT DOCUMENTS

| | | | |
|---|---|---|---|
| 7,659,270 | B2 | 2/2010 | Bachand et al. |
| 8,088,368 | B2 | 1/2012 | Guo et al. |
| 8,303,944 | B2 | 11/2012 | Bachand et al. |
| 8,921,372 | B2 * | 12/2014 | McKinnell et al. |
| 2008/0050336 | A1 | 2/2008 | Bachand et al. |
| 2010/0215618 | A1 | 8/2010 | Carter et al. |
| 2011/0064695 | A1 | 3/2011 | Qiu et al. |
| 2011/0064698 | A1 | 3/2011 | Or et al. |
| 2011/0077280 | A1 | 3/2011 | Bender et al. |
| 2011/0142798 | A1 | 6/2011 | Qiu et al. |
| 2011/0152237 | A1 | 6/2011 | Chen et al. |
| 2011/0274648 | A1 | 11/2011 | Lavoie et al. |
| 2011/0286961 | A1 | 11/2011 | Belema et al. |
| 2011/0300104 | A1 | 12/2011 | Qiu et al. |
| 2012/0114600 | A1 | 5/2012 | McKinnell et al. |
| 2012/0195857 | A1 | 8/2012 | Belema et al. |
| 2013/0028859 | A1 | 1/2013 | Bender et al. |

FOREIGN PATENT DOCUMENTS

| | | | |
|---|---|---|---|
| WO | 2008/021927 | A2 | 2/2008 |
| WO | 2010/094977 | A1 | 8/2010 |
| WO | 2011/079327 | A1 | 6/2011 |
| WO | 2011/091446 | A1 | 7/2011 |
| WO | 2012/027712 | A2 | 3/2012 |
| WO | 2012/048421 | A1 | 4/2012 |

OTHER PUBLICATIONS

International Search Report for PCT/US2012/063181 dated Dec. 18, 2012.

* cited by examiner

*Primary Examiner* — Melenie McCormick
*Assistant Examiner* — Gregg Polansky
(74) *Attorney, Agent, or Firm* — Jeffrey A. Hagenah; Roberta P. Saxon

(57) ABSTRACT

The invention provides compounds of formula (I):

(I)

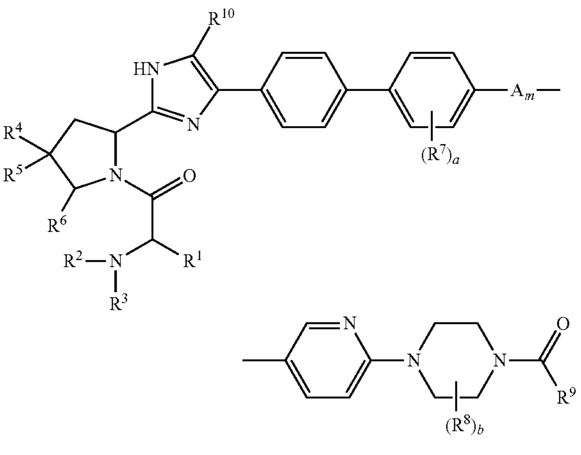

wherein the variables are defined in the specification, or a pharmaceutically-acceptable salt thereof, that are inhibitors of replication of the hepatitis C virus. The invention also provides pharmaceutical compositions comprising such compounds, methods of using such compounds to treat hepatitis C viral infections, and processes and intermediates useful for preparing such compounds.

8 Claims, 1 Drawing Sheet

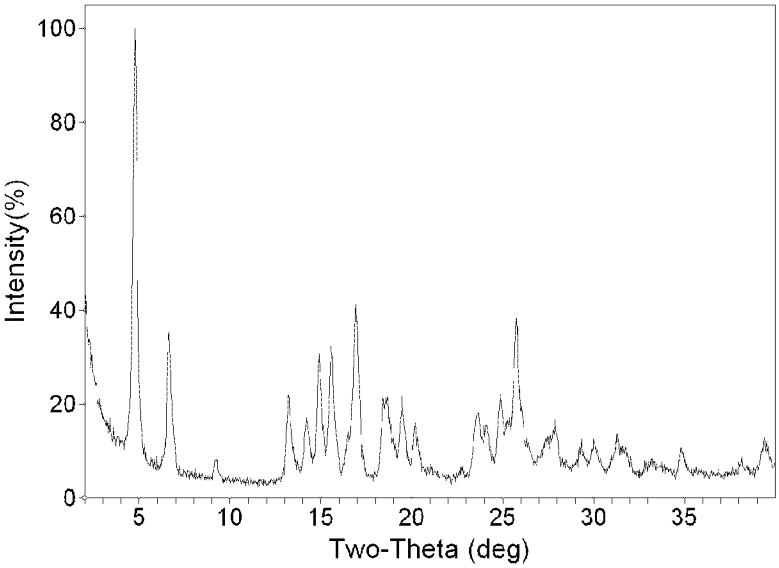
Intensity(%)
100
80
60
40
20
0
5
10
15
20
25
30
35
Two-Theta (deg)

HEPATITIS C VIRUS INHIBITORS

CROSS-REFERENCE TO RELATED APPLICATIONS

This application claims the benefit of U.S. Provisional Application Nos. 61/555,056, filed on Nov. 3, 2011, 61/600,089, filed on Feb. 17, 2012, and 61/637,961, filed on Apr. 25, 2012, the disclosures of which are incorporated herein by reference in their entirety.

BACKGROUND OF THE INVENTION

1. Field of the Invention

The invention is directed to compounds useful as inhibitors of replication of the hepatitis C virus (HCV). The invention is also directed to pharmaceutical compositions comprising such compounds, methods of using such compounds to treat HCV infection, and processes and intermediates useful for preparing such compounds.

2. State of the Art

Recent estimates place the number of people infected with the hepatitis C virus (HCV) worldwide at more than 170 million, including 3 million people in the United States. The infection rate is thought to be roughly 4 to 5 times that of the human immunodeficiency virus (HIV). While in some individuals, the natural immune response is able to overcome the virus, in the majority of cases, a chronic infection is established, leading to increased risk of developing cirrhosis of the liver and hepatocellular carcinomas. Infection with hepatitis C, therefore, presents a serious public health problem.

Prior to mid-2011, the accepted standard of care for HCV involved the use of a pegylated interferon which is believed to act by boosting the body's immune response, together with ribavirin. Unfortunately, the course of treatment is lengthy, typically 48 weeks, often accompanied by serious adverse side effects, including depression, flu-like symptoms, fatigue, and hemolytic anemia, and ineffective in up to 50% of patients. In mid-2011, two HCV protease inhibitors were approved in the United States to be used in combination with interferon and ribavirin. Although better cure rates have been reported, the course of therapy is still lengthy and accompanied by undesirable side effects. Accordingly, there remains a serious unmet need in HCV treatment.

The virus responsible for HCV infection has been identified as a positive-strand RNA virus belonging to the family Flaviviridae. The HCV genome encodes a polyprotein that during the viral lifecycle is cleaved into ten individual proteins, including both structural and non-structural proteins. The six non-structural proteins, denoted as NS2, NS3, NS4A, NS4B, NS5A, and NS5B have been shown to be required for RNA replication. In particular, the NS5A protein appears to play a significant role in viral replication, as well as in modulation of the physiology of the host cell. Effects of NS5A on interferon signaling, regulation of cell growth and apoptosis have also been identified. (Macdonald et al., *Journal of General Virology* (2004), 85, 2485-2502.) Compounds which inhibit the function of the NS5A protein are expected to provide a new approach to HCV therapy.

SUMMARY OF THE INVENTION

In one aspect, the invention provides novel compounds which inhibit replication of the HCV virus.

Accordingly, the invention provides a compound of formula (I):

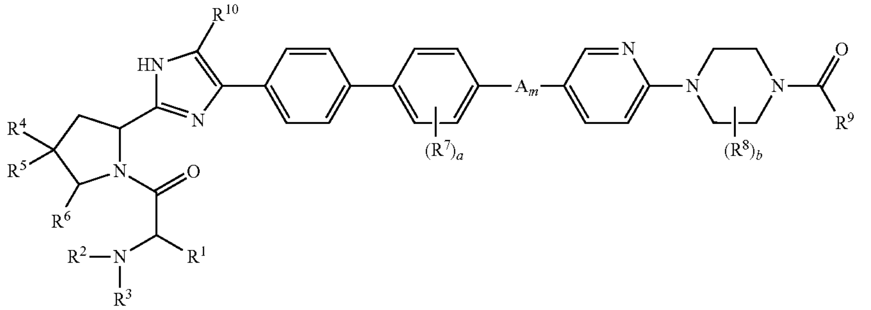

(I)

wherein $R^1$ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with $-OR^a$, amino, $-SR^e$, heterocycle, or heteroaryl, $C_{1-6}$alkoxy is optionally substituted with $-OR^a$, and heterocycle is optionally substituted with $-OR^a$, amino, or $-C(O)OC_{1-6}$alkyl, or with one or two $C_{1-3}$alkyl or =O;

$R^2$ is selected from hydrogen and $C_{1-6}$alkyl;

$R^3$ is selected from hydrogen, $C_{1-6}$alkyl, $-C(O)OC_{1-6}$alkyl, $-C(O)NR^mR^n$, $-C(O)C_{3-6}$cycloalkyl, and $-S(O)_2C_{1-3}$alkyl;

or $R^2$ and $R^3$ together with the nitrogen atom to which they are attached form a heterocycle;

$R^4$ is selected from $C_{1-6}$alkyl, $-NR^bR^c$, $-OR^d$, $-SR^e$, $-S(O)C_{1-3}$alkyl, $-S(O)_2C_{1-3}$alkyl, $-CN$, $-C(O)NR^aR^b$, heterocycle, heteroaryl, and halo, wherein $C_{1-6}$alkyl is optionally substituted with $-OR^a$; and $R^5$ and $R^6$ are hydrogen;

or $R^4$ and $R^5$ are independently $C_{1-6}$alkyl or halo and $R^6$ is hydrogen;

or $R^4$ and $R^5$ taken together form $-(CH_2)_n-$, wherein n is 2, 3, 4, or 5 and $R^6$ is hydrogen;

or $R^4$ and $R^5$ taken together form $-O-(CH_2)_2-O-$ and $R^6$ is hydrogen;

or $R^4$ is hydrogen or $C_{1-3}$alkyl and $R^5$ and $R^6$ taken together form $-(CH_2)_m-$, wherein m is 1, 2, 3, or 4;

or $R^4$ and $R^5$ are each hydrogen and $R^6$ is $C_{1-6}$alkyl;

$R^7$ is selected from halo, $C_{1-3}$alkyl, and $C_{1-3}$alkoxy wherein $C_{1-3}$alkyl and $C_{1-3}$alkoxy are optionally substituted with one, two, three, four, or five halo;

$R^8$ is $C_{1-3}$alkyl, optionally substituted with $-OR^h$;

$R^9$ is selected from $C_{1-6}$alkyl, $C_{3-6}$cycloalkyl, $C_{1-6}$alkoxy, $-NR^fR^g$, heteroaryl, heterocycle, and $-CH_2$-heteroaryl;

wherein:

$C_{1-6}$alkyl is optionally substituted with one or two substituents independently selected from —$OR^h$, —$NR^jR^k$, —NHC(O)$C_{1-3}$alkyl, —NHC(O)O$C_{1-3}$alkyl, —NHC(O)$C_{3-6}$cycloalkyl, $C_{3-6}$cycloalkyl, halo, —NHC(O)$C_{1-3}$alkylC(O)$OR^h$, —NHC(O)$C_{1-3}$alkyl$OR^h$, —NHC(O)NH$C_{1-3}$alkyl, —NHS$(O)_2C_{1-3}$alkyl, and heterocycle;

$C_{1-6}$alkoxy is optionally substituted with —$OR^h$;

any $C_{3-6}$cycloalkyl is optionally substituted with one, two, or three substituents independently selected from $C_{1-3}$alkyl, halo, —$NR^aR^b$, —$OR^h$, and —$CD_3$, wherein any $C_{1-3}$alkyl is optionally substituted with one, two, or three halo;

any heterocycle is optionally substituted with one, two, or three substituents independently selected from $C_{1-3}$alkyl, halo, —C(O)O$C_{1-3}$alkyl, —C(O)$C_{1-6}$alkyl, —C(O)$C_{3-6}$cycloalkyl, —C(O)NH$C_{1-6}$alkyl, —C(O)NH$C_{3-6}$cycloalkyl, —S$(O)_2C_{1-6}$alkyl, and —C(O)$NH_2$; wherein any —C(O)$C_{1-6}$alkyl is optionally substituted with —NHC(O)O$C_{1-3}$alkyl, —$OR^h$, —$NR^jR^k$, or heterocycle, any —C(O)$C_{3-6}$cycloalkyl is optionally substituted with one or two $C_{1-3}$alkyl, and any —C(O)NH$C_{1-6}$alkyl is optionally substituted with —$OR^h$ or $C_{3-6}$cycloalkyl;

any heteroaryl is optionally substituted with one or two $C_{1-3}$alkyl;

$R^a$, $R^b$, $R^c$, $R^h$, $R^j$, $R^k$, $R^m$, and $R^n$ are each independently hydrogen or $C_{1-3}$alkyl;

$R^c$ is hydrogen or $C_{1-6}$alkyl, wherein $C_{1-6}$alkyl is optionally substituted with —$OR^a$ or amino;

$R^d$ is hydrogen or $C_{1-6}$alkyl, wherein $C_{1-6}$alkyl is optionally substituted with —$OR^h$ or with heteroaryl optionally substituted with $C_{1-3}$alkyl;

$R^f$ is hydrogen or $C_{1-6}$alkyl, wherein $C_{1-6}$alkyl is optionally substituted with —$OR^h$;

$R^g$ is selected from hydrogen, $C_{1-6}$alkyl, $C_{1-6}$alkoxy, $C_{3-6}$cycloalkyl, $NR^aR^b$, and heterocycle, wherein $C_{1-6}$alkyl is optionally substituted with —$OR^h$ and heterocycle is optionally substituted with one or two =O;

$R^{10}$ is selected from hydrogen, halo, and $C_{1-3}$alkyl, wherein $C_{1-3}$alkyl is optionally substituted with one, two, or three halo, or with —$OR^h$;

$A_m$ is —NHC(O)— or —C(O)NH— a is 0, 1, or 2; and b is 0, 1 or 2;

or a pharmaceutically-acceptable salt of stereoisomer thereof.

As used hereinafter, the phrase "compound of formula (I)" means a compound of formula (I) or a pharmaceutically acceptable salt thereof; i.e., this phrase means a compound of formula (I) in free base form or in a pharmaceutically acceptable salt form unless otherwise indicated.

The invention also provides a pharmaceutical composition comprising a compound of the invention and a pharmaceutically-acceptable carrier. In addition, the invention provides a pharmaceutical composition comprising a compound of the invention, a pharmaceutically-acceptable carrier and one or more other therapeutic agents useful for treating hepatitis C viral infections.

The invention also provides a method of treating a hepatitis C viral infection in a mammal, the method comprising administering to the mammal a therapeutically effective amount of a compound or of a pharmaceutical composition of the invention. In addition, the invention provides a method of treating a hepatitis C viral infection in a mammal, the method comprising administering to the mammal a compound or a pharmaceutical composition of the invention and one or more other therapeutic agents useful for treating hepatitis C viral infections. Further, the invention provides a method of inhibiting replication of the hepatitis C virus in a mammal, the method comprising administering a compound or a pharmaceutical composition of the invention.

In separate and distinct aspects, the invention also provides synthetic processes and intermediates described herein, which are useful for preparing compounds of the invention.

The invention also provides a compound of the invention as described herein for use in medical therapy, as well as the use of a compound of the invention in the manufacture of a formulation or medicament for treating a hepatitis C viral infection in a mammal.

BRIEF DESCRIPTION OF THE DRAWING

The FIGURE shows a powder x-ray diffraction (PXPD) pattern of crystalline (R)-5-chloro-4-(6-(2-methyl-4-pivaloylpiperazin-1-yl)nicotinamido)-2-(trifluoromethoxy)phenylboronic acid.

DETAILED DESCRIPTION OF THE INVENTION

Among other aspects, the invention provides inhibitors of HCV replication of formula (I), pharmaceutically-acceptable salts thereof, and intermediates for the preparation thereof. The following substituents and values are intended to provide representative examples of various aspects of this invention. These representative values are intended to further define such aspects and are not intended to exclude other values or limit the scope of the invention.

In a specific aspect, $R^1$ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with —$OR^a$, amino, —$SR^e$, heterocycle, or heteroaryl, $C_{1-6}$alkoxy is optionally substituted with —$OR^a$, and heterocycle is optionally substituted with —$OR^a$, amino, or —C(O)O$C_{1-6}$alkyl, or with one or two $C_{1-3}$alkyl or =O.

In another specific aspect, $R^1$ is selected from $C_{1-6}$alkyl, $C_{1-6}$alkoxy, phenyl, $C_{3-6}$cycloalkyl, heterocycle, and heteroaryl, wherein $C_{1-6}$alkyl is optionally substituted with —$OR^a$, amino, —$SR^e$, heterocycle, or heteroaryl, $C_{1-6}$alkoxy is optionally substituted with —$OR^a$, and heterocycle is optionally substituted with —$OR^a$, amino, or —C(O)O$C_{1-6}$alkyl, or with one or two $C_{1-3}$alkyl, wherein $R^a$ is hydrogen or $C_{1-3}$alkyl.

In another specific aspect, $R^1$ is selected from $C_{1-3}$alkyl, phenyl, $C_{5-6}$cycloalkyl, and heterocycle, wherein $C_{1-3}$alkyl is optionally substituted with —$OR^a$, wherein $R^a$ is hydrogen or $C_{1-3}$alkyl, and any heterocycle has six ring atoms and is optionally substituted with one or two $C_{1-3}$alkyl or =O.

In another specific aspect, $R^1$ is selected from $C_{1-6}$alkyl, phenyl, and heterocycle, wherein $C_{1-6}$alkyl is optionally substituted with —$OR^a$, and heterocycle has six ring atoms and is optionally substituted with —$OR^a$ or amino or with one or two methyl. In another specific aspect, $R^1$ is selected from $C_{1-6}$alkyl, phenyl, and $C_{3-6}$cycloalkyl; wherein $C_{1-6}$alkyl is optionally substituted with —$OR^a$; wherein $R^a$ is hydrogen or $C_{1-3}$alkyl.

In another specific aspect, $R^1$ is selected from $C_{1-6}$alkyl, phenyl, and tetrahydropyranyl, wherein $C_{1-6}$alkyl is optionally substituted with —$OR^a$; wherein $R^a$ is hydrogen or $C_{1-3}$alkyl.

In another specific aspect, $R^1$ is selected from $C_{1-6}$alkyl, optionally substituted with hydroxy or methoxy, tetrahydropyran, and phenyl. In another specific aspect, $R^1$ is selected from $C_{1-6}$alkyl and phenyl.

Specific $R^1$ values include isopropyl, phenyl, tetrahydropyran-4-yl, 2,6-dimethyltetrahydropyran-4-yl, 1,1-dioxo-hexahydro-1$\lambda^6$-thiopyran-4-yl, oxetan-3-yl, 1-hydroxyethyl, 1-methoxyethyl, 2-hydroxypropan-2-yl, cyclohexyl, cyclopentyl, thiphen-2-yl, and furan-2-ylmethyl.

In a specific aspect, $R^1$ is $C_{1-3}$ alkyl.

In another specific aspect, $R^1$ is isopropyl.

In yet another specific aspect, $R^1$ is phenyl.

In still another specific aspect, $R^1$ is tetrahydropyranyl.

In still another specific aspect, $R^1$ is tetrahydropyran-4-yl.

In a specific aspect, $R^2$ is hydrogen or $C_{1-6}$alkyl.

In other specific aspects, $R^2$ is hydrogen or $C_{1-3}$alkyl; or $R^2$ is hydrogen.

In a specific aspect, $R^3$ is selected from hydrogen, $C_{1-6}$alkyl, $-C(O)OC_{1-6}$alkyl, $-C(O)NR'''R''$, $-C(O)C_{3-6}$cycloalkyl, and $-S(O)_2C_{1-3}$alkyl; or $R^2$ and $R^3$ together with the nitrogen atom to which they are attached form a heterocycle;

In another specific aspect, $R^3$ is selected from hydrogen, $C_{1-6}$alkyl, $-C(O)OC_{1-6}$alkyl, $-C(O)NR'''R''$, $-C(O)C_{3-6}$cycloalkyl, and $-S(O)_2C_{1-3}$alkyl;

In another specific aspect, $R^3$ is selected from hydrogen, $C_{1-6}$alkyl, and $-C(O)OC_{1-6}$alkyl.

In yet another specific aspect, $R^3$ is $-C(O)OC_{1-3}$alkyl.

In another specific aspect, $R^2$ and $R^3$ together with the nitrogen atom to which they are attached form a heterocycle.

In yet another specific aspect, $R^2$ and $R^3$ together with the nitrogen atom to which they are attached form a piperidinyl ring.

In a specific aspect, $R^1$ is $C_{1-6}$alkyl, $R^2$ is hydrogen, and $R^3$ is $-C(O)OC_{1-6}$alkyl.

In another specific aspect, $R^1$ is isopropyl, $R^2$ is hydrogen, and $R^3$ is $-C(O)OCH_3$.

In yet other specific aspects, $R^1$ is phenyl and $R^2$ and $R^3$ are each $C_{1-3}$alkyl; or $R^1$ is phenyl, $R^2$ is hydrogen, and $R^3$ is $-C(O)OC_{1-3}$alkyl; or $R^1$ is tetrahydropyranyl, $R^2$ is hydrogen, and $R^3$ is $-C(O)OC_{1-3}$alkyl.

In a specific aspect, $R^4$ is selected from $C_{1-6}$alkyl, $-NR^bR^c$, $-OR^d$, $-SR^e$, $-S(O)C_{1-3}$alkyl, $-S(O)_2C_{1-3}$alkyl, $-CN$, $-C(O)NR^aR^b$, heterocycle, heteroaryl, and halo; and $R^5$ and $R^6$ are hydrogen;

In another specific aspect, $R^4$ is selected from $C_{1-6}$alkyl, $-NR^bR^c$, $-OR^d$, $-SR^e$; and $R^5$ and $R^6$ are hydrogen.

In another specific aspect, $R^4$ is selected from $C_{1-6}$alkyl, $-OR^d$, and $-C(O)NR^aR^b$ and $R^5$ and $R^6$ are hydrogen.

In another specific aspect, $R^4$ is selected from $C_{1-3}$alkyl and $-OR^d$, wherein $C_{1-3}$alkyl is optionally substituted with $-OR^a$, wherein $R^a$ and $R^d$ are independently hydrogen or $C_{1-3}$alkyl; and $R^5$ and $R^6$ are hydrogen.

In another specific aspect, $R^4$ is selected from methyl, methoxy, fluoro, $-CH_2OCH_3$, $-C(O)NH_2$, $-CN$, $-NH_2$, $-NH(CH_3)_2$, $-SCH_3$, $-S(O)CH_3$, $-S(O)_2CH_3$, morpholinyl, and pyrrolidin-1-yl and $R^5$ and $R^6$ are hydrogen.

In another specific aspect, $R^4$ is selected from methyl, methoxy, and $-C(O)NH_2$, and $R^5$ and $R^6$ are hydrogen.

In still another aspect, $R^4$ is methyl or methoxy, and $R^5$ and $R^6$ are hydrogen.

In a further aspect, $R^4$ is methyl and $R^5$ and $R^6$ are hydrogen.

In another specific aspect, $R^4$ and $R^5$ are independently $C_{1-6}$alkyl and $R^6$ is hydrogen.

In yet another specific aspect, $R^4$ and $R^5$ are each fluoro.

In yet another specific aspect, $R^4$ and $R^5$ taken together form $-O-(CH_2)_2-O-$ and $R^6$ is hydrogen.

In still another specific aspect, $R^4$ and $R^5$ taken together form $-(CH_2)_n-$, wherein n is 2, 3, 4, or 5.

In additional aspects, $R^4$ is hydrogen and $R^5$ and $R^6$ taken together form $-(CH_2)_m-$, wherein n is 1 or 4; or $R^4$ is hydrogen and $R^5$ and $R^6$ taken together form $-(CH_2)_4-$.

In still further aspects, $R^4$ and $R^5$ are each hydrogen and $R^6$ is $C_{1-6}$alkyl, or $R^4$ and $R^5$ are each hydrogen and $R^6$ is methyl.

In a specific aspect, $R^7$ is selected from halo, $C_{1-3}$alkyl, and $C_{1-3}$alkoxy wherein $C_{1-6}$alkyl and $C_{1-6}$alkoxy are optionally substituted with one, two, three, four, or five halo.

In another specific aspect $R^7$ is selected from halo, $C_{1-3}$alkyl, and $C_{1-3}$alkoxy wherein $C_{1-6}$alkyl and $C_{1-6}$alkoxy are substituted with one, two, or three halo.

In yet another specific aspect, $R^7$ is selected from fluoro, chloro, $-CF_3$, and $-OCF_3$. In a specific aspect, $R^8$ is $C_{1-3}$alkyl, optionally substituted with $-OR^h$; wherein $R^h$ is hydrogen or $C_{1-3}$alkyl.

In a specific aspect, $R^8$ is $C_{1-3}$alkyl.

In another specific aspect, $R^8$ is methyl or hydroxymethyl.

In another specific aspect, $R^8$ is methyl.

In a specific aspect, $R^9$ is defined as in formula (I).

In another specific aspect, $R^9$ is selected from $C_{1-6}$alkyl, $C_{3-6}$cycloalkyl, $C_{1-6}$alkoxy, $-NR^fR^g$, heteroaryl, heterocycle, and $-CH_2-$ heteroaryl; wherein $C_{1-6}$alkyl is optionally substituted with one or two substituents independently selected from $-OR^h$, $-NR^jR^k$, $-NHC(O)C_{1-3}$alkyl, $-NHC(O)OC_{1-3}$alkyl, $-NHC(O)C_{3-6}$cycloalkyl, $C_{3-6}$cycloalkyl, and halo; $C_{1-6}$alkoxy is optionally substituted with $-OR^h$; any $C_{3-6}$cycloalkyl is optionally substituted with one, two, or three substituents independently selected from $C_{1-3}$alkyl, halo, $-NR^aR^b$, $-OR^h$, and $-CD_3$, wherein any $C_{1-3}$alkyl is optionally substituted with one, two, or three halo; any heterocycle is optionally substituted with one, two, or three substituents independently selected from $C_{1-3}$alkyl, halo, $-C(O)OC_{1-3}$alkyl, $-C(O)C_{1-6}$alkyl, $-C(O)C_{3-6}$cycloalkyl, $-C(O)NHC_{1-6}$alkyl, $-C(O)NHC_{3-6}$cycloalkyl, $-S(O)_2C_{1-6}$alkyl, and $-C(O)NH_2$; wherein any $-C(O)C_{1-6}$alkyl is optionally substituted with $-NHC(O)OC_{1-3}$alkyl, $-OR^h$, $-NR^jR^k$, or heterocycle, any $-C(O)C_{3-6}$cycloalkyl is optionally substituted with one or two $C_{1-3}$alkyl, and any $-C(O)NHC_{1-6}$alkyl is optionally substituted with $-OR^h$ or $C_{3-6}$cycloalkyl; any heteroaryl is optionally substituted with one or two $C_{1-3}$alkyl; $R^a$, $R^b$, $R^h$, $R^j$, and $R^k$ are defined as in formula (I), and $R^g$ is selected from hydrogen, $C_{1-6}$alkyl, $C_{1-6}$alkoxy, $C_{3-6}$cycloalkyl, $NR^aR^b$, and heterocycle, wherein $C_{1-6}$alkyl is optionally substituted with $-OR^h$ and heterocycle is optionally substituted with $=O$.

In another specific aspect, $R^9$ is selected from $C_{1-6}$alkyl, $C_{3-6}$cycloalkyl, $-NR^fR^g$, heteroaryl, heterocycle, and $-CH_2$-heteroaryl; wherein any heteroaryl or heterocycle has 5 or 6 ring atoms; any heteroaryl is optionally substituted with $C_{1-3}$alkyl; $C_{1-6}$alkyl is optionally substituted with one or two substituents independently selected from $-OR^h$, $-NR^jR^k$, $-NHC(O)C_{1-3}$alkyl, and $-NHC(O)OC_{1-3}$alkyl; any $C_{3-6}$cycloalkyl is optionally substituted with one or two $C_{1-3}$alkyl; any heterocycle is optionally substituted with one, or two substituents independently selected from $C_{1-3}$alkyl, $-C(O)OC_{1-3}$alkyl, $-C(O)C_{1-6}$alkyl, $-C(O)C_{3-6}$cycloalkyl, $-C(O)NHC_{1-6}$alkyl, and $-C(O)NHC_{3-6}$cycloalkyl; wherein any $-C(O)C_{1-6}$alkyl is optionally substituted with $-NHC(O)OC_{1-3}$alkyl, $-OR^h$, $-NR^jR^k$, or heterocycle; any $-C(O)C_{3-6}$cycloalkyl is optionally substituted with one or two $C_{1-3}$alkyl; and any $-C(O)NHC_{1-6}$alkyl is optionally substituted with $-OR^h$ or $C_{3-6}$cycloalkyl.

In yet another aspect, $R^9$ is selected from $C_{3-4}$cycloalkyl, —$CH_2NR^jR^k$, —$NR^fR^g$, imidazolyl, pyrazolyl, pyrimidinyl, and pyrrolidinyl; wherein $C_{3-4}$cycloalkyl is optionally substituted with one or two $C_{1-3}$alkyl; pyrrolidinyl is optionally substituted with methyl and substituted with a substituent selected from —C(O)O$C_{1-3}$alkyl, —C(O)$C_{1-6}$alkyl, —C(O)NH$C_{1-6}$alkyl, wherein —C(O)$C_{1-6}$alkyl is substituted with —NHC(O)O$C_{1-3}$alkyl, —$OR^h$, —$NR^jR^k$, or heterocycle.

In another specific aspect, $R^9$ is selected from $C_{1-6}$alkyl, $C_{3-6}$cycloalkyl, $NR^fR^g$, wherein $R^f$ and $R^g$ are independently hydrogen or $C_{1-3}$alkyl, heteroaryl, and heterocycle, wherein $C_{1-6}$alkyl is optionally substituted with —$OR^h$, $C_{3-6}$cycloalkyl is optionally substituted with one or two $C_{1-3}$alkyl or halo, any heteroaryl has five or six ring atoms, and any heterocycle has five ring atoms and is optionally substituted with one or two substituents selected from $C_{1-3}$alkyl, —C(O)O $C_{1-3}$alkyl, —C(O)$C_{1-6}$alkyl, —C(O)NH$C_{1-6}$alkyl, and —C(O)$C_{1-3}$alkylNHC(O)$OCH_3$.

Exemplary specific values of $R^9$ within this aspect include —$NHCH_3$, cyclopropyl, 2,2-dimethylcyclopropyl, tert-butyl, 3-hydroxy-2,2-dimethylpropyl, imidazolyl, 2,2-difluorocyclopropyl, 2,2-dichlorocylopropyl, and 2 methylpyrrolidin-2-yl substituted at the nitrogen with —C(O)$NHCH_3$, —C(O)t-Bu, —C(O)$CH_3$, —C(O)iPr, C(O)$CH_2OCH_3$. C(O)t-Bu, or —C(O)CH(iPr)NHC(O)$OCH_3$.

In yet another aspect, $R^9$ is selected from $C_{1-6}$alkyl, optionally substituted with —$OR^h$ wherein $R^h$ is hydrogen or $C_{1-3}$alkyl, and $C_{3-4}$cycloalkyl, optionally substituted with one or two $C_{1-3}$alkyl.

In still another aspect, $R^9$ is selected from —$NHCH_3$, 2,2-dimethylcyclopropyl, tert-butyl, and imidazolyl.

In another specific aspect, $R^9$ is selected from —$NHCH_3$, cyclopropyl, 2,2-dimethylcyclopropyl, tert-butyl, 3-hydroxy-2,2-dimethylpropyl, and imidazolyl.

In a still further aspect, $R^9$ is selected from cyclopropyl, 2,2-dimethylcyclopropyl, tert-butyl, and 3-hydroxy-2,2-dimethylpropyl.

In a specific aspect, $R^{10}$ is hydrogen, halo, $C_{1-3}$alkyl, wherein $C_{1-3}$alkyl is optionally substituted with one, two, or three halo, or with —$OR^h$.

In a specific aspect, $R^{10}$ is hydrogen, halo, or $C_{1-3}$alkyl substituted with one, two, or three halo.

In other specific aspects, $R^{10}$ is hydrogen or halo; or $R^{10}$ is hydrogen, chloro, or fluoro; or $R^{10}$ is hydrogen or —$CH_2OH$.

In another specific aspect, $R^{10}$ is —$CF_3$.

In another specific aspect, $R^{10}$ is chloro.

In yet another specific aspect, $R^{10}$ is hydrogen.

In a still further aspect, $R^{10}$ is —$CH_2OH$.

In a specific aspect, a is 0, 1, or 2.

In another specific aspect, a is 1 or 2.

In a specific aspect, b is 0, 1, or 2.

In another specific aspect, b is 1 or 2.

In yet another specific aspect, b is 1.

In another aspect, the invention provides compounds of formula (II):

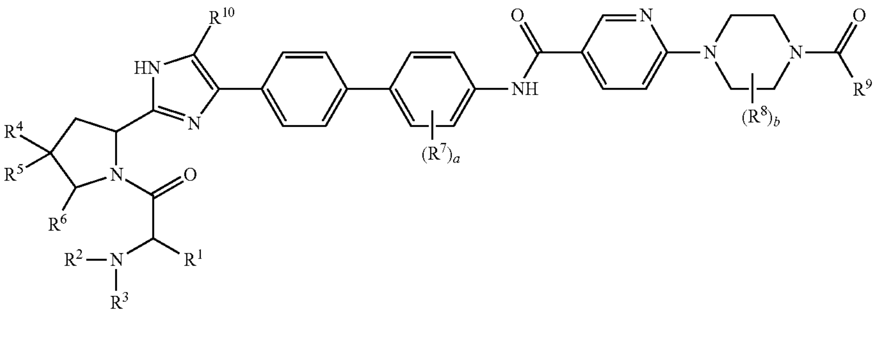

(II)

wherein the variables of formula (II) are as defined herein.

In another aspect, the invention provides compounds of formula (III)

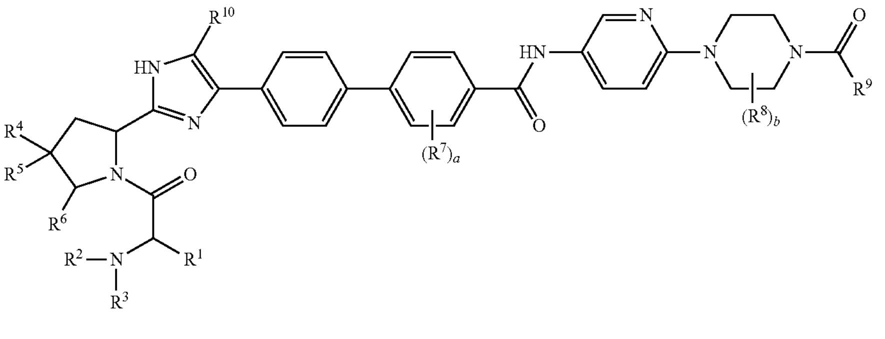

(III)

wherein the variables of formula (III) are as defined herein.

In yet another aspect, the invention provides compounds of formula (IV):

(IV)

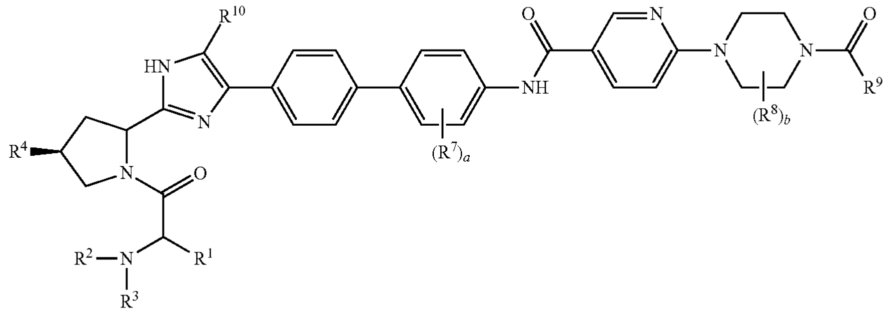

wherein:

$R^1$ is selected from $C_{1-6}$alkyl, optionally substituted with hydroxy or methoxy, tetrahydropyran, and phenyl;

$R^2$ is hydrogen;

$R^3$ is —C(O)O$C_{1-6}$alkyl;

$R^4$ is methyl or methoxy;

a is 1 or 2; and b is 1 or 2;

or a pharmaceutically-acceptable salt thereof.

Within this aspect, are compounds of formula (IVa) and of (IVb):

(IVa)

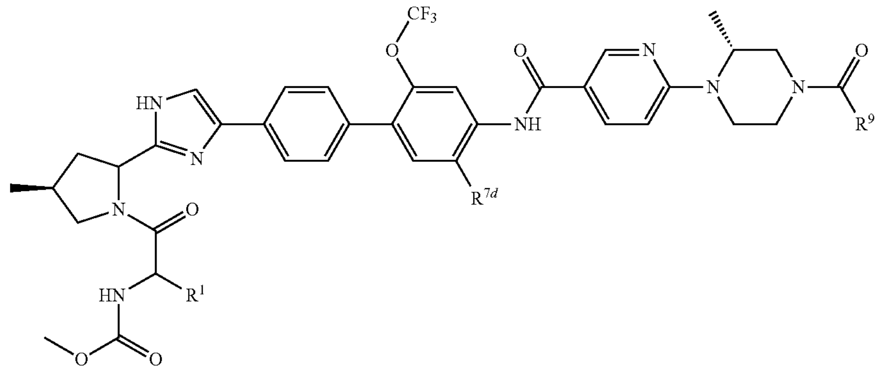

(IVb)

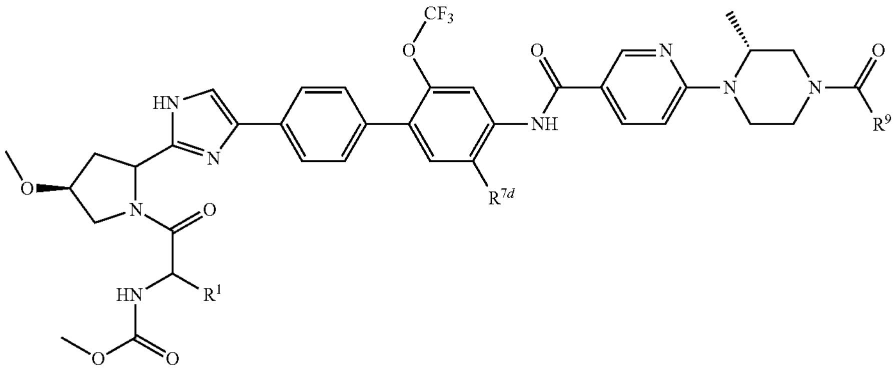

$R^7$ is selected from fluoro, chloro, —$CF_3$, and —$OCF_3$;

$R^8$ is independently methyl or hydroxymethyl;

$R^9$ is selected from —$NHCH_3$, cyclopropyl, 2,2-dimethyl-cyclopropyl, tert-butyl, 3-hydroxy-2,2-dimethylpropyl, and imidazolyl;

$R^{10}$ is hydrogen or hydroxymethyl;

wherein $R^1$ is isopropyl or tetrahydropyranyl, $R^{7d}$ is fluoro or chloro, and $R^9$ is tert-butyl or 3-hydroxy-2,2-dimethylpropyl.

In a further aspect, the invention provides compounds of formula (V):

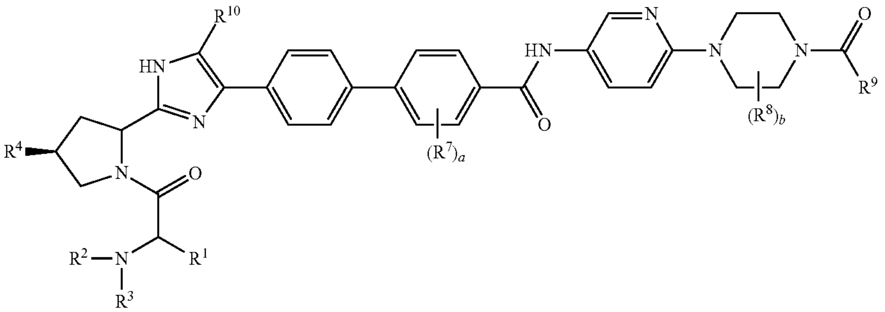

(V)

wherein:

$R^1$ is selected from $C_{1-6}$alkyl, optionally substituted with hydroxy or methoxy, tetrahydropyran, and phenyl;

$R^2$ is hydrogen;

$R^3$ is —C(O)O$C_{1-6}$alkyl;

$R^4$ is methyl or methoxy;

$R^7$ is selected from fluoro, chloro, —$CF_3$, and —$OCF_3$;

$R^8$ is independently methyl or hydroxymethyl;

$R^9$ is selected from —$NHCH_3$, cyclopropyl, 2,2-dimethylcyclopropyl, tert-butyl, 3-hydroxy-2,2-dimethylpropyl, and imidazolyl;

$R^{10}$ is hydrogen or hydroxymethyl;

a is 1 or 2; and b is 1 or 2;

or a pharmaceutically-acceptable salt thereof.

In one aspect, the invention provides the compounds of Examples 1-24 and Tables 1-29 below In another aspect, the invention provides a compound selected from the following compounds

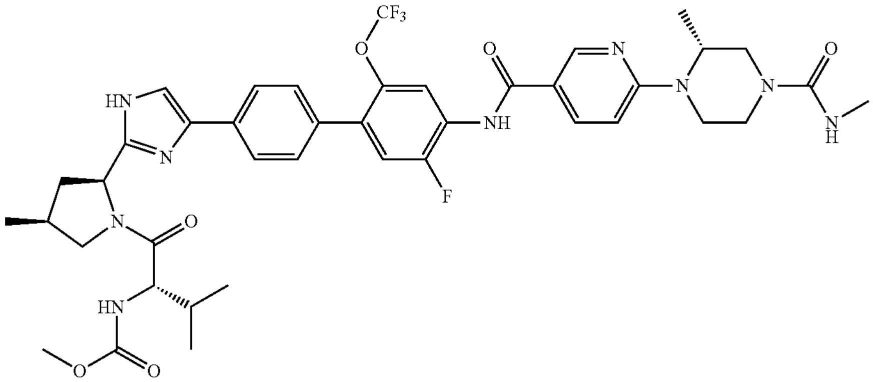

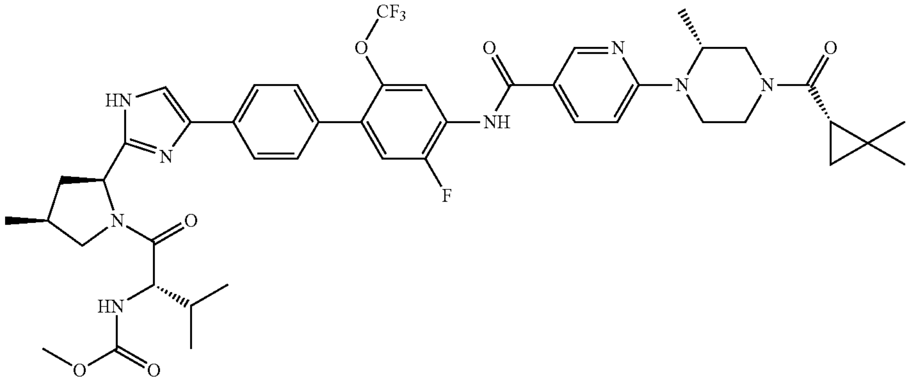

-continued
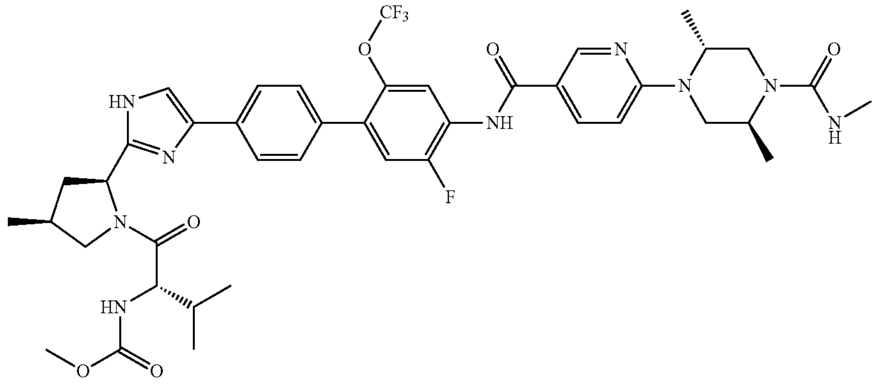
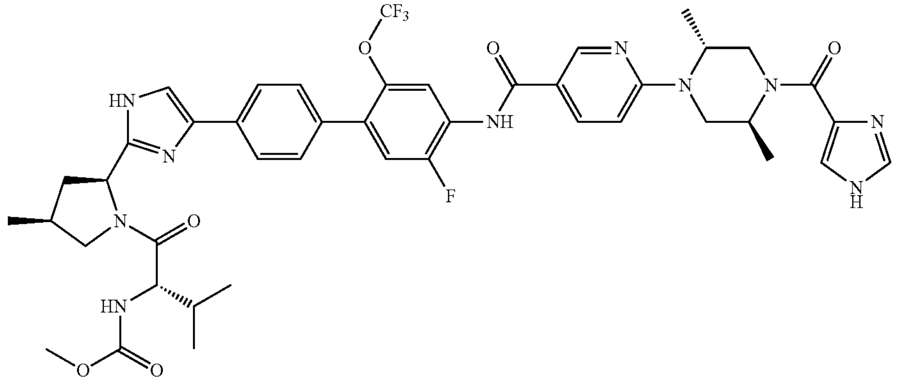
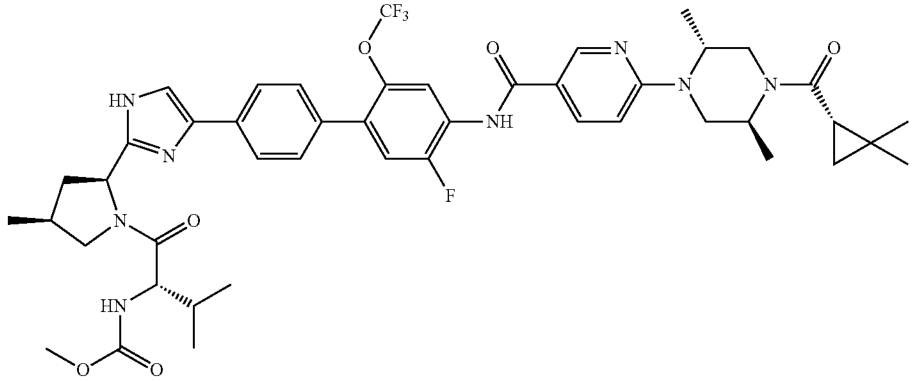
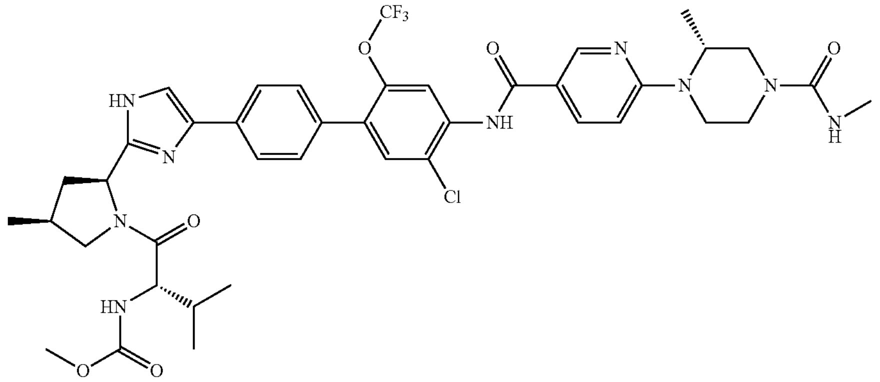

-continued
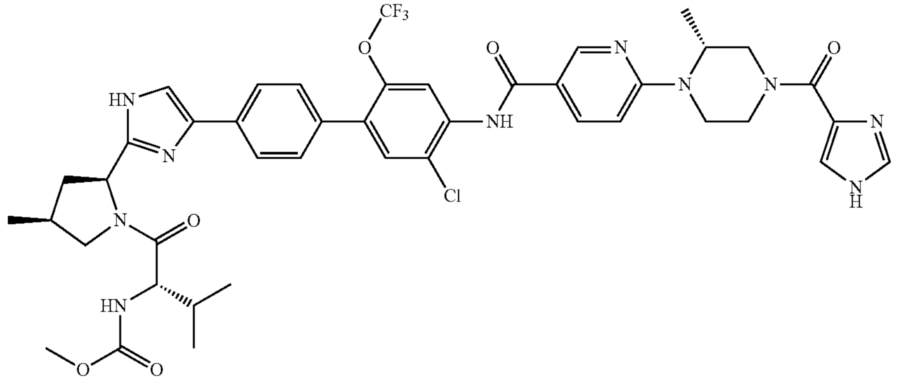
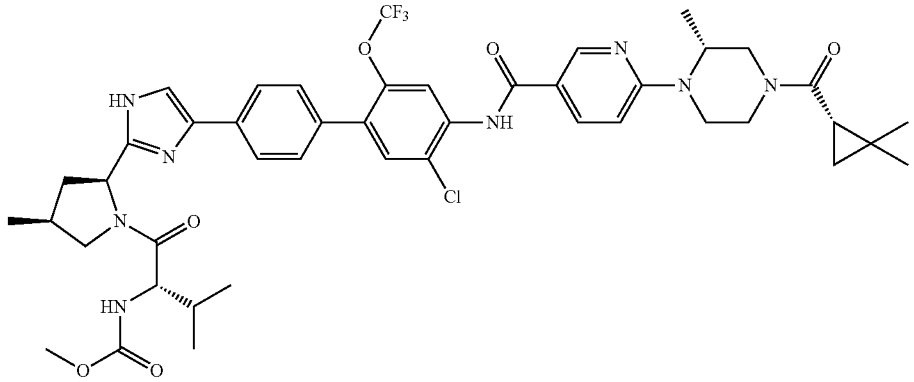
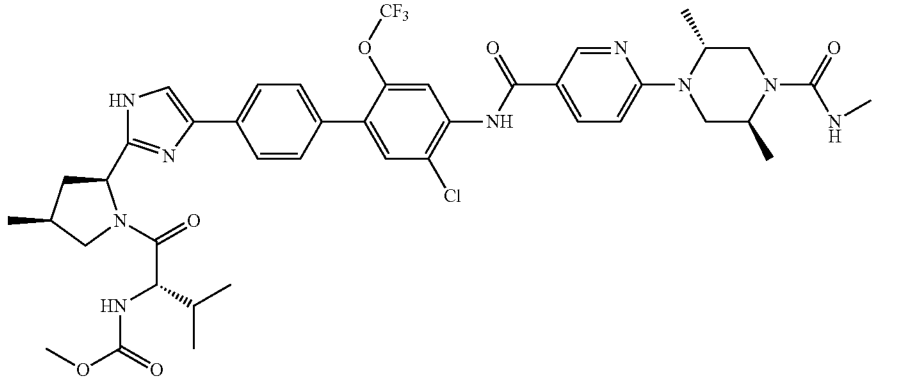
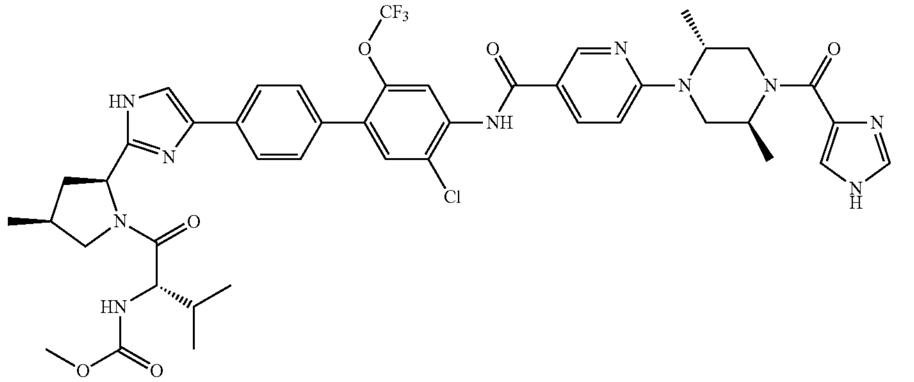

-continued
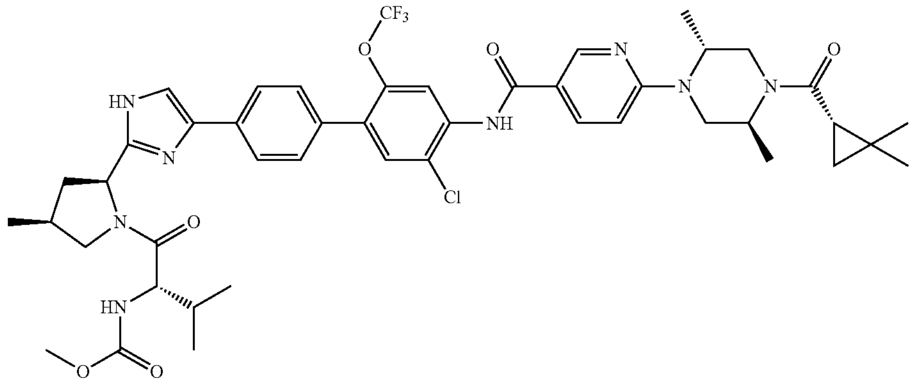
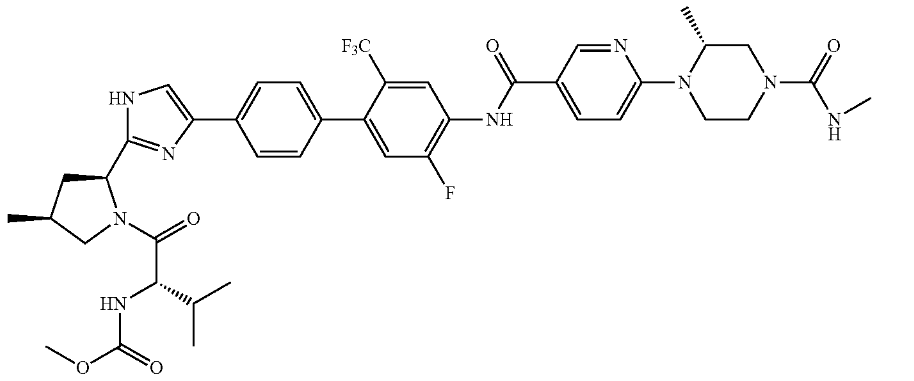
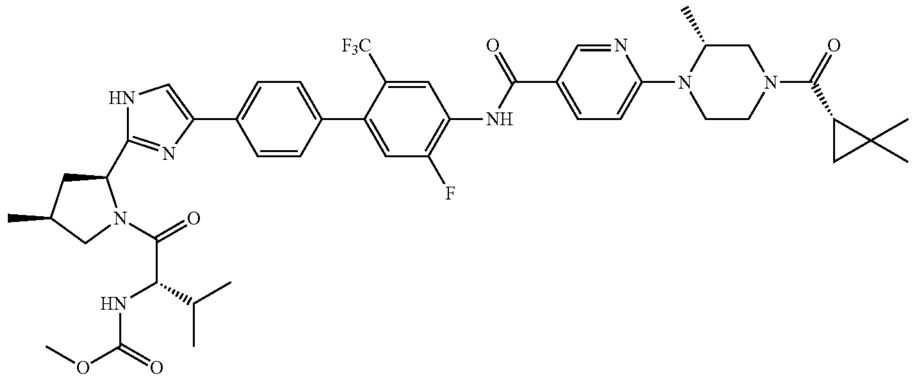
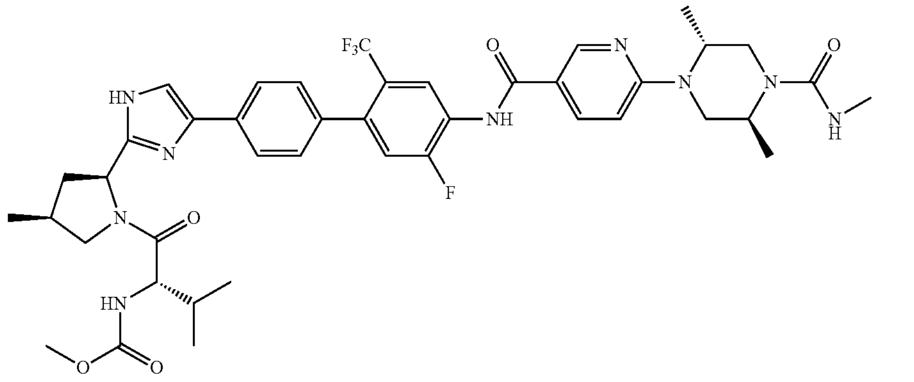

-continued
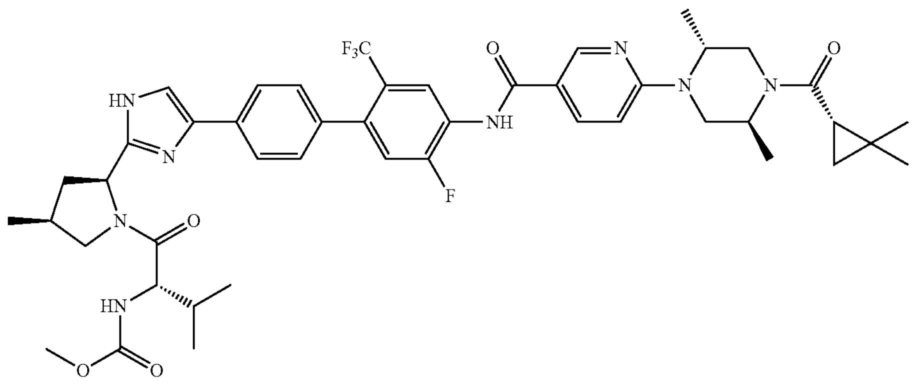
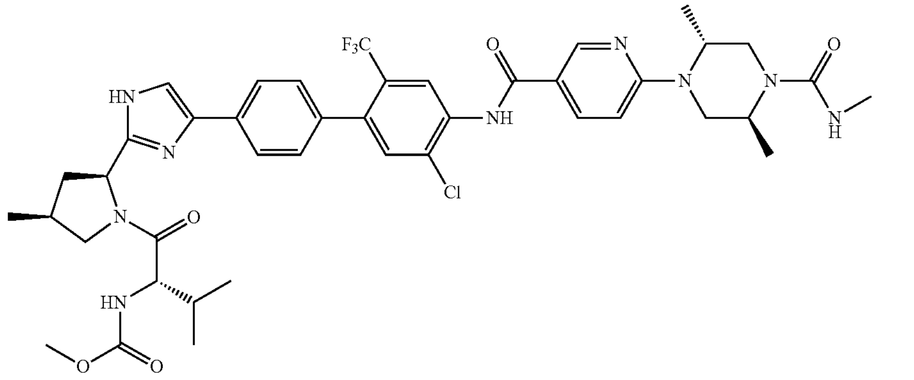
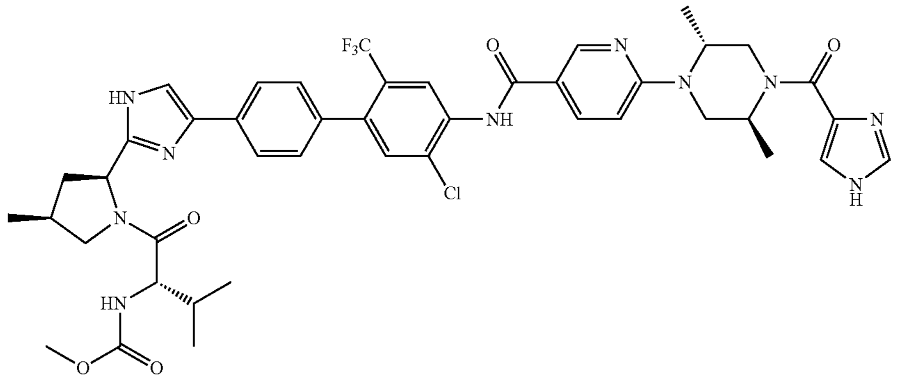
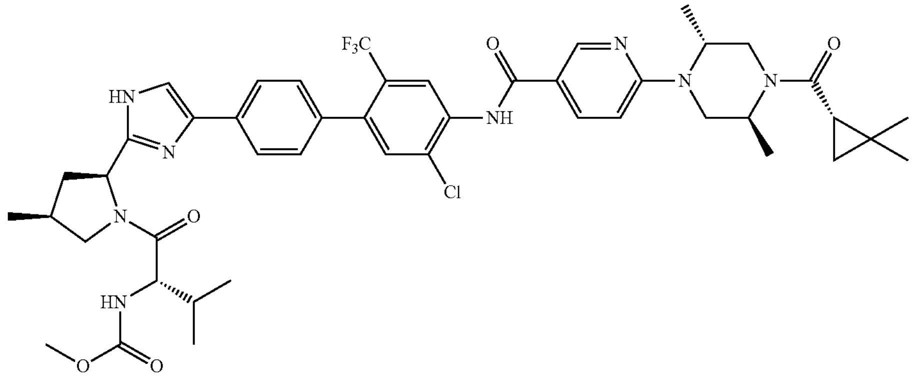

-continued
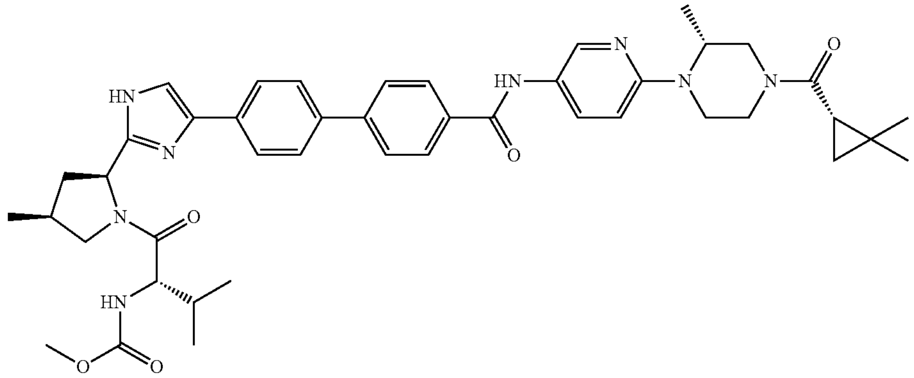
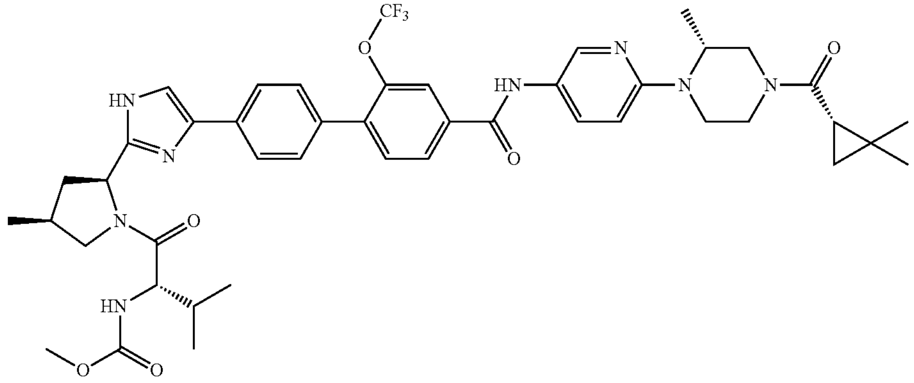
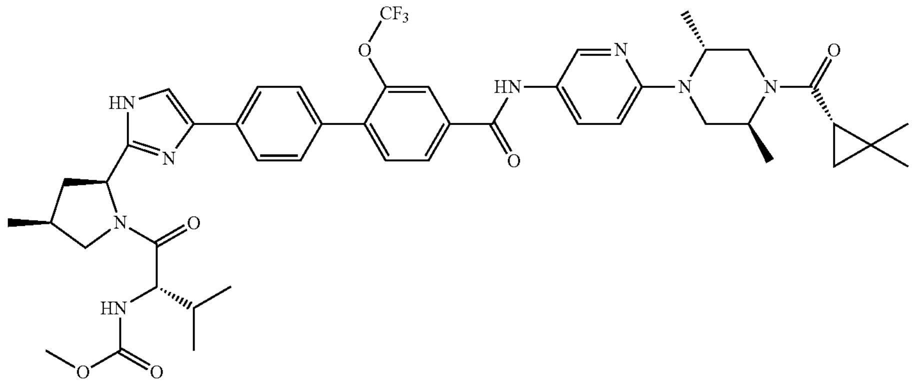
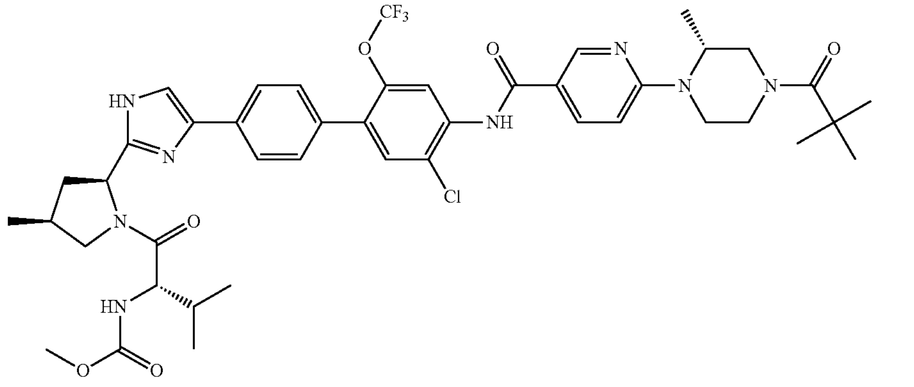

-continued
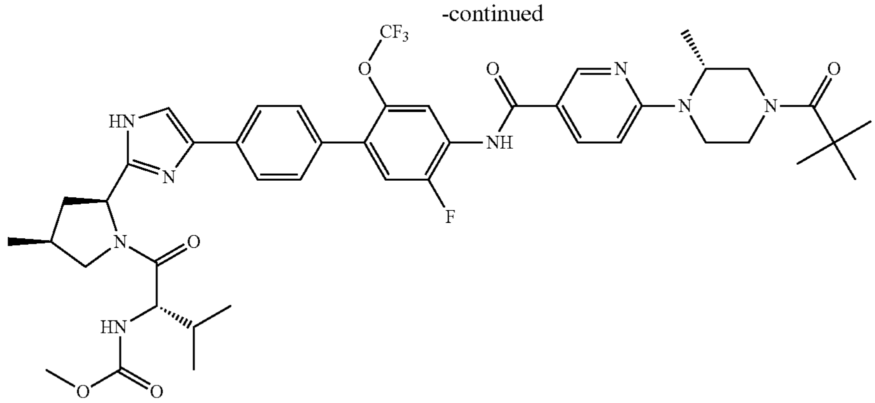
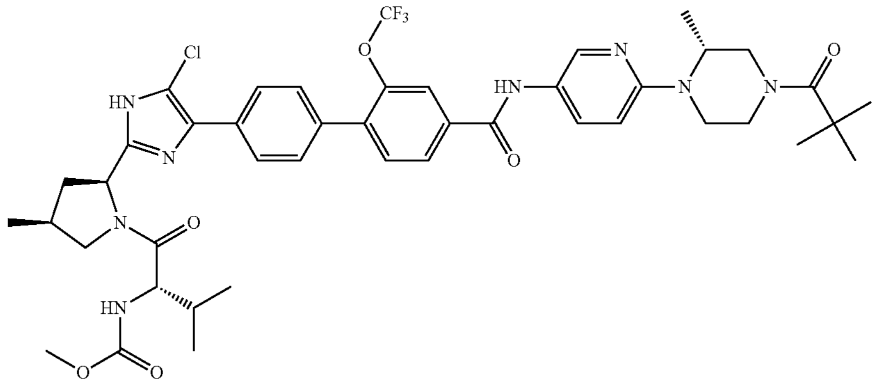
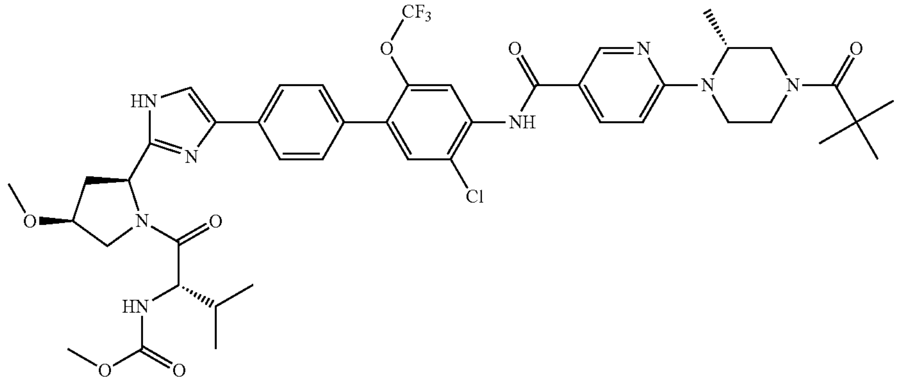
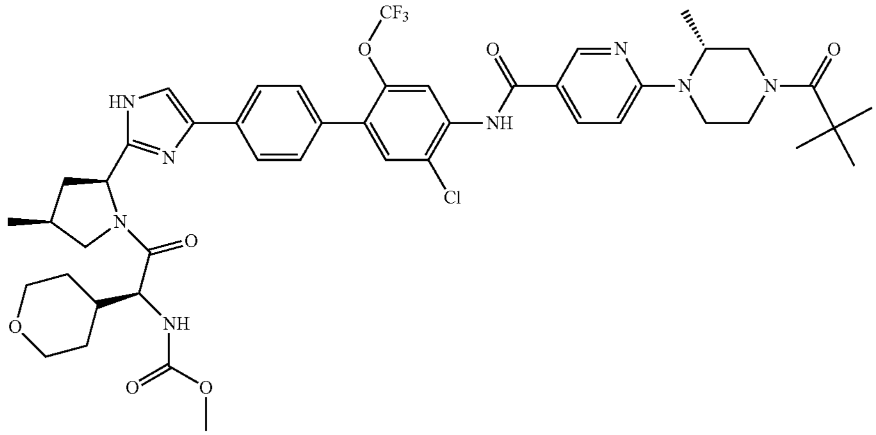

-continued
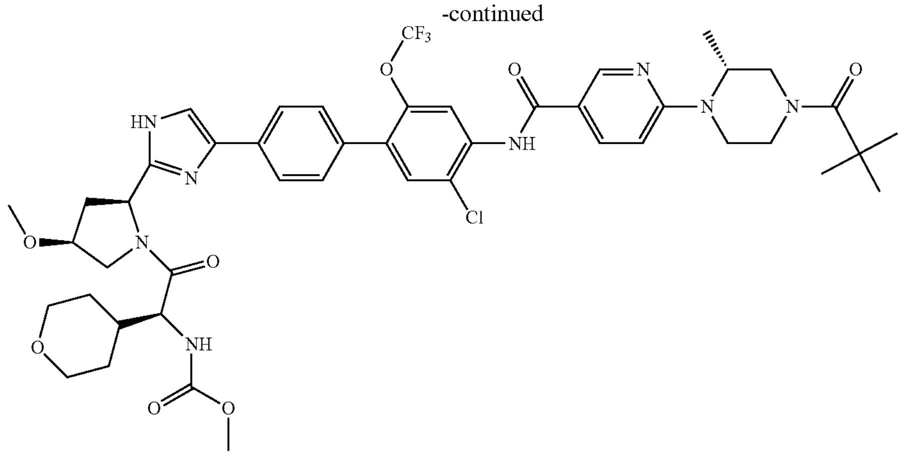
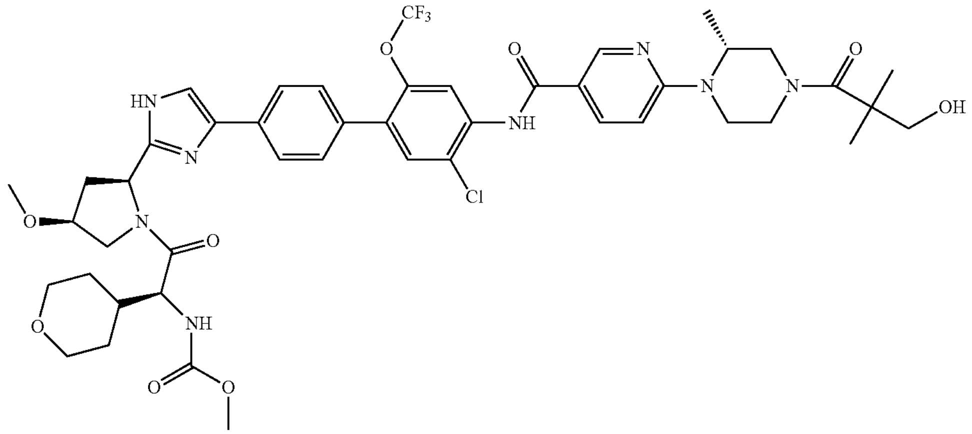
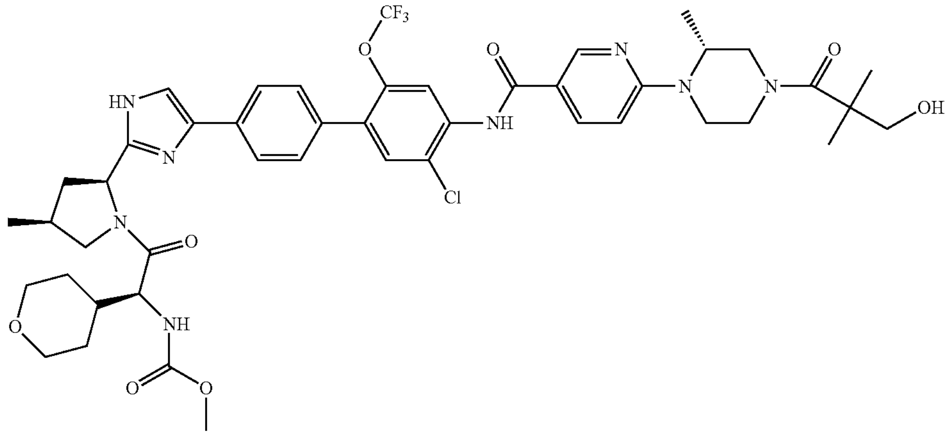
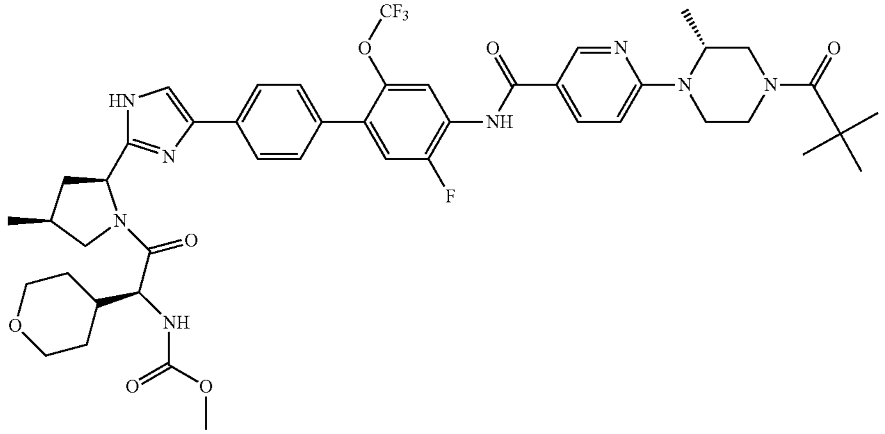

-continued
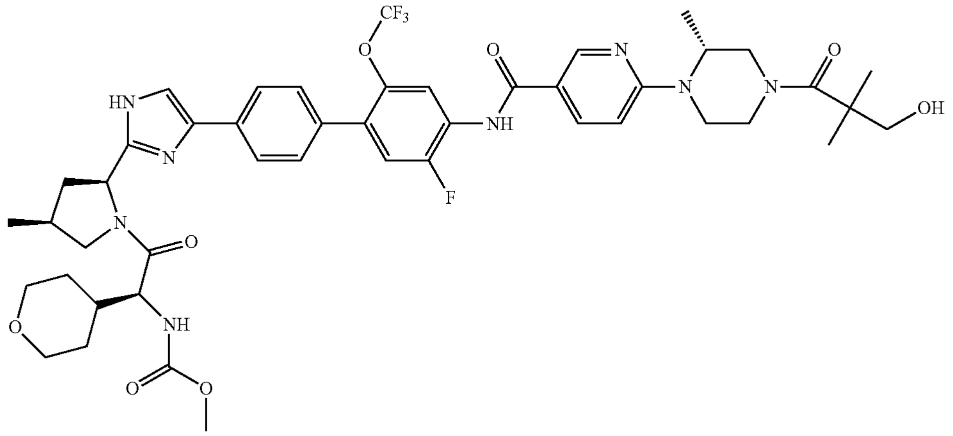
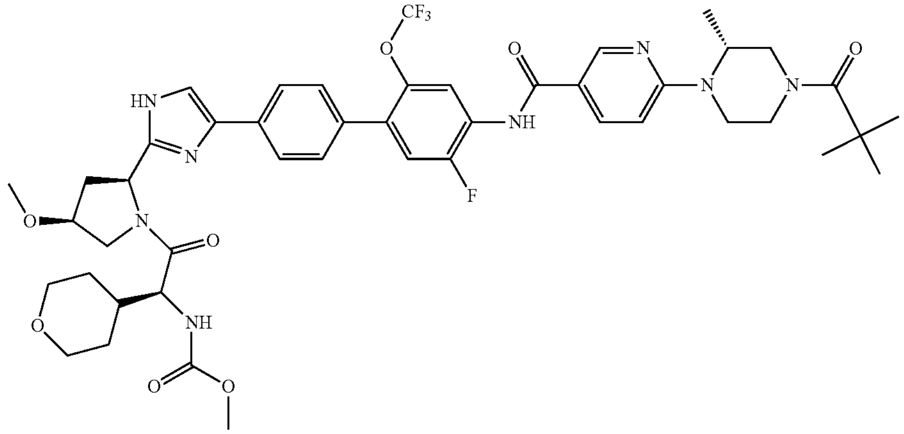
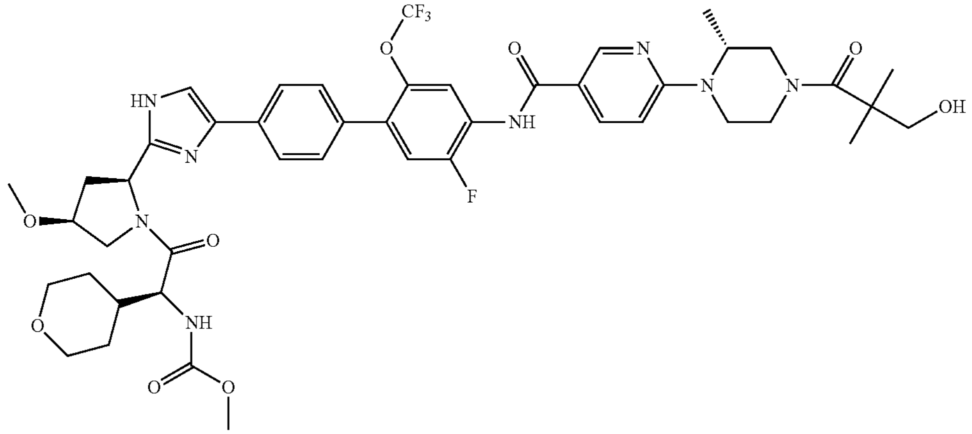
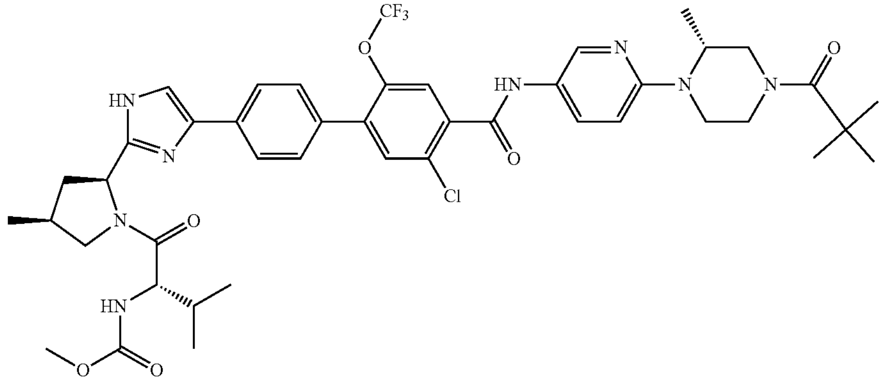

-continued
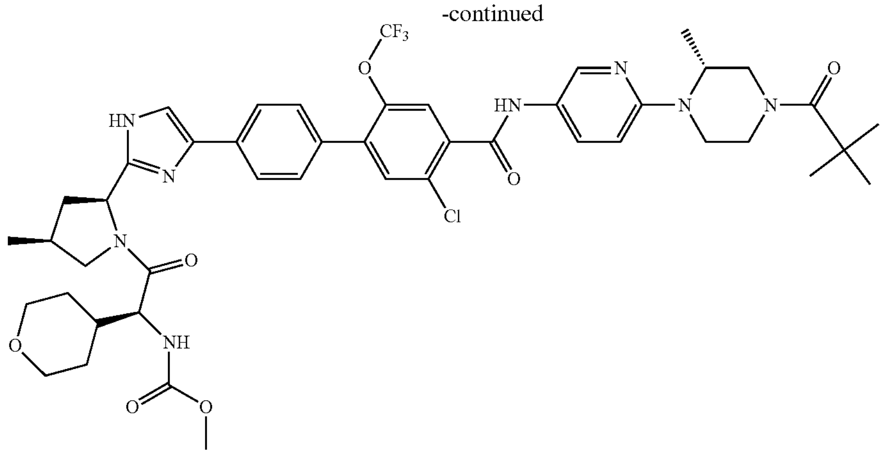
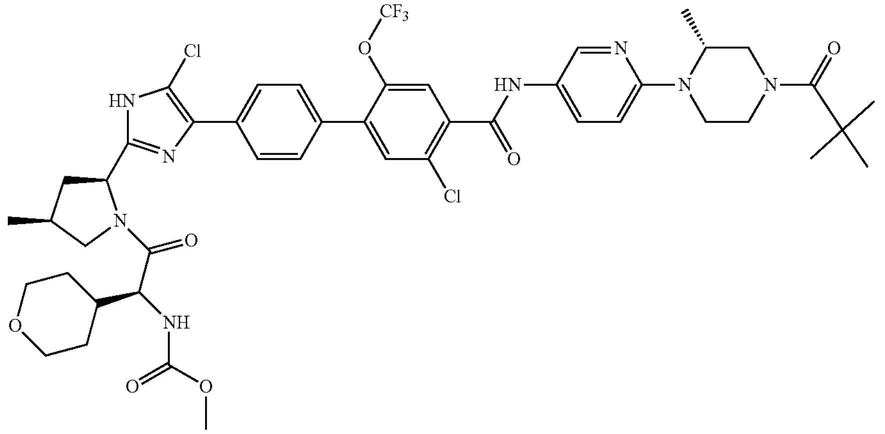
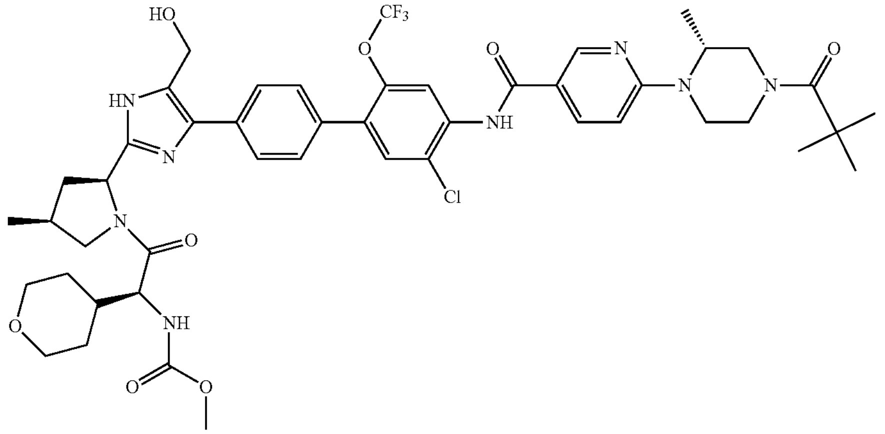
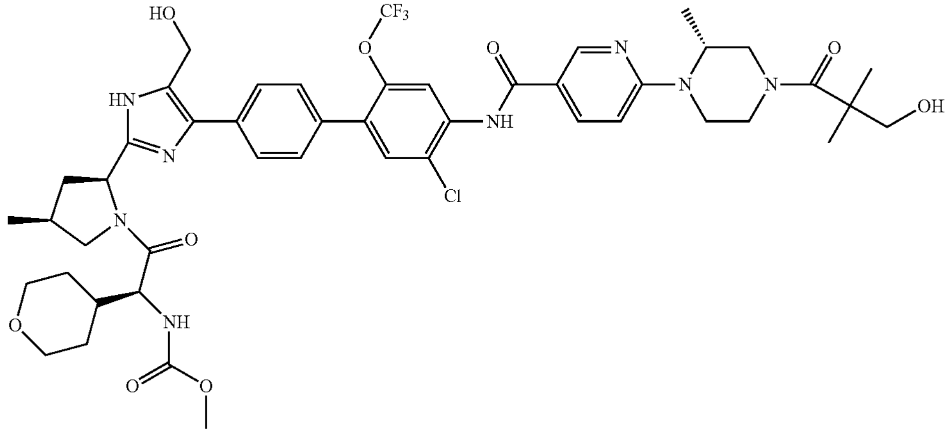

-continued
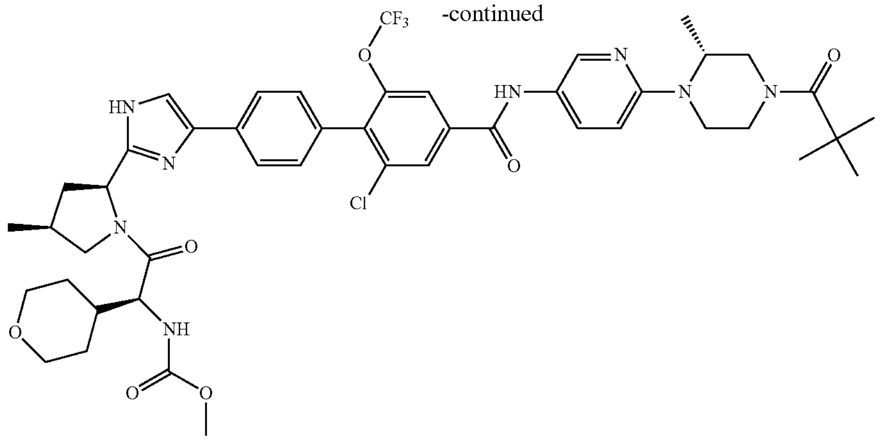
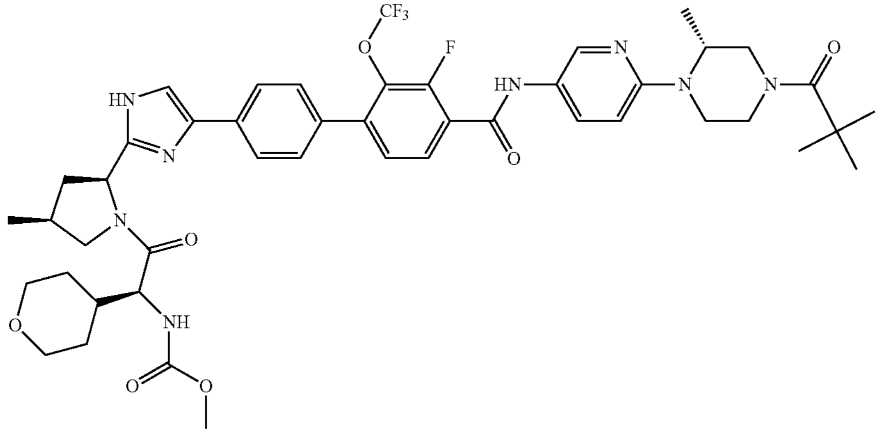
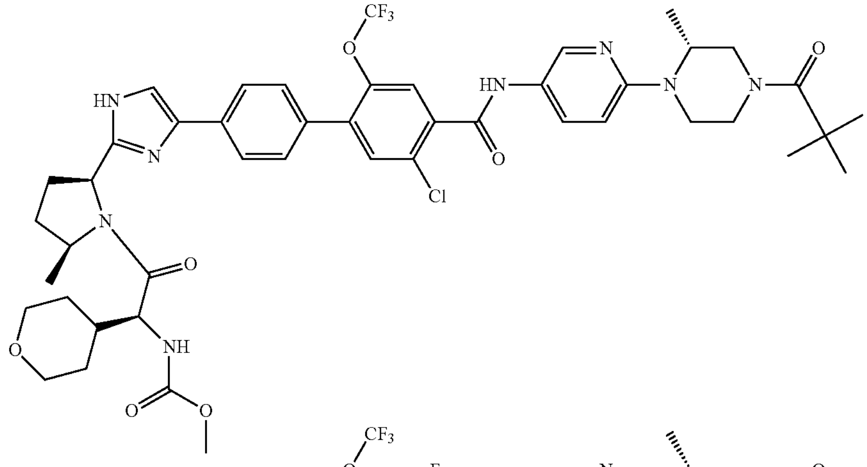
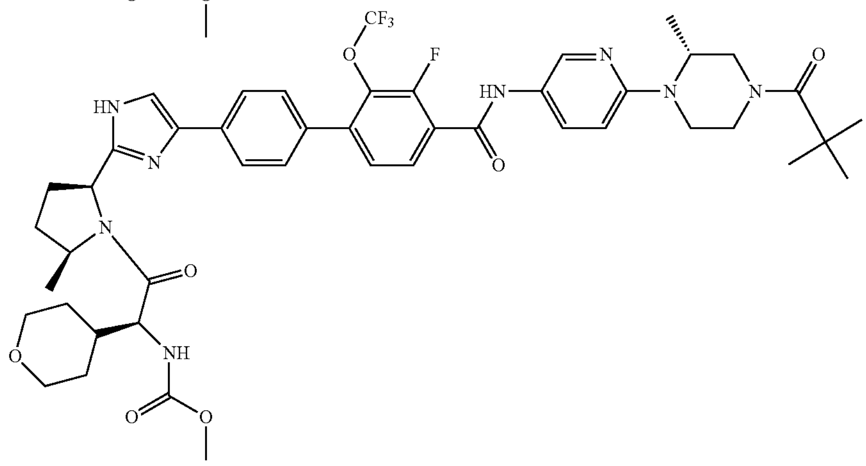

and pharmaceutically-acceptable salts thereof.

Chemical structures are named herein according to IUPAC conventions as implemented in available software packages. For example, the compound of Example 1:

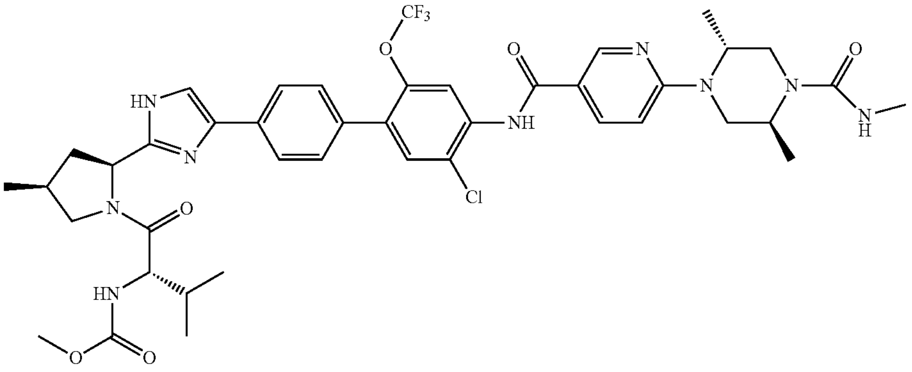

is designated as ((S)-1-{(2S,4S)-2-[4-(5'-chloro-4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester by AutoNom software, (MDL Information Systems, GmbH, Frankfurt, Germany). Equivalently, the compound may be named as methyl (S)-1-((2S,4S)-2-(4-(5'-chloro-4'-(6-((2R,5S)-2,5-dimethyl-4-(methylcarbamoyl)piperazin-1-yl)nicotinamido)-2'-(trifluoromethoxy)biphenyl-4-yl)-1H-imidazol-2-yl)-4-methylpyrrolidin-1-yl)-3-methyl-1-oxobutan-2-ylcarbamate, as provided by ChemDraw software (PerkinElmer, Inc., Cambridge, Mass.).

Furthermore, the imidazole moiety in the structure of formula (I) exists in tautomeric forms, illustrated below for a fragment of the compound of Example 1

A

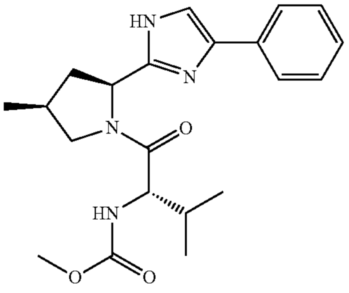

B

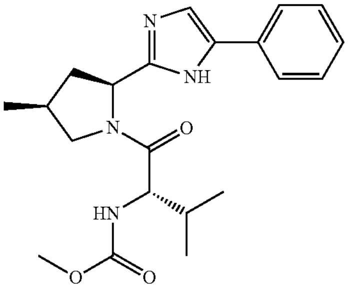

According to the IUPAC convention, these representations give rise to different numbering of the atoms of the imidazole moiety: methyl (S)-3-methyl-1-((2S,4S)-4-methyl-2-(4-phenyl-1H-imidazol-2-yl)pyrrolidin-1-yl)-1-oxobutan-2-ylcarbamate (structure A) vs. methyl (S)-3-methyl-1-((2S,4S)-4-methyl-2-(5-phenyl-1H-imidazol-2-yl)pyrrolidin-1-yl)-1-oxobutan-2-ylcarbamate (structure B). It will be understood that although structures are shown, or named, in a particular form, the invention also includes the tautomer thereof.

The compounds of the invention contain one or more chiral centers and therefore, such compounds (and intermediates thereof) can exist as racemic mixtures; pure stereoisomers (i.e., enantiomers or diastereomers); stereoisomer-enriched mixtures and the like. Chiral compounds shown or named herein without a defined stereochemistry at a chiral center are intended to include any or all possible stereoisomer variations at the undefined stereocenter unless otherwise indicated. The depiction or naming of a particular stereoisomer means the indicated stereocenter has the designated stereochemistry with the understanding that minor amounts of other stereoisomers may also be present unless otherwise indicated, provided that the utility of the depicted or named compound is not eliminated by the presence of another stereoisomer.

Compounds of formula (I) also contain several basic groups (e g, amino groups) and therefore, such compounds can exist as the free base or in various salt forms, such a mono-protonated salt form, a di-protonated salt form, a tri-protonated salt form, or mixtures thereof. All such forms are included within the scope of this invention, unless otherwise indicated.

This invention also includes isotopically-labeled compounds of formula (I), i.e., compounds of formula (I) where an atom has been replaced or enriched with an atom having the same atomic number but an atomic mass different from the atomic mass that predominates in nature. Examples of isotopes that may be incorporated into a compound of formula (I) include, but are not limited to, $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{36}Cl$, and $^{18}F$. Of particular interest are compounds of formula (I) enriched in tritium or carbon-14, which compounds can be used, for example, in tissue distribution studies. Also of particular interest are compounds of formula (I) enriched in deuterium especially at a site of metabolism, which compounds are expected to have greater metabolic stability. Additionally of particular interest are compounds of formula (I) enriched in a positron emitting isotope, such as $^{11}C$, $^{18}$, $^{15}O$ and $^{13}N$, which compounds can be used, for example, in Positron Emission Tomography (PET) studies.

DEFINITIONS

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "alkoxy" means the monovalent group —O-alkyl, where alkyl is defined as above. Representative alkoxy groups include, by way of example, methoxy, ethoxy, propoxy, butoxy, and the like.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl, cyclopentyl, cyclohexyl, cycloheptyl, cyclooctyl, adamantyl, and the like.

The term "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclic groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "heteroaryl" or "heteroaryl ring" means a monovalent aromatic group having from 5 to 10 total ring atoms, wherein the ring contains from 1 to 9 carbon ring atoms and from 1 to 4 ring heteroatoms selected from nitrogen, oxygen, and sulfur. Heteroaryl groups may be monocyclic or multicyclic. Representative heteroaryl groups include, by way of example, pyrroyl, isoxazolyl, isothiazolyl, pyrazolyl, oxazolyl, oxadiazolyl, thiadiazolyl, thiazolyl, imidazolyl, triazolyl, tetrazolyl, furanyl, triazinyl, thienyl, pyridyl (or, equivalently, pyridinyl), pyrimidyl, pyridazinyl, pyrazinyl, indolyl, benzofuranyl, benzothienyl, benzimidazolyl, benzthiazolyl, and the like, where the point of attachment is at any available carbon or nitrogen ring atom. Where the context makes the point of attachment of the heteroaryl group evident, such groups may alternatively be referred to as a non-valent species, i.e. pyrrole, isoxazole, isothiazole, pyrazole, imidazole, etc.

The term "halo" means fluoro, chloro, bromo or iodo.

The term "therapeutically effective amount" means an amount sufficient to effect treatment when administered to a patient in need of treatment.

The term "treatment" as used herein means the treatment of a disease, disorder, or medical condition in a patient (such as hepatitis C viral infection), such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound of formula (I), i.e. a form where one or more amino groups have been protonated by an acid. Typically, the salt is a pharmaceutically acceptable salt, although this is not required for salts of intermediate compounds that are not intended for administration to a patient.

The term "amino-protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like. Numerous protecting groups, and their introduction and removal, are described in T. W. Greene and G. M. Wuts, *Protecting Groups in Organic Synthesis*, Third Edition, Wiley, New York General Synthetic Procedures Compounds of this invention, and intermediates thereof, can be prepared according to the following general methods and procedures using commercially-available or routinely-prepared starting materials and reagents. The substituents and variables (e.g., $R^1$, $R^2$, $R^3$, $R^4$, etc.) used in the following schemes have the same meanings as those defined elsewhere herein unless otherwise indicated. Additionally, compounds having an acidic or basic atom or functional group may be used or may be produced as a salt unless otherwise indicated (in some cases, the use of a salt in a particular reaction will require conversion of the salt to a non-salt form, e.g., a free base, using routine procedures before conducting the reaction).

Although a particular embodiment of the present invention may be shown or described in the following procedures, those skilled in the art will recognize that other embodiments or aspects of the present invention can also be prepared using such procedures or by using other methods, reagents, and starting materials know to those skilled in the art. In particular, it will be appreciated that compounds of the invention may be prepared by a variety of process routes in which reactants are combined in different orders to provide different intermediates en route to producing final products.

In one exemplary method of synthesis, compounds of formula (1-5) in which $A_m$ is defined as —NHC(O)— are prepared as shown in Scheme 1:

where G represents the group

G

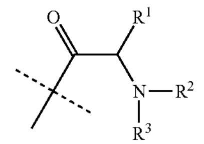

and Pg represents an amino-protecting group. Aniline intermediate 1-1 is reacted with carboxylic acid 1-2 according to typical amide bond formation conditions to provide a protected intermediate of formula 1-3 In some instances, the carboxylic acid 1-2 is first converted to an acid chloride and then reacted with aniline intermediate 1-1 to provide a compound of formula 1-3. As shown in the examples below, the amide bond formation reaction may utilize coupling agents, such as N,N,N',N'-tetramethyl-O-(7-azabenzotriazol-1-yl) uronium hexafluorophosphate (HATU), or as 1,3-dicyclohexylcarbodiimide (DCC), 1-(3-dimethylaminopropyl)-3-ethylcarbodiimide (EDC), or benzotriazol-1-

Scheme 1

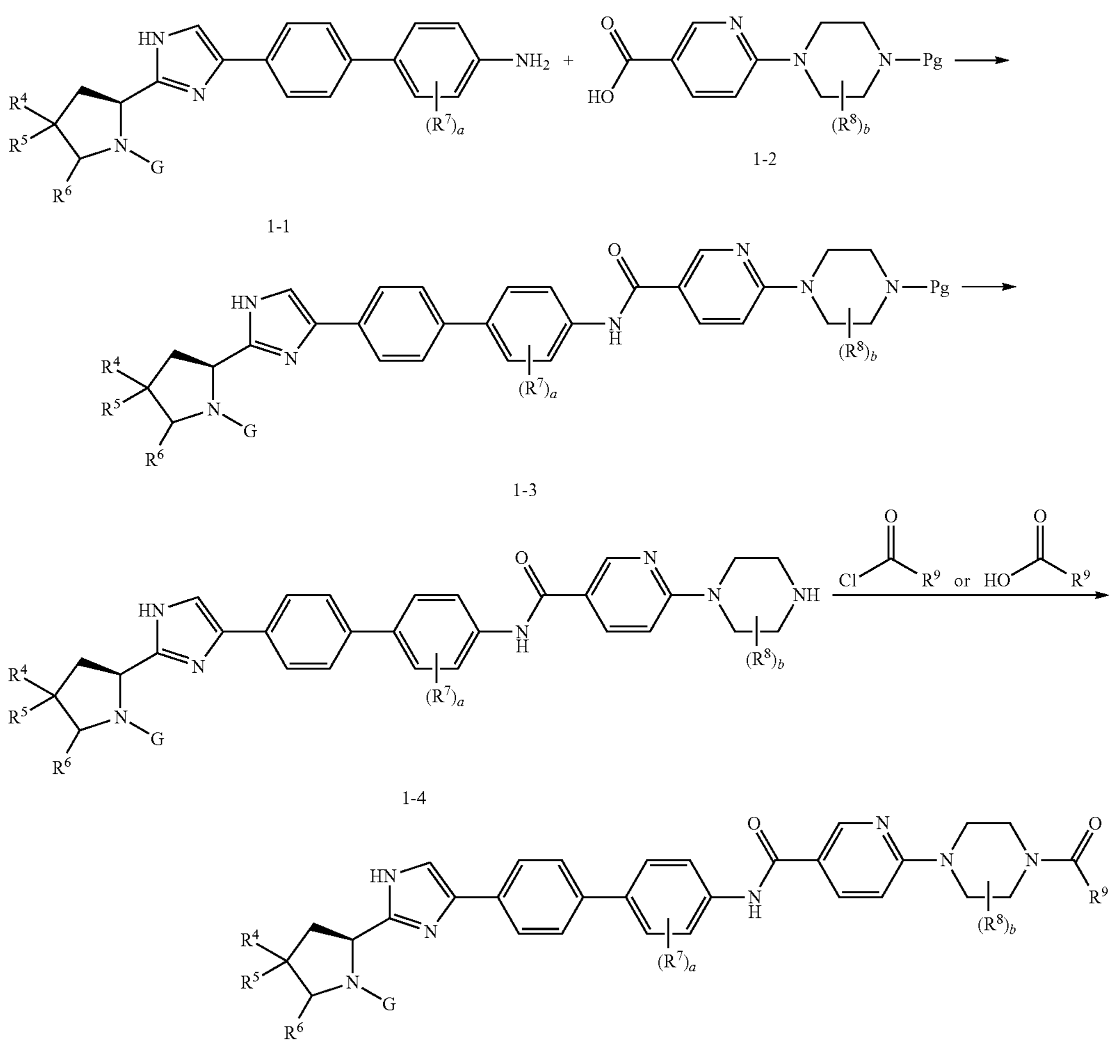

1-1, 1-2, 1-3, 1-4 or 1-5 yloxytripyrrolidino-phosphonium hexafluorophosphate (PyBop), optionally combined with 1-hydroxy-7-azabenzotriazole (HOAt). Preferably, the process of Scheme 1 is used to prepare compounds of formula 1-3 in which $R^7$ is absent (a is 0) or $R^7$ is an electron rich substituent such as an unsubstituted-alkyl or unsubstituted-alkoxy, and the reaction is performed in the presence of coupling agents EDC and HOAt at a temperature of about 50 to about 60° C. Intermediate 1-3 is then deprotected, for example, by treatment with an acid to provide compound 1-4, which is reacted with an acid chloride in the presence of base or with a carboxylic acid under amide bond formation conditions to prepare a compound of the invention of formula 1-5.

It will be readily understood that the final product 1-5 could alternatively be prepared directly by reaction of aniline 1-1 with a compound of formula 1-2'

1-2'

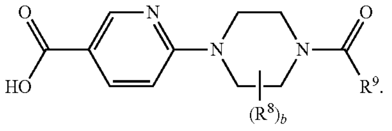

Protected intermediate 1-3 may also be conveniently prepared by alternative processes, for example, as shown in Scheme 2:

In a first step, biphenyl aniline 1-1 is reacted with a fluoropyridine carbonyl chloride 2-1 in the presence of base to provide fluoro intermediate 2-2. The fluoro intermediate is then reacted with an excess of protected piperazine 2-3 to provide protected intermediate 1-3. The reaction typically is performed in the presence of base with heating to a temperature of about 80° C. to about 120° C. for a period of about 4 to about 48 hours.

Yet another alternative process for the preparation of intermediate 1-3 utilizes a Suzuki coupling reaction in the presence of a palladium catalyst (Miyaura and Suzuki, *Chem. Rev.* 1995, 95, 2457-2483). As shown in Scheme 3 below, either coupling partner may bear the boronate moiety. Alternatively, a boronic acid reagent may be used in place of a boronate reagent, such as the pinacol boronate depicted below.

Scheme 2

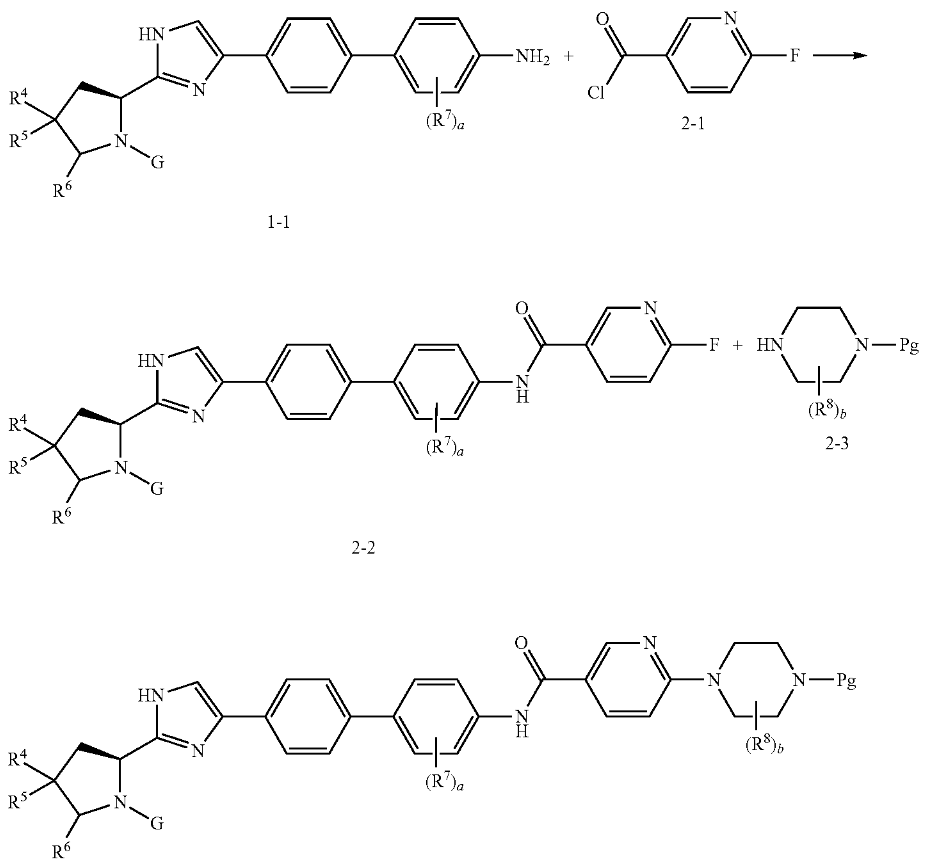

1-1

2-1

2-2

2-3

1-3

Scheme 3A

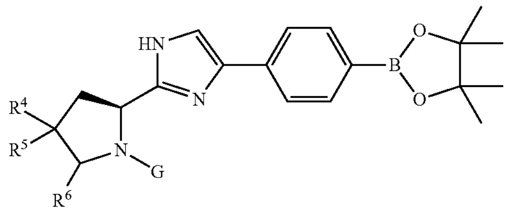

3-1

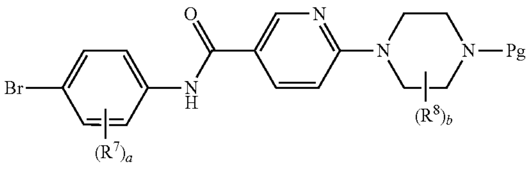

3-2 or

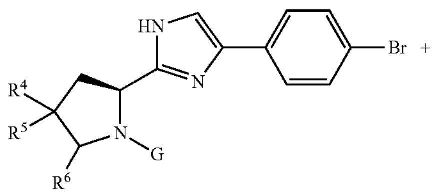

3-3

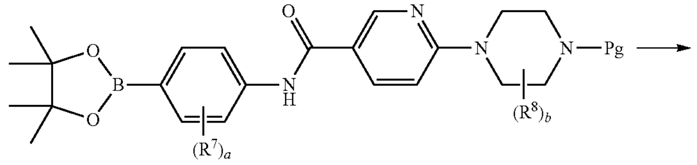

3-4

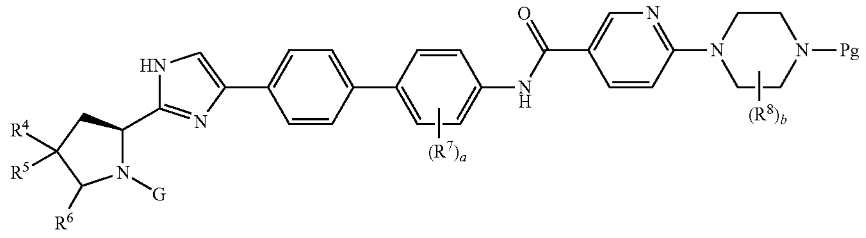

1-3

If protected intermediate 3-2 were replaced by an intermediate 3-2'

3-2'

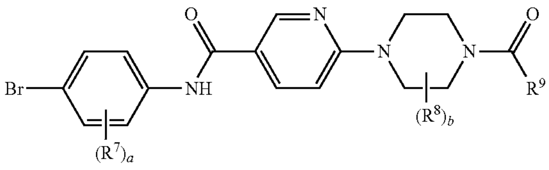

then the Suzuki coupling of the boronate 3-1 in the first alternative of Scheme 3 would directly provide a final compound of the invention.

Analogously, if protected intermediate 3-4 were replaced by a boronate intermediate 3-4' or equivalently a boronic acid intermediate 3-4'', 3-4'

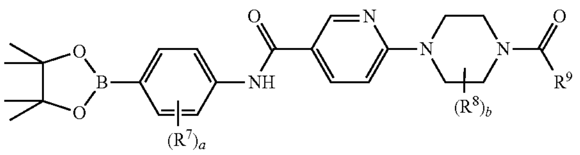

3-4''

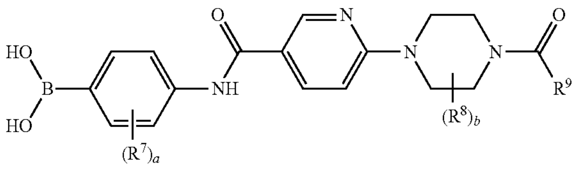

then the Suzuki coupling of the bromo intermediate shown in the second alternative initial step of Scheme 3 would directly provide a compound of the invention. The boronic acid 3-4'' advantageously may be prepared in crystalline form. See, for example, Preparation 44 below.

Another useful sequence for preparation of final compounds of the invention is illustrated in Scheme 3B.

Scheme 3B

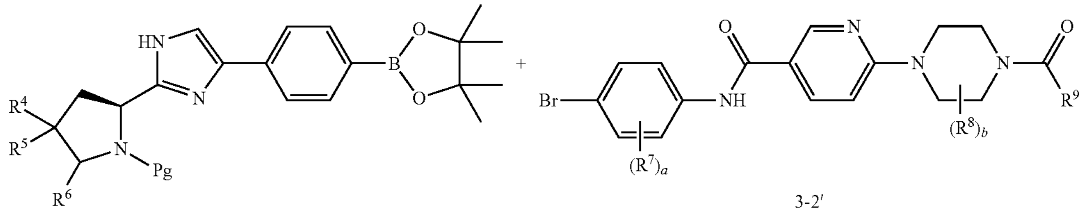

or 3-1'

3-2'

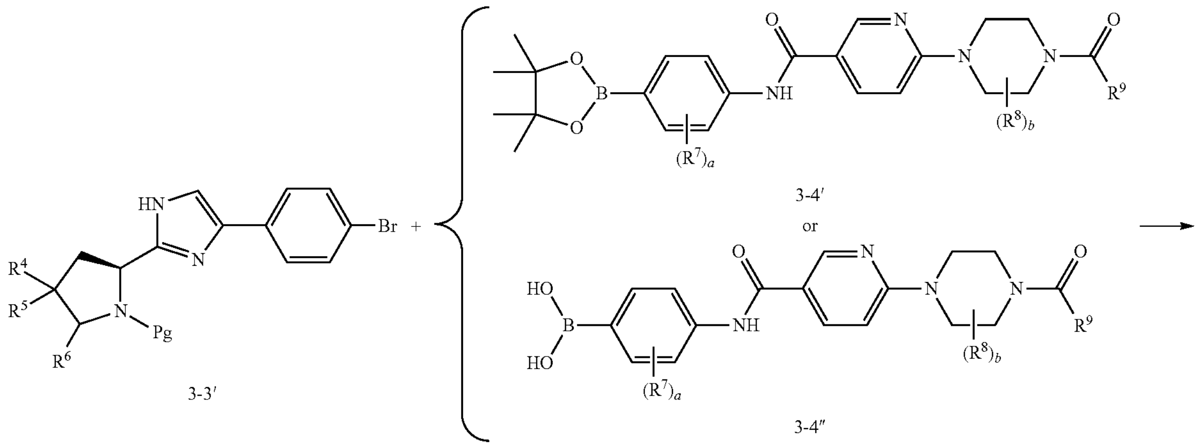

3-4' or 3-3'

3-4''

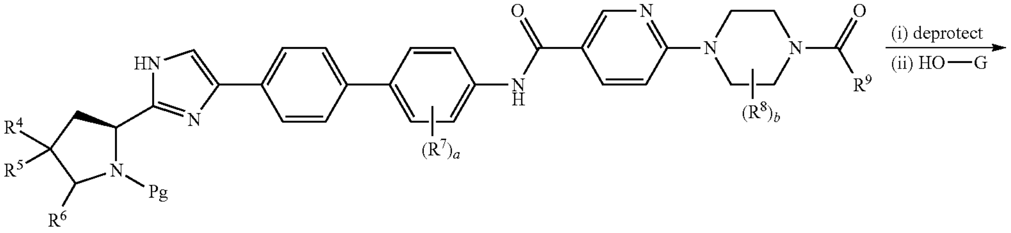

3-5

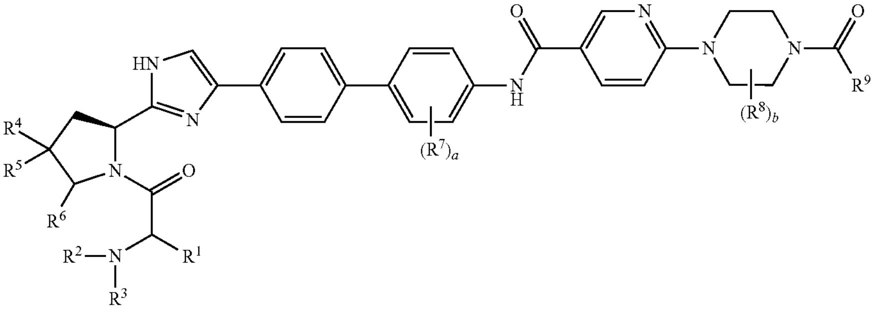

(II')

where a protected form of the Suzuki coupling partners 3-1' or 3-3' in which the nitrogen on the proline bears a protecting group Pg, and intermediates 3-2', 3-4, or 3-4", bearing the substituent $R^9$, are used in the first step to form a protected intermediate 3-5. The protected intermediate 3-5 is (i) deprotected conventionally, and then (ii) reacted with a reagent HO-G to provide a compound of the invention.

The bromo intermediate 3-2 of Scheme 3A may be prepared, for example, by amide coupling of arylamine 4-1 with a fluoropyridine carbonyl chloride 2-1, followed by reaction with a protected piperazine 2-3 as shown in Scheme 4.

Scheme 4

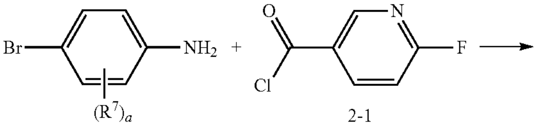

4-1

2-1

-continued

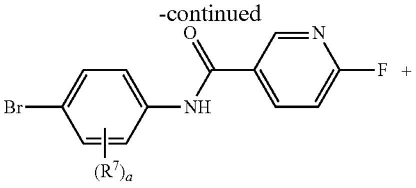

4-2

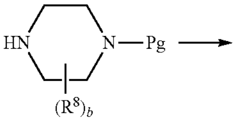

2-3

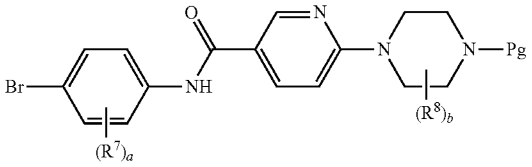

3-2

Alternatively, intermediate 3-2 may be prepared by the reaction of 4-1 with the carboxylic acid intermediate 1-2 as given in Scheme 5.

Scheme 5

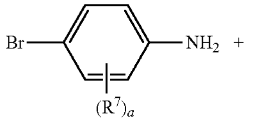

4-1

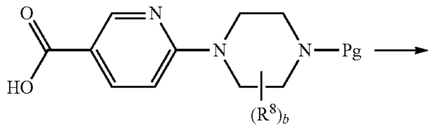

1-2

-continued

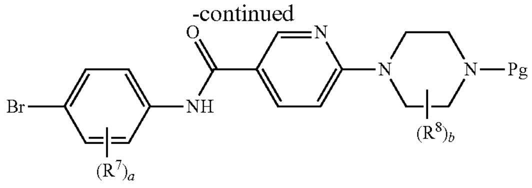

3-2

It will be readily understood that intermediates bearing the substituent $R^9$ may be prepared from the corresponding protected compound. For example, the bromo intermediate 3-2', may be prepared by deprotecting intermediate 3-2 and then reacting with an acid chloride or carboxylic acid as in Scheme 1.

Processes for the preparation of intermediates 1-1 and 1-2 used in process Scheme 1 are given in the following schemes.

Scheme 6

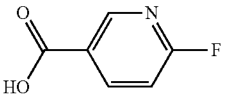

6-1

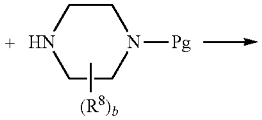

2-3

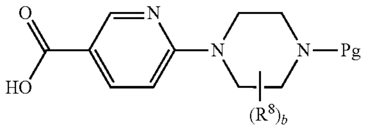

1-2

The reaction in Scheme 6 of a fluoronicotinic acid 6-1 with the protected piperazine 2-3 to provide intermediate 1-2 is typically performed using a Grignard reagent such as isopropylmagnesium chloride at a temperature below about −20° C.

The biaryl aniline intermediate 1-1 may be prepared by the Suzuki coupling reaction of Scheme 7, where, as shown, either coupling partner may bear the boronate moiety.

Scheme 7

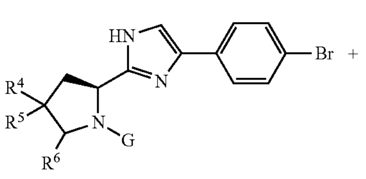

3-3

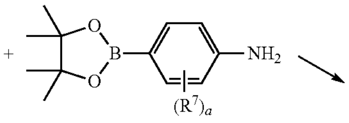

7-1

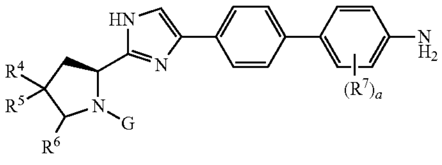

1-1

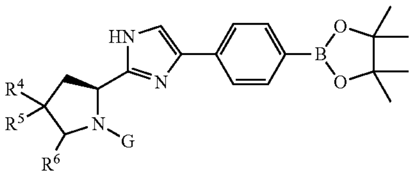

3-1

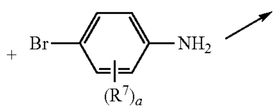

7-2

Intermediates 3-1 and 3-3 used in the Suzuki reaction of Schemes 3 and 7 may be prepared, for example, as shown in Schemes 8 and 9.

Scheme 8

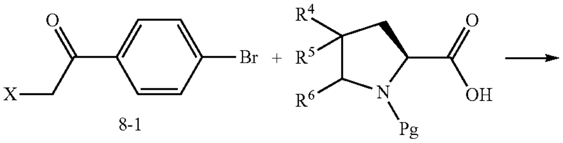

8-1

8-2

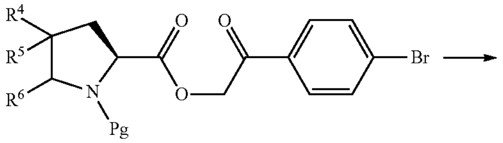

8-3

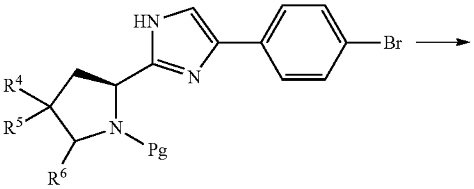

8-4

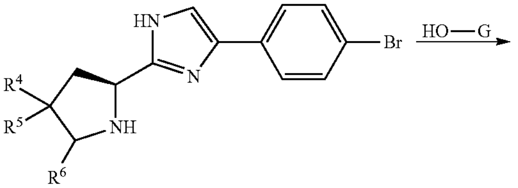

8-5

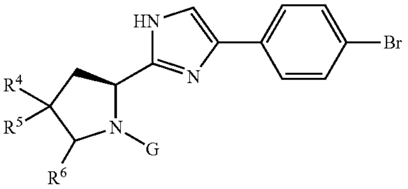

3-3

Reagent 8-1, where X represents bromo or chloro, is reacted with a protected proline carboxylic acid 8-2 to provide intermediate 8-3 which is converted to intermediate 8-4 in the presence of an excess of ammonium acetate. The ring closure reaction typically is performed at a temperature between about 100° C. and about 120° C. for a period of about 4 to about 24 hours. To provide compound 3-3, intermediate 8-4 is typically deprotected and coupled with a reagent HO-G to provide compound 3-3.

Finally, the boronate intermediates of Scheme 3 may be prepared from the corresponding bromo compounds. For example, to provide boronate intermediate 3-1, intermediate 3-3 is reacted with bis(pinacolato)diboron, 9-1, in the presence of a palladium catalyst as shown in Scheme 9.

Scheme 9

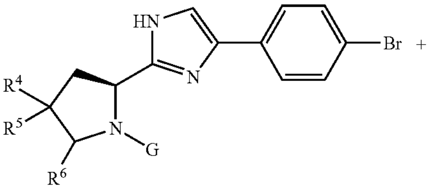

3-3

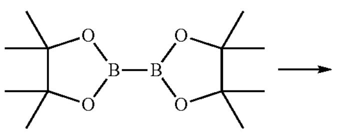

9-1

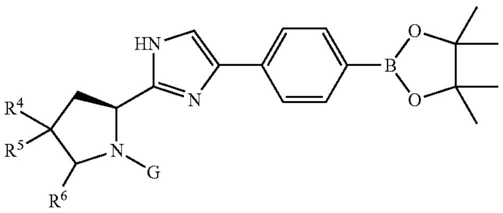

3-1

Similarly, the boronate intermediate 3-4 may be prepared by the reaction of bromo intermediate 3-2 with the diboron 9-1 under similar conditions. Further, a boronic acid Suzuki coupling partner may also be prepared from the corresponding bromo compound by reaction with a borate ester in the presence of a Grignard reagent, e.g. isopropylmagnesium chloride. See, for example, Preparation 44 below.

Compounds of Formula 10-5 in which the variable $A_m$ is defined as —C(O)NH— are prepared by processes analogous to those described above. One exemplary process for the preparation of compounds of Formula 10-5 is shown in Scheme 10.

Scheme 10

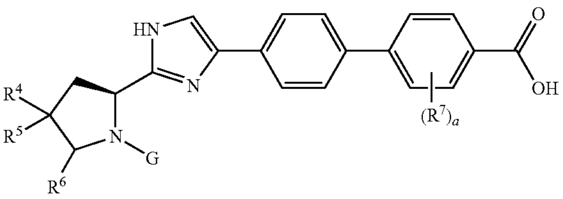

+

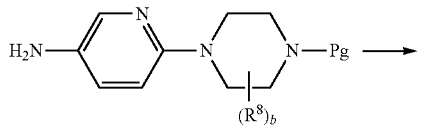

10-2

10-1

-continued

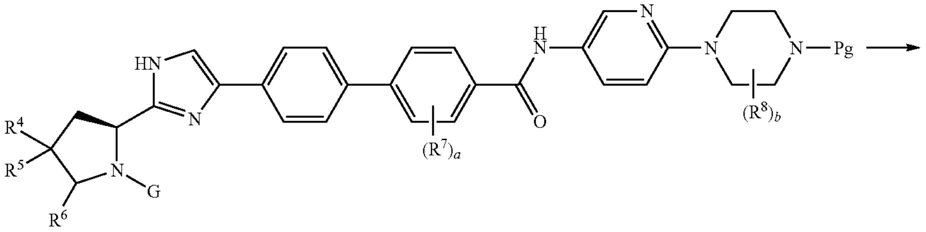

10-3

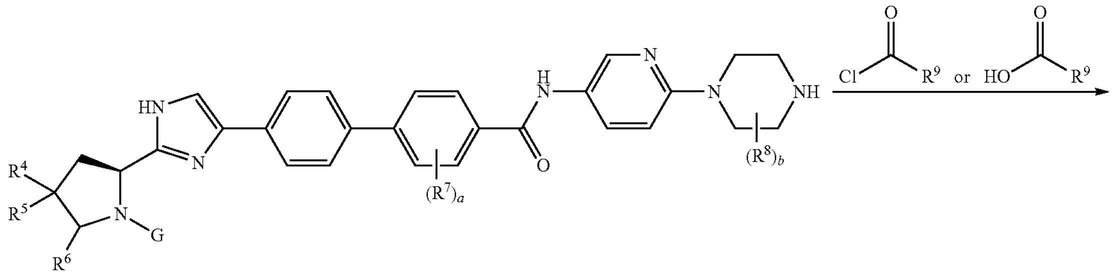

10-4

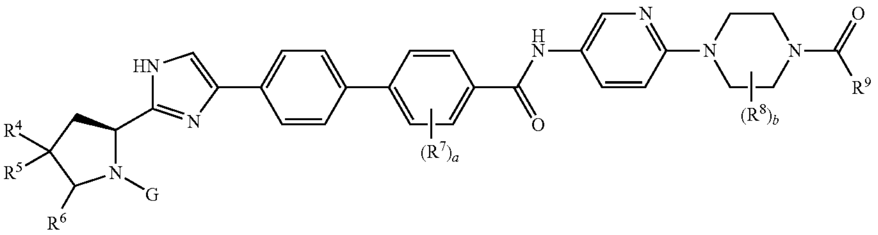

10-5

The acid 10-1 and aminopyridine 10-2 are reacted under amide bond formation conditions to provides a protected intermediate of formula 10-3 which is then deprotected and reacted with an acid chloride or carboxylic acid as in Scheme 1 to provide final compounds of the invention.

The intermediates of Scheme 10 may be prepared by conventional synthetic reactions. For example, the biaryl acid 10-1 may be prepared by the Suzuki coupling of boronate intermediate 3-1 with a bromobenzoic acid ester 11-1 followed by hydrolysis (not shown) to the acid to provide the biaryl acid, as shown in Scheme 11.

Scheme 11

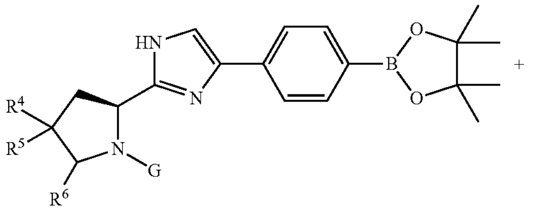

3-1

-continued

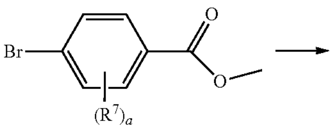

11-1

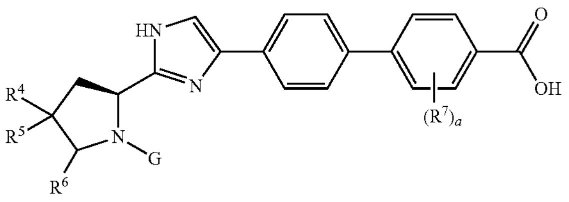

10-1

Alternatively, compounds of formula 10-3 may be prepared by the reaction illustrated in Scheme 12:

Scheme 12

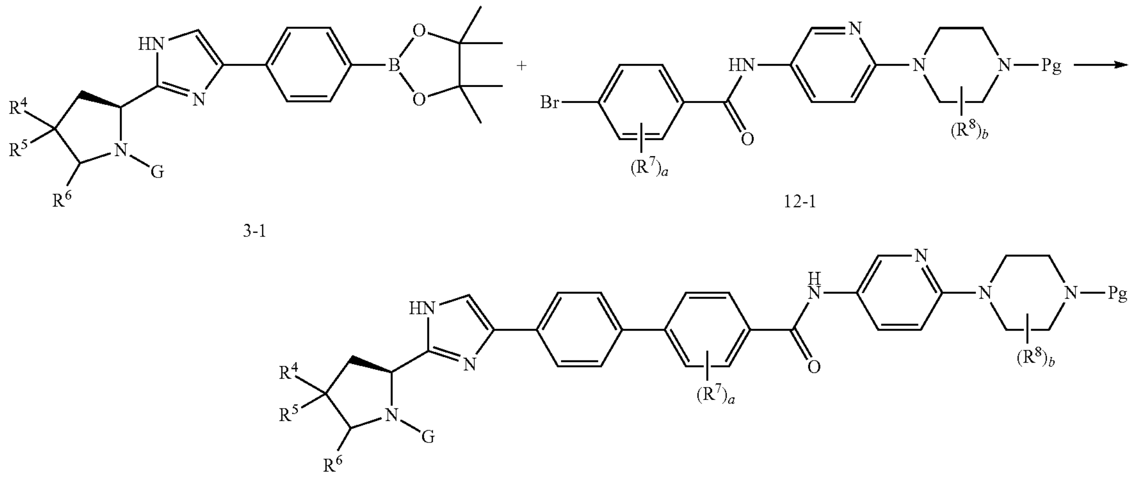

3-1

12-1

10-3 or, alternatively, by the Suzuki coupling reaction of bromo intermediate 3-3 with a boronate or boronic acid analog of 12-1.

Analogously, to the process described in Scheme 3 above, if the protected intermediate 12-1 were replaced by an intermediate 12-1'

12-1'

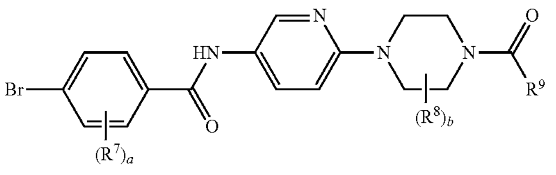

then the reaction of Scheme 12 would directly provide a final compound of the invention.

Bromo intermediate 12-1 may be prepared by the amide coupling of a bromo-benzoic acid 13-1 with intermediate 10-2 as illustrated in Scheme 13.

Scheme 13

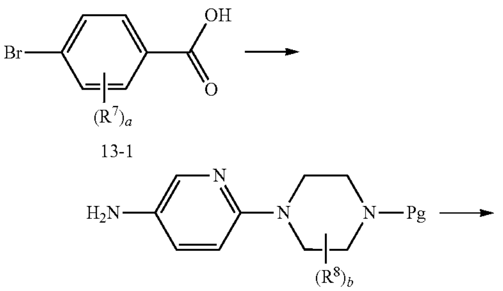

13-1

10-2

-continued

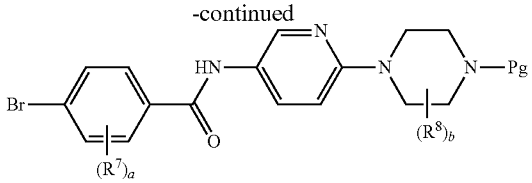

12-1 and the corresponding intermediate 12-1' is prepared from 12-1 by deprotection of 12-1 and reaction with an appropriate acid chloride or carboxylic acid.

Finally, amine intermediate 10-2 is conveniently prepared from a nitro-substituted chloropyridine which is reacted with a protected piperazine 2-3 to provide a protected intermediate 14-2 as shown in Scheme 14.

Scheme 14

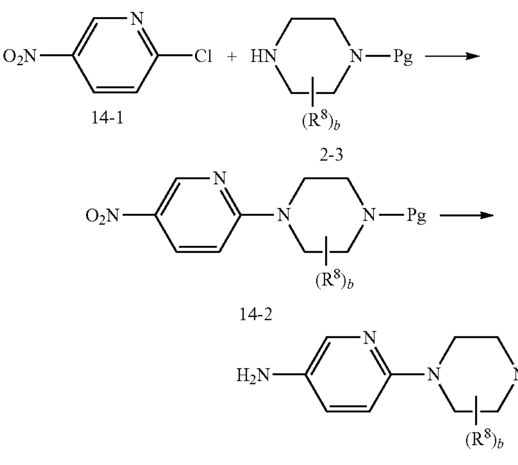

14-1

2-3

14-2

10-2

Reduction of the nitro group to the amine provides intermediate 10-2.

Details regarding specific reaction conditions and other procedures for preparing representative compounds of the invention or intermediates thereto are described in the examples below.

Thus, in one of its method aspects, the invention provides the processes of Schemes 1-14 and variations thereto described above as well as the processes exemplified below.

In a particular method aspect, the invention provides a process illustrated in Scheme 3B, the process comprising: (a) reacting a protected bromo intermediate 3-3' with a boronate 3-4' or boronic acid 3-4" intermediate, to provide a protected intermediate 3-5, (b) deprotecting intermediate 3-5, and (c) reacting the deprotected intermediate with a reagent HO-G, to provide a compound of the invention of the formula (II') or a pharmaceutically-acceptable salt thereof. This aspect includes a process of preparing a compound of formula (II') in which $R^1$ is $C_{1-6}$alkyl or tetrahydropyran, $R^2$ is hydrogen, $R^3$ is —C(O)O$C_{1-6}$alkyl, $R^4$ is methyl or methoxy, $R^5$ and $R^6$ are both hydrogen, $R^7$ is fluoro, chloro, or —$OCF_3$, $R^8$ is methyl, $R^9$ is tert-butyl or 3-hydroxy-2,2-dimethylpropyl, a is 1 or 2, and b is 1. In a particular aspect, a boronic acid 3-4" is used in step (a).

It will further be understood, this disclosure encompasses compounds of formula (I) when prepared by synthetic processes such as those described above and below or by metabolic processes including those occurring in vivo in human or animal body or in vitro.

Pharmaceutical Compositions

The compounds of the invention and pharmaceutically-acceptable salts thereof are typically used in the form of a pharmaceutical composition or formulation. Such pharmaceutical compositions may be administered to a patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a compound of formula (I), where, as defined above, "compound of formula (I)" means a compound of formula (I) or a pharmaceutically-acceptable salt thereof. Optionally, such pharmaceutical compositions may contain other therapeutic and/or formulating agents if desired. When discussing compositions and uses thereof, the "compound of the invention" may also be referred to herein as the "active agent". As used herein, the term "compound of the invention" is intended to include all compounds encompassed by formula (I) as well as the species embodied in formulas (II), (II'), (III), (IV), (IVa), (IVb), and (V) and pharmaceutically-acceptable salts thereof.

The pharmaceutical compositions of the invention typically contain a therapeutically effective amount of a compound of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and antioxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acidmethacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), oleic acid, glycerol, tetrahydrofuryl alcohol, polyethylene glycols and fatty acid esters of sorbitan, and mixtures thereof.

Alternatively, certain liquid formulations can be converted, for example, by spray drying, to a powder, which is used to prepare solid dosage forms by conventional procedures.

Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The compounds of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The compounds of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

The following non-limiting examples illustrate representative pharmaceutical compositions of the present invention.

Oral Solid Dosage Form

A compound of the invention is dissolved in polyethylene glycol acidified to pH≤2 with optional heating to form a solution comprising 10% w/w or 40% w/w active agent. The solution is spray dried to form a powder. The resulting powder is loaded into capsules, for example gelatin or hydroxypropyl methylcellulose capsules, to provide a unit dosage of 14 mg or 56 mg, respectively, active agent per capsule.

Oral Liquid Formulation

A compound of the invention (100 mg) is added to a mixture of ethanol (5 mL), propylene glycol (10 mL), and polyethylene glycol (25 mL). Once dissolution is achieved, acidified distilled water (q.s. to 100 mL) is added to provide a liquid formulation at a concentration of 1 mg/mL active agent.

Lipid Emulsion Formulation

A lipid emulsion formulation comprising a compound of the invention (10%), oleic acid (78%) polyethylene glycol (10%), and polysorbate 20 (2%) w/w is formed by adding a compound of the invention to a mixture of the remaining ingredients.

Lipid Emulsion Formulation

A lipid emulsion formulation comprising a compound of the invention (10%) and oleic acid (90%) w/w is formed by adding a compound of the invention to oleic acid.

Micro-Emulsion Formulation

A compound of the invention (1 g) is dissolved in a mixture of ethanol (2 mL), propylene glycol (2 mL), polyethylene glycol 400 (4 mL), and polyethylene glycol-15 hydroxystearate (4 mL). Acidified distilled water (q.s. to 100 mL) is added to form a self-emulsifying micro-emulsion formulation.

Utility

The compounds of the invention have been shown to inhibit viral replication in HCV replicon assays and therefore are expected to be useful for the treatment of hepatitis C viral infections.

In one aspect, therefore, the invention provides a method of inhibiting replication of the hepatitis C virus in a mammal (e.g., a human), the method comprising administering to the mammal a therapeutically-effective amount of a compound of the invention or of a pharmaceutical composition comprising a pharmaceutically-acceptable carrier and a compound of the invention.

The invention further provides a method of treating hepatitis C viral infections in a mammal (e.g., a human), the method comprising administering to the mammal a therapeutically-effective amount of compound of the invention or of a pharmaceutical composition comprising a pharmaceutically-acceptable carrier and a compound of the invention.

The compounds of the invention may inhibit viral replication by inhibiting the function of the NS5A protein encoded by the HCV genome. In one aspect, therefore, the invention provides a method of inhibiting the NS5A protein of HCV in a mammal, the method comprising administering to the mammal, a compound or a composition of the invention.

When used to treat HCV infections, the compounds of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating HCV infections will range from about 1 to about 2000 mg/day of active agent, including from about 5 to about 300 mg/day and from about 10 to about 200 mg per day of active agent for an average 70 kg human.

Combination Therapy

Compounds of the invention may also be used in combination with one or more agents which act by the same mechanism or by different mechanisms to effect treatment of HCV. Useful classes of agents for combination therapy include, but are not limited to, HCV NS3 protease inhibitors, HCV NS5B nucleoside and non-nucleoside polymerase inhibitors, helicase inhibitors, NS4B protein inhibitors, HCV viral entry inhibitors, cyclophyllin inhibitors, toll-like receptor agonists, inhibitors of heat shock proteins, interfering RNA, antisense RNA, HCV internal ribosome entry site (IRES) inhibitors, thiazolides, nucleoside analogs such as ribavirin and related compounds, interferons and other immunomodulatory agents, inosine 5'-monophosphate dehydrogenase (IMPDH) inhibitors, and other NS5A protein inhibitors. Agents which act to inhibit HCV replication by any other mechanism may also be used in combination with the present compounds.

HCV NS3 protease inhibitors which may be used in combination therapy include, but are not limited to, Incivek® (telaprevir, VX-950), boceprevir (SCH-503034), simeprevir (TMC-435), narlaprevir (SCH-900518), vaniprevir (MK-7009), danoprevir (ITMN-191, R-7227), BI-201335, ABT-450/r, asunaprevir (BMS-650032), GS-9256, GS-9451, sovaprevir (ACH-1625), ACH-2684, BMS-605339, VX-985, PHX-1766, BMS-791325, IDX-320, and MK-5172.

Examples of HCV NS5B nucleoside polymerase inhibitors include, but are not limited to, mericitabine (RG7128), IDX-184, sofosbuvir (GS-7977, PSI-7977), PSI-7851, PSI-938, BMS-986094 (NX-189, INX-08189), RG7348, MK-0608, TMC-649128, HCV-796, and ALS-2200 (VX-135), while, non-nucleoside HCV NS5B polymerase inhibitors, include but are not limited to, filibuvir (PF-8685540), tegobuvir (GS-9190), VX-222, VX-759, setrobuvir (ANA-598), ABT-072, ABT-333, BI-207127, BMS-791325, MK-3281, IDX-37, BMS-824393, TMC-647055.

A wide variety of interferons and pegylated interferons, including alpha, beta, omega, and gamma interferons, having antiviral, antiproliferative or immunomodulatory effects, can be combined with the present compounds. Representative examples include, but are not limited to, Intron® A (interferon-alpha2b), Actimmune® (interferon-gamma-1b), Alferon N, Advaferon®, Roferon-A (interferon alpha-2a) PegIntron® (peginterferon-alpha 2b), Alfaferone, Pegasys® (peginterferon alpha-2a), Alfanative (interferon alpha), Zalbin™ (albinterferon alpha-2b), Infergon® (interferon alfacon-1), Omega DUROS®(omega interferon), Locteron™ (interferon alpha), PEG-rIL-29 (pegylated interferon lambda), and Rebif® (interferon beta-1a).

Nucleoside analog antiviral agents include, but are not limited to, ribavirin (Copegus®, Rebetol®, Virazole®) and Viramidine (taribavirin). Interferons and ribavirin are also provided in in the form of kits which include, for example, but are not limited to, Rebetron® (interferon alpha-2b/ribavirin) and Pegetron® (Peginterferon alpha-2b/ribavirin)

Useful compounds acting by other mechanisms include, but are not limited to: cyclophilin inhibitors, such as DEB-025, SCY-635, NIM-811, and cyclosporine and derivatives; toll-like receptor agonists, such as resiquimod, IMO-2125, and ANA-773, HCV viral entry inhibitors, such as civacir, thiazolides, such as nitazoxanide, and broad-spectrum viral inhibitors, such as, inosine-5'-monophosphate dehydrogenase (IMPDH) inhibitors.

In addition, compounds of the invention may be combined with an NS5A inhibitor, for example, daclatasvir (BMS-790052), AZD-7295, PPI-461, PPI-1301, GS-5885, GSK2336805, ABT-267, ACH-2928, ACH-3102, EDP-239, IDX-719, MK-8742, or PPI-668.

In another aspect, therefore, the invention provides a therapeutic combination for use in the treatment of hepatitis C viral infections, the combination comprising a compound of the invention and one or more other therapeutic agents useful for treating HCV. For example, the invention provides a combination comprising a compound of the invention and one or more agents selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin and related nucleoside analogs. Also provided, therefore, is a pharmaceutical composition comprising a compound of the invention and one or more other therapeutic agents useful for treating HCV.

Further, in a method aspect, the invention provides a method of treating a hepatitis C viral infection in a mammal, the method comprising administering to the mammal a compound of the invention and one or more other therapeutic agents useful for treating HCV.

In another method aspect, the invention provides a method of inhibiting replication of the hepatitis C virus in a mammal, the method comprising administering to the mammal a compound of the invention and one or more other therapeutic agents useful for inhibiting replication of the hepatitis C virus.

For example, in one method aspect, the invention provides a method of treating a hepatitis C viral infection in a mammal, the method comprising administering to the mammal a compound of the invention, an interferon or pegylated interferon, and ribavirin.

In another exemplary method aspect, the invention provides a method of treating a hepatitis C viral infection in a mammal, the method comprising administering to the mammal a compound of the invention, an interferon or pegylated interferon, ribavirin, and an HCV NS3 protease inhibitor.

In still another method aspect, the invention provides a method of treating a hepatitis C viral infection in a mammal, the method comprising administering to the mammal a compound of the invention, an HCV NS3 protease inhibitor, and ribavirin.

Still other all-oral combination therapies useful in other method aspects, include, for example, a compound of the invention and an HCV NS3 protease inhibitor; a compound of the invention and an HCV NS5B nucleoside polymerase inhibitor; a compound of the invention, an HCV NS5B nucleoside polymerase inhibitor, and ribavirin; a compound of the invention, an HCV NS3 protease inhibitor, and an HCV NS5B nucleoside polymerase inhibitor; a compound of the invention, an HCV NS3 protease inhibitor, an HCV NS5B nucleoside polymerase inhibitor and ribavirin; a compound of the invention, an HCV NS3 protease inhibitor, and an HCV NS5B non-nucleoside polymerase inhibitor; and a compound of the invention, an HCV NS3 protease inhibitor, an HCV NS5B non-nucleoside polymerase inhibitor and ribavirin.

In another method aspect, the invention provides a method of inhibiting replication of the hepatitis C virus in a mammal, using a compound of the invention in combination with other agents, as described above.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Finally, the compounds of the invention may also find utility as research tools, for example, for discovering new HCV NS5A protein inhibitors or explicating mechanisms of HCV replication.

Compounds of the invention have been demonstrated to be potent inhibitors of HCV replication in HCV replicon assays, as described in the following examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
DCM=dichloromethane
DIPEA=N,N-diisopropylethylamine
DMA=N,N-dimethylacetamide
DMF=N,N-dimethylformamide
DMP=1,1,1-triacetoxy-1,1-dihydro-1,2-benziodoxol-3(1H)-one (Dess-Martin periodinane)
DMSO=dimethyl sulfoxide
EDC=N-(3-dimethylaminopropyl)-N-ethylcarbodiimide hydrochloride
EtOAc=ethyl acetate
h=hour(s)
HATU=N,N,N',N'-tetramethyl-O-(7-azabenzotriazol-1-yl)uronium hexafluorophosphate
HCTU=2-(6-chloro-1H-benzotriazole-1-yl)-1,1,3,3-tetramethylaminium hexafluorophosphate
HOAt=1-hydroxy-7-azabenzotriazole
min=minute(s)
$Pd(dppf)Cl_2$=dichloro(1,1'-bis(diphenylphosphino)-ferrocene)dipalladium(II)
MTBE=methyl tert-butyl ether
RT=room temperature
TFA=trifluoroacetic acid
THF=tetrahydrofuran
bis(pinacolato)diboron=4,4,5,5,4',4',5',5'-octamethyl-[2,2]bi[[1,3,2]dioxaborolanyl]

Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation. In addition, reaction mixtures were routinely purified by preparative HPLC, typically using C18 or BDS column packings and conventional eluents. Typical preparative HPLC conditions are described below.

Characterization of reaction products was routinely carried out by mass and $^1H$-NMR spectrometry. For NMR analysis, samples were dissolved in deuterated solvent (such as $CD_3OD$, $CDCl_3$, or $d_6$-DMSO), and $^1H$-NMR spectra were acquired with a Varian Gemini 2000 instrument (400 MHz) under standard observation conditions. Mass spectrometric identification of compounds was performed by an electrospray ionization method (ESMS) with an Applied Biosystems (Foster City, Calif.) model API 150 EX instrument or an Agilent (Palo Alto, Calif.) model 1200 LC/MSD instrument.

General Preparative HPLC Conditions

Column: C18, 5 μm. 21.2×150 mm or C18, 5 μm 21×250 or C14 21×150
Column temperature: Room Temperature
Flow rate: 20.0 mL/min
Mobile Phases: A=Water+0.05% TFA
B=ACN+0.05% TFA,
Injection volume: (100-1500 μL)
Detector wavelength: 214 nm Crude compounds were dissolved in 1:1 water:acetic acid at about 50 mg/mL. A 4 minute analytical scale test run was carried out using a 2.1×50 mm C18 column followed by a 15 or 20 minute preparative scale run using 100 μL injection with the gradient based on the % B retention of the analytical scale test run. Exact gradients were sample dependent. Samples with close running impurities were checked with a 21×250 mm C18 column and/or a 21×150 mm C14 column for best separation. Fractions containing desired product were identified by mass spectrometric analysis.

Analytical HPLC

Column: Zorbax Bonus-RP 3.5 μm. 4.6×150 mm
Column temperature: 35° C.
Flow rate: 1.0 mL/min
Injection volume: 5 μL
Sample preparation: Dissolve in 1:1 ACN:water Method A Mobile Phases: A=Water/ACN (98:2)+0.1% TFA
B=Water/ACN (10:90)+0.1% TFA Detector wavelength: 254 nm Gradient: 21 min total (time (min)/% B): 0.5/10, 15/60, 16.5/80, 17/80, 18/10, 21/10

Method B

Mobile Phases: A=Water/ACN (98:2)+0.1% TFA
B=Water/ACN (2:98)+0.5% TFA

Detector wavelength: 214 nm

Gradient: 29 min total (time (min)/% B): 0.5/10, 24/90, 25/90, 26/10, 29/10

Preparation 1: (R)-4-[5-(4-Bromo-2-chloro-5-trifluoromethoxy-phenylcarbamoyl)-pyridin-2-yl]-3-methyl-piperazine-1-carboxylic acid tert-butyl ester

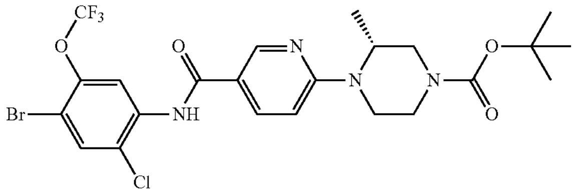 [SMILES: C[C@@H]1CN(C(=O)OC(C)(C)C)CCN1c1ccc(C(=O)Nc2cc(OC(F)(F)F)c(Br)cc2Cl)cn1]

(a) 4-Bromo-2-chloro-5-trifluoromethoxy-phenylamine

To a mixture of 4-bromo-3-trifluoromethoxy-phenylamine (2.0 g, 7.8 mmol) in ACN (60 mL) was slowly added a solution of N-chlorosuccinimide (1.0 g, 7.8 mmol) in ACN (40 mL). The reaction mixture was heated at 60° C. overnight and extracted with ethyl acetate/water. The organic layer was dried over sodium sulfate and purified by flash chromatography (40 g column, 100% hexanes to 10% EtOAc:hexanes) to produce the desired product as an orange-ish colored oil (1.4 g, 64% yield).

(b) N-(4-Bromo-2-chloro-5-trifluoromethoxy-phenyl)-6-fluoro-nicotinamide

To a solution of the product of the previous step (1.2 g, 4.1 mmol) in DCM (5 mL) was slowly added a solution of 2-fluoropyridine-5-carbonyl chloride (0.66 g, 4.1 mmol) in DCM (3 mL) and 20 drops of DMA were added. The reaction mixture was concentrated to form a yellowish solid (2 g). (m/z): $[M+H]^+$ calcd for $C_{13}H_6BrClF_4N_2O_2$ 412.92; 414.92. found 413; 415.

(c) (R)-4-[5-(4-Bromo-2-chloro-5-trifluoromethoxy-phenylcarbamoyl)-pyridin-2-yl]-3-methyl-piperazine-1-carboxylic acid tert-butyl ester To a reaction mixture of the product of the previous step (999 mg, 2.42 mmol) in a mixture of N,N-diisopropylethylamine (0.84 mL, 4.83 mmol;) and DMSO (0.86 mL, 12.08 mmol) was added (R)-3-methyl-piperazine-1-carboxylic acid tert-butyl ester (726 mg, 3.62 mmol) and the reaction mixture was heated at 120° C. overnight and extracted with ethyl acetate/water. The organic layer was dried over sodium sulfate and concentrated under vacuum. The dark oil was dissolved in a small amount of DCM and purified by silica gel chromatography (24 g column, 0-40% ethyl acetate:hexanes) to produce the title intermediate as a white solid (916 mg, 64% yield). (m/z): $[M+H]^+$ calcd for $C_{23}H_{25}BrClF_3N_4O_4$ 593.07; 595.07. found 595.4.

Preparation 2: (R)-4-[5-(4-Bromo-2-chloro-5-trifluoromethoxy-phenylcarbamoyl)-pyridin-2-yl]-3-methyl-piperazine-1-carboxylic acid tert-butyl ester

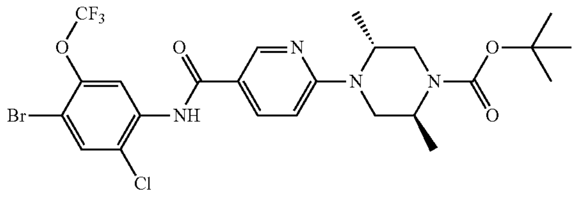 [SMILES: C[C@@H]1CN(C(=O)OC(C)(C)C)[C@@H](C)CN1c1ccc(C(=O)Nc2cc(OC(F)(F)F)c(Br)cc2Cl)cn1]

Following the procedure of Preparation 1 step (c) substituting (2S,5R)-2,5-dimethyl-piperazine-1-carboxylic acid tert-butyl ester (777 mg, 3.62 mmol) for (R)-3-methyl-piperazine-1-carboxylic acid tert-butyl ester, the title intermediate was prepared as a light yellow solid (1118 mg, 76% yield). (m/z): $[M+H]^+$ calcd for $C_{24}H_{27}BrClF_3N_4O_4$ 607.09; 609.08. found 609.3.

Preparation 3: (S)-2-Methoxycarbonylamino-3-methyl-butyric acid

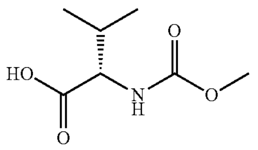

Methylchloroformate (14.5 mL, 0.188 mol) was added over 15 min to a cooled (0-6° C.) mixture of (S)-2-amino-3-methyl-butyric acid (20.0 g, 0.171 mol), NaOH (6.80 g, 0.171 mol) and sodium carbonate (18.1 g, 0.171 mol) in water (200 mL). The cooling bath was removed and the mixture was stirred at ambient temperature overnight. Conc. aqueous HCl (30 mL) was added to the reaction mixture to adjust pH to ~1. A solid formed and the mixture was stirred for 90 min. The mixture was filtered and the solid was dried overnight under reduced pressure at 40° C. to provide the title intermediate (27.8 g, 93% yield). $^1H$ NMR ($CD_3OD$, 400 MHz) δ (ppm) 4.87 (br. s, 4H), 4.05 (d, J=5.49, 1 H), 3.65 (s, 3H), 2.25-2.05 (m, 1H), 0.98 (d, J=6.87, 3H), 0.94 (d, J=6.87, 3H).

Preparation 4: 4-(4-Bromo-phenyl)-2-((2S,4S)-4-methyl-pyrrolidin-2-yl)-1H-imidazole

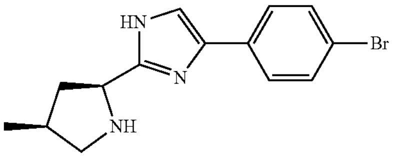 [SMILES: C[C@@H]1CN[C@H](c2nc(-c3ccc(Br)cc3)c[nH]2)C1]

(a) (2S,4S)-4-Methyl-pyrrolidine-1,2-dicarboxylic acid 2-[2-(4-bromophenyl)-2-oxo-ethyl]ester 1-tert-butyl ester To a mixture of p-bromophenacyl bromide (242 mg, 0.87 mmol) in DCM (1.5 mL) and DMA (1.5 mL), under nitrogen, was added (2S,4S)-4-methyl-pyrrolidine-1,2-dicarboxylic acid 1-tert-butyl ester (200 mg, 0.87 mmol) and N,N-diisopropylethylamine (531.8 μL, 3.05 mmol) and the resulting mixture was stirred at 35° C. for 3 h, concentrated under vacuum, dissolved in DCM (30 mL), and washed with water (2×5 ml). The organic layer was dried over magnesium sulfate, filtered, and concentrated under vacuum to provide the title intermediate.

(b) (2S,4S)-2-[4-(4-Bromo-phenyl)-1H-imidazol-2-yl]-4-methyl-pyrrolidine-1-carboxylic acid tert-butyl ester The product of the previous step was dissolved in toluene (20.0 mL), ammonium acetate (1.345 g, 17.45 mmol) was added, and resulting mixture was stirred at 95° C. overnight, concentrated and purified by silica gel chromatography (24 g, 0-80% EtOAc/hexanes)) to give the title product (265 mg) (m/z): $[M+H]^+$ calcd for $C_{19}H_{24}BrN_3O_2$ 406.11; 408.11. found 408.5.

(c) 4-(4-Bromo-phenyl)-2-((2S,4S)-4-methyl-pyrrolidin-2-yl)-1H-imidazole

The product of the previous step was treated with 4 M HCl in 1,4-dioxane (2.0 mL) for 1 h and concentrated by rotary evaporation to provide the di-HCl salt of the title intermediate (224 mg, 68% yield). (m/z): $[M+H]^+$ calcd for $C_{14}H_{16}BrN_3$ 306.06; 308.06. found 306.3.

Preparation 5: ((S)-1-{(2S,4S)-2-[4-(4-Bromo-phenyl)-1H-imidazol-2-yl]-4-methyl-pyrrolidine-1-carbonyl}-2-methyl-propyl)-carbamic acid methyl ester

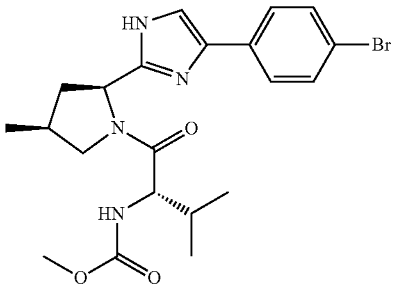 [SMILES: COC(=O)N[C@H](C(=O)N1C[C@@H](C)C[C@H]1c1nc(-c2ccc(Br)cc2)c[nH]1)C(C)C]

A mixture of (S)-2-methoxycarbonylamino-3-methyl-butyric acid (103 mg, 0.59 mmol, Preparation 3) and HATU (270 mg, 0.71 mmol) were stirred in DMA (2 mL) for 10 min and then 4-(4-Bromo-phenyl)-2-((2S,4S)-4-methyl-pyrrolidin-2-yl)-1H-imidazole 2 HCl (224 mg, 0.59 mmol, Preparation 4) and N,N-diisopropylethylamine (0.31 mL, 1.8 mmol) were added. The resulting mixture was stirred at RT overnight, diluted with ethyl acetate (50 mL), and washed with water (2×5 mL). The organic layer was dried over magnesium sulfate, filtered, concentrated and purified by silica gel chromatography (0-100% EtOAc/hexanes)). Fractions with desired product were combined and concentrated to give the title compound (183 mg, 66% yield) (m/z): $[M+H]^+$ calcd for $C_{21}H_{27}BrN_4O_3$ 463.13; 465.12. found 465.3.

Preparation 6: [(S)-2-Methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1-carbonyl)-propyl]carbamic acid methyl ester

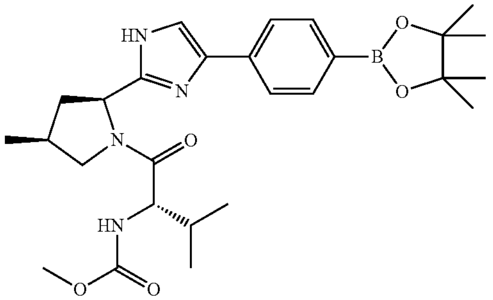

To a solution of ((S)-1-{(2S,4S)-2-[4-(4-bromo-phenyl)-1H-imidazol-2-yl]-4-methyl-pyrrolidine-1-carbonyl}-2-methyl-propyl)-carbamic acid methyl ester (183 mg, 0.39 mmol; Preparation 5) and 4,4,5,5,4',4',5',5'-octamethyl-[2,2']bi[[1,3,2]dioxaborolanyl] (120 mg, 0.47 mmol) in 1,4-dioxane (5 mL) was added potassium acetate (56 mg, 0.59 mmol). The resulting mixture was sparged with nitrogen, Pd(dppf)$Cl_2$.$CH_2Cl_2$ (27 mg, 0.033 mmol) was added, and the reaction mixture was capped and heated at 100° C. overnight. The reaction was cooled to RT and partitioned between EtOAc (50 mL) and water (10 mL). The organic layer was washed with water (5 mL), brine (2 mL), dried over magnesium sulfate, filtered, and concentrated to give a dark-brown oil, which was purified by silica gel chromatography (24 g silica gel, 0-100% EtOAc/hexanes). Fractions with desired product were combined and dried to give the title compound (94 mg, 47% yield) as a white foam. (m/z): $[M+H]^+$ calcd for $C_{27}H_{39}BN_4O_5$ 511.30. found 511.7.

Preparation 7: (2S,5R)-4-[5-(4-Bromo-2-chloro-5-trifluoromethyl-phenylcarbamoyl)-pyridin-2-yl]-2,5-dimethyl-piperazine-1-carboxylic acid tert-butyl ester

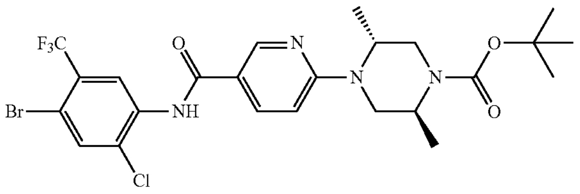 [SMILES: C[C@@H]1CN(C(=O)OC(C)(C)C)[C@@H](C)CN1c1ccc(C(=O)Nc2cc(C(F)(F)F)c(Br)cc2Cl)cn1]

To a solution of 5-amino-2-bromo-4-chlorobenzotrifluoride (466 mg, 1.70 mmol) dissolved in DCM (1 mL) was slowly added a solution of 2-fluoropyridine-5-carbonyl chloride (270 mg, 1.70 mmol) in DCM (1 mL). A few drops of DMA were added and the reaction mixture was concentrated to form N-(4-bromo-2-chloro-5-trifluoromethyl-phenyl)-6-fluoro-nicotinamide as a purple solid.

Half of the solid from the previous step was treated with N,N-diisopropylethylamine (0.5 mL, 3 mmol), DMSO (0.5 mL, 7 mmol) and (2S,5R)-2,5-dimethyl-piperazine-1-carboxylic acid tert-butyl ester (273 mg, 1.27 mmol) and the reaction mixture was heated at 120° C. overnight, concentrated by rotary evaporation, dissolved in a small amount of DCM and purified by silica gel chromatography (0-50% ethyl acetate:hexanes) to produce the title intermediate (288 mg, 29% yield) as a yellow solid. (m/z): $[M+H]^+$ calcd for $C_{24}H_{27}F_4N_4O_4$ 591.09; 593.09. found 593.2.

Preparation 8: ((S)-1-{(S)-8-[4-(4-Bromo-phenyl)-1H-imidazol-2-yl]-1,4-dioxa-7-aza-spiro[4.4]nonane-7-carbonyl}-2-methyl-propyl)-carbamic acid methyl ester

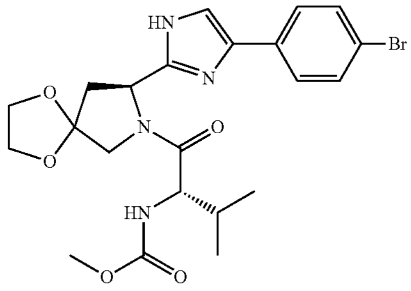 [SMILES: COC(=O)N[C@H](C(=O)N1CC2(C[C@H]1c1nc(-c3ccc(Br)cc3)c[nH]1)OCCO2)C(C)C]

(a) (2S,4R)-4-Hydroxy-1-((S)-2-methoxycarbonylamino-3-methyl-butyryl)-pyrrolidine-2-carboxylic acid methyl ester To a solution of (2S,4R)-4-hydroxy-pyrrolidine-2-carboxylic acid methyl ester in dry DCM (200 mL) was added (S)-2-methoxycarbonylamino-3-methyl-butyric acid (10 g, 55 mmol), HATU (24 g, 63.25 mmol), and triethylamine (16.7 g, 165 mmol. The reaction mixture was stirred at RT overnight. DCM (200 mL) was added and the solution was washed with brine, dried, concentrated and purified by silica gel column chromatography (eluted with petroleum ether: EtOAc 10:1 to 1:4)) to give the title intermediate as a yellow oil (20 g). (m/z): $[M+H]^+$ calcd for $C_{13}H_{22}N_2O_6$ 303.15. found 303.1.

(b) (S)-1-((S)-2-Methoxycarbonylamino-3-methyl-butyryl)-4-oxo-pyrrolidine-2-carboxylic acid methyl ester To a solution of the product of the previous step (15 g, 50 mmol) in DCM (500 mL) was added DMP (60 g) and the reaction mixture was stirred at RT overnight, washed with saturated sodium bicarbonate (3×100 mL), brine (100 mL), dried, concentrated, and purified by silica gel column chromatography (eluted with petroleum ether:EtOAc 1:2) to provide the title intermediate as a yellow oil (7.5 g, 50% yield). (m/z): $[M+H]^+$ calcd for $C_{13}H_{20}N_2O_6$ 301.13. found 301.1.

(c) (S)-7-((S)-2-Methoxycarbonylamino-3-methyl-butyryl)-1,4-dioxa-7-aza-spiro[4.4]nonane-8-carboxylic acid methyl ester To a solution of the product of the previous step (7.5 g, 24.9 mmol) in toluene (100 mL) was added ethane-1,2-diol (7.75 g, 125 mol) and 4-methylbenzenesulfonic acid (860 mg, 5 mmol) and the mixture was stirred at reflux overnight. Ethyl acetate (300 mL) was added and the solution was washed with saturated sodium bicarbonate, dried, concentrated, and purified by silica gel column chromatography (eluted with petroleum ether:EtOAc 1:1) to provide the title intermediate as a yellow solid (3.5 g, 41% yield). (m/z): $[M+H]^+$ calcd for $C_{15}H_{24}N_2O_7$ 345.16. found 345.1.

(d) (S)-7-((S)-2-Methoxycarbonylamino-3-methyl-butyryl)-1,4-dioxa-7-aza-spiro[4.4]nonane-8-carboxylic acid Lithium hydroxide (730 mg, 30.5 mmol) was added to a solution of the product of the previous step (3.0 g, 7.1 mmol) in THF (40 mL) and water (30 mL). The reaction mixture was stirred at RT for 3 h and washed with EtOAc (2×10 mL). The aqueous layer was adjusted to pH 1 with 2 M HCl and extracted with EtOAc (4×50 mL); portions were combined, dried, and concentrated to give the product as a white solid (3 g, 89% yield). (m/z): $[M+H]^+$ calcd for $C_{14}H_{22}N_2O_7$ 331.14. found 331.1.

(e) (S)-7-((S)-2-Methoxycarbonylamino-3-methyl-butyryl)-1,4-dioxa-7-aza-spiro[4.4]nonane-8-carboxylic acid 2-(4-bromo-phenyl)-2-oxo-ethyl ester To a solution of the product of the previous step (2.7 g, 8.17 mmol) in DMF (30 mL) was added 2-bromo-1-(4-bromo-phenyl)-ethanone (2.5 g, 8.99 mmol) and cesium carbonate (5.3 g, 16.34 mmol) and the reaction mixture was stirred at RT for 4 h. Ethyl acetate (150 mL) was added and the solution was washed with brine (3×20 mL), dried, filtered, concentrated, and purified by silica gel column chromatography (eluted with 0 to 50% EtOAc in petroleum ether) to provide the title intermediate as a yellow solid (1.6 g, 37% yield). (m/z): $[M+H]^+$ calcd for $C_{22}H_{27}BrN_2O_8$ 527.11; 529.10. found 527.0; 529.0.

(f) ((S)-1-{(S)-8-[4-(4-Bromo-phenyl)-1H-imidazol-2-yl]-1,4-dioxa-7-aza-spiro[4.4]nonane-7-carbonyl}-2-methyl-propyl)-carbamic acid methyl ester To a solution of the product of the previous step (1.5 g, 2.84 mmol) in toluene (50 mL) was added ammonium acetate (3.3 g, 42.7 mmol) and the solution was stirred at reflux overnight. Ethyl acetate (100 mL) was added and the solution was washed with brine (3×20 mL), dried, filtered, concentrated, and purified by silica gel column chromatography (eluted with 0 to 50% EtOAc in petroleum ether) to provide the title intermediate as a yellow solid (1.0 g, 69% yield). (m/z): $[M+H]^+$ calcd for $C_{22}H_{27}BrN_4O_5$ 507.12; 509.11. found 507.0; 509.0. $^1H$ NMR ($CH_3OD$, 400) δ (ppm) 7.58-7.52 (m, 2H), 7.49-7.42 (m, 2H), 7.31 (s, 1H), 5.18-5.11 (m, 1H), 4.17-3.78 (m, 7H), 3.63 (s, 3H), 2.52-2.42 (m, 2H), 2.01-1.92 (m, 1H), 0.92-0.82 (m, 6H).

Preparation 9: ((S)-1-{(S)-8-[4-(4'-Amino-2'-trifluoromethoxy-biphenyl-4-yl)-1H-imidazol-2-yl]-1,4-dioxa-7-aza-spiro[4.4]nonane-7-carbonyl}-2-methyl-propyl)-carbamic acid methyl ester

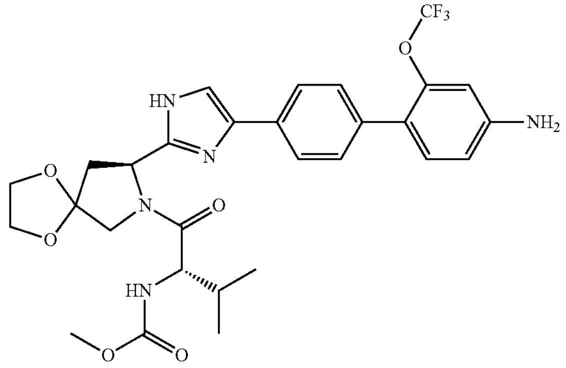 [SMILES: COC(=O)N[C@H](C(=O)N1CC2(C[C@H]1c1nc(-c3ccc(-c4ccc(N)cc4OC(F)(F)F)cc3)c[nH]1)OCCO2)C(C)C]

(a) (4'-{2-[(S)-7-((S)-2-Methoxycarbonylamino-3-methyl-butyryl)-1,4-dioxa-7-aza-spiro[4.4]non-8-yl]-1H-imidazol-4-yl}-2-trifluoromethoxy-biphenyl-4-yl)-carbamic acid tert-butyl ester To a solution of ((S)-1-{(S)-8-[4-(4-bromo-phenyl)-1H-imidazol-2-yl]-1,4-dioxa-7-aza-spiro[4.4]nonane-7-carbonyl}-2-methyl-propyl)-carbamic acid methyl ester (350 mg, 0.69 mmol) in dioxane (8 mL) and water (4 mL) was added [4-(4,4,5,5-tetramethyl-[1,3,2]dioxaborolan-2-yl)-3-trifluoromethoxy-phenyl]-carbamic acid tert-butyl ester (334 mg, 0.83 mmol), sodium carbonate (148 mg, 1.4 mmol), and tetrakis(triphenylphosphine)-palladium(0) (81 mg, 0.07 mmol). The reaction mixture was stirred at reflux for 3 h under nitrogen. Ethyl acetate (50 mL) was added and the solution was washed with brine, dried over sodium sulfate, filtered, and concentrated to give the title intermediate as a yellow solid (650 mg). (m/z): $[M+H]^+$ calcd for $C_{34}H_{49}N_5O_8$ 704.28. found 704.3.

(b) ((S)-1-{(S)-8-[4-(4'-Amino-2'-trifluoromethoxy-biphenyl-4-yl)-1H-imidazol-2-yl]-1,4-dioxa-7-aza-spiro[4.4]nonane-7-carbonyl}-2-methyl-propyl)-carbamic acid methyl ester To a solution of the product of the previous step (610 mg, 0.87 mmol) in DCM (8 mL) was added TFA (1.6 mL) and the reaction mixture was stirred at RT for 1 h. Saturated sodium bicarbonate was added (10 mL) and the solution was extracted with DCM (3×20 mL). The organic layers were combined, dried over sodium sulfate, concentrated and purified by HPLC under acid conditions (0.075% HCl) to provide the di-HCl salt of the title intermediate as a white solid (92 mg). (m/z): $[M+H]^+$ calcd for $C_{29}H_{32}F_3N_5O_6$ 604.23. found 604.2. $^1H$ NMR ($CH_3OD$, 400) δ (ppm) 7.88 (s, 1H), 7.80 (d, 2H), 7.61 (d, 2H), 7.52-7.49 (m, 1H), 7.21-7.16 (m, 2H), 5.38-5.34 (m, 1H), 4.18-4.02 (m, 6H), 3.96-3.90 (m, 1H), 3.65 (s, 3H), 2.71-2.63 (m, 1H), 2.46-2.39 (m, 1H), 2.07-1.94 (m, 1H), 0.93-0.85 (m, 6H).

Preparation 10: ((S)-1-{(2S,4S)-2-[4-(4'-Amino-biphenyl-4-yl)-1H-imidazol-2-yl]-4-hydroxy-pyrrolidine-1-carbonyl}-2-methyl-propyl)-carbamic acid methyl ester

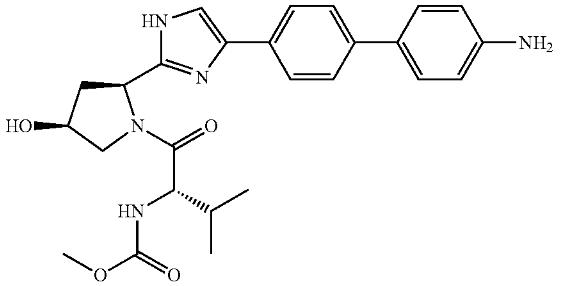 [SMILES: COC(=O)N[C@H](C(=O)N1C[C@@H](O)C[C@H]1c1nc(-c2ccc(-c3ccc(N)cc3)cc2)c[nH]1)C(C)C]

To a solution of ((S)-1-{(2S,4S)-2-[4-(4-bromo-phenyl)-1H-imidazol-2-yl]-4-hydroxy-pyrrolidine-1-carbonyl}-2-methyl-propyl)-carbamic acid methyl ester (1.8 g, 3.87 mmol) in dioxane (30 mL) and water (10 mL), 4-(4,4,5,5-tetramethyl-[1,3,2]dioxaborolan-2-yl)-phenylamine (848 mg, 3.87 mmol), sodium carbonate (820 mg, 7.74 mmol) and $Pd(dppf)Cl_2$ (316 mg, 0.39 mmol) were added and the reaction mixture was heated at reflux for 3 h, cooled to RT, filtered and concentrated, extracted with EtOAc (50 mL), and washed with water (50 mL). The organic layer was dried over sodium sulfate, filtered, concentrated and purified by silica gel column chromatography (eluted with 1% to 3% methanol in DCM) to give the title intermediate (1.45 g, 65% yield). $^1H$ NMR ($CH_3OD$, 400) δ (ppm) 7.70 (m, 2H), 7.67 (m, 2H), 7.45 (m, 2H), 7.29 (s, 1H), 6.80 (d, J=6.8 Hz, 1H), 5.82 (d, J=9.2 Hz, 1H), 5.29 (d, J=8.8 Hz, 1H), 4.59 (s, 1H), 4.34 (d, J=8.8 Hz, 1H), 4.16 (d, J=8.0 Hz, 1H), 3.95-4.04 (m, 1H), 3.79-3.83 (m, 1H), 3.76 (s, 3H), 2.55-2.69 (m, 1H), 2.32 (m, 1H), 1.60-2.03 (m, 1H), 1.00 (m, 3H), 0.3-0.85 (m, 3H).

Preparation 11: (R)-4-(5-Carboxy-pyridin-2-yl)-3-methyl-piperazine-1-carboxylic acid tert-butyl ester

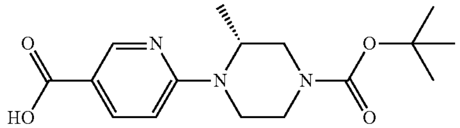 [SMILES: C[C@@H]1CN(C(=O)OC(C)(C)C)CCN1c1ccc(C(=O)O)cn1]

A mixture of 6-fluoronicotinic acid (150 g, 1.063 mol) and (R)-3-methyl-piperazine-1-carboxylic acid tert-butyl ester (234.2 g, 1.169 mol) in tetrahydrofuran (1.75 L) was cooled to −40° C. and then 2 M isopropylmagnesium chloride in tetrahydrofuran (1.196 L, 2.39 mol) was added slowly maintaining the temperature less than −20° C. The reaction mixture was slowly warmed to RT, stirred at RT for 4 h and then 1N HCl (1.75 L) and water (1.175 L) were added. The reaction mixture was extracted with ethyl acetate (4 L). The organic phase was evaporated to provide crude solid (534 g). To the crude solid was added acetone (2 L) and water (200 mL). The resulting reaction mixture was heated to 50° C. and then water (2.8 L) was added slowly. Seed crystals from a previous run at smaller scale were added after ~1 L of water. The reaction mixture was cooled to 20° C. over 3 h, stirred at 20° C. overnight and filtered. The solid was washed with 2:3 acetone:water (2×500 mL) and dried under vacuum to provide the title compound (329 g, 96% yield) as an off-white solid. HPLC Method A: Retention time 9.73 min.

Preparation 12: ((S)-1-{(2S,4S)-2-[4-(4-Bromo-phenyl)-1H-imidazol-2-yl]-4-dimethylamino-pyrrolidine-1-carbonyl}-2-methyl-propyl)-carbamic acid methyl ester

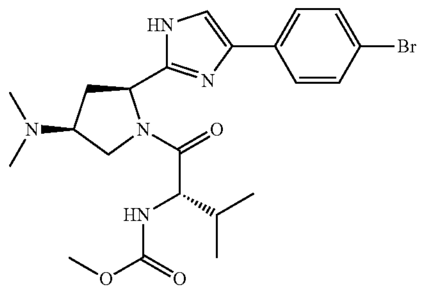 [SMILES: COC(=O)N[C@H](C(=O)N1C[C@@H](N(C)C)C[C@H]1c1nc(-c2ccc(Br)cc2)c[nH]1)C(C)C]

(a) (2S,4R)-4-Methanesulfonyloxy-pyrrolidine-1,2-dicarboxylic acid 1-tert-butyl ester 2-methyl ester To a solution of (2S,4R)-4-hydroxy-pyrrolidine-1,2-dicarboxylic acid 1-tert-butyl ester 2-methyl ester (50 g, 0.2 mol), triethylamine (50.5 g, 0.5 mol) in DCM was added methanesulfonyl chloride (28 g, 0.25 mol) in portions and the reaction mixture was stirred at 0° C. for 20 min and at RT for 1.5 h, and washed with citric acid solution and water. The organic layer was dried over sodium sulfate and concentrated to give the title intermediate (70 g, 97% yield). $^1$H NMR ($CDCl_3$, 400 MHz) δ (ppm) 5.23 (m, 1H), 4.44 (m, 1H), 3.75 (m, 5H), 3.04 (s, 3H), 2.64 (m, 1H), 2.26 (m, 1H), 1.43 (m, 9H).

(b) (2S,4S)-4-Azido-pyrrolidine-1,2-dicarboxylic acid 1-tert-butyl ester 2-methyl ester A mixture of the product of the previous step (70 g, 0.2 mol) and sodium azide (26 g, 0.4 mol) in DMF (800 mL) was stirred at 80° C. overnight. The reaction mixture was adjusted to pH 9-10 with sodium bicarbonate and extracted with DCM. The organic layer was washed with water and brine, dried over sodium sulfate, concentrated, and purified by silica gel chromatography (eluted with petroleum ether:EtOAc 5:1) to give the title intermediate (60 g, 97% yield) as a clear oil. $^1$H NMR ($CDCl_3$, 400 MHz) δ (ppm) 4.33 (m, 1H), 4.11 (m, 1H), 3.73 (s, 3H), 3.44 (m, 1H), 2.44 (m, 1H), 2.16 (m, 1H), 1.43 (m, 9H).

(c) (2S,4S)-4-Amino-pyrrolidine-1,2-dicarboxylic acid 1-tert-butyl ester 2-methyl ester A mixture of the product of the previous step (60 g, 0.2 mol) and palladium on carbon (7 g) in methanol (700 mL) was degassed under vacuum, purged with hydrogen several times, stirred under hydrogen (40 psi) at RT overnight and filtered. The filtrate was concentrated to give the title intermediate (45 g) as a brown oil. (m/z): $[M+H]^+$ calcd for $C_{11}H_{20}N_2O_4$ 245.14. found 245.1.

(d) (2S,4S)-4-Dimethylamino-pyrrolidine-1,2-dicarboxylic acid 1-tert-butyl ester 2-methyl ester To a solution of the product of the previous step (28 g, 57 mmol) and formaldehyde (20 g, 240 mmol) in methanol (500 mL) was added sodium triacetoxyborohydride (36 g, 170 mmol) in portions at RT and the reaction mixture was stirred at RT overnight under nitrogen and then concentrated. The residue was washed with water and extracted with DCM (2×500 mL). The organic layer was washed with water and brine, dried over sodium sulfate, concentrated, and purified by silica gel chromatography (eluted with petroleum ether: EtOAc 1:2, 1% $NH_4OH$) to give the title product (8 g, 50% yield) as a clear oil. $^1$H NMR ($CDCl_3$, 400) δ (ppm) 4.09 (m, 2H), 3.73 (s, 3H), 3.53 (m, 1H), 2.58 (m, 2H), 2.26 (s, 6H), 1.88 (m, 1H), 1.42 (m, 9H).

(e) (2S,4S)-4-Dimethylamino-pyrrolidine-1,2-dicarboxylic acid 1-tert-butyl ester A solution of the product of the previous step (8.0 g, 30 mmol) and sodium hydroxide (5.8 g, 150 mmol) in methanol: water 3:1 (120 mL) was stirred at RT overnight under nitrogen and concentrated. The water phase was adjusted to pH 5-6 with 3 N HCl and lyophilized. The solid was washed with methanol and filtered. The filtrate was concentrated to give the title intermediate (8 g) as a white solid. $^1$H NMR ($CDCl_3$, 400) δ (ppm) 4.09 (m, 2H), 3.73 (m, 2H), 3.53 (m, 1H), 2.78 (s, 6H), 2.58 (m, 1H), 2.21 (m, 1H), 1.42 (m, 9H).

(f) (2S,4S)-2-[2-(4-Bromo-phenyl)-2-oxo-ethylcarbamoyl]-4-dimethylamino-pyrrolidine-1-carboxylic acid tert-butyl ester A mixture of the product of the previous step (5.0 g, 16 mmol), 2-amino-1-(4-bromo-phenyl)-ethanone HCl (4.0 g, 16 mmol) 3-(diethoxyphosphoryloxy)-1,2,3-benzotrazin-4 (3H)-one (DEPBT) (6.0 g, 20 mmol), and DIPEA (6.0 g, 48 mmol) in DMF (150 mL) was stirred at RT overnight. The reaction mixture was washed with water and extracted with DCM (2×500 mL). The organic layer was washed with water and brine, dried over sodium sulfate, concentrated, and purified by silica gel chromatography (eluted with DCM:methanol 10:1) to give the title intermediate (2.3 g) which was purified by HPLC to give the title intermediate as a clear oil (1 g, 97% purity) and (750 mg, 70% purity).

(g) {(3S,5S)-5-[4-(4-Bromo-phenyl)-1H-imidazol-2-yl]-pyrrolidin-3-yl}-dimethyl-amine A mixture of the product of the previous step (1.25 g, 2.75 mmol) and ammonium acetate (4.2 g, 55 mmol) in toluene (50 mL) was stirred at 100-120° C. overnight under nitrogen. The reaction mixture was washed with water and the water phase was extracted with DCM (2×100 mL). The organic layer was washed with water and brine, dried over sodium sulfate, concentrated, and purified by silica gel chromatography (eluted with DCM:methanol 10:1) to give (2S,4S)-2-[4-(4-bromo-phenyl)-1H-imidazol-2-yl]-4-dimethylamino-pyrrolidine-1-carboxylic acid tert-butyl ester (1.7 g) as a brown solid.

A mixture of the product of the previous step (1.7 g, 2.3 mmol) in HCl and methanol (50 mL was stirred at RT for 1 h and concentrated to give the title intermediate (1.5 g) as a brown solid. (m/z): $[M+H]^+$ calcd for $C_{15}H_{19}BrN_4$ 335.08. found 334.9.

(h) ((S)-1-{(2S,4S)-2-[4-(4-Bromo-phenyl)-1H-imidazol-2-yl]-4-dimethylamino-pyrrolidine-1-carbonyl}-2-methyl-propyl)-carbamic acid methyl ester A mixture of the product of the previous step (1.5 g, 2.3 mmol), (S)-2-methoxycarbonyl-amino-3-methyl-butyric acid (0.6 g, 3.5 mmol), HATU (1.3 g, 3.5 mmol), and N,N-diisopropylethylamine (0.9 g, 6.9 mmol) in DCM (50 mL) was stirred at RT overnight. The reaction mixture was washed with water and extracted with DCM (2×100 mL). The organic layer was washed with water and brine, dried over sodium sulfate, concentrated, and purified by silica gel chromatography (eluted with DCM:methanol 10:1) to give the title intermediate (0.8 g, 65% yield) as a brown solid. (m/z): [M+H]$^+$ calcd for $C_{22}H_{30}BrN_5O_3$ 492.15. found 492.1.

Preparation 13: (R)-3-Methyl-4-{5-[4-(4,4,5,5-tetramethyl-1,3,2-dioxaborolan-2-yl)-phenylcarbamoyl]-pyridin-2-yl}-piperazine-1-carboxylic acid tert-butyl ester

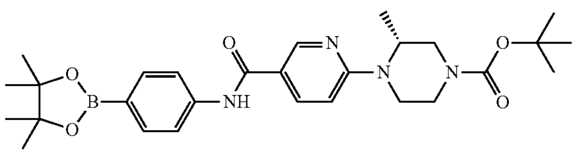 [SMILES: C[C@@H]1CN(C(=O)OC(C)(C)C)CCN1c1ccc(C(=O)Nc2ccc(B3OC(C)(C)C(C)(C)O3)cc2)cn1]

A solution of (R)-4-(5-carboxy-pyridin-2-yl)-3-methyl-piperazine-1-carboxylic acid tert-butyl ester (200 mg, 0.6 mmol) and EDC (140 mg, 0.75 mmol) and HOAt (100 mg, 0.75 mmol) dissolved in DMF (4.6 mL) was stirred for 30 min and 4-(4,4,5,5-tetramethyl-1,3,2-dioxaborolan-2-yl)aniline (140 mg, 0.62 mmol) and N,N-diisopropylethylamine (130 μL, 0.75 mmol) were added. The reaction mixture was stirred at RT overnight and extracted with ethyl acetate/water. The organic layer was dried over sodium sulfate, filtered, concentrated, and purified by silica gel chromatography (eluted with 0-70% ethyl acetate:hexanes) to provide the title intermediate (250 mg, 80% yield). (m/z): [M+H]$^+$ calcd for $C_{28}H_{39}BN_4O_5$ 523.30. found 523.5.

Preparation 14: 4-Bromo-3-trifluoromethoxy-benzoic acid methyl ester

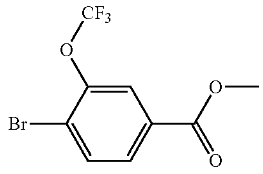 [SMILES: COC(=O)c1ccc(Br)c(OC(F)(F)F)c1]

A mixture of 4-amino-3-(trifluoromethoxy)benzoic acid (504.1 mg, 2.28 mmol), methanol (7.6 mL) and 4.0 M HCl in 1,4-dioxane (5.7 mL) was stirred at RT over the weekend, concentrated, evaporated with EtOAc (3×10 mL), and dried under vacuum to give a brownish solid. The solid was dissolved in a mixture of acetonitrile (23 mL) and water (2.3 mL). Copper(II) bromide (595 mg, 2.66 mmol) and tert-butyl nitrite (0.39 mL, 3.32 mmol) were added to the reaction mixture which was heated at 70° C. for 1.5 h, cooled to RT and diluted with EtOAc (70 mL). The organic layer was washed with saturated sodium bicarbonate (2×15 mL), brine (2×15 mL), dried over sodium sulfate, filtered and concentrated to give a brownish oil, which was purified by silica gel chromatography (24 g silica gel, 0-50% EtOAc/Hexanes). Desired fractions were combined and concentrated to give the title intermediate (281 mg, 41% yield) as a yellowish oil.

Preparation 15: 4'-{2-[(2S,4S)-1-((S)-2-Methoxycarbonylamino-3-methyl-butyryl)-4-methyl-pyrrolidin-2-yl]-1H-imidazol-4-yl}-2-trifluoromethoxy-biphenyl-4-carboxylic acid

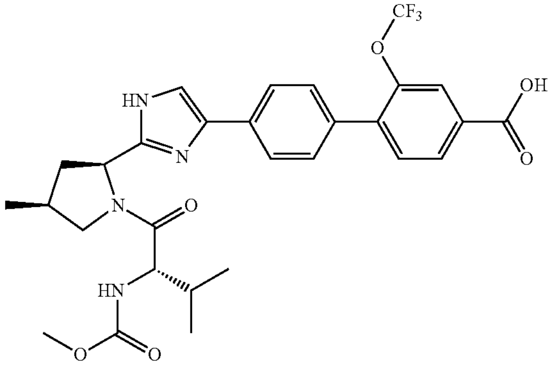 [SMILES: COC(=O)N[C@H](C(=O)N1C[C@@H](C)C[C@H]1c1nc(-c2ccc(-c3ccc(C(=O)O)cc3OC(F)(F)F)cc2)c[nH]1)C(C)C]

To a mixture of 4-bromo-3-trifluoromethoxy-benzoic acid methyl ester (161 mg, 0.54 mmol; Preparation 14), [(S)-2-methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester (250 mg, 0.49 mmol) and potassium carbonate (304 mg, 2.20 mmol) at RT was added toluene (1.2 mL) followed by water (0.61 mL). The resulting mixture was degassed and flushed with nitrogen and $Pd(dppf)Cl_2$ (24 mg, 0.029 mmol) was added under an atmosphere of nitrogen. The reaction mixture was capped and held at 100° C. overnight, cooled to RT and partitioned between EtOAc (10 mL) and water (2 mL). The organic layer was dried over sodium sulfate, filtered and concentrated to give a brownish oil which was purified by silica gel chromatograph (12 g silica gel, 0-100% EtOAc/Hexanes). Desired fractions were combined and concentrated to give a light reddish oil.

The oily residue from the previous step was dissolved in a mixture of methanol (4.9 mL) and water (2 mL) and treated with lithium hydroxide monohydrate (123 mg, 2.94 mmol) at 65° C. for 1 hr. The reaction mixture was concentrated, dissolved in 1:1 acetic acid:water (1.5 mL), filtered and purified by reverse phase HPLC. Desired fractions were combined and freeze dried to give the TFA salt of the title intermediate (221 mg, 64% yield) as a white solid. (m/z): $[M+H]^+$ calcd for $C_{29}H_{31}F_3N_4O_6$ 589.22. found 589.

Preparation 16: (2S,5R)-4-(5-Amino-pyridin-2-yl)-2,5-dimethyl-piperazine-1-carboxylic acid tert-butyl ester

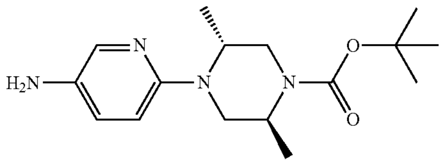 [SMILES: C[C@@H]1CN(C(=O)OC(C)(C)C)[C@@H](C)CN1c1ccc(N)cn1]

(a) (2S,5R)-2,5-Dimethyl-4-(5-nitro-pyridin-2-yl)-piperazine-1-carboxylic acid tert-butyl ester A mixture of 2-chloro-5-nitropyridine (1.0 g, 6.3 mmol), (2S,5R)-2,5-dimethyl-piperazine-1-carboxylic acid tert-butyl ester (1.4 g, 6.3 mmol), and potassium carbonate (1.7 g, 13 mmol) was stirred in DMSO (5.0 mL, 70 mmol) at 100° C. overnight. The reaction mixture was filtered thru a silica gel pad, which was washed with EtOAc (200 mL). The filtrate was washed with water (2×10 mL), concentrated, and purified by silica gel chromatography (eluted with ethyl acetate/hexane=0 to 80%) to give the title intermediate (1.724 g, 81% yield) as a yellow solid.

(b) (2S,5R)-4-(5-Amino-pyridin-2-yl)-2,5-dimethyl-piperazine-1-carboxylic acid ten-butyl ester A solution of the product of the previous step in methanol (250 mL) was degassed, then 20% palladium hydroxide on carbon (170 mg, 10% by weight) was added and reaction mixture was degassed three times, and hydrogenated under a balloon of hydrogen overnight. The reaction mixture was filtered thru a Celite® pad. The filtrate was concentrated and purified by silica gel chromatography (eluted with 3% triethylamine in ethyl acetate/hexanes 0 to 80%) to give the title intermediate (1.3 g, 67% yield) as a dark purple solid. (m/z): $[M+H]^+$ calcd for $C_{16}H_{26}N_4O_2$ 307.21. found 307.6.

Preparation 17: [(R)-4-(5-Amino-pyridin-2-yl)-3-methyl-piperazin-1-yl]-((S)-2,2-dimethyl-cyclopropyl)-methanone

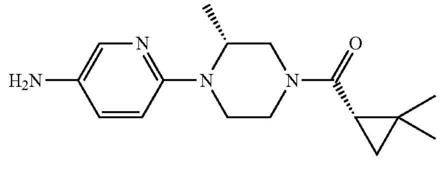 [SMILES: C[C@@H]1CN(C(=O)[C@H]2CC2(C)C)CCN1c1ccc(N)cn1]

(a) (R)-3-Methyl-4-(5-nitro-pyridin-2-yl)-piperazine-1-carboxylic acid tert-butyl ester In each of two separate reactions, a mixture of 2-chloro-5-nitropyridine (1.0 g, 6.3 mmol), (R)-3-methyl-piperazine-1-carboxylic acid tert-butyl ester (1.4 g, 6.9 mmol), and potassium carbonate (1.31 g, 9.46 mmol) in DMSO (20 mL) was heated at 100° C. overnight. The reaction mixtures were cooled to RT, filtered through silica gel, and eluted with EtOAc (150 mL). The filtrate was washed with water (2×20 mL) and brine (20 mL), dried over sodium sulfate, filtered, and concentrated to give a brownish oil, which was purified by silica gel chromatography (40 g silica gel, 0-60% EtOAc/Hexanes). Desired fractions were combined and concentrated to provide the title intermediate (1.39 g each) as a yellowish solid. (m/z): $[M+H]^+$ calcd for $C_{15}H_{22}N_4O_4$ 323.16. found 323.3.

(b) (R)-2-Methyl-1-(5-nitro-pyridin-2-yl)-piperazine

The product of the previous step (2.79 g, 8.65 mmol) was treated with 4 M of HCl in 1,4-dioxane (65 mL) and stirred at RT for 1 h, concentrated to produce a yellow solid and evaporated twice with EtOAc to provide the di-HCl salt of the title intermediate (2.20 g, 86% yield).

(c) ((S)-2,2-Dimethyl-cyclopropyl)-[(R)-3-methyl-4-(5-nitro-pyridin-2-yl)-piperazin-1-yl]-methanone The product of the previous step (1.5 g, 6.7 mmol) was dissolved in DMA (65 mL) and N,N-Diisopropylethylamine (3.5 mL) was added followed by (S)-(+)-2,2-dimethylcyclopropane carboxylic acid (0.93 mL, 8.1 mmol) and then HATU (3.1 g, 8.1 mmol). The reaction mixture was stirred at RT overnight, diluted in EtOAc and washed with water and brine. The organic layer was dried over sodium sulfate, filtered and concentrated to produce a yellow oil, which was purified by silica chromatography (0-60% EtOAc:hexanes) to produce the title intermediate (1.29 g, 60% yield) as a yellow solid. (m/z): $[M+H]^+$ calcd for $C_{16}H_{22}N_4O_3$ 319.17. found 319.2.

(d) [(R)-4-(5-Amino-pyridin-2-yl)-3-methyl-piperazin-1-yl]-((S)-2,2-dimethyl-cyclopropyl)-methanone A solution of the product of the previous step (200 mg, 0.63 mmol) in methanol (6 mL) was degassed with nitrogen for 15 min and then 5% platinum on Carbon wet 65.25% (491 mg, 0.063 mmol) was added and the reaction mixture was bubbled with hydrogen for 15 min and stirred under hydrogen atmosphere for 1.5 h at RT. The reaction mixture was degassed under nitrogen and filtered through Celite, washed with EtOAc and concentrated to yield a dark red oil, which was purified by silica gel chromatography (0-100% ethyl acetate: hexanes) to provide the title intermediate as a light red solid (83 mg, 46% yield). (m/z): $[M+H]^+$ calcd for $C_{16}H_{24}N_4O$ 289.20. found 289.4.

Preparation 18: 4-(4-Bromo-phenyl)-2-((2S,4S)-4-methylsulfanyl-pyrrolidin-2-yl)-1H-imidazole

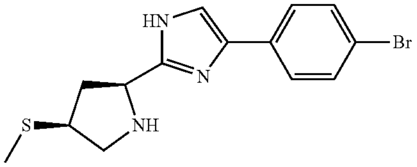 [SMILES: CS[C@@H]1CN[C@H](c2nc(-c3ccc(Br)cc3)c[nH]2)C1]

(a) (2S,4S)-2-[4-(4-Bromo-phenyl)-1H-imidazol-2-yl]-4-methylsulfanyl-pyrrolidine-1-carboxylic acid tert-butyl ester To a solution of (2S,4S)-4-methylsulfanyl-pyrrolidine-1,2-dicarboxylic acid 1-tert-butyl ester (250 mg, 0.96 mmol) and p-bromophenacyl bromide (266 mg, 0.96 mmol) in DCM (10 mL) under nitrogen was added N,N-diisopropylethylamine (0.58 mL, 3.35 mmol) and the resulting mixture was stirred at 35° C. for 3 h, concentrated under vacuum, dissolved in DCM (30 mL), and washed with water (2×5 mL). The organic layer was dried over magnesium sulfate, filtered, and concentrated under vacuum.

The crude intermediate from the previous step was dissolved in toluene (75.0 mL), and then ammonium acetate (1.475 g, 19.13 mmol) was added, and the resulting mixture was stirred at 100° C. overnight, concentrated and purified by silica gel chromatograph (12 g silica, 0 to 60% EtOAc/hexane) to give the title intermediate (410 mg, 98% yield). (m/z): $[M+H]^+$ calcd for $C_{19}H_{24}BrN_3O_2S$ 438.08; 440.08. found 440.

(b) 4-(4-Bromo-phenyl)-2-((2S,4S)-4-methylsulfanyl-pyrrolidin-2-yl)-1H-imidazole The product of the previous step was treated with 4 M HCl in 1,4-dioxane (2.0 mL) for 1 h and concentrated by rotary evaporation to provide the di-HCl salt of the title intermediate (368 mg, 93% yield). (m/z): $[M+H]^+$ calcd for $C_{14}H_{16}BrN_3S$ 338.02; 340.02. found 340.

Preparation 19: ((S)-1-{(2S,4S)-2-[4-(4-Bromo-phenyl)-1H-imidazol-2-yl]-4-methylsulfanyl-pyrrolidine-1-carbonyl}-2-methyl-propyl)-carbamic acid methyl ester

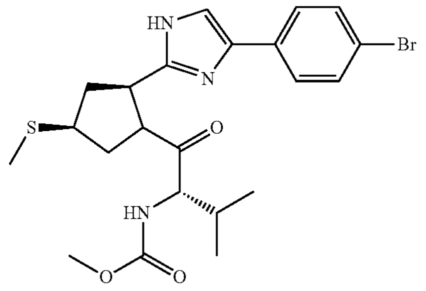

A mixture of (S)-2-methoxycarbonylamino-3-methyl-butyric acid (156 mg, 0.89 mmol) and HATU (407 mg, 1.07 mmol) was stirred in DMA (3.0 mL) for 10 min, then 4-(4-bromo-phenyl)-2-((2S,4S)-4-methylsulfanyl-pyrrolidin-2-yl)-1H-imidazole di-HCl (367 mg, 0.89 mmol; Preparation 18) and N,N-diisopropylethylamine (777.3 μL, 4.46 mmol) were added. The resulting mixture was stirred at RT overnight, concentrated, and purified by silica gel chromatography (0 to 90% EtOAc/hexane). Fractions with desired product were combined and concentrated to give the title intermediate (366 mg, 82% yield). (m/z): $[M+H]^+$ calcd for $C_{21}H_{27}BrN_4O_3S$ 495.10; 497.10. found 495.

Preparation 20: [(S)-2-Methyl-1-((2S,4S)-4-methylsulfanyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester

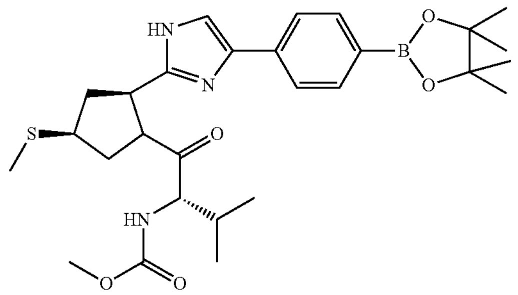

To a solution of ((S)-1-{(2S,4S)-2-[4-(4-bromo-phenyl)-1H-imidazol-2-yl]-4-methylsulfanyl-pyrrolidine-1-carbonyl}-2-methyl-propyl)-carbamic acid methyl ester (320 mg, 0.65 mmol, Preparation 19) and 4,4,5,5,4',4',5',5'-octamethyl-[2,2']bi[[1,3,2]dioxaborolanyl] (246 mg, 0.97 mmol in 1,4-dioxane (5 mL) was added potassium acetate (114 mg, 1.16 mmol). The resulting mixture was sparged with nitrogen. 1,1'-bis(diphenylphosphino)ferrocene-palladium(II) dichloride dichloromethane (47 mg, 0.058 mmol) was added, and reaction mixture was capped and heated at 100° C. overnight. The reaction mixture was cooled to RT and partitioned between EtOAc (50 mL) and water (10 mL). The organic layer was washed with water (5 mL) and brine (2 mL), dried over magnesium sulfate, filtered, and concentrated to give a dark-brown oil, which was purified by silica gel chromatography (24 g silica gel, 0-100% EtOAc/Hexanes). Fractions with desired product were combined and dried to give the title intermediate (120 mg, 34% yield) (m/z): $[M+H]^+$ calcd for $C_{27}H_{39}BN_4O_5S$ 543.27. found 543.

Preparation 21: 4'-{2-[(2S,4S)-1-((S)-2-Methoxycarbonylamino-3-methyl-butyryl)-4-methylsulfanyl-pyrrolidin-2-yl]-1H-imidazol-4-yl}-2-trifluoromethoxy-biphenyl-4-carboxylic acid

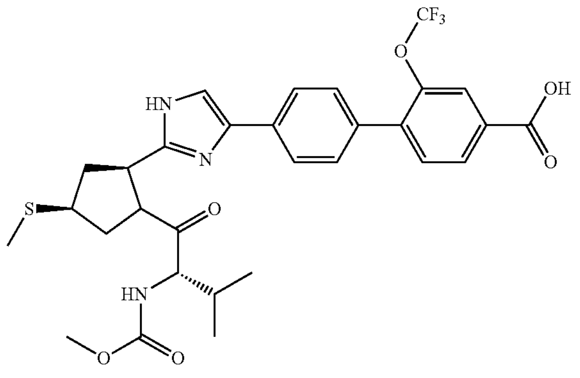

To a mixture of 4-bromo-3-trifluoromethoxy-benzoic acid methyl ester (36 mg, 0.12 mmol; Preparation 14), [(S)-2-methyl-1-((2S,4S)-4-methylsulfanyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester (60 mg, 0.11 mmol; Preparation 20) and potassium carbonate (69 mg, 0.50 mmol) at RT was added toluene (0.27 mL) followed by water (0.14 mL). The resulting mixture was degassed and flushed with nitrogen and $Pd(dppf)Cl_2$ (5.4 mg, 0.006 mmol) was added under an atmosphere of nitrogen. The reaction mixture was capped and held at 100° C. overnight, cooled to RT and partitioned between EtOAc (10 mL) and water (2 mL). The organic layer was dried over sodium sulfate, filtered, and concentrated to give a brownish oil, which was purified by silica gel chromatography (12 g silica gel, 0-100% EtOAc/Hexanes). Desired fractions were combined and concentrated to give a light reddish oil.

The oily residue from previous step was dissolved in a mixture of methanol (1.1 mL) and water (0.4 mL) and treated with lithium hydroxide monohydrate (28 mg, 0.66 mmol) at 65° C. for 1 h. The reaction mixture was concentrated, dissolved in 1:1 acetic acid:water (1.5 mL), filtered and purified by reverse phase HPLC. Desired fractions were combined and freeze dried to give the TFA salt of the title intermediate (37 mg, 46% yield) as a white solid. (m/z): $[M+H]^+$ calcd for $C_{29}H_{31}F_3N_4O_6S$ 621.19. found 621.

Preparation 22: (2S,5R)-4-[5-(4-Bromo-2-fluoro-5-trifluoromethoxy-phenylcarbamoyl)-pyridin-2-yl]-2,5-dimethyl-piperazine-1-carboxylic acid tert-butyl ester

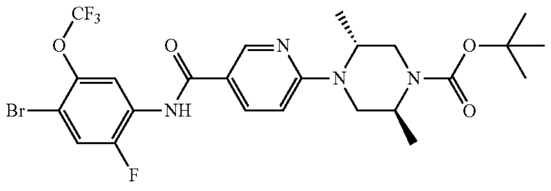

To a solution of 4-bromo-2-fluoro-5-trifluoromethoxy-phenylamine (500 mg, 2 mmol) dissolved in DCM (1 mL) was slowly added a solution of 2-fluoropyridine-5-carbonyl chloride (290 mg, 1.8 mmol) in DCM (1 mL). A few drops of DMA were added and the reaction mixture was concentrated to form N-(4-bromo-2-fluoro-5-trifluoromethoxy-phenyl)-6-fluoro-nicotinamide as a purple solid.

The solid from the previous step was dissolved in a mixture of N,N-diisopropylethylamine (0.7 mL, 4 mmol) and DMSO (0.7 mL, 10 mmol) and (2S,5R)-2,5-dimethyl-piperazine-1-carboxylic acid tert-butyl ester (590 mg, 2.7 mmol) was added and the reaction mixture heated at 120° C. overnight, concentrated by rotary evaporation, dissolved in a small amount of DCM and purified by silica gel chromatography (0-40% ethyl acetate:hexanes) to produce the title intermediate (613 mg, 57% yield) as a white solid. (m/z): $[M+H]^+$ calcd for $C_{24}H_{27}F_4N_4O_4$ 591.12. found 591.4.

Preparation 23: 4'-{2-[(S)-7-((S)-2-Methoxycarbonylamino-3-methyl-butyryl)-1,4-dioxa-7-aza-spiro[4.4]non-8-yl]-1H-imidazol-4-yl}-biphenyl-4-carboxylic acid

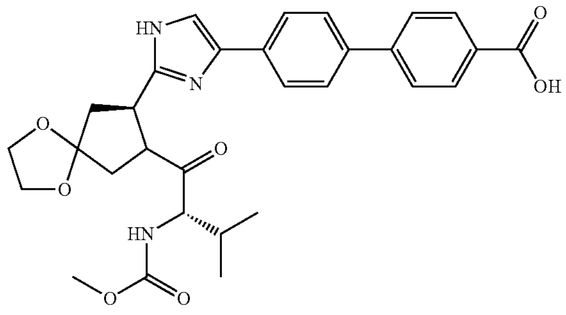

To a solution of ((S)-1-{(S)-8-[4-(4-Bromo-phenyl)-1H-imidazol-2-yl]-1,4-dioxa-7-aza-spiro[4.4]nonane-7-carbonyl}-2-methyl-propyl)-carbamic acid methyl ester (450 mg, 0.89 mmol) in dioxane (8 mL) and water (4 mL) was added 4-boronobenzoic acid (154 mg, 0.93 mmol), sodium carbonate (189 mg, 1.78 mmol), and tetrakis(triphenylphosphine)-palladium(0) (104 mg, 0.09 mmol) and the reaction mixture was stirred at reflux for 3 h under nitrogen. The pH was adjusted to 1 with 2 M HCl, and the reaction mixture was extracted with EtOAc (3×20 mL). The organic layers were combined, dried over sodium sulfate, concentrated and purified by flash chromatography (eluted with methanol in DCM, 0 to 7%) to provide the title intermediate as a yellow solid (330 mg, 68% yield). (m/z): $[M+H]^+$ calcd for $C_{29}H_{32}N_4O_7$ 549.23. found 549.3. $^1H$ NMR ($CH_3OD$, 400) δ (ppm) 8.13-8.11 (m, 2H), 7.90-7.78 (m, 7H), 5.39-5.34 (m, 1H), 4.19-3.91 (m, 7H), 3.66 (s, 3H), 2.72-2.65 (m, 1H), 2.48-2.41 (m, 1H), 2.12-1.95 (m, 1H), 0.92-0.85 (m, 6H).

Preparation 24: (R)-4-[5-(4-Bromo-2-fluoro-5-trifluoromethoxy-phenylcarbamoyl)-pyridin-2-yl]-3-methyl-piperazine-1-carboxylic acid tert-butyl ester

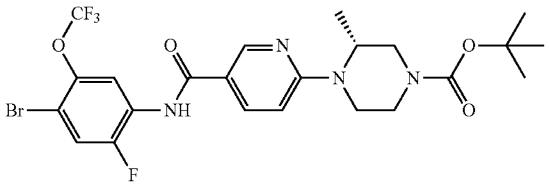 [SMILES: C[C@@H]1CN(C(=O)OC(C)(C)C)CCN1c1ccc(C(=O)Nc2cc(OC(F)(F)F)c(Br)cc2F)cn1]

(a) 4-Bromo-2-fluoro-5-trifluoromethoxy-phenylamine

To a mixture of 2-fluoro-5-(trifluoromethoxy)aniline (2 g, 10 mmol) dissolved in DMF (4 mL) was slowly added a solution of N-bromosuccinimide (2.2 g, 12 mmol) dissolved in DMF (5 mL). The reaction mixture was stirred at RT for 1 h, concentrated and extracted with ethyl acetate/water. The organic layer was washed with brine, partitioned, dried over sodium sulfate, filtered, concentrated, and purified by silica chromatography (100% hexanes) to produce the title intermediate as a red oil (2 g, 70% yield). (m/z): $[M+H]^+$ calcd for $C_7H_4BrF_4NO$ 273.94; 275.94. found 276.2.

(b) N-(4-Bromo-2-fluoro-5-trifluoromethoxy-phenyl)-6-fluoro-nicotinamide

To a solution of the product of the previous step (2 g, 7 mmol) dissolved in DCM (10 mL) was slowly added a solution of 2-fluoropyridine-5-carbonyl chloride (1.2 g, 7.3 mmol) in DCM (10 mL) and DMA (60 drops). The reaction mixture was concentrated to provide the title intermediate as a purple solid. (m/z): $[M+H]^+$ calcd for $C_{13}H_6BrF_5N_2O_2$ 396.95; 398.95. found 399.0.

(c) (R)-4-[5-(4-Bromo-2-fluoro-5-trifluoromethoxy-phenylcarbamoyl)-pyridin-2-yl]-3-methyl-piperazine-1-carboxylic acid tert-butyl ester The solid from the previous step was dissolved in a mixture of N,N-diisopropylethylamine (3 mL, 20 mmol) and DMSO (3 mL) and (R)-3-methyl-piperazine-1-carboxylic acid tert-butyl ester (2.2 g, 11 mmol) was added. The reaction mixture was heated at 120° C. overnight, concentrated by rotary evaporation, dissolved in a small amount of DCM, and purified by silica gel chromatography (0-40% ethyl acetate:hexanes) to produce the title intermediate as a white solid (3.6 g, 80% yield). (m/z): $[M+H]^+$ calcd for $C_{23}H_{25}BrF_4N_4O_4$ 577.10; 579.10. found 577.5, 580.3.

Preparation 25: 4'-{5-Chloro-2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-carboxylic acid

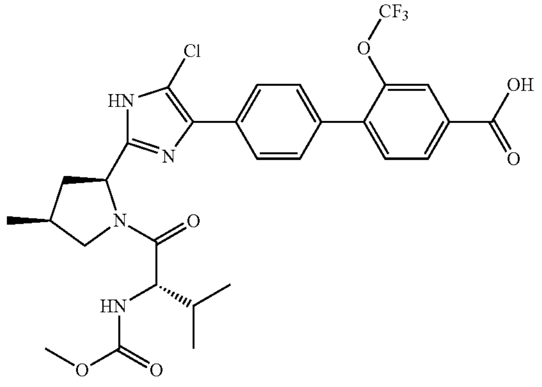 [SMILES: COC(=O)N[C@H](C(=O)N1C[C@@H](C)C[C@H]1c1nc(-c2ccc(-c3ccc(C(=O)O)cc3OC(F)(F)F)cc2)c(Cl)[nH]1)C(C)C]

A mixture of 4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-carboxylic acid (124 mg, 0.21 mmol) and N-chlorosuccinimide (28 mg, 0.21 mmol) was stirred in acetonitrile (2.0 mL) and N,N-dimethylacetamide (0.2 mL) at 60° C. overnight. The reaction mixture was concentrated by rotary evaporation, dissolved in 1:1 acetic acid:water (8 mL) and purified by reverse phase HPLC to provide the TFA salt of the title compound (48 mg). (m/z): $[M+H]^+$ calcd for $C_{29}H_{30}ClF_3N_4O_6$ 623.18. found 623.2.

Preparation 26: ((S)-1-{(2S,4S)-2-[4-(4-Bromo-phenyl)-1H-imidazol-2-yl]-4-methoxy-pyrrolidine-1-carbonyl}-2-methyl-propyl)-carbamic acid methyl ester

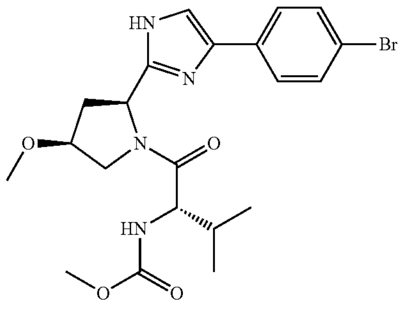 [SMILES: COC(=O)N[C@H](C(=O)N1C[C@@H](OC)C[C@H]1c1nc(-c2ccc(Br)cc2)c[nH]1)C(C)C]

(a) (2S,4S)-2-[4-(4-Bromo-phenyl)-1H-imidazol-2-yl]-4-methoxy-pyrrolidine-1-carboxylic acid tert-butyl ester To a solution of (2S,4S)-4-methoxy-pyrrolidine-1,2-dicarboxylic acid 1-tert-butyl ester (900 mg, 3.67 mmol), and p-bromophenacyl bromide (1.02 g, 3.67 mmol) in DCM (20 mL) under nitrogen, was added N,N-diisopropylethylamine (1.92 mL, 11.01 mmol). The resulting mixture was stirred at 35° C. for 3 h and concentrated under vacuum. The crude intermediate was dissolved in toluene (150 mL), ammonium acetate (5.66 g, 73.39 mmol) was added, and the resulting mixture was stirred at 95° C. overnight, and washed with water (2×10 mL). The organic layer was dried over magnesium sulfate, filtered, concentrated and purified by silica gel chromatography (24 g, ethyl acetate/hexanes 0 to 60%) to give the title intermediate (1.49 g, 96% yield).

(b) 4-(4-Bromo-phenyl)-2-((2S,4S)-4-methoxy-pyrrolidin-2-yl)-1H-imidazole

The product of the previous step was treated with 4 M HCl in 1,4-dioxane (2 mL) for 1 h and concentrated by rotary evaporation to give the di-HCl salt of the title intermediate (1.40 g, 97% yield). (m/z): $[M+H]^+$ calcd for $C_{14}H_{16}BrN_3O$ 322.05; 324.05. found 324.

(c) ((S)-1-{(2S,4S)-2-[4-(4-Bromo-phenyl)-1H-imidazol-2-yl]-4-methoxy-pyrrolidine-1-carbonyl}-2-methyl-propyl)-carbamic acid methyl ester A mixture of (S)-2-methoxycarbonylamino-3-methyl-butyric acid (643 mg, 3.67 mmol) and HATU (1.67 g, 4.40 mmol) were stirred in DMA (5 mL) for 10 min, and then the product of the previous step (1.40 g, 3.54 mmol) and N,N-diisopropylethylamine (1.92 mL, 11.01 mmol) were added, and the resulting mixture was stirred at room temperature overnight, concentrated by rotary evaporation, dissolved in ethyl acetate (100 mL), and washed with water (2×10 mL). The organic layer was dried over magnesium sulfate, filtered, concentrated, and purified by silica gel chromatography (ethyl acetate/hexanes 30 to 80%) to give the title product (1.38 g, 79% yield). (m/z): $[M+H]^+$ calcd for $C_{21}H_{27}BrN_4O_4$ 479.12; 481.12. found 481.

Preparation 27: [(S)-1-((2S,4S)-4-Methoxy-2-{4-[4-(4,4,5,5-tetramethyl-1,3,2-dioxaborolan-2-yl)-phenyl]-1H-imidazol-2-yl}-pyrrolidine-1-carbonyl)-2-methyl-propyl]-carbamic acid methyl ester

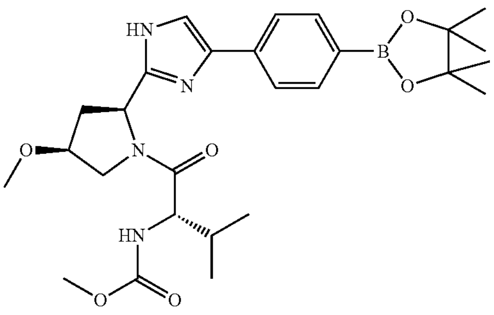

A solution of ((S)-1-{(2S,4S)-2-[4-(4-bromo-phenyl)-1H-imidazol-2-yl]-4-methoxy-pyrrolidine-1-carbonyl}-2-methyl-propyl)-carbamic acid methyl ester (1.05 g, 2.18 mmol; Preparation 26), 4,4,5,5,4',4',5',5'-octamethyl-[2,2']bi[[1,3,2]dioxaborolanyl] (0.83 g, 3.27 mmol), and potassium acetate (0.39 g, 3.93 mmol) in 1,4-dioxane (5 mL) was purged with nitrogen for 5 min, then $Pd(dppf)Cl_2$ (95.80 mg, 0.13 mmol) was added, and the resulting mixture was stirred at 100° C. for 3 h, diluted with ethyl acetate (50 mL), and filtered through a pad of celite and silica gel. The pad was washed with ethyl acetate (150 ml); the filtrate was concentrated and purified by silica gel chromatography (ethyl acetate/hexanes 30 to 100%) to give the title intermediate (669 mg 58% yield). (m/z): $[M+H]^+$ calcd for $C_{27}H_{39}BN_4O_6$ 527.30. found 527.2.

Preparation 28: ((S)-1-{(2S,4S)-2-[4-(5'-Chloro-4'-4{[6-((R)-2-methyl-piperazin-1-yl)-pyridine-3-carbonyl]-amino}-2'-trifluoromethoxy-biphenyl-4-yl)-1H-imidazol-2-yl]-4-methoxy-pyrrolidine-1-carbonyl}-2-methyl-propyl)-carbamic acid methyl ester (a) (R)-4-[5-(5-Chloro-4'-{2-[(2S,4S)-4-methoxy-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-3-methyl-piperazine-1-carboxylic acid tert-butyl ester To a solution of [(S)-1-((2S,4S)-4-methoxy-2-{4-[4-(4,4,5,5-tetramethyl-1,3,2-dioxaborolan-2-yl)-phenyl]-1H-imidazol-2-yl}-pyrrolidine-1-carbonyl)-2-methyl-propyl]-carbamic acid methyl ester (100 mg, 0.19 mmol, Preparation 27) and (R)-4-[5-(4-bromo-2-chloro-5-trifluoromethoxy-phenylcarbamoyl)-pyridin-2-yl]-3-methyl-piperazine-1-carboxylic acid tert-butyl ester (110 mg, 0.19 mmol) dissolved in toluene (1.18 mL) and water (0.43 mL) was added potassium carbonate (127 mg, 0.92 mmol). The reaction mixture was sparged under nitrogen for 15 min and $Pd(dppf)Cl_2CH_2Cl_2$ (13.55 mg, 0.017 mmol) was added and the reaction mixture was sparged with nitrogen and heated at 90° C. overnight, cooled to RT, diluted with EtOAc and washed with water and brine to produce a dark colored solid, which was purified by silica gel chromatography (12 g silica, EtOAc/hexanes 40 to 100%) to produce the title intermediate (35.3 mg, 21% yield) as a yellowish colored solid. (m/z): $[M+H]^+$ calcd for $C_{44}H_{52}ClF_3N_8O_8$ 913.35. found 913.3.

(b) ((S)-1-{(2S,4S)-2-[4-(5'-Chloro-4'-{[6-((R)-2-methyl-piperazin-1-yl)-pyridine-3-carbonyl]-amino}-2'-trifluoromethoxy-biphenyl-4-yl)-1H-imidazol-2-yl]-4-methoxy-pyrrolidine-1-carbonyl}-2-methyl-propyl)-carbamic acid methyl ester The product of the previous step was treated with 4 M HCl in 1,4-dioxane (0.92 mL) and HCl (0.28 mL) and the reaction mixture was stirred at RT for 1 h, concentrated and evaporated with ethyl acetate (2×) to produce the tri-HCl salt of the title intermediate (38.5 mg, 23% yield). (m/z): $[M+H]^+$ calcd for $C_{39}H_{44}ClF_3N_8O_6$ 813.30. found 813.3.

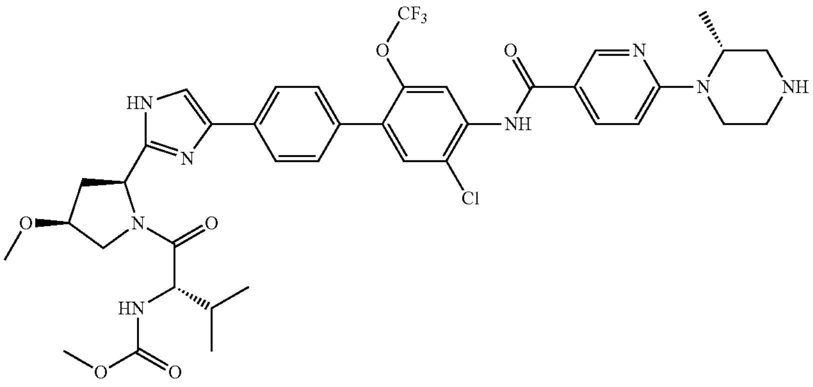 [SMILES: COC(=O)N[C@H](C(=O)N1C[C@@H](OC)C[C@H]1c1nc(-c2ccc(-c3cc(Cl)c(NC(=O)c4ccc(N5CCNC[C@H]5C)nc4)cc3OC(F)(F)F)cc2)c[nH]1)C(C)C]

Preparation 29: (S)-Methoxycarbonylamino-(tetrahydro-pyran-4-yl)-acetic acid

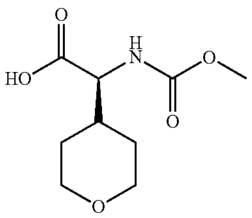

A solution of (S)-amino-(tetrahydro-pyran-4-yl)-acetic acid (200 mg, 1.26 mmol) in saturated aqueous sodium bicarbonate solution (2.46 mL, 25.13 mmol) was stirred until all solids were dissolved. Methyl chloroformate (0.19 mL, 2.51 mmol) was added dropwise, the reaction mixture was stirred for 30 min, and 1N HCl was added to adjust pH to 1. The reaction mixture was extracted with ethyl acetate (3x5 mL) and the organic extracts were dried over sodium sulfate, filtered, concentrated and dried overnight under vacuum to give the title intermediate (248 mg, 91% yield) as a white, sticky solid. (m/z): $[M+H]^+$ calcd for $C_9H_{15}NO_5$ 218.10. found 218.1.

Preparation 30: N-(4-Bromo-2-chloro-5-trifluoromethoxy-phenyl)-6-[(R)-4-(2,2-dimethyl-propionyl)-2-methyl-piperazin-1-yl]-nicotinamide

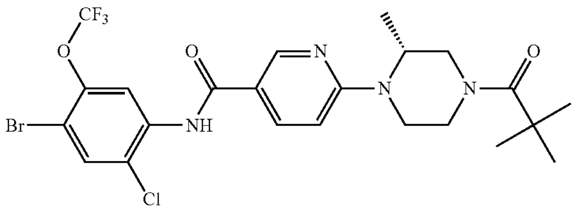 [SMILES: C[C@@H]1CN(C(=O)C(C)(C)C)CCN1c1ccc(C(=O)Nc2cc(OC(F)(F)F)c(Br)cc2Cl)cn1]

(a) N-(4-Bromo-2-chloro-5-trifluoromethoxy-phenyl)-6-((R)-2-methyl-piperazin-1-yl)-nicotinamide A solution of (R)-4-[5-(4-bromo-2-chloro-5-trifluoromethoxy-phenylcarbamoyl)-pyridin-2-yl]-3-methyl-piperazine-1-carboxylic acid tert-butyl ester (600 mg, 1.01 mmol) and 4 M HCl in 1,4-dioxane (5.05 mL) and HCl (1.55 mL) was stirred at RT for 1 h, concentrated, and evaporated with ethyl acetate (2×) to produce the di-HCl salt of the title intermediate (625.5 mg), (m/z): $[M+H]^+$ calcd for $C_{18}H_{17}BrClF_3N_4O_2$ 493.02; 495.02. found 494.9.

(b) N-(4-Bromo-2-chloro-5-trifluoromethoxy-phenyl)-6-[(R)-4-(2,2-dimethyl-propionyl)-2-methyl-piperazin-1-yl]-nicotinamide The solid from the previous step was dissolved in DMA (6.58 mL) and DIPEA (0.88 mL, 5.05 mmol) was added, followed by 2,2-dimethylpropanoyl chloride (130.53 μL, 1.06 mmol) and the reaction mixture was stirred at RT for 1 h. The reaction mixture was concentrated by rotary evaporation, to produce a yellow oil which was dissolved in a small amount of DCM and purified by silica gel chromatography (24 g column, 0-40% ethyl acetate:hexanes) to produce the title intermediate (552 mg, 94% yield) as a white solid. (m/z): $[M+H]^+$ calcd for $C_{23}H_{25}BrClF_3N_4O_3$ 577.08; 579.08. found 579.0.

Preparation 31: N-{5-Chloro-4'-[2-((2S,4S)-4-methyl-pyrrolidin-2-yl)-1H-imidazol-4-yl]-2-trifluoromethoxy-biphenyl-4-yl}-6-[(R)-4-(2,2-dimethyl-propionyl)-2-methyl-piperazin-1-yl]-nicotinamide

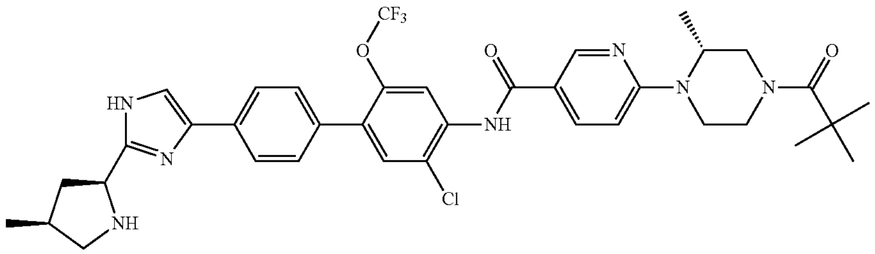 [SMILES: C[C@@H]1CN[C@H](c2nc(-c3ccc(-c4cc(Cl)c(NC(=O)c5ccc(N6CCN(C(=O)C(C)(C)C)C[C@H]6C)nc5)cc4OC(F)(F)F)cc3)c[nH]2)C1]

(a) (2S,4S)-4-methyl-2-{4-[4-(4,4,5,5-tetramethyl-[1,3,2]dioxaborolan-2-yl)-phenyl]-1H-imidazol-2-yl}-pyrrolidine-1-carboxylic acid tert-butyl ester To a solution of (2S,4S)-2-[4-(4-bromo-phenyl)-1H-imidazol-2-yl]-4-methyl-pyrrolidine-1-carboxylic acid tert-butyl ester (1.0 g, 2.5 mmol) and bis(pinacolato)diboron (656 mg, 2.58 mmol) and potassium acetate (362 mg, 3.69 mmol) was added degassed toluene (5.77 mL). The reaction mixture was sparged with nitrogen for 15 min and 1,1'-bis(diphenylphosphino)ferrocene-palladium(ii)dichloride dichloromethane (60.3 mg, 0.074 mmol) was added and the reaction mixture was stirred, purged with nitrogen, and heated to 90° C. for 3 h to provide the title intermediate.

(b) (2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-pyrrolidine-1-carboxylic acid tert-butyl ester To the reaction mixture of the previous step was added degassed water (2.75 mL) and potassium carbonate (1.87 g, 13.54 mmol), and N-(4-bromo-2-chloro-5-trifluoromethoxy-phenyl)-6-[(R)-4-(2,2-dimethyl-propionyl)-2-methyl-piperazin-1-yl]-nicotinamide (1.49 g, 2.58 mmol; Preparation 30). The reaction mixture was purged with nitrogen, Pd(dppf)$Cl_2CH_2Cl_2$ (30.2 mg, 0.037 mmol) was added and the mixture was purged again, heated to 95° C. overnight, cooled to RT, diluted with EtOAc, filtered through a combined pad of Celite® and silica gel, flushed several times with EtOAc, and washed with water and brine to produce a dark colored solid. The residue was purified by silica gel chromatography (40 g column, 40% to 100% EtOAc/hexane,) to provide the title intermediate (890 mg, 44% yield) as a yellow solid. (m/z): $[M+H]^+$ calcd for $C_{42}H_{49}ClF_3N_7O_5$ 824.34. found 824.3

(c) N-{5-Chloro-4'-[2-((2S,4S)-4-methyl-pyrrolidin-2-yl)-1H-imidazol-4-yl]-2-trifluoromethoxy-biphenyl-4-yl}-6-[(R)-4-(2,2-dimethyl-propionyl)-2-methyl-piperazin-1-yl]-nicotinamide The solid from the previous step was treated with 4 M HCl in 1,4-dioxane (12.3 mL) and HCl (3.8 mL) and the reaction mixture was stirred at RT for 1 h, concentrated and evaporated with ethyl acetate (2×) to produce the tri-HCl salt of the title intermediate (913 mg, 44% yield). (m/z): $[M+H]^+$ calcd for $C_{37}H_{41}ClF_3N_7O_3$ 724.29. found 724.3.

Preparation 32 N-{5-Chloro-4'-[2-((2S,4S)-4-methoxy-pyrrolidin-2-yl)-1H-imidazol-4-yl]-2-trifluoromethoxy-biphenyl-4-yl}-6-[(R)-4-(2,2-dimethyl-propionyl)-2-methyl-piperazin-1-yl]-nicotinamide

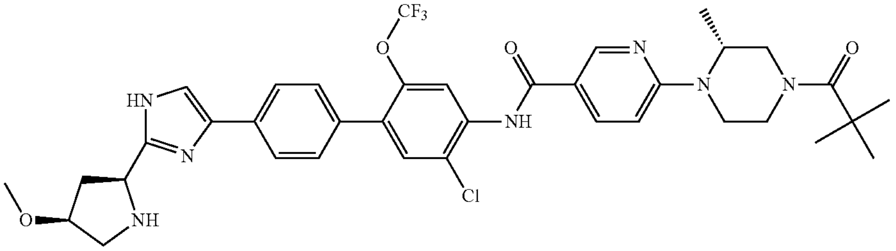 [SMILES: CO[C@@H]1CN[C@H](c2nc(-c3ccc(-c4cc(Cl)c(NC(=O)c5ccc(N6CCN(C(=O)C(C)(C)C)C[C@H]6C)nc5)cc4OC(F)(F)F)cc3)c[nH]2)C1]

Following a process analogous to that of Preparation 31 at the 0.71 mmol scale, substituting (2S,4S)-2-[4-(4-bromo-phenyl)-1H-imidazol-2-yl]-4-methoxy-pyrrolidine-1-carboxylic acid tert-butyl ester for (2S,4S)-2-[4-(4-bromo-phenyl)-1H-imidazol-2-yl]-4-methyl-pyrrolidine-1-carboxylic acid tert-butyl ester in step (a), the tri-HCl salt of the title intermediate was prepared (146 mg, 24% yield). (m/z): $[M+H]^+$ calcd for $C_{37}H_{41}ClF_3N_7O_4$ 740.29. found 740.2.

Preparation 33: N-(4-Bromo-2-chloro-5-trifluoromethoxy-phenyl)-6-[(R)-4-(3-hydroxy-2,2-dimethyl-propionyl)-2-methyl-piperazin-1-yl]-nicotinamide

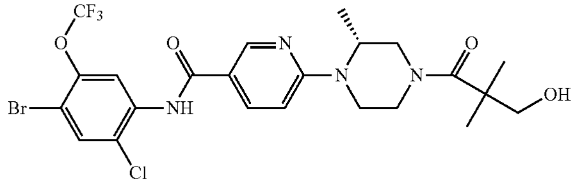 [SMILES: C[C@@H]1CN(C(=O)C(C)(C)CO)CCN1c1ccc(C(=O)Nc2cc(OC(F)(F)F)c(Br)cc2Cl)cn1]

(a) N-(4-Bromo-2-chloro-5-trifluoromethoxy-phenyl)-6-((R)-2-methyl-piperazin-1-yl)-nicotinamide (R)-4-[5-(4-bromo-2-chloro-5-trifluoromethoxy-phenylcarbamoyl)-pyridin-2-yl]-3-methyl-piperazine-1-carboxylic acid tert-butyl ester (500 mg, 0.84 mmol) was treated with 4 M HCl in 1,4-dioxane (4.2 mL) and HCl (1.3 mL) and stirred at RT for 1 h. The reaction mixture was concentrated and dissolved in ethyl acetate and coevaporated (2×) to produce the di-HCl salt of the title intermediate as a yellow solid. (m/z): $[M+H]^+$ calcd for $C_{18}H_{17}BrClF_3N_4O_2$ 493.02; 495.02. found 494.9.

(b) N-(4-Bromo-2-chloro-5-trifluoromethoxy-phenyl)-6-[(R)-4-(3-hydroxy-2,2-dimethyl-propionyl)-2-methyl-piperazin-1-yl]-nicotinamide To a solution of 2,2-dimethyl-3-hydroxypropionic acid (119 mg, 1.01 mmol) in DMF (4.6 mL, 58.9 mmol) was added HATU (384 mg, 1.0 mmol). The reaction mixture was stirred at RT for 15 min, the product of the previous step (534 mg) was added followed by DIPEA (0.73 mL, 4.2 mmol) and the mixture was stirred at RT for 3 h, and concentrated by rotary evaporation to produce a yellow/orange oil which was dissolved in a small amount of DCM and purified by silica chromatography 2 (4 g column, 0-80% ethyl acetate:hexanes) to produce the title intermediate (495 mg) as a white solid. (m/z): $[M+H]^+$ calcd for $C_{23}H_{25}BrClF_3N_4O_4$ 593.07; 595.07. found 595.4.

Preparation 34: N-{5-Chloro-4'-[2-((2S,4S)-4-methoxy-pyrrolidin-2-yl)-1H-imidazol-4-yl]-2-trifluoromethoxy-biphenyl-4-yl}-6-[(R)-4-(3-hydroxy-2,2-dimethyl-propionyl)-2-methyl-piperazin-1-yl]-nicotinamide

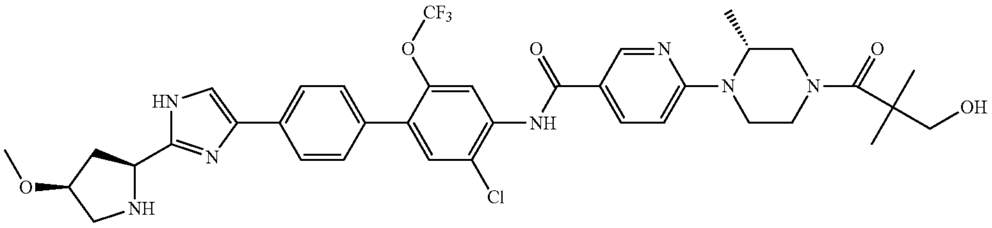 [SMILES: CO[C@@H]1CN[C@H](c2nc(-c3ccc(-c4cc(Cl)c(NC(=O)c5ccc(N6CCN(C(=O)C(C)(C)CO)C[C@H]6C)nc5)cc4OC(F)(F)F)cc3)c[nH]2)C1]

(a) (2S,4S)-4-Methoxy-2-{4-[4-(4,4,5,5-tetramethyl-[1,3,2]dioxaborolan-2-yl)-phenyl]-1H-imidazol-2-yl}-pyrrolidine-1-carboxylic acid tert-butyl ester To a solution of (2S,4S)-2-[5-(4-Bromo-phenyl)-1H-imidazol-2-yl]-4-methoxy-pyrrolidine-1-carboxylic acid tert-butyl ester (335 mg, 0.79 mmol), bis(pinacolato)diboron (212 mg, 0.83 mmol) and potassium acetate (117 mg, 1.19 mmol) was added degassed toluene (1.86 mL). The resulting mixture was sparged with nitrogen for 15 min, $Pd(dppf)Cl_2CH_2Cl_2$ (19.4 mg, 0.024 mmol) was added, and the reaction mixture was stirred, purged with nitrogen, and heated to 90° C. for 4 h to provide the title intermediate. (m/z): $[M+H]^+$ calcd for $C_{25}H_{36}BN_3O_5$ 470.27. found 470.1.

(b) (2S,4S)-2-{4-[5'-Chloro-4'-({6-[(R)-4-(3-hydroxy-2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methoxy-pyrrolidine-1-carboxylic acid tert-butyl ester To the reaction mixture of the previous step was added degassed water (0.89 mL), potassium carbonate (603 mg, 4.36 mmol), and N-(4-bromo-2-chloro-5-trifluoromethoxy-phenyl)-6-[(R)-4-(3-hydroxy-2,2-dimethyl-propionyl)-2-methyl-piperazin-1-yl]-nicotinamide (495 mg, 0.84 mmol; Preparation 33). The reaction mixture was purged with nitrogen, $Pd(dppf)Cl_2CH_2Cl_2$ (9.72 mg, 0.012 mmol) was added; the mixture was purged again and heated to 95° C. overnight, cooled to RT, diluted with EtOAc, filtered through a combined pad of Celite® and silica gel, flushed several times with EtOAc, and washed with water and brine to produce a dark colored oil. The residue was purified by silica gel chromatography (24 g silica gel, 40% to 100% EtOAc/hexane, 5-25 min then 0-10% methanol:EtOAc 10-30 min) to produce the title intermediate (211 mg, 31% yield) as a yellow solid. (m/z): $[M+H]^+$ calcd for $C_{42}H_{49}ClF_3N_7O_7$ 856.33. found 856.2.

(c) N-{5-Chloro-4'-[2-((2S,4S)-4-methoxy-pyrrolidin-2-yl)-1H-imidazol-4-yl]-2-trifluoromethoxy-biphenyl-4-yl}-6-[(R)-4-(3-hydroxy-2,2-dimethyl-propionyl)-2-methyl-piperazin-1-yl]-nicotinamide The solid from the previous step (211 mg) was treated with 4 M HCl in 1,4-dioxane (4.0 mL) and HCl (1.2 mL) and the reaction mixture was stirred at RT for 1 h, concentrated, and evaporated with ethyl acetate (2×) to produce the tri-HCl salt of the title intermediate (230 mg, 33% yield). (m/z): $[M+H]^+$ calcd for $C_{37}H_{41}ClF_3N_2O_5$ 756.283. found 756.2.

Preparation 35: 4'-{2-[(2S,4S)-4-Methanesulfinyl-1-((S)-2-methoxycarbonylamino-3-methyl-butyryl)-pyrrolidin-2-yl]-1H-imidazol-4-yl}-2-trifluoromethoxy-biphenyl-4-carboxylic acid

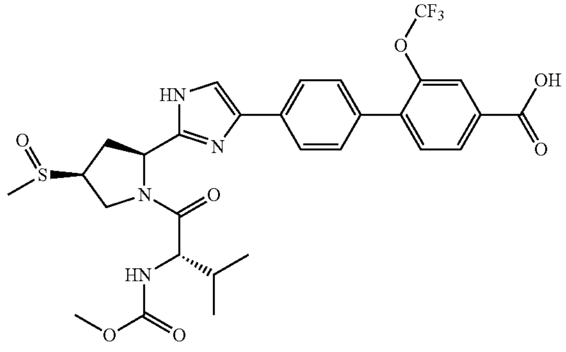 [SMILES: COC(=O)N[C@H](C(=O)N1C[C@@H](S(C)=O)C[C@H]1c1nc(-c2ccc(-c3ccc(C(=O)O)cc3OC(F)(F)F)cc2)c[nH]1)C(C)C]

(a) 4'-{2-[(2S,4S)-1-((S)-2-Methoxycarbonylamino-3-methyl-butyryl)-4-methylsulfanyl-pyrrolidin-2-yl]-1H-imidazol-4-yl}-2-trifluoromethoxy-biphenyl-4-carboxylic acid methyl ester To a mixture of 4-bromo-3-trifluoromethoxy-benzoic acid methyl ester (184 mg, 0.62 mmol), [(S)-2-methyl-1-((2S,4S)-4-methylsulfanyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester (300 mg, 0.55 mmol) and potassium carbonate (344 mg, 2.49 mmol) at RT was added toluene (1.35 mL) followed by water (0.69 mL). The reaction mixture was purged with nitrogen, Pd(dppf) $Cl_2CH_2Cl_2$ (27.4 mg, 0.034 mmol) was added under an atmosphere of nitrogen. The reaction vial was capped and heated at 100° C. overnight, cooled to RT and partitioned between EtOAc (10 mL) and water (2 mL). The organic layer was dried over sodium sulfate, filtered and concentrated to give a brownish oil which was purified by silica gel chromatography (12 g silica gel, 0-100% EtOAc/Hexanes). Desired fractions were combined and concentrated to give the title intermediate as an orange oil. (m/z): $[M+H]^+$ calcd for $C_{30}H_{33}F_3N_4O_6S$ 635.21. found 635.

(b) 4'-{2-[(2S,4S)-4-Methanesulfinyl-1-((S)-2-methoxycarbonylamino-3-methyl-butyryl)-pyrrolidin-2-yl]-1H-imidazol-4-yl}-2-trifluoromethoxy-biphenyl-4-carboxylic acid The oily residue from the previous step was dissolved in a mixture of ACN (0.29 mL) and DMA (0.03 mL) and treated with N-chlorosuccinimide (74 mg, 0.55 mmol) at 65° C. for 1 h. The reaction mixture was cooled to RT and treated with saturated sodium bicarbonate (3 mL), and extracted with EtOAc (5 mL). The organic layer was concentrated, dissolved in a mixture of methanol (2 mL) and water (0.5 mL) and treated with lithium hydroxide monohydrate (139 mg, 3.32 mmol) at 65° C. for 1 h, cooled to RT, concentrated, dissolved in 1:1 acetic acid:water (6 mL) and purified by reverse phase HPLC. Desired fractions were combined and freeze dried to provide the TFA salt of the title intermediate (117 mg, 28% yield) as a white solid. (m/z): $[M+H]^+$ calcd for $C_{29}H_{31}F_3N_4O_7S$ 637.19. found 637.

Preparation 36: 4'-{2-[(2S,4S)-4-Methanesulfonyl-1-((S)-2-methoxycarbonylamino-3-methyl-butyryl)-pyrrolidin-2-yl]-1H-imidazol-4-yl}-2-trifluoromethoxy-biphenyl-4-carboxylic acid

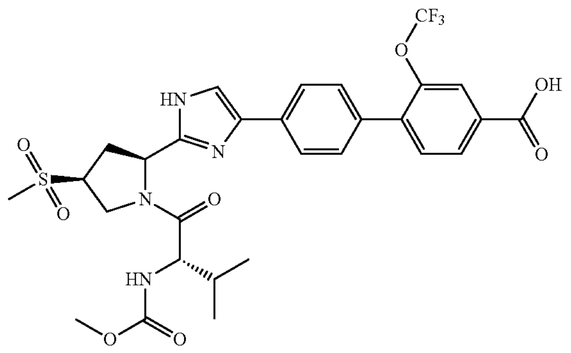 [SMILES: COC(=O)N[C@H](C(=O)N1C[C@@H](S(C)(=O)=O)C[C@H]1c1nc(-c2ccc(-c3ccc(C(=O)O)cc3OC(F)(F)F)cc2)c[nH]1)C(C)C]

Potassium peroxymonosulfate sulfate (66 mg, 0.11 mmol) was added to a solution of 4'-{2-[(2S,4S)-4-methanesulfinyl-1-((S)-2-methoxycarbonylamino-3-methyl-butyryl)-pyrrolidin-2-yl]-1H-imidazol-4-yl}-2-trifluoromethoxy-biphenyl-4-carboxylic acid TFA (67 mg, 0.09 mmol; Preparation 35) in methanol (5 mL) and water (1 mL). The reaction mixture was stirred at RT for 2 h, filtered, concentrated, dissolved in 1:1 acetic acid:water (5 mL), filtered, and purified by reverse phase HPLC. Desired fractions were combined and freeze dried to provide the TFA salt of the title intermediate (55 mg, 80% yield). (m/z): $[M+H]^+$ calcd for $C_{29}H_{31}F_3N_4O_8S$ 653.18. found 653.2.

Preparation 37: ((S)-1-{(2S,4S)-2-[4-(4-Bromo-phenyl)-1H-imidazol-2-yl]-4-morpholin-4-yl-pyrrolidine-1-carbonyl}-2-methyl-propyl)-carbamic acid methyl ester

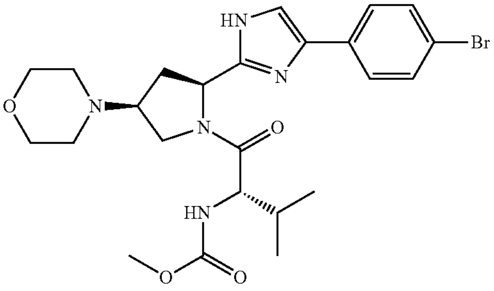 [SMILES: COC(=O)N[C@H](C(=O)N1C[C@@H](N2CCOCC2)C[C@H]1c1nc(-c2ccc(Br)cc2)c[nH]1)C(C)C]

(a) (2S,4R)-4-(Toluene-4-sulfonyloxy)-pyrrolidine-1,2-dicarboxylic acid 1-tert-butyl ester 2-methyl ester To a solution of methyl (2S,4R)—N-tert-butoxycarbonyl-4-hydroxy-2-pyrrolidinecarboxylate (4.68 g, 19.1 mmol) in DCM (47 mL) at RT was added DIPEA (3.66 mL, 21.0 mmol) and 4-dimethylaminopyridine (233 mg, 1.91 mmol) followed by p-toluenesulfonyl chloride (3.82 g, 20.1 mmol). The reaction mixture was stirred at RT overnight, washed with 1N HCl (2 mL), saturated sodium bicarbonate (2 mL), and brine (2 mL), dried over sodium sulfate, filtered and concentrated to give a yellowish oil, which was purified by silica gel chromatography (80 g silica, 0-100% EtOAc/Hexanes). Desired fractions were combined and concentrated to give the title intermediate (1.74 g, 23% yield) as a colorless oil.

(b) (2S,4S)-4-Morpholin-4-yl-pyrrolidine-1,2-dicarboxylic acid 1-tert-butyl ester 2-methyl ester A mixture of the product of the previous step (908 mg, 2.27 mmol) and morpholine (3.96 mL, 45.46 mmol) was heated at 70° C. overnight, concentrated by rotary evaporation, dissolved in water (3 mL) and extracted with EtOAc (3×2 mL). The aqueous layer was saturated with brine and 1N aq NaOH (1 mL) was added. The aqueous mixture was extracted with EtOAc (3 mL). Combined organic layers were dried over sodium sulfate, filtered, and concentrated to give the title intermediate as a colorless oil. (m/z): $[M+H]^+$ calcd for $C_{15}H_{26}N_2O_5$ 315.18. found 315.

(c) (2S,4S)-4-Morpholin-4-yl-pyrrolidine-1,2-dicarboxylic acid 1-tert-butyl ester The product of the previous step was dissolved in methanol (3 mL) and water (1 mL) at RT and treated with lithium hydroxide monohydrate (191 mg, 4.55 mmol) for 30 min. The reaction mixture was concentrated, treated with EtOAc (3 mL) and acidified to pH-6 with 2 N HCl. The aqueous layer was freeze dried to give the title intermediate as a light brownish foam. (m/z): $[M+H]^+$ calcd for $C_{14}H_{24}N_2O_5$ 301.17. found 301.

(d) (2S,4S)-4-Morpholin-4-yl-pyrrolidine-1,2-dicarboxylic acid 2-[2-(4-bromo-phenyl)-2-oxo-ethyl] ester 1-tert-butyl ester The foam from the previous step was treated with DCM (11.7 mL, 181.8 mmol) and DIPEA (0.32 mL, 1.82 mmol) and then p-bromophenacyl bromide (505 mg, 1.82 mmol) was added. The resulting mixture was heated at 35° C. for 1 h and concentrated to give the title compound as a yellowish solid. (m/z): $[M+H]^+$ calcd for $C_{22}H_{29}BrN_2O_6$ 497.12; 499.12. found 499.

(e) (2S,4S)-2-[4-(4-Bromo-phenyl)-1H-imidazol-2-yl]-4-morpholin-4-yl-pyrrolidine-1-carboxylic acid tert-butyl ester The solid from the previous step was mixed with ammonium acetate (2.80 g, 36.36 mmol) and DIPEA (0.48 mL, 2.73 mmol) in toluene (55 mL) and the reaction mixture was heated at 110° C. overnight, cooled to RT, and concentrated. The resulting residue was purified by silica gel chromatography (12 g silica gel, 0-100% EtOAc/Hexanes). Desired fractions were combined and concentrated to give the title intermediate (133 mg, 15% yield over steps (b) through (e)) as a brownish foam. (m/z): $[M+H]^+$ calcd for $C_{22}H_{29}BrN_4O_3$ 477.14; 479.14. found 477.

(f) ((S)-1-{(2S,4S)-2-[4-(4-Bromo-phenyl)-1H-imidazol-2-yl]-4-morpholin-4-yl-pyrrolidine-1-carbonyl}-2-methyl-propyl)-carbamic acid methyl ester The product of the previous step (133 mg, 0.28 mmol) was treated with 4 M HCl in 1,4-dioxane (2 mL) at RT for 30 min. The reaction mixture was concentrated, and evaporated with EtOAc (3×2 mL) to give a brownish foam. The foam was dissolved in DMF (2.5 mL) and treated with (S)-2-methoxycarbonylamino-3-methyl-butyric acid (49 mg, 0.28 mmol) and HATU (106 mg, 0.28 mmol) at RT over the weekend. The reaction mixture was diluted with EtOAc (5 mL) and washed with water (2 mL). The organic layer was dried over sodium sulfate, filtered and concentrated to give a brownish oil, which was purified by silica gel chromatography (4 g silica gel, 0-100% EtOAc/Hexanes then 10% MeOH/EtOAc, (3% $Et_3N$ in MeOH)). Desired fractions were combined and concentrated to give the title intermediate (57 mg, 38% yield) as a yellowish oil. (m/z): $[M+H]^+$ calcd for $C_{24}H_{32}BrN_5O_4$ 534.16; 536.16. found 534.

Preparation 38: (2S,4S)-4-Cyano-pyrrolidine-1,2-dicarboxylic acid 1-tert-butyl ester

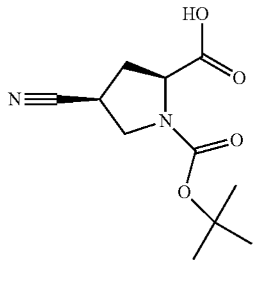 [SMILES: CC(C)(C)OC(=O)N1C[C@@H](C#N)C[C@H]1C(=O)O]

(a) (2S,4R)-4-Hydroxy-pyrrolidine-1,2-dicarboxylic acid 1-tert-butyl ester 2-methyl ester To a solution of (2S,4R)-4-hydroxy-pyrrolidine-2-carboxylic acid methyl ester HCl (10 g, 55.1 mmol) in DCM (100 mL) was added triethylamine (16.73 g, 165.3 mmol) and di-tert-butyl dicarbonate (14.41 g, 66.1 mmol). The reaction mixture was stirred at RT overnight, concentrated, and purified by column chromatography (3:1 petroleum ether:EtOAc) to give the title intermediate (12 g, 89% yield) $^1H$ NMR (400 MHz, $CDCl_3$): δ(ppm) 4.48 (m, 1H), 4.38 (m, 1H), 3.72 (s, 3H), 3.63 (m, 1H), 3.45 (m, 1H), 2.29 (m, 1H), 2.06 (m, 2H), 1.39 (s, 9H).

(b) (2S,4R)-4-Methanesulfonyloxy-pyrrolidine-1,2-dicarboxylic acid 1-tert-butyl ester 2-methyl ester To the product of the previous step (12 g, 48.9 mmol) dissolved in dry DCM (100 mL) was added triethylamine (14.87 g, 147 mmol) in an ice bath and then methanesulfonyl chloride (6.72 g, 58.7 mmol) was added dropwise. The reaction mixture was stirred at 0° C. for 1 h, poured into ice water, and extracted with DCM (3×). The combined organic layers were washed with $NaHCO_3$, water and brine, dried over $Na_2SO_4$, and concentrated to give the title intermediate (15 g). (m/z): $[M+H-100]^+$ calcd for $C_{12}H_{21}NO_7S$ 224.10. found 224.

(c) (2S,4S)-4-Cyano-pyrrolidine-1,2-dicarboxylic acid 1-tert-butyl ester 2-methyl ester A mixture of the product of the previous step (15 g, 46.4 mmol) and sodium cyanide (22.74 g, 464 mmol) was stirred in DMSO (200 mL), heated at 55° C. for 3 days under nitrogen, cooled to RT, and poured into ice water. The mixture was extracted with EtOAc (3×) and the combined organic extracts were washed three times with water and brine, dried over $Na_2SO_4$, and concentrated. The residue was purified by column chromatography (3:1 petroleum ether: EtOAc) to give the title intermediate (3 g, 25% yield). $^1H$ NMR (400 MHz, $CDCl_3$): δ(ppm) 4.38 (m, 1H), 3.93 (m, 1H), 3.73 (s, 3H), 3.65 (m, 1H), 3.08 (m, 1H), 2.24-2.70 (m, 2H), 1.45 (m, 9H).

(d) (2S,4S)-4-Cyano-pyrrolidine-1,2-dicarboxylic acid 1-tert-butyl ester

To a solution of the product of the previous step (3 g, 11.8 mmol) in methanol (50 mL) was added an aqueous solution of 4 M NaOH (5.9 mL). The mixture was stirred at RT overnight under nitrogen and concentrated. The residue was adjusted to pH 2 with 1M HCl and the aqueous solution was extracted with DCM (3×50 mL). The combined organic phase was washed with brine, dried over $Na_2SO_4$, filtered and concentrated to give the title intermediate (2 g). $^1H$ NMR (400 MHz, $CDCl_3$): δ(ppm) 9.45 (br, 1H), 4.33-4.52 (m, 1H), 3.59-3.98 (m, 2H), 3.13-3.30 (m, 1H), 2.36-2.74 (m, 2H), 1.49 (m, 9H).

Preparation 39: (3S,5S)-5-[4-(4-Bromo-phenyl)-1H-imidazol-2-yl]-pyrrolidine-3-carbonitrile

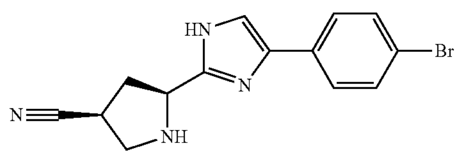 [SMILES: N#C[C@@H]1CN[C@H](c2nc(-c3ccc(Br)cc3)c[nH]2)C1]

(a) (2S,4S)-4-Cyano-pyrrolidine-1,2-dicarboxylic acid 2-[2-(4-bromo-phenyl)-2-oxo-ethyl]ester 1-tert-butyl ester To a solution of the product of Preparation 38 (2 g, 8.3 mmol) in acetonitrile (50 mL) was added DIPEA (3.22 g, 25.0 mmol) and 2-bromo-1-(4-bromo-phenyl)-ethanone (2.31 g, 8.3 mmol). The reaction mixture was stirred at RT overnight under nitrogen. The reaction mixture was concentrated and the residue was dissolved in EtOAc (30 mL) and water (30 mL). The aqueous layer was extracted with EtOAc (2×30 mL).

The combined organic layers were washed with water and brine, dried over $Na_2SO_4$, filtered, concentrated, and purified by column chromatography (10-30% EtOAc in petroleum ether) to give the title intermediate (900 mg, 25% yield). (m/z): $[M+H-100]^+$ calcd for $C_{19}H_{21}BrN_2O_6$ 337.06; 339.06. found 339.

(b) (2S,4S)-2-[4-(4-Bromo-phenyl)-1H-imidazol-2-yl]-4-cyano-pyrrolidine-1-carboxylic acid tert-butyl ester To a solution of the product of the previous step (900 mg, 2.1 mmol) in toluene (30 mL) was added ammonium acetate (3.21 g, 41.2 mmol). The reaction mixture was heated at reflux for 1.5 h under nitrogen. The mixture was concentrated and the residue was dissolved in EtOAc (50 mL) and water (50 mL). The aqueous layer was extracted with EtOAc (2×50 mL). The combined organic layers were dried over $Na_2SO_4$, filtered, concentrated, and purified by column chromatography (10-50% EtOAc in petroleum ether) to give the title intermediate (400 mg, 46% yield). (m/z): $[M+H]^+$ calcd for $C_{19}H_{21}BrN_4O_2$ 417.09; 419.09. found 417.

(c) (3S,5S)-5-[4-(4-Bromo-phenyl)-1H-imidazol-2-yl]-pyrrolidine-3-carbonitrile

The product of the previous step (400 mg, 0.96 mmol) was dissolved in HCl/dioxane (10 mL) and the mixture was stirred at RT for 1 h. The reaction mixture was concentrated to give the HCl salt of the title intermediate (340 mg). (m/z): $[M+H]^+$ calcd for $C_{19}H_{21}BrN_4O_2$ 317.03; 319.03. found 317; 319.

Preparation 40: [(S)-1-((2S,4S)-4-Cyano-2-{4-[4-(4,4,5,5-tetramethyl-[1,3,2]dioxaborolan-2-yl)-phenyl]-1H-imidazol-2-yl}-pyrrolidine-1-carbonyl)-2-methyl-propyl]-carbamic acid methyl ester

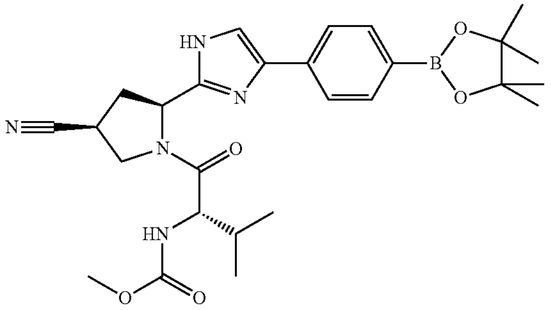 [SMILES: COC(=O)N[C@H](C(=O)N1C[C@@H](C#N)C[C@H]1c1nc(-c2ccc(B3OC(C)(C)C(C)(C)O3)cc2)c[nH]1)C(C)C]

(a) ((S)-1-{(2S,4S)-2-[4-(4-Bromo-phenyl)-1H-imidazol-2-yl]-4-cyano-pyrrolidine-1-carbonyl}-2-methyl-propyl)-carbamic acid methyl ester The product of Preparation 39 (340 mg, 0.96 mmol) was dissolved in DCM (20 mL) and DIPEA (620 mg, 4.80 mmol) was added followed by 2-methoxycarbonylamino-3-methyl-butyric acid (168 mg, 0.96 mmol) and HATU (365 mg, 0.96 mmol). The reaction mixture was stirred at RT for 1 h under nitrogen, diluted with DCM, and washed with aqueous bicarbonate solution, water (30 mL), and brine (30 mL), dried over $Na_2SO_4$, filtered, concentrated and purified by column chromatography (30-100% EtOAc in petroleum ether) to give the title intermediate (350 mg, 77% yield). (m/z): $[M+H]^+$ calcd for $C_2H_{24}BrN_5O_3$ 474.11; 476.11. found 474; 476.

(b) [(S)-1-((2S,4S)-4-Cyano-2-{4-[4-(4,4,5,5-tetramethyl-[1,3,2]dioxaborolan-2-yl)-phenyl]-1H-imidazol-2-yl}-pyrrolidine-1-carbonyl)-2-methyl-propyl]-carbamic acid methyl ester To a solution of ((S)-1-{(2S,4S)-2-[4-(4-bromo-phenyl)-1H-imidazol-2-yl]-4-cyano-pyrrolidine-1-carbonyl}-2-methyl-propyl)-carbamic acid methyl ester (450 mg, 0.95 mmol), bis(pinacolato)diboron (362 mg, 1.42 mmol), and potassium acetate (186 mg, 1.90 mmol) in dioxane (20 mL) was added $Pd(dppf)Cl_2$—$CH_2Cl_2$ (78 mg, 0.095 mmol) and the mixture was degassed with nitrogen and heated at reflux overnight under nitrogen. The cooled mixture was filtered through Celite® and washed with EtOAc. The filtrate was washed with water and brine, dried over $Na_2SO_4$, filtered, concentrated, and purified by column chromatography (20-100% EtOAc in petroleum ether) to give the title intermediate (320 mg, 65% yield). (m/z): $[M+H]^+$ calcd for $C_{27}H_{36}BN_5O_5$ 522.28. found 522. $^1H$ NMR (400 MHz, MeOD): δ(ppm) 7.72 (m, 2H), 7.64 (m, 2H), 7.36 (s, 1H), 5.14 (m, 1H), 4.60

(m, 1H), 4.11 (m, 1H), 3.99 (m, 1H), 3.63 (s, 3H), 3.45 (m, 1H), 2.85 (m, 1H), 2.52 (m, 1H), 2.00 (m, 1H), 1.34 (s, 12H), 0.84 (m, 6H).

Preparation 41: (2S,5S)-5-Methyl-pyrrolidine-1,2-dicarboxylic acid 1-tert-butyl ester

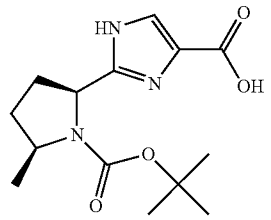 [SMILES: C[C@H]1CC[C@@H](c2nc(C(=O)O)c[nH]2)N1C(=O)OC(C)(C)C]

(a) (S)-2-tert-Butoxycarbonylamino-5-oxo-hexanoic acid ethyl ester

A solution of (S)-5-oxo-pyrrolidine-1,2-dicarboxylic acid 1-tert-butyl ester 2-ethyl ester (20 g, 10 mmol) in dry THF (150 mL) was cooled to −50° C., and then methylmagnesium bromide (31 mL, 93.28 mmol) was added dropwise at a temperature between −50 and −44° C. in 30 min. The reaction mixture was stirred at −43° C. for 2 h and placed in a freezer (ca. −20° C.) overnight. The mixture was quenched with sat. $NH_4Cl$ solution and extracted with EtOAc. The combined organic layers were dried over $Na_2SO_4$, filtered and concentrated under reduced pressure to give the crude product, which was purified by column chromatography (8:1-3:1 petroleum ether:EtOAc) to give the title intermediate (38 g) as light yellow oil. $^1H$ NMR (400 MHz, $CDCl_3$): δ(ppm) 5.11-5.09 (m, 1H), 4.25-4.24 (m, 1H), 4.19 (q, J=7.2 Hz, 2H), 2.63-2.52 (m, 2H), 2.15 (s, 3H), 2.12-2.08 (m, 1H), 1.92-1.82 (m, 1H), 1.44 (s, 9H), 1.28 (t, J=7.2 Hz, 3H).

(b) (S)-5-Methyl-3,4-dihydro-2H-pyrrole-2-carboxylic acid ethyl ester

To a solution of the product of the previous step (5 g, 18.29 mmol) in dry DCM (10 mL) was added TFA (7.5 mL) and the reaction mixture was stirred at ambient temperature for 3 h. The mixture was concentrated to give the title intermediate (7 g). $^1H$ NMR (400 MHz, $CDCl_3$): δ(ppm) 5.14-5.09 (m, 1H), 4.29-4.25 (m, 2H), 3.21-3.17 (m, 2H), 2.77-2.69 (m, 1H), 2.62 (s, 3H), 2.49-2.41 (m, 1H), 1.32-1.29 (m, 3H).

(c) (2S,5S)-5-Methyl-pyrrolidine-1,2-dicarboxylic acid 1-tert-butyl ester 2-ethyl ester The product of the previous step (4 g) was dissolved in ethanol (40 mL) and 10% Pd/C (400 mg) was added. The reaction mixture was stirred at 35° C. under 55 psi of hydrogen overnight. After filtration, the filtrate was concentrated under reduced pressure to give 2.62 g of crude product, which was added to a mixture of triethylamine (4.6 mL) and 4-dimethylaminopyridine (DMAP) (102 mg, 0.83 mmol) in dry DCM (10 mL). Then, di-tert-butyl dicarbonate (4 g, 18.33 mmol) was added and the reaction mixture was stirred at RT overnight. The reaction mixture was washed with 1N HCl solution and brine. The organic layer was dried over $Na_2SO_4$, filtered and concentrated under reduced pressure to give the residue, which was purified by column chromatography (8:1-3:1 petroleum ether:EtOAc) to give the title intermediate (2 g) as a colorless oil. $^1H$ NMR (400 MHz, $CDCl_3$): δ(ppm) 4.53-4.50 (m, 1H), 4.30 (q, J=7.2 Hz, 1H), 3.93-3.87 (m, 1H), 2.52-2.42 (m, 1H), 2.31-2.19 (m, 2H), 1.71-1.60 (m, 1H), 1.52-1.50 (m, 3H), 1.32 (t, J=7.2 Hz, 3H).

(d) (2S,5S)-5-Methyl-pyrrolidine-1,2-dicarboxylic acid 1-tert-butyl ester

A mixture of the product of the previous step (2 g, 7.77 mmol) and lithium hydroxide (466 mg, 23.3 mmol) in 3:1 methanol:water (24 mL) was stirred at RT overnight, and concentrated. The residue was dissolved in water and extracted with EtOAc (2×20 mL). The aqueous layer was adjusted to pH 2 with 1N HCl and extracted with 3:1 DCM: methanol (3×24 mL) to give the title intermediate (1.7 g) as a white crystal.

Preparation 42: 4-(4-Bromo-phenyl)-2-((2S,5S)-5-methyl-pyrrolidin-2-yl)-1H-imidazole

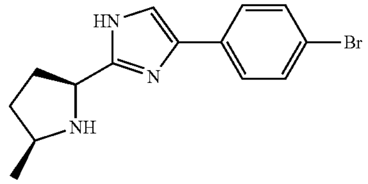 [SMILES: C[C@H]1CC[C@@H](c2nc(-c3ccc(Br)cc3)c[nH]2)N1]

(a) (2S,5S)-5-Methyl-pyrrolidine-1,2-dicarboxylic acid 2-[2-(4-bromo-phenyl)-2-oxo-ethyl]ester 1-tert-butyl ester A mixture of the product of Preparation 41 (1.7 g, 7.41 mmol), 2-bromo-1-(4-bromo-phenyl)-ethanone (2.08 g, 7.49 mmol) and DIPEA (2.87 g, 22.23 mmol) in ACN (50 mL) was stirred under nitrogen at RT for 2 h. The reaction mixture was concentrated under reduced pressure to give the title intermediate (3.16 g).

(b) (2S,5S)-2-[4-(4-Bromo-phenyl)-1H-imidazol-2-yl]-5-methyl-pyrrolidine-1-carboxylic acid tert-butyl ester A mixture of the product of the previous step (3.16 g, 7.41 mmol) and ammonium acetate (17 g, 222.3 mmol) in toluene (50 mL) was refluxed under nitrogen overnight. The reaction mixture was washed with water and extracted with EtOAc. The combined organic layers were dried over $Na_2SO_4$, filtered and concentrated under reduced pressure to give the residue, which was purified by column chromatography (10:1-5:1 petroleum ether:EtOAc) to give the title intermediate (3.06 g) as a solid.

(c) 4-(4-Bromo-phenyl)-2-((2S,5S)-5-methyl-pyrrolidin-2-yl)-1H-imidazole

The product of the previous step (3.06 g, 7.53 mmol) was dissolved in EtOAc (10 mL) and HCl/dioxane solution (20 mL) was added slowly. The reaction mixture was stirred at RT for 3 h, and concentrated under reduced pressure to give the residue, which was partitioned between sat. $NaHCO_3$ and DCM. The combined organic layers were dried over $Na_2SO_4$, filtered and concentrated under reduced pressure to give the title intermediate (2.5 g) as a solid.

Preparation 43: [(S)-2-Methyl-1-((2S,5S)-2-methyl-5-{4-[4-(4,4,5,5-tetramethyl-[1,3,2]dioxaborolan-2-yl)-phenyl]-1H-imidazol-2-yl}-pyrrolidine-1-carbonyl)-propyl]carbamic acid methyl ester

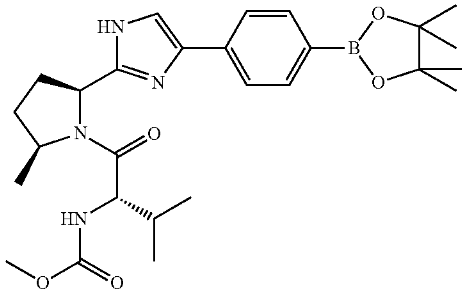

(a) ((S)-1-{(2S,5S)-2-[4-(4-Bromo-phenyl)-1H-imidazol-2-yl]-5-methyl-pyrrolidine-1-carbonyl}-2-methyl-propyl)-carbamic acid methyl ester A mixture of the product of Preparation 42 (2.5 g, 8.16 mmol), 2-methoxycarbonyl-amino-3-methyl-butyric acid (1.72 g, 9.79 mmol), HATU (3.72 g, 9.79 mmol) and DIPEA (3.16 g, 24.48 mmol) in DCM (50 mL) was stirred at RT overnight. The reaction mixture was washed with water and brine and extracted with EtOAc. The combined organic layers were dried over $Na_2SO_4$, filtered, and concentrated under reduced pressure to give the residue, which was purified by column chromatography (3:1-1:1 petroleum ether:EtOAc) to give the title intermediate (1.5 g, 85% purity) as a solid. $^1H$ NMR (400 MHz, $CD_3OD$): δ(ppm) 7.73-7.33 (m, 5H), 5.36 (m, 0.5H), 5.10-5.05 (m, 0.5H), 4.75-4.71 (m, 0.5H), 4.23-4.08 (m, 1H), 3.69-3.67 (m, 3H), 2.82-2.80 (m, 0.5H), 2.35-2.33 (m, 0.5H), 2.17-1.91 (m, 4H), 1.5-1.48 (m, 0.5H), 1.27-0.84 (m, 9H).

(b) [(S)-2-Methyl-1-((2S,5S)-2-methyl-5-{4-[4-(4,4,5,5-tetramethyl-[1,3,2]dioxaborolan-2-yl)-phenyl]-1H-imidazol-2-yl}-pyrrolidine-1-carbonyl)-propyl]-carbamic acid methyl ester A mixture of the product of the previous step (1.5 g, 3.24 mmol), bis(pinacolato)diboron (988 mg, 3.89 mmol), potassium acetate (954 mg, 9.72 mmol) and $Pd(dppf)Cl_2$ (150 mg) in dioxane (50 mL) was refluxed under nitrogen for 3 h. The reaction mixture was concentrated under reduced pressure to give the residue, which was partitioned between water and EtOAc. The combined organic layers were washed with brine, dried over $Na_2SO_4$, filtered, and concentrated under reduced pressure to give the residue, which was purified by column chromatography to give the title intermediate (1.1 g). (m/z): $[M+H]^+$ calcd for $C_{27}H_{39}BN_4O_5$ 511.3. found 511.3. $^1H$ NMR (400 MHz, $CDCl_3$): δ(ppm) 7.78 (s, 4H), 7.44-7.38 (m, 1H), 5.52-5.45 (m, 1H), 5.3-5.18 (m, 1H), 4.23-4.20 (m, 1H), 3.79-3.68 (m, 3H), 2.39-1.50 (m, 5H), 1.35-1.29 (m, 12H), 1.27-0.78 (m, 9H).

Preparation 44: (R)-5-chloro-4-(6-(2-methyl-4-pivaloylpiperazin-1-yl)nicotinamido)-2-(trifluoromethoxy)phenylboronic acid

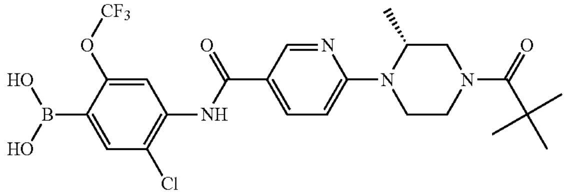 [SMILES: C[C@@H]1CN(C(=O)C(C)(C)C)CCN1c1ccc(C(=O)Nc2cc(OC(F)(F)F)c(B(O)O)cc2Cl)cn1]

Under an atmosphere of nitrogen, a mixture of N-(4-bromo-2-chloro-5-trifluoromethoxy-phenyl)-6-[(R)-4-(2,2-dimethyl-propionyl)-2-methyl-piperazin-1-yl]-nicotinamide (20.0 g, 34.6 mmol) and tetrahydrofuran (200 mL) was cooled to 0° C. and then 1.3 M isopropylmagnesium chloride lithium chloride complex in tetrahydrofuran (79.9 mL, 104 mmol) was added dropwise at 0-10° C. After 2.5 h, boric acid, trimethyl ester (12.0 mL, 106 mmol) was added dropwise, and then 1 N HCl (105 mL) was added and the reaction mixture was stirred overnight. The reaction mixture was extracted with EtOAc (250 mL); the organic layer was washed with water, sat. aq. $NaHCO_3$, dried over $MgSO_4$, and evaporated to give crude product (22.8 g). To the crude product was added ethanol (230 mL) and then slowly water (57.5 mL). The resulting mixture was stirred for 10 days and filtered to give the title intermediate as a crystalline solid (10.7 g, 57% yield).

A powder x-ray diffraction pattern of a crystalline sample of (R)-5-chloro-4-(6-(2-methyl-4-pivaloylpiperazin-1-yl)nicotinamido)-2-(trifluoromethoxy)phenylboronic acid prepared by the above process is shown in the FIGURE. The pattern was obtained with a Thermo ARL X'Tra X-ray diffractometer using Cu-Kα radiation (λ=1.54051 Å) with output voltage of 45 kV and current of 40 mA. The sample was scanned in 2θ-2θ mode from 2° to 40° in 2θ with a step size of 0.03° and a scan speed of 2.0° per minute. Observed PXRD two-theta peak positions and d-spacings are given in the following table (only peaks having a relative peak height (H %) of about 8% or greater are listed).

| 2-Theta | d(Å) | Height | H % |
|---|---|---|---|
| 4.77 | 18.51 | 1579 | 100.0 |
| 6.66 | 13.26 | 513 | 32.5 |
| 13.24 | 6.68 | 323 | 20.5 |
| 14.23 | 6.22 | 140 | 8.8 |
| 14.92 | 5.93 | 314 | 19.9 |
| 15.58 | 5.68 | 419 | 26.5 |
| 16.93 | 5.23 | 617 | 39.1 |
| 18.57 | 4.77 | 291 | 18.4 |
| 19.47 | 4.56 | 183 | 11.6 |
| 20.21 | 4.39 | 137 | 8.7 |
| 23.63 | 3.76 | 191 | 12.1 |

-continued

| 2-Theta | d(Å) | Height | H % |
|---|---|---|---|
| 24.06 | 3.70 | 126 | 8.0 |
| 24.91 | 3.57 | 147 | 9.3 |
| 25.76 | 3.46 | 529 | 33.5 |
| 27.84 | 3.20 | 165 | 10.5 |
| 31.36 | 2.85 | 137 | 8.7 |

Preparation 45: [(S)-2-{(2S,4S)-2-[4-(4-Bromo-phenyl)-1H-imidazol-2-yl]-4-methyl-pyrrolidin-1-yl}-2-oxo-1-(tetrahydropyran-4-yl)-ethyl]-carbamic acid methyl ester

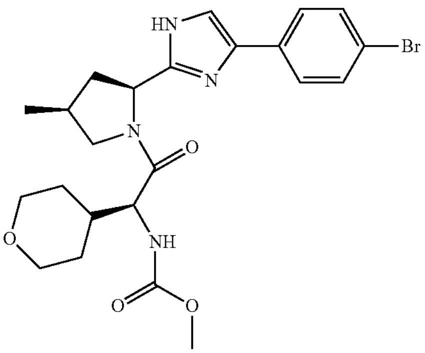 [SMILES: COC(=O)N[C@H](C(=O)N1C[C@@H](C)C[C@H]1c1nc(-c2ccc(Br)cc2)c[nH]1)C1CCOCC1]

(a) 4-(4-Bromo-phenyl)-2-((2S,4S)-4-methyl-pyrrolidin-2-yl)-1H-imidazole (2S,4S)-2-[4-(4-bromo-phenyl)-1H-imidazol-2-yl]-4-methyl-pyrrolidine-1-carboxylic acid tert-butyl ester (0.65 g, 1.6 mmol) was treated with 4 M HCl in 1,4-dioxane (4 mL, 20 mmol) at 50° C. for 1 h. The reaction mixture was concentrated and dissolved in ethyl acetate and evaporated with ethyl acetate (2×) to produce the HCl salt of the title intermediate as a yellow solid.

(b) [(S)-2-{(2S,4S)-2-[4-(4-Bromo-phenyl)-1H-imidazol-2-yl]-4-methyl-pyrrolidin-1-yl}-2-oxo-1-(tetrahydropyran-4-yl)-ethyl]-carbamic acid methyl ester The yellow solid from the previous step was dissolved in DMA (3 mL) and DIPEA (1.4 mL, 8.0 mmol) was added. A solution of 0.5 M (S)-methoxycarbonylamino-(tetrahydro-pyran-4-yl)-acetic acid in DMA (4.0 mL, 2.0 mmol) and HATU (760 mg, 2.0 mmol) were added. The reaction mixture was stirred at RT for 1 h, dissolved in ethyl acetate (100 mL) and washed with water (300 mL). The aqueous layer was extracted with ethyl acetate (100 mL). The combined organic layer was washed with brine, dried over sodium sulfate, filtered, concentrated, and purified by silica gel chromatography (0-100% ethyl acetate:hexanes) to produce the title intermediate as a light colored solid. (760 mg, 94% yield). (m/z): $[M+H]^+$ calcd for $C_{23}H_{29}BrN_4O_4$ 505.14; 507.14. found 506.95.

Preparation 46: [(S)-2-((2S,4S)-4-Methyl-2-{4-[4-(4,4,5,5-tetramethyl-1,3,2-dioxaborolan-2-yl)-phenyl]-1H-imidazol-2-yl}-pyrrolidin-1-yl)-2-oxo-1-(tetrahydro-pyran-4-yl)-ethyl]-carbamic acid methyl ester

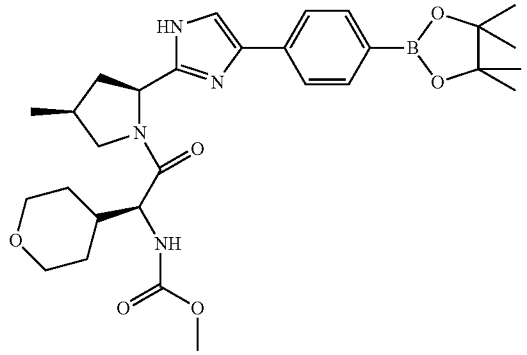 [SMILES: COC(=O)N[C@H](C(=O)N1C[C@@H](C)C[C@H]1c1nc(-c2ccc(B3OC(C)(C)C(C)(C)O3)cc2)c[nH]1)C1CCOCC1]

The product of Preparation 45 (760 mg, 1.5 mmol), bis (pinacolato)diboron (570 mg, 2.2 mmol) and potassium acetate (220 mg, 2.2 mmol) were mixed with 1,4-dioxane (5 mL). The resulting suspension was sparged under nitrogen and then $Pd(dppf)Cl_2CH_2Cl_2$ (61 mg, 0.075 mmol) was added. The reaction mixture was heated at 100° C. overnight, cooled to RT and filtered through a stacked pad of silica gel and Celite®. The pad was washed with EtOAc (180 mL). The filtrate was concentrated to give a black oil which was purified by silica gel chromatography (24 g silica gel disposable column, eluted with 0-100% EtOAc:hexanes). Desired fractions were combined and concentrated to give the title intermediate (544 mg, 65% yield) as a yellowish foam. (m/z): $[M+H]^+$ calcd for corresponding boronic acid $C_{23}H_{31}BN_4O_6$ 471.23. found 471.05.

Preparation 47: (R)-4-(5-Amino-pyridin-2-yl)-3-methyl-piperazine-1-carboxylic acid tert-butyl ester

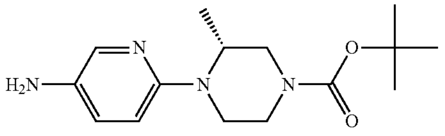 [SMILES: C[C@@H]1CN(C(=O)OC(C)(C)C)CCN1c1ccc(N)cn1]

(a) (R)-3-Methyl-4-(5-nitropyridin-2-yl)-piperazine-1-carboxylic acid tert-butyl ester A mixture of 2-chloro-5-nitropyridine (1.0 g, 6.3 mmol), (R)-3-methyl-piperazine-1-carboxylic acid tert-butyl ester (1.26 g, 6.31 mmol), and potassium carbonate (2.18 g, 15.77 mmol) was stirred in DMSO (5 mL) at 120° C. overnight. The reaction mixture was concentrated under rotary evaporation and mixed with water (50 mL). The resulting precipitate was filtered, washed with water (3×10 mL) and air-dried to provide the title intermediate.

(b) (R)-4-(5-Amino-pyridin-2-yl)-3-methyl-piperazine-1-carboxylic acid tert-butyl ester A solution of the product of the previous step in methanol (150 mL) was degassed several times, then palladium hydroxide on carbon (20 weight %, 200 mg, 0.29 mmol) was added, and resulting mixture was degassed, hydrogenated overnight under a balloon of hydrogen, degassed again, and filtered thru Celite®. The filter pad was washed with methanol (3×5 mL). The filtrate was concentrated and purified by silica gel chromatography (20-80% EtOAc:hexanes) to provide the title intermediate (1514 mg; 82% yield). (m/z): $[M+H]^+$ calcd for $C_{15}H_{24}N_4O_2$ 293.19. found 293.1.

Preparation 48: 4-Bromo-2-chloro-5-trifluoromethoxy-benzoic acid methyl ester

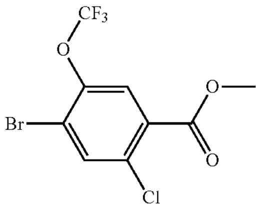 [SMILES: COC(=O)c1cc(OC(F)(F)F)c(Br)cc1Cl]

(a) 2-Chloro-5-trifluoromethoxy-benzoic acid methyl ester

A mixture of 2-bromo-1-chloro-4-trifluoromethoxy-benzene (5 g, 18.2 mmol), triethylamine (5.51 g, 54.5 mmol), and $Pd(dppf)Cl_2$ (1.33 g, 1.82 mmol) in methanol (200 mL) was stirred at 80° C. under carbon monoxide (50 Psi) overnight, filtered, and concentrated under vacuum. The residue was purified by silica gel chromatography (5% EtOAc in petroleum ether) to give the title intermediate as a colorless liquid (3.4 g, 74% yield).

(b) (2-Chloro-5-trifluoromethoxy-phenyl)-methanol

To a solution of the product of the previous step (2.9 g, 11.4 mmol) in THF (30 mL) was added $NaBH_4$ (2.59 g, 68.3 mmol). The resulting mixture was stirred for 15 min at 70° C., methanol (10 mL) was then added dropwise during 0.5 h and the mixture was stirred for 2 h at 70° C. The reaction mixture was cooled to RT, and quenched with sat. $NH_4Cl$. The organic layer was separated and the aqueous layer was extracted with EtOAc. The combined organics were dried over sodium sulfate, filtered, and concentrated to give the title intermediate. (2.3 g, 98% yield). (m/z): $[M-OH]^+$ calcd for $C_8H_6ClF_3O_2$ 209.0. found 209.0

(c) (4-Bromo-2-chloro-5-trifluoromethoxy-phenyl)-methanol

To a solution of (2-chloro-5-trifluoromethoxy-phenyl)-methanol (16.3 g, 71.94 mmol) in sulfuric acid (200 mL) and water (60 mL) was added bromine (12.65 g, 79.13 mmol), followed by silver sulfate (12.34 g, 39.57 mmol). The reaction mixture was stirred at RT for 1 h, poured onto ice, and then extracted with EtOAc (3×100 mL). The organic layers were combined, dried over $Na_2SO_4$ and concentrated to afford crude product, which was purified by flash chromatography (0-10% EtOAc in petroleum ether) to give the title intermediate (6.0 g, 27% yield). (m/z): $[M-OH]^+$ calcd for $C_8H_5BrClF_3O_2$ 286.91; 288.91. found 289.0.

(d) 4-Bromo-2-chloro-5-trifluoromethoxy-benzoic acid methyl ester

To a solution of (4-bromo-2-chloro-5-trifluoromethoxy-phenyl)-methanol (6.6 g, 21.61 mmol) in methanol (70 mL) was added 2-methyl-prop-2-yl-hydroperoxide (14.4 mL, 86.42 mmol), and potassium iodide (0.72 g, 4.32 mmol), The reaction mixture was stirred under reflux for 48 h and sat. sodium thiosulfate (20 mL) was added. The reaction mixture was concentrated and extracted with EtOAc (3×100 mL). The organic layers were combined, washed with brine, dried over sodium sulfate, concentrated, and purified by HPLC to provide the title intermediate (2.86 g, 39% yield). (m/z): $[M+H]^+$ calcd for $C_9H_5BrClF_3O_3$ 332.91; 334.91. found 332.9; 334.9. $^1H$ NMR (400 MHz, $CDCl_3$): δ(ppm) 7.79 (s, 1H), 7.77 (s, 1H), 3.94 (s, 3H).

Preparation 49: (R)-4-[5-(4-Bromo-2-chloro-5-trifluoromethoxy-benzoylamino)-pyridin-2-yl]-3-methyl-piperazine-1-carboxylic acid tert-butyl ester

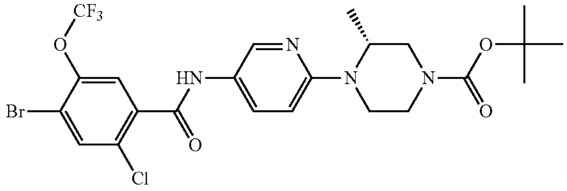 [SMILES: C[C@@H]1CN(C(=O)OC(C)(C)C)CCN1c1ccc(NC(=O)c2cc(OC(F)(F)F)c(Br)cc2Cl)cn1]

(a) 4-Bromo-2-chloro-5-trifluoromethoxy-benzoic acid

To a mixture of 4-bromo-2-chloro-5-trifluoromethoxy-benzoic acid methyl ester (1.0 g, 3.0 mmol, Preparation 48) dissolved in methanol (4 mL) and water (4 mL) was added lithium hydroxide (360 mg, 15 mmol). The reaction mixture was stirred at 60° C. for 1 h and concentrated. The reaction mixture was adjusted to acidic pH with 1 N HCl, dissolved in EtOAc (60 mL) and washed with water (60 mL). The aqueous layer was extracted with EtOAc (60 mL). The combined organic layers were washed with brine, dried over sodium sulfate, filtered, and concentrated to produce the title intermediate (966 mg, 100% yield) as a white powder.

(b) (R)-4-[5-(4-Bromo-2-chloro-5-trifluoromethoxy-benzoylamino)-pyridin-2-yl]-3-methyl-piperazine-1-carboxylic acid tert-butyl ester The white powder from the previous step (300 mg) was dissolved in DMF (2.5 mL) and HATU (480 mg, 1.3 mmol) was added, followed by DIPEA (550 μL, 3.2 mmol) and 0.5 M (R)-4-(5-amino-pyridin-2-yl)-3-methyl-piperazine-1-carboxylic acid tert-butyl ester in DMA (2.1 mL, 1.0 mmol; Preparation 47) The reaction mixture was stirred at room temperature overnight, dissolved in EtOAc (60 mL) and washed with water (120 mL). The aqueous layer was extracted with EtOAc (60 mL). The combined organic layer was washed with brine (60 mL), isolated and dried over sodium sulfate, filtered, concentrated, and purified by silica gel chromatography (40 g silica, 0-40% ethyl acetate:hexanes) to produce the title intermediate (491 mg, 80% yield) as a colored solid. (m/z): $[M+H]^+$ calcd for $C_{23}H_{25}BrClF_3N_4O_4$ 593.07; 595.07. found 595.0.

Preparation 50: 4-bromo-3-chloro-5-(trifluoromethoxy)benzoic acid

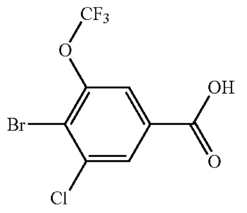 [SMILES: O=C(O)c1cc(Cl)c(Br)c(OC(F)(F)F)c1]

(a) 4-Amino-3-trifluoromethoxybenzoic acid methyl ester

A mixture of 4-amino-3-(trifluoromethoxy)benzoic acid (5.0 g, 22.61 mmol), methanol (75 mL) and 4.0 M HCl in 1,4-dioxane (56.53 mL, 226.1 mmol) was stirred at RT for 2 days. The reaction mixture was concentrated and the resulting residue was coevaporated with EtOAc (3×20 mL), and further dried under vacuum to give the HCl salt of the title intermediate as an off-white solid (6.9 g). Structure confirmed by NMR.

(b) 4-Amino-3-chloro-5-trifluoromethoxy-benzoic acidmethyl ester

The product of the previous step (200.0 mg, 0.74 mmol) was dissolved in a mixture of ACN (9.44 mL) and DMA (0.944 mL) at RT. To this stirred solution was added N-chlorosuccinimide (108.2 mg, 0.81 mmol). The resulting mixture was heated at 60° C. for 1 h, cooled to RT and partitioned between EtOAc (20 mL) and saturated sodium bicarbonate (4 mL). The organic layer was washed with saturated sodium bicarbonate (4 mL) and brine (4 mL), dried over sodium sulfate, filtered, and concentrated to give a yellowish oil, which was purified by silica gel chromatography (12 g silica gel, 0-40% EtOAc/hexanes) to give the title intermediate as a white solid (173.8 mg, 88% yield). Structure confirmed by NMR.

(c) 4-Bromo-3-chloro-5-trifluoromethoxy-benzoic acidmethyl ester

To a solution of the product of the previous step (173.8 mg, 0.65 mmol) in a mixture of ACN (7.74 mL) and water (0.80 mL) at RT was added copper(II) bromide (198.7 mg, 0.89 mmol) followed by tert-butyl nitrite (0.13 mL, 1.11 mmol) dropwise. The resulting mixture was heated at 60° C. for 1 h. The reaction mixture was cooled to RT and partitioned between EtOAc (10 mL) and water (2 mL). The organic layer was washed with water (4 mL), brine (4 mL), dried over sodium sulfate, filtered, and concentrated to give a brownish oil which was purified by silica gel chromatography (12 g silica gel, 0-30% EtOAc/hexanes) to give the title intermediate as a white solid (163.7 mg, 76% yield). Structure confirmed by NMR.

(d) 4-bromo-3-chloro-5-(trifluoromethoxy)benzoic acid

The product of the previous step (75.6 mg, 0.23 mmol) was dissolved in a mixture of methanol (0.7 mL) and water (0.2 mL) and treated with lithium hydroxide (21.7 mg, 0.91 mmol) at 75° C. for 30 min. The reaction mixture was concentrated, diluted with water (3 mL), then acidified to pH~1 with 1 N HCl, and extracted with EtOAc (5 mL). The organic layer was washed with water (2 mL) and brine (2 mL), dried over sodium sulfate, filtered and concentrated to give a white solid, which was used directly in Preparation 51.

Preparation 51: (R)-4-bromo-3-chloro-N-(6-(2-methyl-4-pivaloylpiperazin-1-yl)pyridin-3-yl)-5-(trifluoromethoxy)benzamide

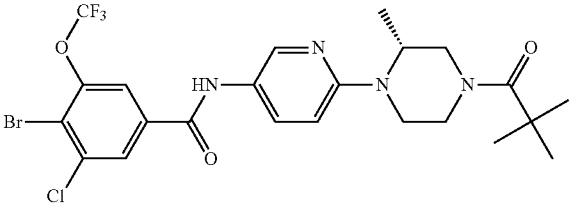 [SMILES: C[C@@H]1CN(C(=O)C(C)(C)C)CCN1c1ccc(NC(=O)c2cc(Cl)c(Br)c(OC(F)(F)F)c2)cn1]

(a) (R)-tert-butyl 4-(5-(4-bromo-3-chloro-5-(trifluoromethoxy)benzamido)pyridin-2-yl)-3-methylpiperazine-1-carboxylate To a mixture of (R)-tert-butyl 4-(5-aminopyridin-2-yl)-3-methylpiperazine-1-carboxylate (59.9 mg, 0.21 mmol) and 4-bromo-3-chloro-5-(trifluoromethoxy)benzoic acid (65.5 mg, 0.21 mmol; Preparation 50) in DMA (0.5 mL) at RT was added HATU (86 mg, 0.23 mmol) followed by DIPEA (0.11 mL, 0.62 mmol). The reaction mixture was stirred at RT for 1 h, partitioned between EtOAc (10 mL) and water (2 mL). The organic layer was washed with water (2 mL), dried over sodium sulfate, filtered and concentrated to give the title intermediate as a dark purplish oil. (m/z): $[M+H]^+$ calcd for $C_{23}H_{25}BrClF_3N_4O_4$ 593.07; 595.07. found 595.

(b) (R)-4-bromo-3-chloro-N-(6-(2-methylpiperazin-1-yl)pyridin-3-yl)-5-(trifluoromethoxy)-benzamide To the oily residue from the previous step (122 mg, 0.21 mmol) was added 4 N HCl in dioxane (0.51 mL, 2.05 mmol). The reaction mixture was held at RT overnight, concentrated, evaporated with EtOAc (3×2.0 mL), and dried under vacuum to give the di-HCl salt of the title intermediate as a purplish solid. (m/z): $[M+H]^+$ calcd for $C_{18}H_{17}BrClF_3N_4O_2$ 493.02; 495.02. found 495.

(c) (R)-4-bromo-3-chloro-N-(6-(2-methyl-4-pivaloylpiperazin-1-yl)pyridin-3-yl)-5-(trifluoromethoxy)benzamide The product of the previous step (116 mg, 0.21 mmol) was dissolved in a mixture of DCM (2 mL) and DIPEA (0.14 mL, 0.82 mmol) at RT. Pivaloyl chloride (24.7 mg, 0.21 mmol) was added. The reaction mixture was stirred at RT for 10 min and then purified by silica gel chromatography (12 g silica gel, 0-40% EtOAc/hexanes) to give the title intermediate (80.3 mg, 68% yield) as a light yellowish solid. (m/z): $[M+H]^+$ calcd for $C_{18}H_{17}BrClF_3N_4O_2$ 577.08; 579.07. found 579.

Preparation 52: 4-bromo-2-fluoro-3-(trifluoromethoxy)benzoic acid

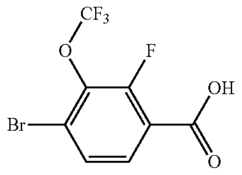 [SMILES: O=C(O)c1ccc(Br)c(OC(F)(F)F)c1F]

(a) 4-bromo-2-fluoro-3-(trifluoromethoxy)aniline

To a solution of 2-fluoro-3-(trifluoromethoxy)aniline (1.0 g, 5.13 mmol) dissolved in DMF (2 mL) at 0° C. was slowly added a solution of cold N-bromosuccinimide (0.91 g, 5.13 mmol) dissolved in DMF (6 mL) over 5 min. The reaction mixture was stirred at 0° C. for 1 h, extracted with EtOAc (125 mL) and washed with water (3×25 mL). The combined aqueous layers were extracted with EtOAc (75 mL). The combined organic layers were washed with brine (25 mL), dried over sodium sulfate, filtered, and concentrated to produce the title compound as a dark colored liquid (1.27 g, 90% yield). (m/z): $[M+H]^+$ calcd for $C_7H_4BrF_4NO$ 273.94. found 273.8.

(b) 4-bromo-2-fluoro-3-(trifluoromethoxy)benzonitrile

A mixture of water (3 mL) and sulfuric acid (0.59 mL) was cooled to 10° C. and the product of the previous step (1.27 g, 4.62 mmol) was added and stirred for 30 min at less than 15° C. The mixture was cooled to below 3° C., a solution of sodium nitrite (0.36 g, 5.22 mmol) in water (0.75 mL) was added, keeping the temperature below 3° C. and the reaction mixture was stirred for 45 min. The reaction mixture was added to a hot slurry (80° C.) of sodium carbonate (1.35 g, 12.75 mmol), copper(I) cyanide (0.42 g, 4.71 mmol) and sodium cyanide (0.36 g, 7.39 mmol) in water (3.27 mL) and the reaction mixture was heated at 65° C. for 2 h. Hexanes (80 mL) was added and the aqueous phase was extracted with hexanes (2×60 mL). The combined organic layer was washed with brine, dried over sodium sulfate, filtered, concentrated, and purified by silica gel chromatography (0-5% EtOAc: hexanes over 40 min) Fractions 33-39 were combined and concentrated to provide the title compound (258.6 mg, 20% yield).

(c) 4-bromo-2-fluoro-3-(trifluoromethoxy)benzoic acid

To a solution of the product of the previous step (258.6 mg, 0.91 mmol) in dioxane (2 mL) was added water (0.8 mL) and sulfuric acid (1.2 mL). The reaction mixture was heated at 110° C. overnight, and extracted with DCM (80 mL) and water (20 mL). The aqueous layer was extracted with DCM (2×30 mL). The combined organic layer was washed with water (2×30 mL), then with brine (30 mL), dried over sodium sulfate, and filtered, and concentrated to provide the title intermediate (275 mg) as a colored solid. (m/z): $[M+H]^+$ calcd for $C_8H_3BrF_4O_3$ 302.92. found 302.8.

Preparation 53: (R)-4-bromo-2-fluoro-N-(6-(2-methyl-4-pivaloylpiperazin-1-yl)pyridin-3-yl)-3-(trifluoromethoxy)benzamide

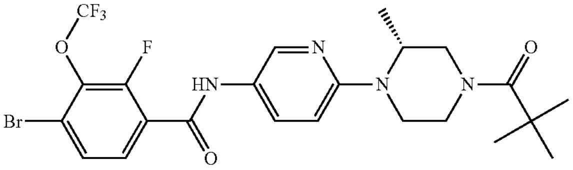 [SMILES: C[C@@H]1CN(C(=O)C(C)(C)C)CCN1c1ccc(NC(=O)c2ccc(Br)c(OC(F)(F)F)c2F)cn1]

(a) (R)-tert-butyl 4-(5-(4-bromo-2-fluoro-3-(trifluoromethoxy)benzamido)pyridin-2-yl)-3-methylpiperazine-1-carboxylate To a solution of 4-bromo-2-fluoro-3-(trifluoromethoxy) benzoic acid (150 mg, 0.50 mmol, Preparation 52), (R)-tert-butyl 4-(5-aminopyridin-2-yl)-3-methylpiperazine-1-carboxylate (145 mg, 0.50 mmol), and HATU (235 mg, 0.62 mmol) dissolved in DMF (1 mL) was added DIPEA (0.43 mL, 2.48 mmol). The reaction mixture was stirred at RT for 1 h, extracted with EtOAc (80 mL) washed with water (3×20 mL) and brine (20 mL), dried over sodium sulfate, filtered, concentrated, and purified by silica gel chromatography (12 g silica gel, 0-40% EtOAc:hexanes over 20 min), to provide the title intermediate (203 mg, 71% yield) as a yellow solid. (m/z): $[M+H]^+$ calcd for $C_{23}H_{25}BrF_4N_4O_4$ 577.10; 579.10. found 579.0.

(b) (R)-4-bromo-2-fluoro-N-(6-(2-methylpiperazin-1-yl)pyridin-3-yl)-3-(trifluoromethoxy)-benzamide To the product of the previous step (203 mg, 0.35 mmol) was added 4.0 M HCl in dioxane (3 mL) and the reaction mixture was stirred at RT for 1 h, concentrated and evaporated with EtOAc (2×) to produce the di-HCl salt of the title intermediate (189.3 mg, 98% yield) as a yellow solid. (m/z): $[M+H]^+$ calcd for $C_{18}H_{17}BrF_4N_4O_2$ 477.05; 479.05. found 476.9.

(c) (R)-4-bromo-2-fluoro-N-(6-(2-methyl-4-pivaloylpiperazin-1-yl)pyridin-3-yl)-3-(trifluoromethoxy)benzamide To a solution of the product of the previous step (189.3 mg, 0.34 mmol) and DIPEA (0.18 mL, 1.03 mmol) dissolved in DMF (1 mL) was added pivaloyl chloride (0.042 mL 0.34 mmol) and the reaction mixture was stirred at RT overnight, concentrated, and purified by silica gel chromatography (0-40% EtOAc:hexanes over 25 min), to provide the title intermediate (128.6 mg, 67% yield) as a white solid. (m/z): $[M+H]^+$ calcd for $C_{23}H_{25}BrF_4N_4O_3$ 561.10; 563.10. found 563.0.

Preparation 54: (2S,4S)-tert-butyl 2-(4-(4-bromophenyl)-1H-imidazol-2-yl)-4-(methoxymethyl)pyrrolidine-1-carboxylate

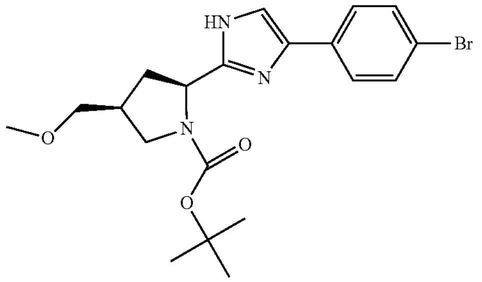 [SMILES: COC[C@H]1C[C@@H](c2nc(-c3ccc(Br)cc3)c[nH]2)N(C(=O)OC(C)(C)C)C1]

(a) (S)-1-tert-butyl 2-methyl 4-oxopyrrolidine-1,2-dicarboxylate

To a solution of (2S,4R)-1-tert-butyl 2-methyl 4-hydroxypyrrolidine-1,2-dicarboxylate (40 g, 157 mmol) in DCM (500 mL) was added DMP (80 g, 189 mmol) at 0° C. and the reaction mixture was stirred at RT for 4 h, quenched with $NaHSO_3$, extracted with DCM and washed with $NaHCO_3$. The organic phase was concentrated to provide the title intermediate (33 g, 89% yield) as a colorless oil. $^1H$ NMR (400 MHz, $CDCl_3$): δ(ppm) 1.51 (s, 9H), 2.550-2.597 (d, 1H, J=18.8 Hz), 2.876-2.944 (t, 1H, J=13.6 Hz), 3.895 (s, 3H), 3.766-3.895 (m, 1H), 4.696-4.814 (m, 1H).

(b) (S,E)-1-tert-butyl 2-methyl 4-(methoxymethylene)pyrrolidine-1,2-dicarboxylate Potassium carbonate (200 g, 2.17 mmol) was added to a solution of (S)-1-tert-butyl 2-methyl 4-oxopyrrolidine-1,2-dicarboxylate (88 g, 362 mmol) and dimethyl 1-diazo-2-oxopropylphosphonate (200 g, 1.04 mol) in methanol (1 L) at 0° C. and the reaction mixture was stirred at RT overnight, quenched, concentrated, poured into water, extracted with DCM, and purified by column chromatography to provide the title intermediate (18 g, 17% yield) as a yellow oil. $^1H$ NMR (400 MHz, $CDCl_3$): δ(ppm) 1.406-1.457 (d, 9H, J=20.4 Hz), 2.502-2.520 (m, 1H), 2.601-2.631 (m, 1H), 2.720-2.782 (m, 1H), 3.578 (s, 3H), 3.707 (s, 3H), 3.952-3.983 (m, 1H), 4.302-4.375 (m, 1H), 4.471-4.490 (m, 1H), 5.810-5.968 (m, 1H).

(c) (2S,4S)-1-tert-butyl 2-methyl 4-(methoxymethyl) pyrrolidine-1,2-dicarboxylate A solution of (5,E)-1-tert-butyl 2-methyl 4-(methoxymethylene)pyrrolidine-1,2-dicarboxylate (9 g, 33.21 mmol), magnesium oxide (12 g, 33.21 mmol) and palladium on carbon (3 g) in methanol (100 mL) was held under a steady flow of hydrogen at RT for 2 h, and filtered. The organic phase was concentrated to provide the title intermediate (9 g, 100% yield) as a colorless oil. $^1H$ NMR (400 MHz, $(CD_3)_2S{=}O$): δ(ppm) 1.367 (s, 9H), 1.620-1.670 (m, 1H), 1.904-1.953 (m, 1H), 3.110-3.140 (s, 3H, J=12 Hz), 3.255-3.360 (m, 2H), 3.523-3.561 (m, 1H), 3.653 (s, 3H), 4.241-4.283 (m, 1H).

(d) (2S,4S)-1-(tert-butoxycarbonyl)-4-(methoxymethyl)pyrrolidine-2-carboxylic acid A solution of (2S,4S)-1-tert-butyl 2-methyl 4-(methoxymethyl)pyrrolidine-1,2-dicarboxylate (18 g, 66.91 mmol) and lithium hydroxide (3.37 g, 80.3 mmol) in THF (50 mL), methanol (50 mL), and water (50 mL) was stirred at RT for 2 h. The reaction mixture was adjusted to ph 6 and extracted with 10:1 DCM:methanol. The organic phase was dried over sodium sulfate and concentrated to provide the title intermediate (17 g, 84% yield) as a colorless oil). $^1H$ NMR (400 MHz, $CDCl_3$): δ(ppm) 1.398-1.451 (d, 9H, J=21.2 Hz), 1.625-1.754 (m, 1H), 2.226-2.652 (m, 3H), 3.251-3.458 (m, 1H), 3.316 (s, 3H), 3.316-3.462 (m, 2H), 3.556-3.750 (m, 2H), 4.405-4.445 (m, 1H), 7.652 (s, 1H).

(e) (2S,4S)-2-(2-(4-bromophenyl)-2-oxoethyl) 1-tert-butyl 4-(methoxymethyl)pyrrolidine-1,2-dicarboxylate To a solution of (2S,4S)-1-(tert-butoxycarbonyl)-4-(methoxymethyl)pyrrolidine-2-carboxylic acid (10 g, 38.61 mmol) in DCM (100 mL) was added (2-bromo-1-(4-bromophenyl)-ethanone (11.8 g, 42.47 mmol) and triethylamine (7.8 g, 77.22 mmol). The reaction mixture was stirred at RT for 3 h. Water was added and the mixture was extracted with EtOAc. The organic phase was dried over sodium sulfate, concentrated, and purified by column chromatography to provide the title intermediate (12 g, 56% yield) as a colorless oil. $^1H$ NMR (400 MHz, $CDCl_3$): δ(ppm) 1.438-1.466 (d, 9H, J=11.2 Hz), 2.024-2.056 (t, 1H, J=12.8 Hz), 2.553 (s, 2H), 3.214-3.776 (m, 6H), 4.410-4.850 (t, 1H, J=15 Hz), 5.155-5.549 (m, 1H), 7.270-7.278 (t, 1H, J=1.6 Hz), 7.636-7.654 (d, 1H, J=7.2 Hz), 7.765-7.774 (d, 1H, J=3.6 Hz).

(f) (2S,4S)-tert-butyl 2-(4-(4-bromophenyl)-1H-imidazol-2-yl)-4-(methoxymethyl)pyrrolidine-1-carboxylate Ammonium acetate (77 g, 1 mol) was added to a solution of (2S,4S)-2-(2-(4-bromophenyl)-2-oxoethyl) 1-tert-butyl 4-(methoxymethyl)pyrrolidine-1,2-dicarboxylate (11 g, 25.11 mmol) in toluene (150 mL) and the reaction mixture was refluxed overnight and concentrated. Water (50 mL) was added, the reaction mixture was adjusted to pH 8, and extracted with EtOAc. The organic phase was dried over sodium sulfate, concentrated, and purified by column chromatography to provide the title intermediate (3 g, 31% yield) as a white solid. $^1H$ NMR (400 MHz, $CDCl_3$) δ(ppm) 1.316-1.535 (m, 9H), 2.457-2.630 (m, 4H), 2.808 (d, 1H), 3.202-3.223 (d, 1H, J=8.4 Hz), 3.404-3.565 (m, 6H), 3.832-3.877 (m, 1H), 5.019-5.054 (t, 1H, J=14 Hz), 7.056-7.592 (m, 6H).

Example 1

((S)-1-{(2S,4S)-2-[4-(5'-Chloro-4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester The solid from the previous step was treated with 4 M HCl in 1,4-dioxane (2.5 mL) and HCl (0.6 mL) and stirred at RT for 1 h. The reaction mixture was concentrated, dissolved in 1:1 acetic acid:water (6 mL) and purified by reverse phase HPLC. Fractions containing desired compound were combined and lyophilized to produce the tri-TFA salt of the title intermediate (99 mg, 26% yield) as a white powder. (m/z): $[M+H]^+$ calcd for $C_{40}H_{46}ClF_3N_8O_5$ 811.32. found 811.0.

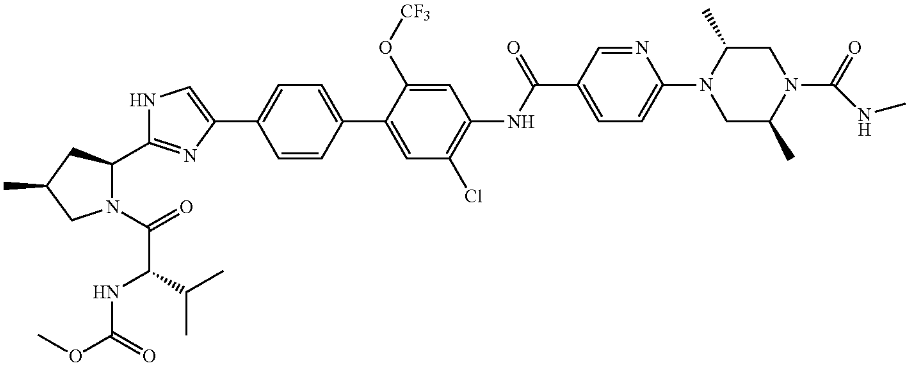

(a) ((S)-1-{(2S,4S)-2-[4-(5'-Chloro-4'-{[6-((2R,5S)-2,5-dimethyl-piperazin-1-yl)-pyridine-3-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester To a solution of [(S)-2-Methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1-carbonyl)-propyl]carbamic acid methyl ester (168 mg, 0.33 mmol) and (2S,5R)-4-[5-(4-bromo-2-chloro-5-trifluoromethoxy-phenylcarbamoyl)-pyridin-2-yl]-2,5-dimethyl-piperazine-1-carboxylic acid tert-butyl ester (200 mg, 0.33 mmol) dissolved in toluene (2.1 mL) and water (0.36 mL) was added potassium carbonate (227 mg, 1.65 mmol). The reaction mixture was sparged under nitrogen for 15 min. Tetrakis(triphenylphosphine)palladium(0) (45.6 mg, 0.039 mmol) was added and the reaction mixture was sparged with nitrogen and heated at 100° C. overnight. The reaction mixture was diluted with ethyl acetate and washed with water and brine. The organic layer was dried over sodium sulfate, filtered and concentrated to produce a brownish solid.

(b) ((S)-1-{(2S,4S)-2-[4-(5'-Chloro-4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester The product of the previous step was dissolved in DMA and 0.5 M methylaminoformyl chloride in DMA (34.7 μL, 0.017 mmol) was added followed by N,N-diisopropylethylamine (0.015 mL, 0.087 mmol) and the reaction mixture was stirred at RT overnight, concentrated by rotary evaporation, dissolved in 1:1 acetic acid:water (1.5 mL) and purified by reverse phase HPLC to provide the di-TFA salt of the title compound (15 mg, 79% yield). (m/z): $[M+H]^+$ calcd for $C_{42}H_{49}ClF_3N_9O_6$ 868.35. found 868.6.

Example 2

[(S)-1-((2S,4S)-2-{4-[5'-Chloro-4'-({6-[(R)-4-((S)-2,2-dimethyl-cyclopropanecarbonyl)-2-methyl-piperazin-1-yl]-pyridine-3-carbonyl}-amino)-2'-trifluoromethoxy-biphenyl-4-yl]-1H-imidazol-2-yl}-4-methyl-pyrrolidine-1-carbonyl)-2-methyl-propyl]-carbamic acid methyl ester

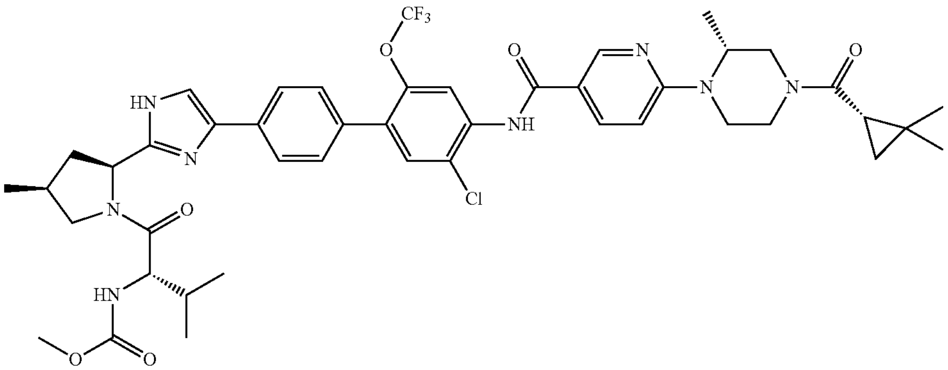

(a) ((S)-1-{(2S,4S)-2-[4-(5'-Chloro-4'-{[6-((R)-2-methyl-piperazin-1-yl)-pyridine-3-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester Following the general procedure of Example 1(a) at the 0.30 mmol scale, substituting (R)-4-[5-(4-bromo-2-chloro-5-trifluoromethoxy-phenylcarbamoyl)-pyridin-2-yl]-3-methyl-piperazine-1-carboxylic acid tert-butyl ester for (2S,5R)-4-[5-(4-bromo-2-chloro-5-trifluoromethoxy-phenylcarbamoyl)-pyridin-2-yl]-2,5-dimethyl-piperazine-1-carboxylic acid tert-butyl ester, with, alternative purification by evaporation with ethyl acetate (2×) the tri-HCl salt of the title intermediate was prepared (101 mg, 29% yield). (m/z): $[M+H]^+$ calcd for $C_{39}H_{44}ClF_3N_8O_5$ 797.31. found 797.

(b) [(S)-1-((2S,4S)-2-{4-[5'-Chloro-4'-({6-[(R)-4-((S)-2,2-dimethyl-cyclopropanecarbonyl)-2-methyl-piperazin-1-yl]-pyridine-3-carbonyl}-amino)-2'-methoxy-biphenyl-4-yl]-1H-imidazol-2-yl}-4-methyl-pyrrolidine-1-carbonyl)-2-methyl-propyl]-carbamic acid methyl ester To a solution of 0.5 M (S)-(+)-2,2-dimethylcyclopropane carboxylic acid in DMA (41.6 μL, 0.02 mmol) was added HATU (7.9 mg, 0.02). The reaction mixture was stirred for 15 min and then the product of the previous step (20 mg, 0.02 mmol) was added followed by N,N-diisopropylethylamine (0.015 mL, 0.09 mmol) and the reaction mixture was stirred at 55° C. overnight, concentrated, dissolved in 1:1 acetic acid: water (1.5 mL) and purified by reverse phase HPLC to provide the di-TFA salt of the title compound (16 mg, 78% yield). (m/z): $[M+H]^+$ calcd for $C_{45}H_{52}ClF_3N_8O_6$ 893.37. found 893.6.

Example 3

[(S)-1-((2S,4S)-2-{4-[5'-Chloro-4'-({6-[(2R,5S)-4-(1H-imidazole-4-carbonyl)-2,5-dimethyl-piperazin-1-yl]-pyridine-3-carbonyl}-amino)-2'-trifluoromethyl-biphenyl-4-yl]-1H-imidazol-2-yl}-4-methyl-pyrrolidine-1-carbonyl)-2-methyl-propyl]-carbamic acid methyl ester

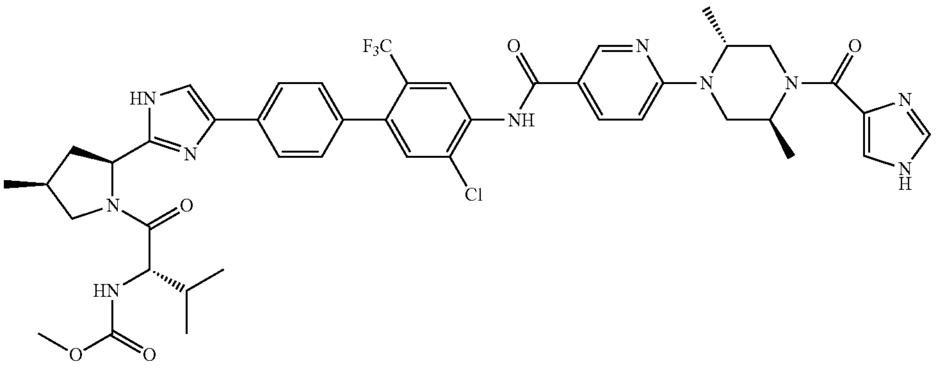 [SMILES: COC(=O)N[C@H](C(=O)N1C[C@@H](C)C[C@H]1c1nc(-c2ccc(-c3cc(Cl)c(NC(=O)c4ccc(N5C[C@H](C)N(C(=O)c6c[nH]cn6)C[C@H]5C)nc4)cc3C(F)(F)F)cc2)c[nH]1)C(C)C]

(a) ((S)-1-{(2S,4S)-2-[4-(5'-Chloro-4'-{[6-((2R,5S)-2,5-dimethyl-piperazin-1-yl)-pyridine-3-carbonyl]-amino}-2'-trifluoromethyl-biphenyl-4-yl)-1H-imidazol-2-yl]-4-methyl-pyrrolidine-1-carbonyl}-2-methyl-propyl)-carbamic acid methyl ester Following the procedure of Example 1 at the 0.24 mmol scale, substituting (2S,5R)-4-[5-(4-Bromo-2-chloro-5-trifluoromethyl-phenylcarbamoyl)-pyridin-2-yl]-2,5-dimethyl-piperazine-1-carboxylic acid tert-butyl ester for (2S,5R)-4-[5-(4-bromo-2-chloro-5-trifluoromethoxy-phenylcarbamoyl)-pyridin-2-yl]-2,5-dimethyl-piperazine-1-carboxylic acid tert-butyl ester, the tri-TFA salt of the title intermediate was prepared (116 mg, 54% yield). (m/z): $[M+H]^+$ calcd for $C_{40}H_{46}ClF_3N_8O_4$ 795.33. found 795.4.

(b) [(S)-1-((2S,4S)-2-{4-[5'-Chloro-4'-({6-[(2R,5S)-4-(1H-imidazole-4-carbonyl)-2,5-dimethyl-piperazin-1-yl]-pyridine-3-carbonyl}-amino)-2'-trifluoromethyl-biphenyl-4-yl]-1H-imidazol-2-yl}-4-methyl-pyrrolidine-1-carbonyl)-2-methyl-propyl]-carbamic acid methyl ester To a solution of the product of the previous step (12 mg, 0.013 mmol) and N,N-diisopropylethylamine (23 μL, 0.13 mmol) dissolved in DMA (0.5 mL) was added imidazol-4-carboxylic acid (1.5 mg, 0.013 mmol) and HATU (7.6 mg, 0.02 mmol) and the reaction mixture was stirred at 50° C. for 2 hours, concentrated and dissolved in 1:1 acetic acid:water (1.5 mL) and purified by reverse phase HPLC to provide the tri-TFA salt of the title compound (5 mg). (m/z): $[M+H]^+$ calcd for $C_{44}H_{48}ClF_3N_{10}O_5$ 889.35. found 889.6.

Example 4

Methyl (S)-1-((S)-8-(4-(4'-(6-((R)-4-((S)-2,2-dimethylcyclopropanecarbonyl)-2-methylpiperazin-1-yl) nicotinamido)-2'-(trifluoromethoxy)biphenyl-4-yl)-1H-imidazol-2-yl)-1,4-dioxa-7-azaspiro[4.4]nonan-7-yl)-3-methyl-1-oxobutan-2-ylcarbamate

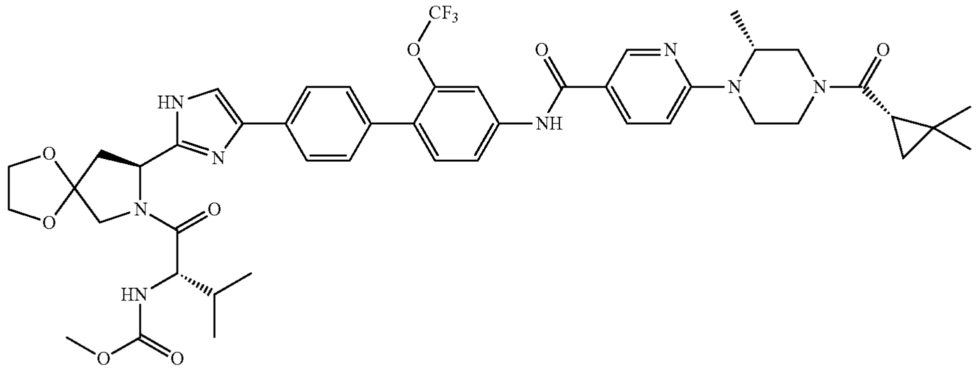 [SMILES: COC(=O)N[C@H](C(=O)N1CC2(C[C@H]1c1nc(-c3ccc(-c4ccc(NC(=O)c5ccc(N6CCN(C(=O)[C@H]7CC7(C)C)C[C@H]6C)nc5)cc4OC(F)(F)F)cc3)c[nH]1)OCCO2)C(C)C]

To a solution of ((S)-1-{(S)-8-[4-(4'-Amino-2'-trifluoromethoxy-biphenyl-4-yl)-1H-imidazol-2-yl]-1,4-dioxa-7-aza-spiro[4.4]nonane-7-carbonyl}-2-methyl-propyl)-carbamic acid methyl ester 2HCl (92.0 mg, 0.136 mmol; Preparation 9) in DCM (1.36 mL) and DMA (0.14 mL) at RT was added N,N-diisopropylethylamine (94.7 μL, 0.54 mmol) and 2-fluoropyridine-5-carbonyl chloride (228 mg, 0.143 mmol), The reaction mixture was stirred for 30 min at RT and concentrated.

The residue from the previous step was dissolved in DMSO (2.0 mL) and treated with (R)-3-methyl-piperazine-1-carboxylic acid tert-butyl ester (136 mg, 0.680 mmol) and N,N-diisopropylethylamine (0.237 mL, 1.36 mmol) at 120° C. overnight.

The reaction mixture was concentrated and treated with 4 M HCl in 1,4-Dioxane (1.0 mL, 4.0 mmol) at RT for 30 min. The reaction mixture was concentrated, dissolved in 1:1 acetic acid:water (6 mL), filtered and purified by reverse phase HPLC. Desired fractions were combined and freeze dried to give a white solid (48 mg, 30% yield).

To a mixture of (S)-(+)-2,2-dimethylcyclopropane carboxylic acid (1.75 mg, 0.015 mmol) in DMA (0.5 mL) at RT was added the product of the previous step (3-TFA salt form) (16 mg, 0.014 mmol) and N,N-diisopropylethylamine (12.1 μL, 0.070 mmol) and the reaction mixture was stirred at RT overnight, dissolved in 1:1 acetic acid:water (1.5 mL), filtered and purified by reverse phase HPLC to provide the di-TFA salt of the title compound (6 mg). (m/z): $[M+H]^+$ calcd for $C_{46}H_{53}F_3N_8O_8$ 903.39. found 904.0.

Example 5

(S)-2-{(R)-4-[5-(4'-{2-[(2S,4S)-4-Hydroxy-1-((S)-2-methoxycarbonyl-amino-3-methyl-butyryl)-pyrrolidin-2-yl]-1H-imidazol-4-yl}-biphenyl-4-ylcarbamoyl)-pyridin-2-yl]-3-methyl-piperazine-1-carbonyl}-2-methyl-pyrrolidine-1-carboxylic acid methyl ester

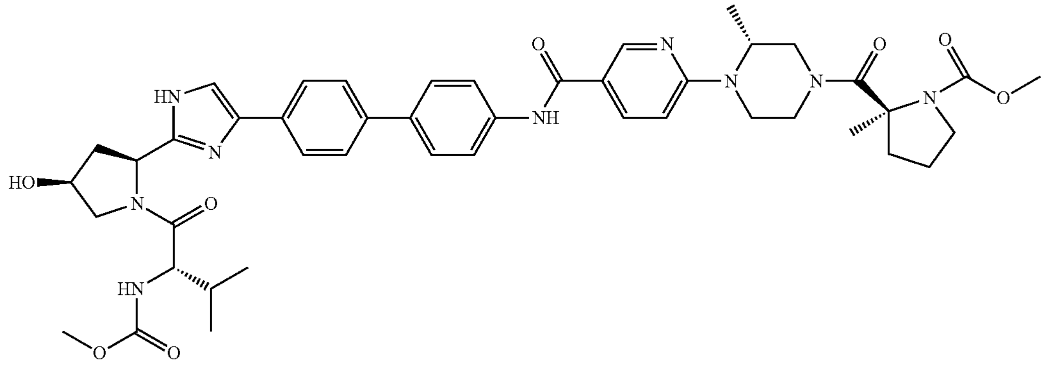 [SMILES: COC(=O)N[C@H](C(=O)N1C[C@@H](O)C[C@H]1c1nc(-c2ccc(-c3ccc(NC(=O)c4ccc(N5CCN(C(=O)[C@]6(C)CCCN6C(=O)OC)C[C@H]5C)nc4)cc3)cc2)c[nH]1)C(C)C]

(a) (S)-1-{(2S,4S)-4-Hydroxy-2-[4-(4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester A solution of (R)-4-(5-carboxy-pyridin-2-yl)-3-methyl-piperazine-1-carboxylic acid tert-butyl ester (130 mg, 0.42 mmol), EDC (120 mg, 0.63 mmol) and HOAt (86 mg, 0.63 mmol) dissolved in DMA (3.9 mL) was stirred at room temperature for 30 min and then ((S)-1-{(2S,4S)-2-[4-(4'-Amino-biphenyl-4-yl)-1H-imidazol-2-yl]-4-hydroxy-pyrrolidine-1-carbonyl}-2-methyl-propyl)-carbamic acid methyl ester (200 mg, 0.40 mmol; Preparation 10) was added followed by N,N-diisopropylethylamine (0.18 mL, 1.0 mmol). The reaction mixture was stirred at RT over the weekend, and extracted with EtOAc and water. The organic layer was dried over sodium sulfate, filtered and evaporated under vacuum.

The brown oil from the previous step was treated with 4 M HCl in 1,4-dioxane (3.1 mL) and HCl (1.15 mL) and stirred at room temperature for 1 h. The reaction mixture was concentrated and evaporated with ethyl acetate (2×) to produce a brown oil. The oil was dissolved in 1:1 acetic acid:water (4 mL), filtered, and purified by reverse phase HPLC to produce the tri-TFA salt of the desired product (276 mg). (m/z): $[M+H]^+$ calcd for $C_{37}H_{44}N_8O_5$ 681.34. found 681.4.

(b) (S)-2-{(R)-4-[5-(4'-{2-[(2S,4S)-4-Hydroxy-1-((S)-2-methoxycarbonyl-amino-3-methyl-butyryl)-pyrrolidin-2-yl]-1H-imidazol-4-yl}-biphenyl-4-yl-carbamoyl)-pyridin-2-yl]-3-methyl-piperazine-1-carbonyl}-2-methyl-pyrrolidine-1-carboxylic acid methyl ester The product of the previous step (20.0 mg, 0.029 mmol) was dissolved in DMA (1 mL) and N,N-diisopropylethylamine (0.015 mL, 0.088 mmol) was added. To the reaction mixture was added 0.5 M (S)-2-methyl-pyrrolidine-1,2-dicarboxylic acid 1-methyl ester in DMA (70.5 μL, 0.035 mmol) followed by HATU (13 mg, 0.035 mmol). The reaction mixture stirred at RT overnight, concentrated, dissolved in 1:1 acetic acid:water (1.5 mL) and purified by reverse phase HPLC to provide the di-TFA salt of the title compound (16.8 mg, 56% yield). (m/z): $[M+H]^+$ calcd for $C_{45}H_{55}N_9O_8$ 850.42. found 850.4.

Example 6

((S)-1-{(2S,4S)-2-[4-(4'-{[6-((R)-4-Cyclopropanecarbonyl-2-methyl-piperazin-1-yl)-pyridine-3-carbonyl]-amino}-biphenyl-4-yl)-1H-imidazol-2-yl]-4-dimethylamino-pyrrolidine-1-carbonyl}-2-methyl-propyl)-carbamic acid methyl ester

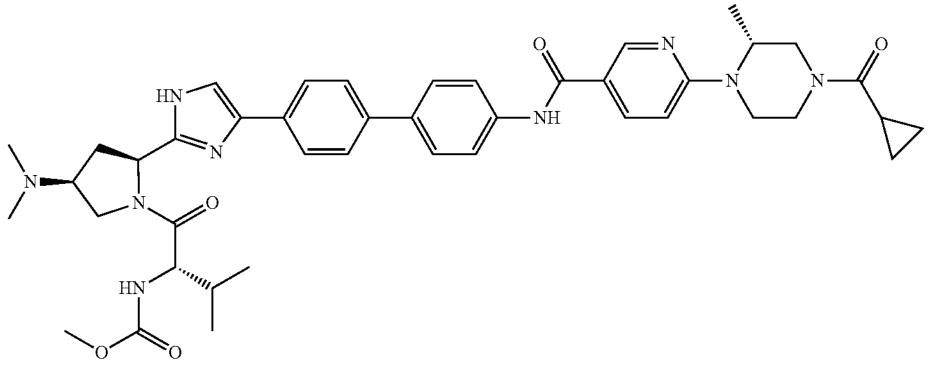 [SMILES: COC(=O)N[C@H](C(=O)N1C[C@@H](N(C)C)C[C@H]1c1nc(-c2ccc(-c3ccc(NC(=O)c4ccc(N5CCN(C(=O)C6CC6)C[C@H]5C)nc4)cc3)cc2)c[nH]1)C(C)C]

(a) ((S)-1-{(2S,4S)-4-Dimethylamino-2-[4-(4'-{[6-((R)-2-methyl-piperazin-1-yl)-pyridine-3-carbonyl]-amino}-biphenyl-4-yl)-1H-imidazol-2-yl]-pyrrolidine-1-carbonyl}-2-methyl-propyl)-carbamic acid methyl ester A solution of ((S)-1-{(2S,4S)-2-[4-(4-bromo-phenyl)-1H-imidazol-2-yl]-4-dimethylamino-pyrrolidine-1-carbonyl}-2-methyl-propyl)-carbamic acid methyl ester (135 mg, 0.27 mmol; Preparation 12) and (R)-3-methyl-4-{5-[4-(4,4,5,5-tetramethyl-1,3,2-dioxaborolan-2-yl)-phenylcarbamoyl]-pyridin-2-yl}-piperazine-1-carboxylic acid tert-butyl ester (140 mg, 0.27 mmol; Preparation 13) dissolved in 1,2-dimethoxyethane (2.85 mL) and water (0.99 mL) was sparged under nitrogen. Sodium bicarbonate (86.4 mg, 1.03 mmol) was added, followed by tetrakis(triphenylphosphine)palladium(0) (48 mg, 0.041 mmol) and the reaction mixture was sealed under nitrogen and heated at 90° C. overnight and extracted with ethyl acetate/water. The organic layer was dried over sodium sulfate, filtered, and concentrated to produce a yellow oil.

The yellow oil from the previous step was treated with 4 M HCl in 1,4-dioxane (3 mL) and stirred at RT for 1 h, concentrated, dissolved in 1:1 acetic acid:water (4 mL) and purified by reverse phase HPLC to produce the tri-TFA salt of the title intermediate (100 mg, 30% yield). (m/z): $[M+H]^+$ calcd for $C_{39}H_{49}N_9O_4$ 708.39. found 708.9.

(b) ((S)-1-{(2S,4S)-2-[4-(4'-{[6-((R)-4-Cyclopropanecarbonyl-2-methyl-piperazin-1-yl)-pyridine-3-carbonyl]-amino}-biphenyl-4-yl)-1H-imidazol-2-yl]-4-dimethylamino-pyrrolidine-1-carbonyl}-2-methyl-propyl)-carbamic acid methyl ester To a solution of the product of the previous step (10 mg, 0.01 mmol) and N,N-diisopropylethylamine (8.3 μL, 0.048 mmol) dissolved in DMA (0.3 mL) was added cyclopropanecarbonyl chloride (0.86 μL, 0.0095 mmol) and the reaction mixture was stirred at RT overnight, concentrated, dissolved in 1:1 acetic acid:water (1.5 mL) and purified by reverse phase HPLC to provide the tri-TFA salt of the title compound (6.9 mg). (m/z): $[M+H]^+$ calcd for $C_{43}H_{53}N_9O_5$ 776.42. found 776.4.

Example 7

((S)-1-{(2S,4S)-2-[4-(4'-{6-[(2R,5S)-4-((S)-2,2-Dimethyl-cyclopropanecarbonyl)-2,5-dimethyl-piperazin-1-yl]-pyridin-3-ylcarbamoyl}-2'-trifluoromethoxy-biphenyl-4-yl)-1H-imidazol-2-yl]-4-methyl-pyrrolidine-1-carbonyl}-2-methyl-propyl)-carbamic acid methyl ester

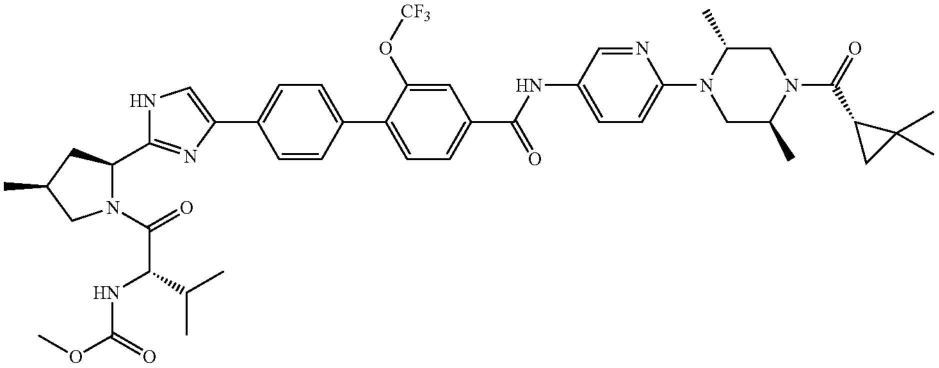

(a) {(S)-1-[(2S,4S)-2-(4-{4'-[6-((2R,5S)-2,5-Dimethyl-piperazin-1-yl)-pyridin-3-ylcarbamoyl]-2'-trifluoromethoxy-biphenyl-4-yl}-1H-imidazol-2-yl)-4-methyl-pyrrolidine-1-carbonyl]-2-methyl-propyl}-carbamicacid methyl ester To a mixture of 4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-carboxylic acid TFA (80 mg, 0.11 mmol; Preparation 15) and (2S,5R)-4-(5-amino-pyridin-2-yl)-2,5-dimethyl-piperazine-1-carboxylic acid tert-butyl ester (416 mg, 0.14 mmol; Preparation 16) in DMF (1 mL) at RT was added HATU (56.8 mg, 0.15 mmol) followed by N,N-diisopropylethylamine (0.12 mL, 0.68 mmol). The reaction mixture was stirred at RT overnight, and partitioned between EtOAc (10 mL) and water (3 mL). The organic layer was washed with water (3 mL), dried over sodium sulfate, filtered and concentrated to give a brownish red oil.

The oily residue from previous step was treated with 4 M HCl in 1,4-dioxane (1.0 mL) at RT for 30 min. The reaction mixture was concentrated, evaporated with EtOAc (3x3 mL) dissolved in a mixture of ACN and water and freeze dried to give the tri-HCl salt of the title intermediate (124 mg) as a reddish solid. (m/z): $[M+H]^+$ calcd for $C_{40}H_{47}F_3N_8O_5$ 777.36. found 777.

(b) ((S)-1-{(2S,4S)-2-[4-(4'-{6-[(2R,5S)-4-((S)-2,2-Dimethyl-cyclopropanecarbonyl)-2,5-dimethyl-piperazin-1-yl]-pyridin-3-ylcarbamoyl}-2'-trifluoromethoxy-biphenyl-4-yl)-1H-imidazol-2-yl]-4-methyl-pyrrolidine-1-carbonyl}-2-methyl-propyl)-carbamic acid methyl ester To a mixture of (S)-(+)-2,2-dimethylcyclopropane carboxylic acid (2.6 mg, 0.023 mmol) and HATU (8.58 mg, 0.023 mmol) in DMF (0.5 mL) at RT was added the product of the previous step (20.0 mg, 0.023 mmol) followed by N,N-diisopropylethylamine (31.4 μL, 0.180 mmol). The reaction mixture was stirred at RT overnight, concentrated, dissolved in 1:1 acetic acid:water (1.5 mL) and purified by reverse phase HPLC to provide the di-TFA salt of the title compound (10 mg). (m/z): $[M+H]^+$ calcd for $C_{46}H_{55}F_3N_8O_6$ 873.42. found 873.8.

Example 8

((S)-1-{(2S,4S)-2-[4-(4'-{6-[(R)-4-((S)-2,2-Dimethyl-cyclopropanecarbonyl)-2-methyl-piperazin-1-yl]-pyridin-3-ylcarbamoyl}-2'-trifluoromethoxy-biphenyl-4-yl)-1H-imidazol-2-yl]-4-methyl-pyrrolidine-1-carbonyl}-2-methyl-propyl)-carbamic acid methyl ester

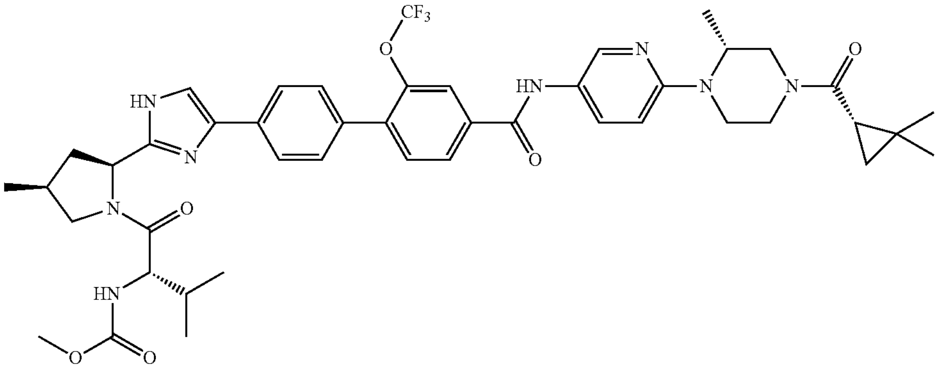

To a mixture of 4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-carboxylic acid TFA (11.4 mg, 0.016 mmol) and HATU (6.8 mg, 0.018 mmol) in DMF (0.5 mL) at RT was added [(R)-4-(5-amino-pyridin-2-yl)-3-methyl-piperazin-1-yl]-((S)-2,2-dimethyl-cyclopropyl)-methanone (5.1 mg, 0.018 mmol, Preparation 17) followed by N,N-diisopropylethylamine (14.07 μL, 0.081 mmol). The reaction mixture was stirred at RT overnight, concentrated, dissolved in 1:1 acetic acid:water (1.5 mL) and purified by reverse phase HPLC to provide the di-TFA salt of the title compound (9 mg). (m/z): $[M+H]^+$ calcd for $C_{45}H_{53}F_3N_8O_6$ 859.40. found 859.4.

Example 9

((S)-1-{(2S,4S)-2-[4-(4'-{6-[(R)-4-((S)-2,2-Dimethyl-cyclopropanecarbonyl)-2-methyl-piperazin-1-yl]-pyridin-3-ylcarbamoyl}-2'-trifluoromethoxy-biphenyl-4-yl)-1H-imidazol-2-yl]-4-methylsulfanyl-pyrrolidine-1-carbonyl}-2-methyl-propyl)-carbamic acid methyl ester

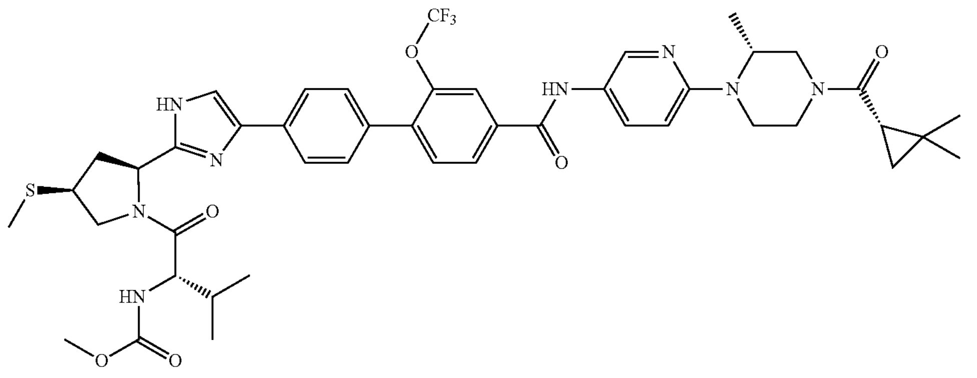

(a) {(S)-2-Methyl-1-[(2S,4S)-2-(4-{4'-[6-((R)-2-methyl-piperazin-1-yl)-pyridin-3-ylcarbamoyl]-2'-trifluoromethoxy-biphenyl-4-yl}-1H-imidazol-2-yl)-4-methylsulfanyl-pyrrolidine-1-carbonyl]-propyl}-carbamic acid methyl ester To a mixture of 4'-{2-[(2S,4S)-1-((S)-2-methoxycarbonylamino-3-methyl-butyryl)-4-methylsulfanyl-pyrrolidin-2-yl]-1H-imidazol-4-yl}-2-trifluoromethoxy-biphenyl-4-carboxylic acid TFA (37 mg, 0.05 mmol; Preparation 21) and (R)-4-(5-amino-pyridin-2-yl)-3-methyl-piperazine-1-carboxylic acid tert-butyl ester (16 mg, 0.06 mmol) in DMF (0.5 mL) at RT was added HATU (21 mg, 0.06 mmol) followed by N,N-Diisopropylethylamine (44.3 μL, 0.25 mmol). The resulting mixture was stirred at RT overnight. The reaction mixture was partitioned between EtOAc (5 mL) and water (2 mL). The organic layer was washed with water (2 mL), dried over sodium sulfate, filtered and concentrated to give a brownish red oil.

The oily residue from previous step was treated with 4 M of HCl in 1,4-dioxane (1.0 mL) at RT for 30 min. The reaction mixture was concentrated, evaporated with EtOAc (3×2 mL), dissolved in a mixture of ACN and water, and freeze dried to give the tri-HCl salt of the title intermediate (57 mg) as a brownish solid. (m/z): $[M+H]^+$ calcd for $C_{45}H_{53}F_3N_8O_6S$ 891.38. found 891.

(b) ((S)-1-{(2S,4S)-2-[4-(4'-{6-[(R)-4-((S)-2,2-Dimethyl-cyclopropanecarbonyl)-2-methyl-piperazin-1-yl]-pyridin-3-ylcarbamoyl}-2'-trifluoromethoxy-biphenyl-4-yl)-1H-imidazol-2-yl]-4-methylsulfanyl-pyrrolidine-1-carbonyl}-2-methyl-propyl)-carbamic acid methyl ester To a mixture of (S)-(+)-2,2-dimethylcyclopropane carboxylic acid (2.7 mg, 0.023 mmol) and HATU (8.8 mg, 0.023 mmol) in DMF (0.5 mL) at RT was added the product of the previous step (19.1 mg, 0.021 mmol) followed by N,N-diisopropylethylamine (18.4 μL, 0.11 mmol). The reaction mixture was stirred at RT overnight, concentrated, dissolved in 1:1 acetic acid:water (1.5 mL) and purified by reverse phase HPLC to provide the di-TFA salt of the title compound (11 mg). (m/z): $[M+H]^+$ calcd for $C_{45}H_{53}F_3N_8O_6S$ 891.38. found 891.

Example 10

[(S)-1-((2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-pyrrolidine-1-carbonyl)-2-methyl-propyl]-carbamic acid methyl ester

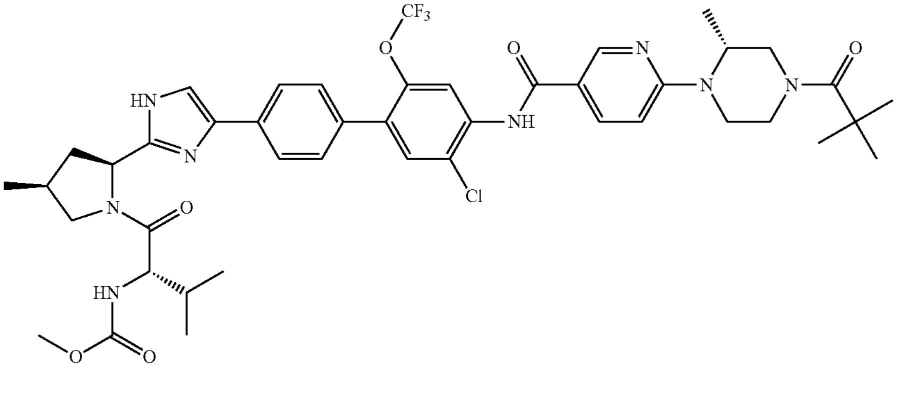 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C]

(a) (R)-4-[5-(5-Chloro-4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-ylcarbamoyl)-pyridin-2-yl]-3-methyl-piperazine-1-carboxylic acid tert-butyl ester To a solution of [(S)-2-methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester (155 mg, 0.30 mmol) and (R)-4-[5-(4-bromo-2-chloro-5-trifluoromethoxy-phenylcarbamoyl)-pyridin-2-yl]-3-methyl-piperazine-1-carboxylic acid tert-butyl ester (180 mg, 0.30 mmol, Preparation 1) dissolved in toluene (1.9 mL) and water (0.33 mL) was added potassium carbonate (210 mg, 1.52 mmol). The reaction mixture was sparged under nitrogen. Tetrakis(triphenylphosphine)palladium(0) (42 mg, 0.036 mmol) was added and the reaction mixture was sparged with nitrogen and heated at 100° C. overnight. The reaction mixture was diluted with ethyl acetate and washed with water and brine. The organic layer was dried over sodium sulfate, filtered, and concentrated to produce the title intermediate as a brownish solid. (m/z): $[M+H]^+$ calcd for $C_{44}H_{52}ClF_3N_8O$, 897.36. found 897.

(b) ((S)-1-{(2S,4S)-2-[4-(5'-Chloro-4'-{[6-((R)-2-methyl-piperazin-1-yl)-pyridine-3-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester The solid from the previous step (431 mg, 0.48 mmol) was treated with 4 M HCl in 1,4-dioxane (2 mL) and the reaction mixture was stirred at 50° C. for 30 min, concentrated, and evaporated with ethyl acetate (2×) to produce the tri-HCl salt of the title intermediate as a yellow solid (426 mg, 0.47 mmol). (m/z): $[M+H]^+$ calcd for $C_{39}H_{44}ClF_3N_8O_5$ 797.31. found 797.8.

(c) [(S)-1-((2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-pyrrolidine-1-carbonyl)-2-methyl-propyl]-carbamic acid methyl ester To a solution of the product of the previous step (12 mg, 0.014 mmol) in DMF (0.5 mL) was added N,N-diisopropylethylamine (0.024 mL, 0.14 mmol) followed by 2,2-dimethylpropanoyl chloride (1.7 μL, 0.014 mmol). The reaction mixture was stirred at RT for 30 min, concentrated, dissolved in 1:1 acetic acid:water (1.5 mL) and purified by reverse phase HPLC to provide the di-TFA salt of the title compound (7 mg). (m/z): $[M+H]^+$ calcd for $C_{44}H_{52}ClF_3N_8O_6$ 881.37. found 881.8.

Example 11

[(S)-1-((2S,4S)-2-{4-[4'-({6-[(R)-4-(2,2-Dimethyl-propionyl)-2-methyl-piperazin-1-yl]-pyridine-3-carbonyl}-amino)-5'-fluoro-2'-trifluoromethoxy-biphenyl-4-yl]-1H-imidazol-2-yl}-4-methyl-pyrrolidine-1-carbonyl)-2-methyl-propyl]-carbamic acid methyl ester

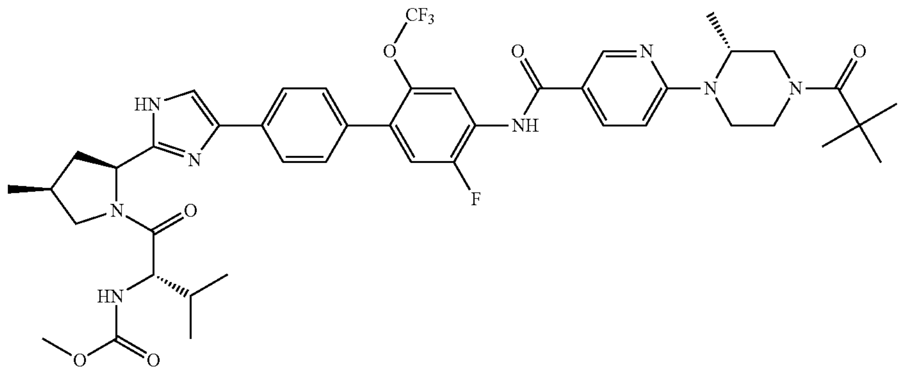 [SMILES: COC(=O)N[C@H](C(=O)N1C[C@@H](C)C[C@H]1c1nc(-c2ccc(-c3cc(F)c(NC(=O)c4ccc(N5CCN(C(=O)C(C)(C)C)C[C@H]5C)nc4)cc3OC(F)(F)F)cc2)c[nH]1)C(C)C]

(a) (R)-4-[5-(5-Fluoro-4'-{2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-ylcarbamoyl)-pyridin-2-yl]-3-methyl-piperazine-1-carboxylic acid tert-butyl ester To a solution of [(S)-2-methyl-1-((2S,4S)-4-methyl-2-{4-[4-(4,4,5,5-tetramethyl-1,3,2-dioxaborolan-2-yl)-phenyl]-1H-imidazol-2-yl}-pyrrolidine-1-carbonyl)-propyl]-carbamic acid methyl ester (170 mg, 0.33 mmol) and (R)-4-[5-(4-bromo-2-fluoro-5-trifluoromethoxy-phenylcarbamoyl)-pyridin-2-yl]-3-methyl-piperazine-1-carboxylic acid tert-butyl ester (192 mg, 0.33 mmol, Preparation 24) dissolved in toluene (2.1 mL) and water (0.8 mL) was added potassium carbonate (230 mg, 1.67 mmol). The reaction mixture was sparged with nitrogen, $Pd(dppf)Cl_2CH_2Cl_2$ (25 mg, 0.03 mmol) was added and the reaction mixture was sparged with nitrogen and heated at 90° C. overnight. The reaction mixture was cooled to RT, filtered through a pad of Celite® and silica gel and washed with EtOAc. The filtrate was washed with water and brine to produce a brownish colored oil. The residue was purified by silica gel chromatography (24 g, 40% to 100% EtOAc/hexanes) to produce the title intermediate as a yellowish solid (227 mg, 78% yield). (m/z): $[M+H]^+$ calcd for $C_{44}H_{52}F_4N_8O_7$ 881.39. found 881.4.

(b) ((S)-1-{(2S,4S)-2-[4-(5'-Fluoro-4'-{[6-((R)-2-methyl-piperazin-1-yl)-pyridine-3-carbonyl]-amino}-2'-trifluoromethoxy-biphenyl-4-yl)-1H-imidazol-2-yl]-4-methyl-pyrrolidine-1-carbonyl}-2-methyl-propyl)-carbamic acid methyl ester The solid from the previous step (227 mg) was treated with 4 M HCl in 1,4-dioxane (1.67 mL) and HCl (0.51 mL) and the reaction mixture was stirred at RT for 1 h. The reaction mixture was concentrated and evaporated with ethyl acetate (2×) to produce the tri-HCl salt of the title intermediate as a yellow solid. (237 mg, 80% yield). (m/z): $[M+H]^+$ calcd for $C_{39}H_{44}F_4N_8O_5$ 781.34. found 781.3.

(c) [(S)-1-((2S,4S)-2-{4-[4'-({6-[(R)-4-(2,2-Dimethyl-propionyl)-2-methyl-piperazin-1-yl]-pyridine-3-carbonyl}-amino)-5'-fluoro-2'-trifluoromethoxy-biphenyl-4-yl]-1H-imidazol-2-yl}-4-methyl-pyrrolidine-1-carbonyl)-2-methyl-propyl]-carbamic acid methyl ester To the product of the previous step (15 mg, 0.017 mmol) dissolved in DMA (1 mL) was added N,N-diisopropylethylamine (14.4 μL, 0.083 mmol) followed by 2,2-dimethylpropanoyl chloride (24 mg, 0.020 mmol) and the reaction mixture was stirred at RT overnight, concentrated, dissolved in 1:1 acetic acid:water (1.5 mL) and purified by reverse phase HPLC to provide the di-TFA salt of the title compound (15 mg, 81% yield). (m/z): $[M+H]^+$ calcd for $C_{44}H_{52}F_4N_8O_6$ 865.39. found 865.8.

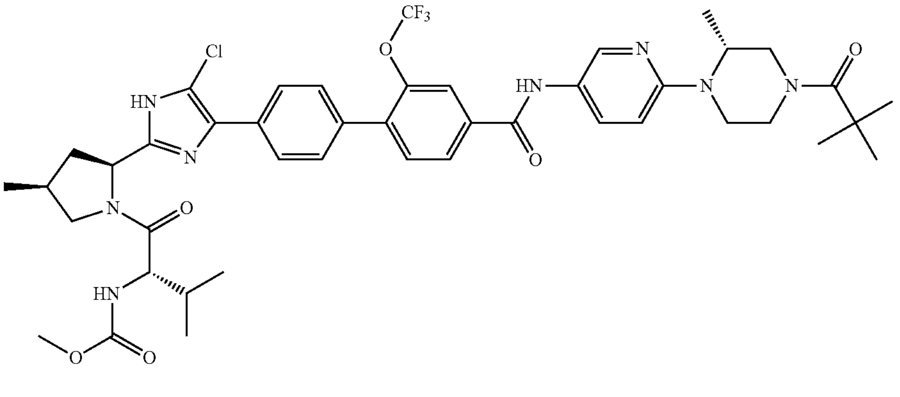 [SMILES: COC(=O)N[C@H](C(=O)N1C[C@@H](C)C[C@H]1c1nc(-c2ccc(-c3ccc(C(=O)Nc4ccc(N5CCN(C(=O)C(C)(C)C)C[C@H]5C)nc4)cc3OC(F)(F)F)cc2)c(Cl)[nH]1)C(C)C]

(a) {(S)-1-[(2S,4S)-2-(5-Chloro-4-{4'-[6-((R)-2-methyl-piperazin-1-yl)-pyridin-3-ylcarbamoyl]-2'-trifluoromethoxy-biphenyl-4-yl}-1H-imidazol-2-yl)-4-methyl-pyrrolidine-1-carbonyl}-2-methyl-propyl]-carbamic acid methyl ester To a mixture of 4'-{5-chloro-2-[(2S,4S)-1-((S)-2-methoxycarbonylamino-3-methyl-butyryl)-4-methyl-pyrrolidin-2-yl]-1H-imidazol-4-yl}-2-trifluoromethoxy-biphenyl-4-carboxylic acid TFA (48 mg, 0.06 mmol; Preparation 25) and HATU (27 mg, 0.07 mmol) in DMF (1 mL) at RT was added 4-(5-amino-pyridin-2-yl)-3-methyl-piperazine-1-carboxylic acid tert-butyl ester (21 mg, 0.07 mmol followed by N,N-diisopropylethylamine (67.6 μL, 0.39 mmol). The reaction mixture was stirred for 1 h, and partitioned between EtOAc (10 mL) and water (3 mL). The organic layer was washed with water (2 mL), dried over sodium sulfate, filtered, and concentrated to give a dark oil, which was purified by silica gel chromatography (0-100% EtOAc/Hexanes). Desired fractions were combined and concentrated to give a yellowish oil.

The oily residue from previous step was treated with 4 M HCl in 1,4-dioxane (1.0 mL) at RT for 30 min. The reaction mixture was concentrated, evaporated with EtOAc (2×2 mL) and dried under vacuum to give the tri-HCl salt of the title intermediate (47 mg) as a light yellowish solid. (m/z): $[M+H]^+$ calcd for $C_{39}H_{44}ClF_3N_8O_5$ 797.31. found 797.

(b) ((S)-1-{(2S,4S)-2-[5-Chloro-4-(4'-{6-[(R)-4-(2,2-dimethyl-propionyl)-2-methyl-piperazin-1-yl]-pyridin-3-ylcarbamoyl}-2'-trifluoromethoxy-biphenyl-4-yl)-1H-imidazol-2-yl]-4-methyl-pyrrolidine-1-carbonyl}-2-methyl-propyl)-carbamic acid methyl ester To a mixture of the product of the previous step (12 mg, 0.013 mmol) and N,N-diisopropylethylamine (13.6 μL, 0.078 mmol) in DMF (0.5 mL) at RT was added 2,2-dimethylpropanoyl chloride (1.92 μL, 0.016 mmol). The reaction mixture was stirred at RT for 1 h, concentrated, dissolved in 1:1 acetic acid:water (1.5 mL) and purified by reverse phase HPLC to provide the di-TFA salt of the title compound (6 mg). (m/z): $[M+H]^+$ calcd for $C_{44}H_{52}ClF_3N_8O_6$ 881.37. found 881.8.

Example 13

((S)-1-{(2S,4S)-2-[4-(4'-{[6-((R)-4-tert-Butyl-2-methyl-piperazin-1-yl)-pyridine-3-carbonyl]-amino}-5'-chloro-2'-trifluoromethoxy-biphenyl-4-yl)-1H-imidazol-2-yl]-4-methoxy-pyrrolidine-1-carbonyl}-2-methyl-propyl)-carbamic acid methyl ester

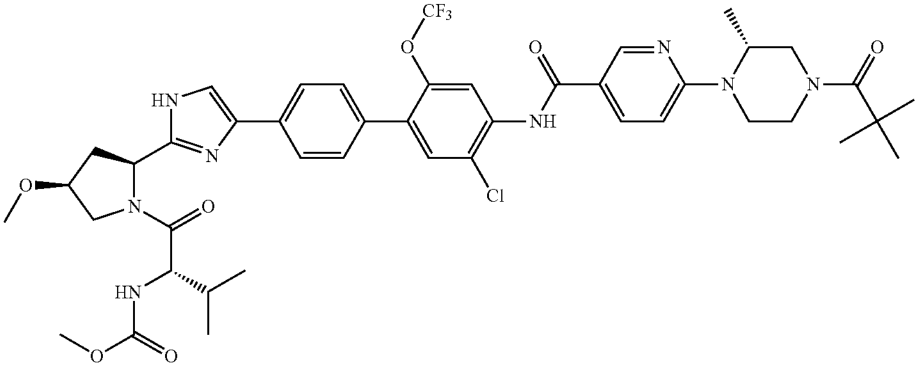 [SMILES: COC(=O)N[C@H](C(=O)N1C[C@@H](OC)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C]

To a solution of ((S)-1-{(2S,4S)-2-[4-(5'-chloro-4'-{[6-((R)-2-methyl-piperazin-1-yl)-pyridine-3-carbonyl]-amino}-2'-trifluoromethoxy-biphenyl-4-yl)-1H-imidazol-2-yl]-4-methoxy-pyrrolidine-1-carbonyl}-2-methyl-propyl)-carbamic acid methyl ester tri-HCl (10 mg, 0.01 mmol; Preparation 28) in DMA (1 mL) was added N,N-diisopropylethylamine (9.44 μL, 0.05 mmol) followed by 2,2-dimethyl-propanoyl chloride (1.31 mg, 0.01 mmol). The reaction mixture was stirred at RT overnight, concentrated by rotary evaporation, dissolved in 1:1 acetic acid:water (1.5 mL) and purified by reverse phase HPLC to provide the di-TFA salt of the title compound (7 mg, 51% yield) (m/z): $[M+H]^+$ calcd for $C_{44}H_{52}ClF_3N_8O_7$ 897.36. found 897.8.

Example 14A

[(S)-2-((2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-pyrrolidin-1-yl)-2-oxo-1-(tetrahydro-pyran-4-yl)-ethyl]-carbamic acid methyl ester

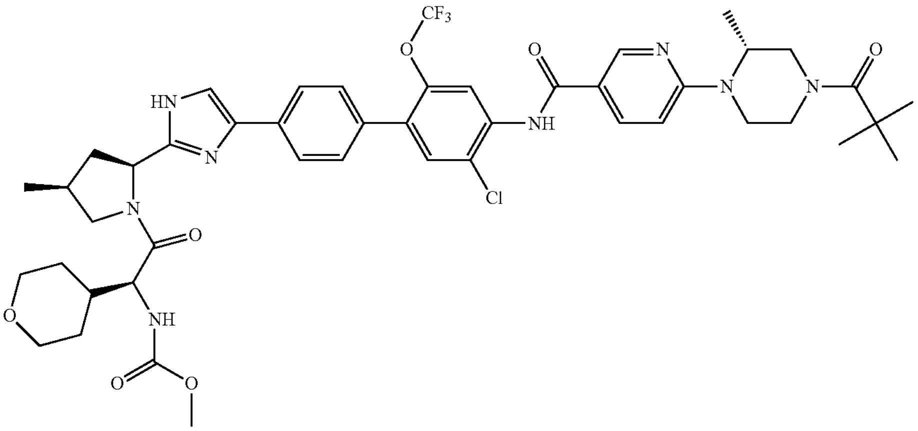 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C1CCOCC1]

To a solution of (S)-methoxycarbonylamino-(tetrahydro-pyran-4-yl)-acetic acid (9.4 mg, 0.046 mmol; Preparation 29) in DMA (5 mL) was added HATU (45.3 mg, 0.12 mmol). The reaction mixture was stirred at RT for 15 min, and N-{5-chloro-4'-[2-((2S,4S)-4-methyl-pyrrolidin-2-yl)-1H-imidazol-4-yl]-2-trifluoromethoxy-biphenyl-4-yl}-6-[(R)-4-(2,2-dimethyl-propionyl)-2-methyl-piperazin-1-yl]-nicotinamide tri-HCl (30.0 mg, 0.036 mmol; Preparation 31 was added followed by DIPEA (86.4 μL, 0.50 mmol). The reaction mixture was stirred at RT overnight, concentrated by rotary evaporation, dissolved in 1:1 acetic acid:water (1.5 mL) and purified by reverse phase HPLC to provide the di-TFA salt of the title compound (14 mg, 37% yield). (m/z): $[M+H]^+$ calcd for $C_{46}H_{54}ClF_3N_8O_7$ 923.38. found 923.8.

Example 14B

[(S)-2-((2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-pyrrolidin-1-yl)-2-oxo-1-(tetrahydro-pyran-4-yl)-ethyl]-carbamic acid methyl ester (a) (2S,4S)-tert-butyl 2-(4-(5'-chloro-4'-(6-((R)-2-methyl-4-pivaloylpiperazin-1-yl)nicotinamido)-2'-(trifluoromethoxy)-[1,1'-biphenyl]-4-yl)-1H-imidazol-2-yl)-4-methylpyrrolidine-1-carboxylate To a round bottom flask was added (2S,4S)-tert-butyl 2-(4-(4-bromophenyl)-1H-imidazol-2-yl)-4-methylpyrrolidine-1-carboxylate (10 g, 24.61 mmol), (R)-(5-chloro-4-(6-(2-methyl-4-pivaloylpiperazin-1-yl)nicotinamido)-2-(trifluoromethoxy)phenyl)boronic acid (14.16 g, 26.1 mmol), sodium bicarbonate (7.24 g, 86 mmol), bis(di-tert-butyl(4-dimethylaminophenyl)phosphine)dichloropalladium(II) (0.17 g, 0.246 mmol), 2 methyltetrahydrofuran (120 mL) and water (44.3 mL) to give a suspension. The reaction mixture was degassed with nitrogen for 10 min then heated at 70° C. overnight. Water (60 mL) was added and the layers were separated. The organic layer was washed with brine, dried over $Na_2SO_4$, and evaporated to give crude product (27.3 g). The crude product was purified by flash chromatography (300 g silica gel, 20-100% EtOAc (50 min), then 100% EtOAc (20 min)) to give the title intermediate (18.8 g; 93% yield) HPLC Method B: Retention time 14.99 min.

(b) N-(5-chloro-4'-(2-((2S,4S)-4-methylpyrrolidin-2-yl)-1H-imidazol-4-yl)-2-(trifluoromethoxy)-[1,1'-biphenyl]-4-yl)-6-((R)-2-methyl-4-pivaloylpiperazin-1-yl)nicotinamide A solution of the product of the previous step (18.8 g, 22.81 mmol) and DCM (82 mL) was cooled to 5° C. and then TFA (26.4 mL) was added. The reaction mixture was stirred overnight and concentrated. To the reaction mixture was added MTBE (300 mL), 1 N HCl (200 mL), and water (100 mL). The organic phase was extracted with 0.5 N HCl (100 mL). The combined aqueous phase was basified with 50% NaOH aqueous solution (17 mL), and extracted with isopropyl acetate (500 mL). The organic layer was dried over $Na_2SO_4$ and evaporated to give the title intermediate (13.6 g, 82% yield)). HPLC Method B: Retention time 11.75 min.

(c) [(S)-2-((2S,4S)-2-{4-[5 ({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methyl-pyrrolidin-1-yl)-2-oxo-1-(tetrahydro-pyran-4-yl)-ethyl]-carbamic acid methyl ester A solution of the product of the previous step (10 g, 13.81 mmol), (S)-2-((methoxycarbonyl)amino)-2-(tetrahydro-2H-pyran-4-yl)acetic acid (3.15 g, 14.50 mmol) and DMF (120 mL) was cooled to 0-10° C. and then HCTU (6.00 g, 14.50 mmol) was added, followed by DIPEA (4.82 ml, 27.6 mmol). The reaction mixture was stirred at RT overnight. Ethyl acetate (250 mL) and water (150 mL) were added; the organic layer was washed with sat. $Na_2CO_3$ (100 mL) and brine, dried over $Na_2SO_4$, and evaporated to give a first crude product (23.7 g). To the first crude product was added methanol (85 mL) and 2 N LiOH (7 mL). After 45 min, the reaction mixture was dried over $Na_2SO_4$ and evaporated to give a second crude product which was purified by flash chromatography (300 g silica gel, 1-8% methanol/DCM over 30 min then 8% over 20 min) to give a solid product (7.7 g). To the solid product was added THF (30 mL) and the resulting solution was added dropwise to hexane (165 mL). The resulting mixture was filtered and dried under vacuum overnight to provide the title compound (6.48 g, 49% yield) as a solid. HPLC Method B: Retention time 14.47 min.

Example 15A

[(S)-2-((2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methoxy-pyrrolidin-1-yl)-2-oxo-1-(tetrahydro-pyran-4-yl)-ethyl]-carbamic acid methyl ester

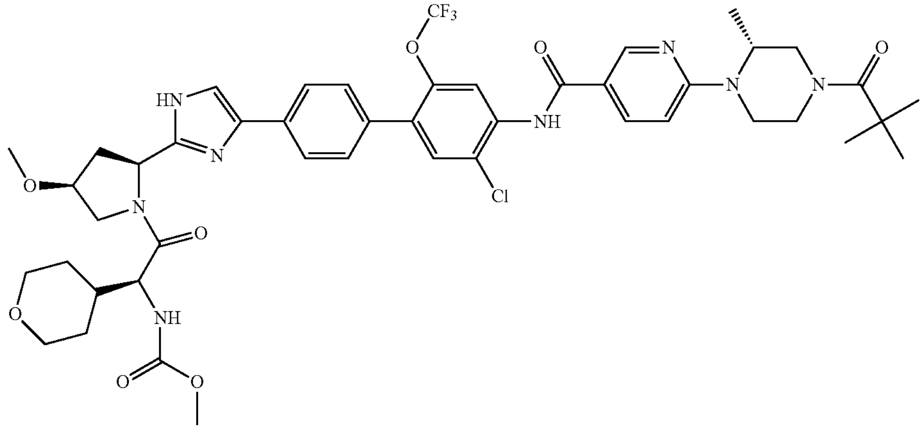 [SMILES: COC(=O)N[C@H](C(=O)N1C[C@@H](OC)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C1CCOCC1]

To a solution of (S)-methoxycarbonylamino-(tetrahydro-pyran-4-yl)-acetic acid (9.4 mg, 0.046 mmol; Preparation 29) in DMA (1 mL) was added HATU (6.4 mg, 0.017 mmol). The reaction mixture was stirred at RT for 15 min, and N-{5-chloro-4'-[2-((2S,4S)-4-methoxy-pyrrolidin-2-yl)-1H-imidazol-4-yl]-2-trifluoromethoxy-biphenyl-4-yl}-6-[(R)-4-(2,2-dimethyl-propionyl)-2-methyl-piperazin-1-yl]-nicotinamide tri-HCl (12.0 mg, 0.014 mmol; Preparation 32)

was added followed by DIPEA (12.3 μL, 0.07 mmol). The reaction mixture was stirred at RT overnight, concentrated by rotary evaporation, dissolved in 1:1 acetic acid:water (1.5 mL) and purified by reverse phase HPLC to provide the di-TFA salt of the title compound (9 mg, 56% yield). (m/z): $[M+H]^+$ calcd for $C_{46}H_{54}ClF_3N_8O_8$ 939.37. found 939.8.

Example 15B

[(S)-2-((2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methoxy-pyrrolidin-1-yl)-2-oxo-1-(tetrahydro-pyran-4-yl)-ethyl]-carbamic acid methyl ester (a) (2S,4S)-2-{4-[5'-Chloro-4'-({6-[(R)-4-(3-hydroxy-2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methoxy-pyrrolidine-1-carboxylic acid tert-butyl ester To a round bottom flask was added (2S,4S)-2-[4-(4-bromo-phenyl)-1H-imidazol-2-yl]-4-methoxy-pyrrolidine-1-carboxylic acid tert-butyl ester (5.0 g, 11.8 mmol) and (R)-5-chloro-4-(6-(2-methyl-4-pivaloylpiperazin-1-yl) nicotinamido)-2-(trifluoromethoxy)phenylboronic acid (6.75 g, 12.4 mmol; Preparation 44), potassium carbonate (5.73 g, 41.4 mmol), and bis(di-tert-butyl(4-dimethylaminophenyl)-phosphine)dichloropalladium(II) (0.092 g, 0.130 mmol), followed by degassed tetrahydrofuran (50 mL) and water (1.28 mL). The reaction mixture was degassed with nitrogen for 5 min then heated at 65° C. for 4 h, and cooled to RT. Water (100 mL) was added and the reaction mixture was extracted with EtOAc (200 mL). The organic layer was washed with NaOH (2×100 mL), water (2×200 mL) and brine, dried over $Na_2SO_4$ and evaporated to give crude product (12.25 g). The crude product was purified by flash chromatography (150 g silica gel, 50-100% EtOAc (10 min), then 100% EtOAc (30 min)) to give the title intermediate (4.2 g; 41% yield) HPLC Method B: Retention time 15.29 min.

(b) N-{5-Chloro-4'-[2-((2S,4S)-4-methoxy-pyrrolidin-2-yl)-1H-imidazol-4-yl]-2-trifluoromethoxy-biphenyl-4-yl}-6-[(R)-4-(2,2-dimethyl-propionyl)-2-methyl-piperazin-1-yl]-nicotinamide A solution of the product of the previous step (4.2 g, 5.00 mmol) and DCM (18.01 mL) was cooled to 5° C. and then TFA (5.78 mL) was added. The reaction mixture was stirred overnight and concentrated. Ethyl acetate (80 mL) was added; the reaction mixture was washed with 1 N NaOH (2×80 mL), water, and brine; dried over $Na_2SO_4$, and evaporated to give the title intermediate (3.56 g, 96% yield)). HPLC Method B: Retention time 12.33 min.

(c) [(S)-2-((2S,4S)-2-{4-[5'-Chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methoxy-pyrrolidin-1-yl)-2-oxo-1-(tetrahydro-pyran-4-yl)-ethyl]-carbamic acid methyl ester A solution of the product of the previous step (3.56 g, 4.81 mmol), (S)-2-((methoxycarbonyl)amino)-2-(tetrahydro-2H-pyran-4-yl)acetic acid (1.097 g, 5.05 mmol) and DMF (43 mL) was cooled to 0-10° C. and then HCTU (2.089 g, 5.05 mmol) was added, followed by DIPEA (1.68 mL, 9.62 mmol). The reaction mixture was stirred at RT for 3 h. Ethyl acetate (150 mL) and water (100 mL) were added; the organic layer was washed with sat. $Na_2CO_3$ (100 mL) and brine, dried over $Na_2SO_4$, and evaporated to give the crude product (5.4 g), which was purified by flash chromatography (133 g silica gel, EtOAc to 10% MeOH/EtOAc (15 min) then 10% MeOH/EOAc (15 min)) to give the title compound (2.8 g, 61% yield) which was dried under vacuum overnight. HPLC Method B: Retention time 13.70 min.

Example 16

[(S)-2-((2S,4S)-2-{4-[5'-Chloro-4'-({6-[(R)-4-(3-hydroxy-2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-4-methoxy-pyrrolidin-1-yl)-2-oxo-1-(tetrahydro-pyran-4-yl)-ethyl]-carbamic acid methyl ester

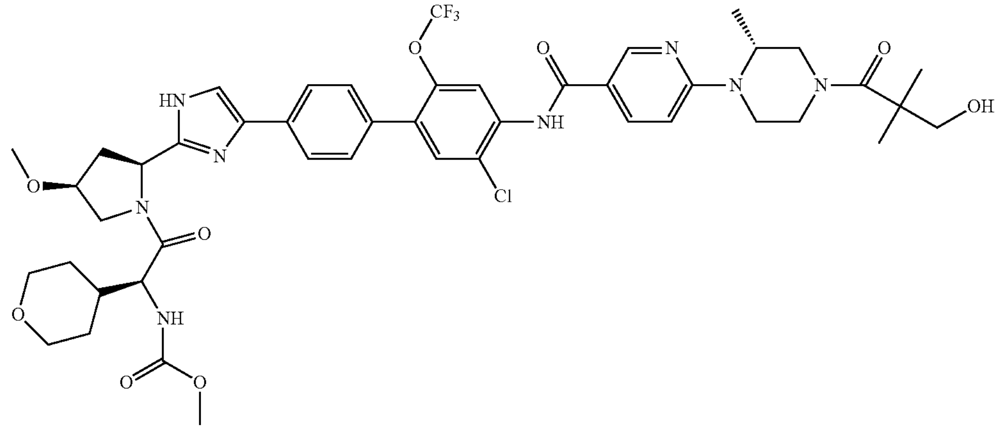 [SMILES: COC(=O)N[C@H](C(=O)N1C[C@@H](OC)C[C@H]1c1nc(-c2ccc(-c3cc(Cl)c(NC(=O)c4ccc(N5CCN(C(=O)C(C)(C)CO)C[C@H]5C)nc4)cc3OC(F)(F)F)cc2)c[nH]1)C1CCOCC1]

To a solution of (S)-methoxycarbonylamino-(tetrahydro-pyran-4-yl)-acetic acid (37.6 mg, 0.17 mmol) in DMA (1 mL) was added HATU (65.9 mg, 0.17 mmol). The reaction mixture was stirred for 15 min and N-{5-chloro-4'-[2-((2S,4S)-4-methoxy-pyrrolidin-2-yl)-1H-imidazol-4-yl]-2-trifluoromethoxy-biphenyl-4-yl}-6-[(R)-4-(3-hydroxy-2,2-dimethyl-propionyl)-2-methyl-piperazin-1-yl]-nicotinamide 3HCl (100 mg, 0.12 mmol; Preparation 34) was added followed by DIPEA (0.10 mL, 0.58 mmol) and the reaction mixture was stirred at RT overnight, concentrated by rotary evaporation, dissolved in 1:1 acetic acid:water (4 mL) and purified by reverse phase HPLC. Fractions containing the desired compound were combined and lyophilized to provide the di-TFA salt of the title compound (65.2 mg) as a white powder. Impure fractions were lyophilized, dissolved in 1:1 acetic acid:water (1.5 mL) and purified by reverse phase HPLC to provide additional di-TFA salt of the title compound (75 mg total, 55% yield). (m/z): $[M+H]^+$ calcd for $C_{46}H_{54}ClF_3N_8O_9$ 955.37. found 955.8.

Example 17

(R)-4-[5-(5-Chloro-4'-{2-[(2S,4S)-4-cyano-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-3-methyl-piperazine-1-carboxylic acid tert-butyl ester

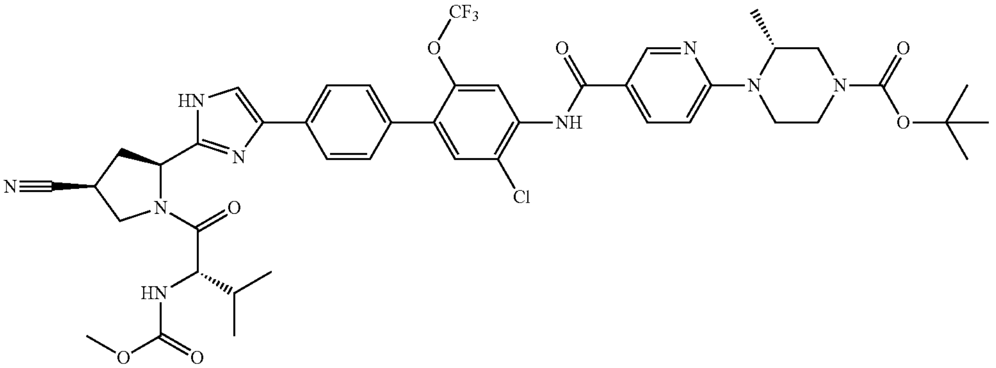 [SMILES: COC(=O)N[C@H](C(=O)N1C[C@@H](C#N)C[C@H]1c1nc(-c2ccc(-c3cc(Cl)c(NC(=O)c4ccc(N5CCN(C(=O)OC(C)(C)C)C[C@H]5C)nc4)cc3OC(F)(F)F)cc2)c[nH]1)C(C)C]

A solution of [(S)-1-((2S,4S)-4-cyano-2-{4-[4-(4,4,5,5-tetramethyl-[1,3,2]dioxaborolan-2-yl)-phenyl]-1H-imidazol-2-yl}-pyrrolidine-1-carbonyl)-2-methyl-propyl]-carbamic acid methyl ester (0.10 g, 0.19 mmol), (R)-4-[5-(4-bromo-2-chloro-5-trifluoromethoxy-phenylcarbamoyl)-pyridin-2-yl]-3-methyl-piperazine-1-carboxylic acid tert-butyl ester (113.9 mg, 0.19 mmol) and potassium carbonate (119.3 mg, 0.86 mmol) in toluene (0.46 mL) and water (0.24 mL, 13.56 mmol) was degassed with nitrogen for 20 min and then $Pd(dppf)Cl_2CH_2Cl_2$ (6.27 mg, 0.0076 mmol) was added and the reaction was degassed with nitrogen for 15 min. The reaction mixture was heated at 100° C. for 12 h, concentrated under vacuum, and purified by reverse phase HPLC. The pure fractions were combined and concentrated under vacuum to afford the di-TFA salt of the title compound (13 mg, 6% yield). (m/z): $[M+H]^+$ calcd for $C_{44}H_{49}ClF_3N_9O_7$ 908.34. found 908.7.

Example 18

[(S)-1-((2S,4S)-4-Carbamoyl-2-{4-[5'-chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-pyrrolidine-1-carbonyl)-2-methyl-propyl]-carbamic acid methyl ester

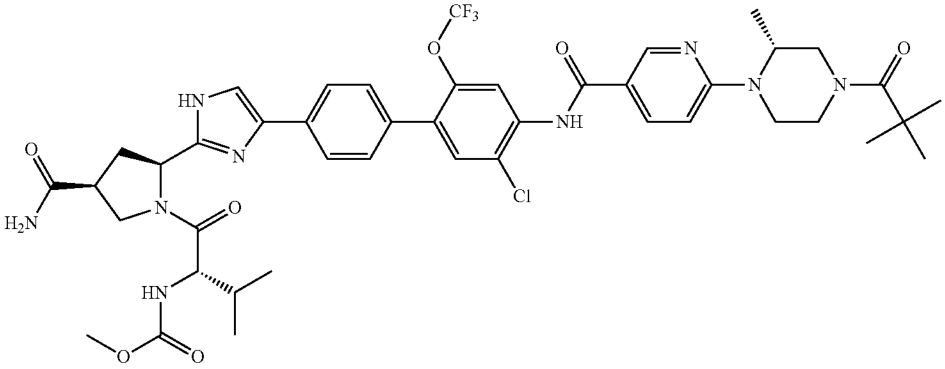 [SMILES: COC(=O)N[C@H](C(=O)N1C[C@@H](C(N)=O)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C]

(a) ((S)-1-{(2S,4S)-4-Carbamoyl-2-[4-(5'-chloro-4'-{[6-((R)-2-methyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester A solution of (R)-4-[5-(5-chloro-4'-{2-[(2S,4S)-4-cyano-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-3-methyl-piperazine-1-carboxylic acid tert-butyl ester 2 TFA (6.3 mg, 0.0055 mmol; Example 17) in 4.0 M HCl in 1,4-dioxane (0.14 mL) was stirred at RT for 1 h and concentrated under vacuum to provide the title intermediate as a yellow powder. (m/z): $[M+H]^+$ calcd for $C_{39}H_{43}ClF_3N_9O_6$ 826.30. found 826.5.

(b) ([(S)-1-((2S,4S)-4-Carbamoyl-2-{4-[5'-chloro-4'-({6-[(R)-4-(2,2-dimethyl-propionyl)-2-methyl-piperazin-1-yl]-pyridine-3-carbonyl}-amino)-2'-trifluoromethoxy-biphenyl-4-yl]-1H-imidazol-2-yl}-pyrrolidine-1-carbonyl)-2-methyl-propyl]-carbamic acid methyl ester The product of the previous step was dissolved in DMA (0.28 mL, 2.99 mmol), and 2,2-dimethylpropanoyl chloride (0.68 μL, 0.0055 mmol) and DIPEA (4.83 μL, 0.028 mmol) were subsequently added. The solution was stirred at RT for 1 h, concentrated under vacuum, dissolved in a 1:1 acetic acid:ACN solution (1.5 mL), and purified by reverse phase HPLC to provide the di-TFA salt of the title compound (4 mg, 57% yield). (m/z): $[M+H]^+$ calcd for $C_{44}H_{51}ClF_3N_9O_7$ 910.36. found 910.8.

Example 19

Methyl ((S)-2-((2S,4S)-2-(4-(5'-chloro-4'-((6-((R)-2-methyl-4-pivaloylpiperazin-1-yl)pyridin-3-yl)carbamoyl)-2'-(trifluoromethoxy)-[1,1'-biphenyl]-4-yl)-1H-imidazol-2-yl)-4-methylpyrrolidin-1-yl)-2-oxo-1-(tetrahydro-2H-pyran-4-yl)ethyl)carbamate (a) (R)-tert-butyl 4-(5-(5-Chloro-4'-(2-((2S,4S)-1-((S)-2-((methoxycarbonyl)amino)-2-(tetrahydro-2H-pyran-4-yl)acetyl)-4-methylpyrrolidin-2-yl)-1H-imidazol-4-yl)-2-(trifluoromethoxy)-[1,1'-biphenyl]-4-ylcarboxamido)pyridin-2-yl)-3-methylpiperazine-1-carboxylate To a mixture of toluene (1 mL) and water (0.4 mL) was added methyl ((S)-2-((2S,4S)-4-methyl-2-(5-(4-(4,4,5,5-tetramethyl-1,3,2-dioxaborolan-2-yl)phenyl)-1H-imidazol-2-yl)pyrrolidin-1-yl)-2-oxo-1-(tetrahydro-2H-pyran-4-yl)ethyl)carbamate (90 mg, 0.16 mmol; Preparation 46), (R)-tert-butyl 4-(5-(4-bromo-2-chloro-5-(trifluoromethoxy)benzamido)pyridin-2-yl)-3-methylpiperazine-1-carboxylate (97 mg, 0.16 mmol; Preparation 49) and potassium carbonate (118 mg, 0.86 mmol). The reaction mixture was sparged under nitrogen, $Pd(dppf)Cl_2$ (7.17 mg, 9.77 μmol) was added and the reaction mixture was sparged under nitrogen, sealed, heated at 90° C. overnight, and extracted with ethyl acetate, water, and brine. The organic layer was dried over sodium sulfate, filtered, concentrated, and purified by silica gel chromatography (12 g column, 0-100% ethyl acetate:hexanes) to produce the title intermediate (70.3 mg, 45.9% yield) as a yellow solid. (m/z): $[M+H]^+$ calcd for $C_{46}H_{54}ClF_3N_8O_8$ 939.37. found 939.30.

(b) Methyl ((S)-2-((2S,4S)-2-(4-(5'-chloro-4'-((6-((R)-2-methylpiperazin-1-yl)pyridin-3-yl)carbamoyl)-2'-(trifluoromethoxy)-[1,1'-biphenyl]-4-yl)-1H-imidazol-2-yl)-4-methylpyrrolidin-1-yl)-2-oxo-1-(tetrahydro-2H-pyran-4-yl)ethyl)carbamate The product of the previous step (70.3 mg, 0.075 mmol) was treated with 4 M HCl in dioxane (1 mL, 0.075 mmol) and stirred at RT for 1 h. The reaction mixture was concentrated and evaporated with ethyl acetate (2×) to produce the tri-HCl salt of the title intermediate (70.5 mg, 99% yield) as a yellow solid. (m/z): $[M+H]^+$ calcd for $C_{41}H_{46}ClF_3N_8O_6$ 839.32. found 839.20.

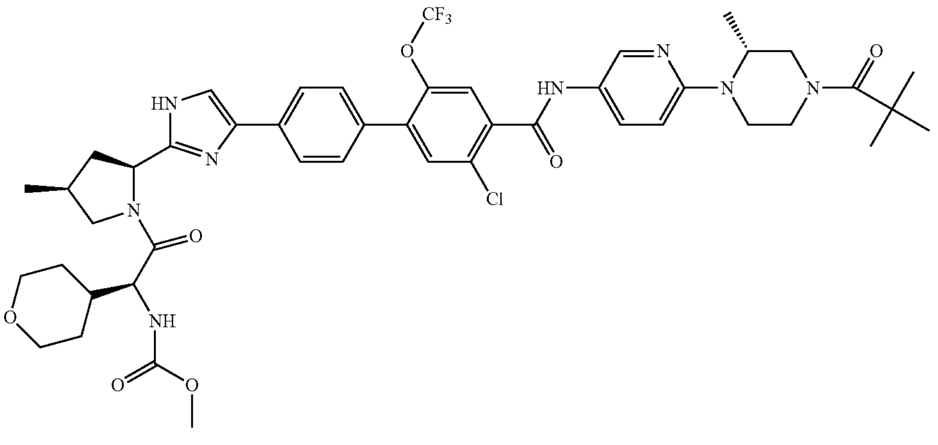 [SMILES: COC(=O)N[C@H](C(=O)N1C[C@@H](C)C[C@H]1c1nc(-c2ccc(-c3cc(Cl)c(C(=O)Nc4ccc(N5CCN(C(=O)C(C)(C)C)C[C@H]5C)nc4)cc3OC(F)(F)F)cc2)c[nH]1)C1CCOCC1]

(c) Methyl ((S)-2-((2S,4S)-2-(4-(5'-chloro-4'-((6-((R)-2-methyl-4-pivaloylpiperazin-1-yl)pyridin-3-yl)carbamoyl)-2'-(trifluoromethoxy)-[1,1'-biphenyl]-4-yl)-1H-imidazol-2-yl)-4-methylpyrrolidin-1-yl)-2-oxo-1-(tetrahydro-2H-pyran-4-yl)ethyl)carbamate To a solution of the product of the previous step (70.5 mg, 0.074 mmol) and DIPEA (0.091 ml, 0.52 mmol) dissolved in DMF (0.5 ml) was added pivaloyl chloride (9.0 mg, 0.075 mmol). The reaction mixture was stirred at RT for 30 min. The reaction mixture was concentrated, dissolved in 1:1 acetic acid:water (1.5 mL) and purified by reverse-phase HPLC. Fractions containing desired product were freeze dried to produce the di-TFA salt of the title compound as a white powder (32.0 mg, 37.2% yield). (m/z): $[M+H]^+$ calcd for $C_{46}H_{54}ClF_3N_8O_2$ 923.38. found 923.30.

Example 20

Methyl ((S)-2-((2S,4S)-2-(4-(2'-chloro-4'-((6-((R)-2-methyl-4-pivaloylpiperazin-1-yl)pyridin-3-yl)carbamoyl)-6'-(trifluoromethoxy)-[1,1'-biphenyl]-4-yl)-1H-imidazol-2-yl)-4-methylpyrrolidin-1-yl)-2-oxo-1-(tetrahydro-2H-pyran-4-yl)ethyl)carbamate

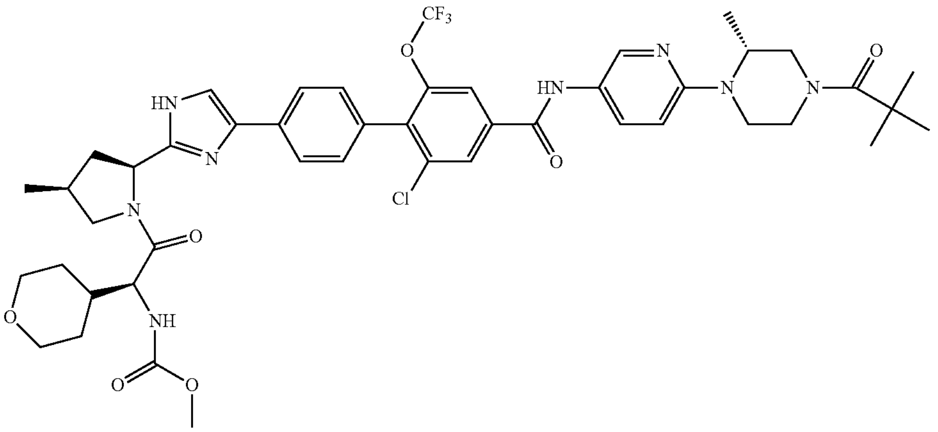 [SMILES: COC(=O)N[C@H](C(=O)N1C[C@@H](C)C[C@H]1c1nc(-c2ccc(-c3c(Cl)cc(C(=O)Nc4ccc(N5CCN(C(=O)C(C)(C)C)C[C@H]5C)nc4)cc3OC(F)(F)F)cc2)c[nH]1)C1CCOCC1]

(a) (2S,4S)-tert-butyl 2-(4 (2' chloro 4' ((6 ((R)-2 methyl-4-pivaloylpiperazin-1-yl)pyridin-3-yl)carbamoyl)-6'-(trifluoromethoxy)-[1,1'-biphenyl]-4-yl)-1H-imidazol-2-yl)-4-methylpyrrolidine-1-carboxylate To a mixture of (R)-4-bromo-3-chloro-N-(6-(2-methyl-4-pivaloylpiperazin-1-yl)pyridin-3-yl)-5-(trifluoromethoxy)benzamide (80.3 mg, 0.14 mmol; Preparation 51) and (2S,4S)-tert-butyl 4-methyl-2-(4-(4-(4,4,5,5-tetramethyl-1,3,2-dioxaborolan-2-yl)phenyl)-1H-imidazol-2-yl)pyrrolidine-1-carboxylate (63.0 mg, 0.14 mmol) in a mixture of toluene (0.9 mL) and water (0.3 mL) was added potassium carbonate (86 mg, 0.63 mmol). The reaction mixture was flushed with nitrogen, $PdCl_2(dppf)$ (6.1 mg, 8.34 μmol) was added. The reaction mixture was capped, heated at 100° C. overnight, cooled to RT and partitioned between EtOAc (5 mL) and water (2 mL). The organic layer was dried over sodium sulfate, filtered and concentrated to give a brown oil, which was purified by silica gel chromatography (12 g silica gel, 0-100% EtOAc/hexanes). Desired fractions were combined and concentrated to give the title intermediate (58.1 mg, 51% yield) as a yellowish oil. (m/z): $[M+H]^+$ calcd for $C_{42}H_{49}ClF_3N_2O_5$ 824.34. found 824.

(b) 2-chloro-N-(6-((R)-2-methyl-4-pivaloylpiperazin-1-yl)pyridin-3-yl)-4'-(2-((2S,4S)-4-methylpyrrolidin-2-yl)-1H-imidazol-4-yl)-6-(trifluoromethoxy)-[1,1'-biphenyl]-4-carboxamide To the product of the previous step (58.1 mg, 0.07 mmol) was added 4.0 N HCl in dioxane (0.18 mL, 0.70 mmol). After 30 min, the reaction mixture was concentrated and evaporated with EtOAc (3×3 mL) to give the di-HCl salt of the title intermediate as a yellowish solid. (m/z): $[M+H]^+$ calcd for $C_{32}H_{41}ClF_3N_2O_3$ 724.29. found 724.

(c) Methyl ((S)-2-((2S,4S)-2-(4-(2'-chloro-4'-((6-((R)-2-methyl-4-pivaloylpiperazin-1-yl)pyridin-3-yl)carbamoyl)-6'-(trifluoromethoxy)-[1,1'-biphenyl]-4-yl)-1H-imidazol-2-yl)-4-methylpyrrolidin-1-yl)-2-oxo-1-(tetrahydro-2H-pyran-4-yl)ethyl)carbamate To a mixture of the product of the previous step (65.8 mg, 0.083 mmol) and (S)-2-((methoxycarbonyl)amino)-2-(tetrahydro-2H-pyran-4-yl)acetic acid (19.7 mg, 0.091 mmol) in DMA (0.5 mL) at RT was added HATU (34.5 mg, 0.091 mmol) and DIPEA (0.043 mL, 0.248 mmol). The reaction mixture was stirred at RT overnight, concentrated, dissolved in 1:1 acetic acid:water (1.5 mL), filtered and purified by reverse phase HPLC. Desired fractions were combined and freeze dried to give the di-TFA salt of the title compound (38.9 mg, 37% yield) as a white solid. (m/z): $[M+H]^+$ calcd for $C_{46}H_{54}ClF_3N_8O_7$ 923.38. found 923.6.

Example 21

Methyl ((S)-2-((2S,4S)-2-(4-(3'-fluoro-4'-((6-((R)-2-methyl-4-pivaloyl-piperazin-1-yl)pyridin-3-yl)carbamoyl)-2'-(trifluoromethoxy)-[1,1'-biphenyl]-4-yl)-1H-imidazol-2-yl)-4-methylpyrrolidin-1-yl)-2-oxo-1-(tetrahydro-2H-pyran-4-yl)ethyl)carbamate

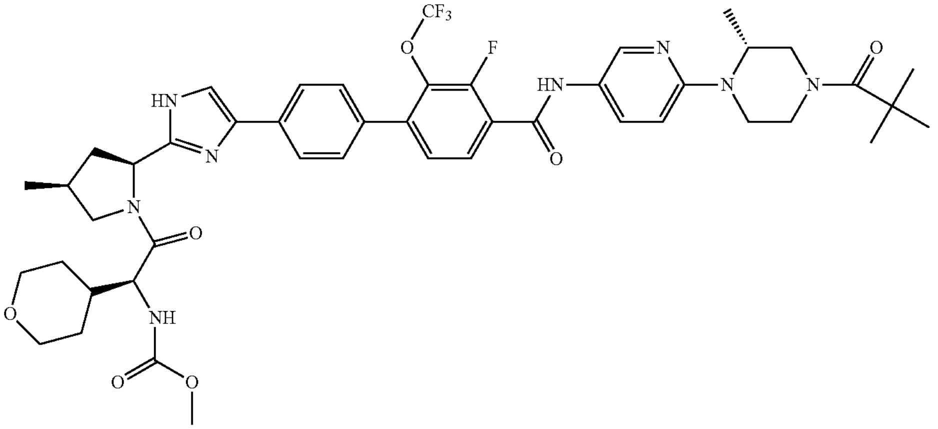 [SMILES: COC(=O)N[C@H](C(=O)N1C[C@@H](C)C[C@H]1c1nc(-c2ccc(-c3ccc(C(=O)Nc4ccc(N5CCN(C(=O)C(C)(C)C)C[C@H]5C)nc4)c(F)c3OC(F)(F)F)cc2)c[nH]1)C1CCOCC1]

(a) (2S,4S)-tert-butyl 2-(4 (3' fluoro 4'-((6 ((R)-2-methyl-4-pivaloylpiperazin-1-yl)pyridin-3-yl)carbamoyl)-2'-(trifluoromethoxy)-[1,1'-biphenyl]-4-yl)-1H-imidazol-2-yl)-4-methylpyrrolidine-1-carboxylate To a solution of (2S,4S)-tert-butyl 4-methyl-2-(4-(4-(4,4,5,5-tetramethyl-1,3,2-dioxaborolan-2-yl)phenyl)-1H-imidazol-2-yl)pyrrolidine-1-carboxylate (68.6 mg, 0.15 mmol) and (R)-4-bromo-2-fluoro-N-(6-(2-methyl-4-pivaloylpiperazin-1-yl)pyridin-3-yl)-3-(trifluoromethoxy)benzamide (85 mg, 0.15 mmol, Preparation 52) and potassium carbonate (110 mg, 0.80 mmol) in a mixture of toluene (1.8 mL) and water (0.6 mL) was added $PdCl_2$(dppf) (6.7 mg, 9.08 μmol). The mixture was sparged under nitrogen for 2 min and heated at 100° C. overnight and extracted with EtOAc and water. The organic layer was dried over sodium sulfate, filtered, concentrated, and purified by silica gel chromatography (12 g silica, 0-100% EtOAc:hexanes over 20 min), to provide the title intermediate (86.9 mg, 71% yield) as a yellow solid. (m/z): $[M+H]^+$ calcd for $C_{42}H_{49}F_4N_7O_5$ 808.37. found 808.7.

(b) 3-fluoro-N-(6-((R)-2-methyl-4-pivaloylpiperazin-1-yl)pyridin-3-yl)-4'-(2-((2S,4S)-4-methylpyrrolidin-2-yl)-1H-imidazol-4-yl)-2-(trifluoromethoxy)-[1,1'-biphenyl]-4-carboxamide To the product of the previous step (86.9 mg, 0.11 mmol) was added 4 N HCl in dioxane (2 mL, 8.00 mmol). The reaction mixture was stirred at RT for 1 h, concentrated, and evaporated with EtOAc (2×) to produce the di-HCl salt of the title intermediate (83 mg, 99% yield) as a yellow solid. (m/z): $[M+H]^+$ calcd for $C_{37}H_{41}F_4N_7O_3$ 708.32. found 708.3.

(c) Methyl ((S)-2-((2S,4S)-2-(4-(3'-fluoro-4'-((6-((R)-2-methyl-4-pivaloyl-piperazin-1-yl)pyridin-3-yl)carbamoyl)-2'-(trifluoromethoxy)-[1,1'-biphenyl]-4-yl)-1H-imidazol-2-yl)-4-methylpyrrolidin-1-yl)-2-oxo-1-(tetrahydro-2H-pyran-4-yl)ethyl)carbamate To a solution of the product of the previous step (83 mg, 0.11 mmol) and DIPEA (0.094 mL, 0.54 mmol) in DMF (1 mL) was added (S)-2-((methoxycarbonyl)amino)-2-(tetrahydro-2H-pyran-4-yl)acetic acid (23 mg, 0.108 mmol) and HATU (51 mg, 0.14 mmol). The reaction mixture was stirred at RT for 1 h, concentrated, dissolved in 1:1 acetic acid:water (1.5 mL) and purified by preparative HPLC to provide the di-TFA salt of the title compound (67.1 mg). (m/z): $[M+H]^+$ calcd for $C_{46}H_{54}F_4NH_8O_7$ 907.41. found 907.6.

Using synthetic methods similar to those exemplified above, the compounds of Examples 22-24 may be prepared.

Example 22

Methyl (S)-2-((2S,4S)-2-(4-(5'-chloro-4'-(6-((R)-2-methyl-4-pivaloylpiperazin-1-yl)nicotinamido)-2'-(trifluoromethoxy)biphenyl-4-yl)-1H-imidazol-2-yl)-4-methylpyrrolidin-1-yl)-1-((2S,6S)-2,6-dimethyltetrahydro-2H-pyran-4-yl)-2-oxoethylcarbamate

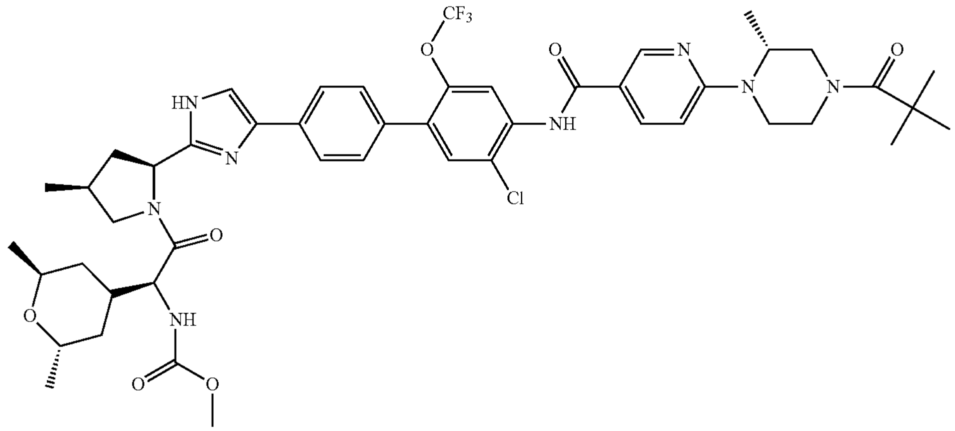 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C1C[C@H](C)O[C@@H](C)C1]

Example 23

Methyl (S)-2-((2S,4S)-2-(4-(5'-chloro-4'-(6-((R)-2-methyl-4-pivaloylpiperazin-1-yl)pyridin-3-ylcarbamoyl)-2'-(trifluoromethoxy)biphenyl-4-yl)-1H-imidazol-2-yl)-4-methylpyrrolidin-1-yl)-1-((2S,6S)-2,6-dimethyltetrahydro-2H-pyran-4-yl)-2-oxoethylcarbamate

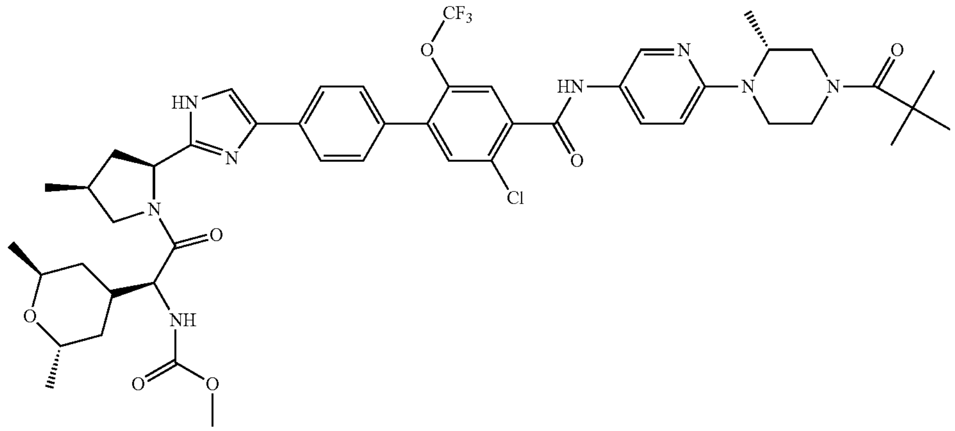 [SMILES: COC(=O)N[C@H](C(=O)N1C[C@@H](C)C[C@H]1c1nc(-c2ccc(-c3cc(Cl)c(C(=O)Nc4ccc(N5CCN(C(=O)C(C)(C)C)C[C@H]5C)nc4)cc3OC(F)(F)F)cc2)c[nH]1)C1C[C@H](C)O[C@@H](C)C1]

Example 24

Methyl (S)-2-((2S,5S)-2-(4-(3'-fluoro-4'-(6-((R)-2-methyl-4-pivaloylpiperazin-1-yl)pyridin-3-ylcarbamoyl)-2'-(trifluoromethoxy)biphenyl-4-yl)-1H-imidazol-2-yl)-5-methylpyrrolidin-1-yl)-2-oxo-1-(tetrahydro-2H-pyran-4-yl)ethylcarbamate

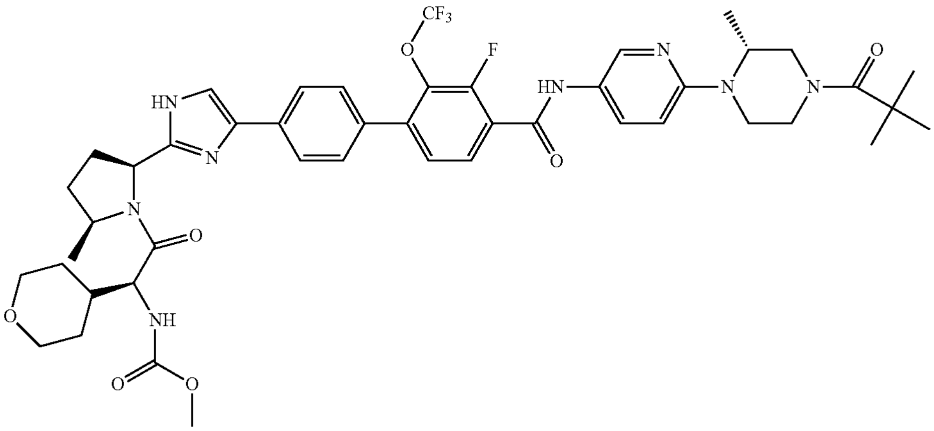 [SMILES: COC(=O)N[C@H](C(=O)N1[C@@H](C)CC[C@H]1c1nc(-c2ccc(-c3ccc(C(=O)Nc4ccc(N5CCN(C(=O)C(C)(C)C)C[C@H]5C)nc4)c(F)c3OC(F)(F)F)cc2)c[nH]1)C1CCOCC1]

Also using similar synthetic methods, the compounds of Tables 1-29 were prepared where a blank in any column denotes hydrogen and the symbol (R) or (S) in any column denotes the orientation of the corresponding chiral carbon atom.

TABLE 1

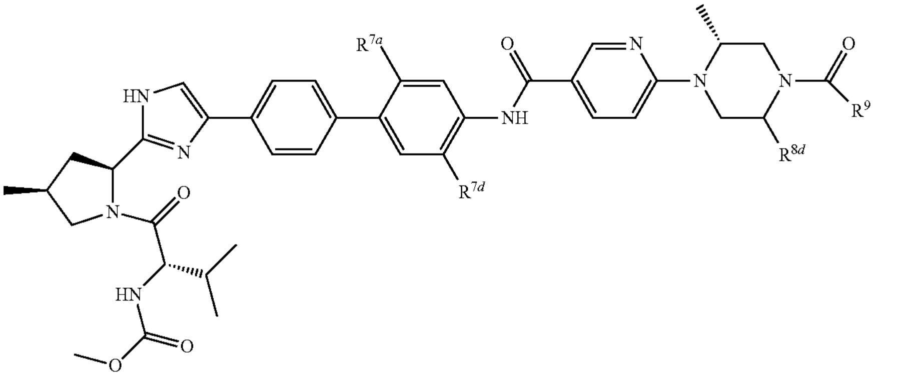

| Ex No. | $R^{7a}$ | $R^{7d}$ | $R^{8d(\#)}$ | $R^9$ | Formula | Calc [M + H]$^+$ | Found [M + H]$^+$ |
|---|---|---|---|---|---|---|---|
| 1-1 | $OCF_3$ | F | | $NHCH_3$ | $C_{41}H_{47}F_4N_9O_6$ | 838.36 | 838.8 |
| 1-2 | $OCF_3$ | F | | (a) | $C_{52}H_{64}F_4N_{10}O_9$ | 1049.48 | 1050.2 |
| 1-3 | $OCF_3$ | F | | 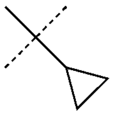 | $C_{43}H_{48}F_4N_8O_6$ | 849.36 | 850.0 |
| 1-4 | $CF_3$ | F | | (a) | $C_{52}H_{64}F_4N_{10}O_8$ | 1033.48 | 1032.6 |
| 1-5 | $CF_3$ | F | | 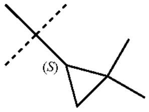 | $C_{45}H_{52}F_4N_8O_5$ | 861.40 | 860.6 |

TABLE 1-continued

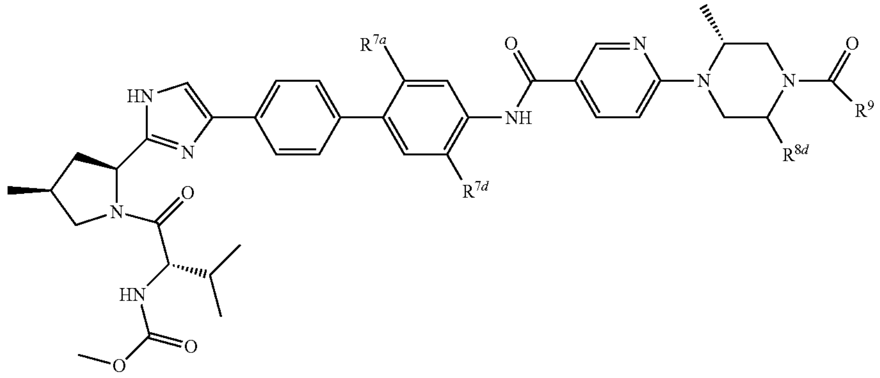

| Ex No. | $R^{7a}$ | $R^{7d}$ | $R^{8d(\#)}$ | $R^9$ | Formula | Calc [M + H]+ | Found [M + H]+ |
|---|---|---|---|---|---|---|---|
| 1-6 | $CF_3$ | F | $CH_3$ | (a) | $C_{53}H_{66}F_4N_{10}O_8$ | 1047.50 | 1046.6 |
| 1-7 | $CF_3$ | F | $CH_3$ | 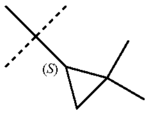 | $C_{46}H_{54}F_4N_8O_5$ | 875.42 | 874.6 |
| 1-8 | $CF_3$ | F | $CH_3$ | $NHCH_3$ | $C_{42}H_{49}F_4N_9O_5$ | 836.38 | 835.6 |
| 1-9 | $CF_3$ | F | | $NHCH_3$ | $C_{41}H_{47}F_4N_9O_5$ | 822.36 | 821.6 |
| 1-10 | $OCF_3$ | F | | 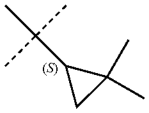 | $C_{45}H_{52}F_4N_8O_6$ | 877.39 | 877 |
| 1-11 | $CF_3$ | Cl | $CH_3$ | 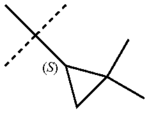 | $C_{46}H_{54}ClF_3N_8O_5$ | 891.39 | 891.6 |
| 1-12 | $CF_3$ | Cl | $CH_3$ | $NHCH_3$ | $C_{42}H_{49}ClF_3N_9O_5$ | 852.35 | 852.6 |
| 1-13 | $OCF_3$ | F | $CH_3$ | 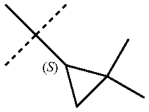 | $C_{46}H_{54}F_4N_8O_6$ | 891.41 | 890.6 |
| 1-14 | $OCF_3$ | F | $CH_3$ | 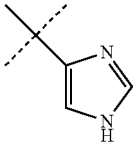 | $C_{44}H_{48}F_4N_{10}O_6$ | 889.37 | 888.6 |
| 1-15 | $OCF_3$ | F | $CH_3$ | 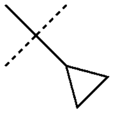 | $C_{44}H_{50}F_4N_8O_6$ | 863.38 | 862.6 |
| 1-16 | $OCF_3$ | F | $CH_3$ | $NHCH_3$ | $C_{42}H_{49}F_4N_9O_6$ | 852.37 | 851.6 |
| 1-17 | $OCF_3$ | Cl | | $NHCH_3$ | $C_{41}H_{47}ClF_3N_9O_6$ | 854.33 | 854.6 |
| 1-18 | $OCF_3$ | Cl | | 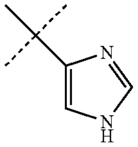 | $C_{43}H_{46}ClF_3N_{10}O_6$ | 891.32 | 891.6 |

TABLE 1-continued
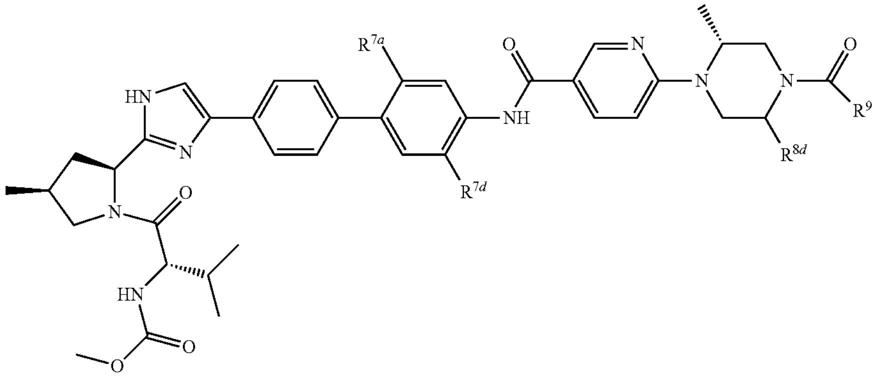
| Ex No. | $R^{7a}$ | $R^{7d}$ | $R^{8d(\#)}$ | $R^9$ | Formula | Calc [M + H]$^+$ | Found [M + H]$^+$ |
|---|---|---|---|---|---|---|---|
| 1-19 | $OCF_3$ | Cl | $CH_3$ | 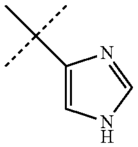 | $C_{44}H_{48}ClF_3N_{10}O_6$ | 905.34 | 905.6 |
| 1-20 | $OCF_3$ | Cl | $CH_3$ | 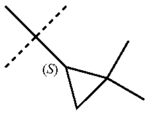 | $C_{46}H_{54}ClF_3N_8O_6$ | 907.38 | 907.6 |
| 1-21 | $CF_3$ | F | ($CH_3$ | 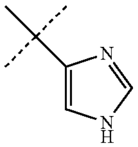 | $C_{44}H_{48}F_4N_{10}O_5$ | 873.37 | 873.6 |
| 1-22 | $OCF_3$ | Cl | | 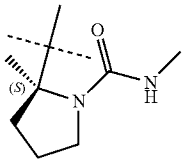 | $C_{47}H_{56}ClF_3N_{10}O_7$ | 965.4 | 966.0 |
| 1-23 | $OCF_3$ | Cl | $CH_3$ | 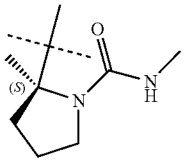 | $C_{48}H_{58}ClF_3N_{10}O_7$ | 979.41 | 980.0 |
| 1-24 | $OCF_3$ | F | $CH_3$ | 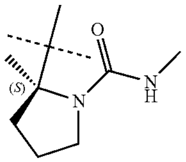 | $C_{48}H_{58}F_4N_{10}O_7$ | 963.44 | 963.6 |
| 1-25 | $OCF_3$ | F | | 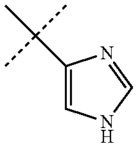 | $C_{43}H_{46}F_4N_{10}O_6$ | 875.35 | 875.8 |

TABLE 1-continued
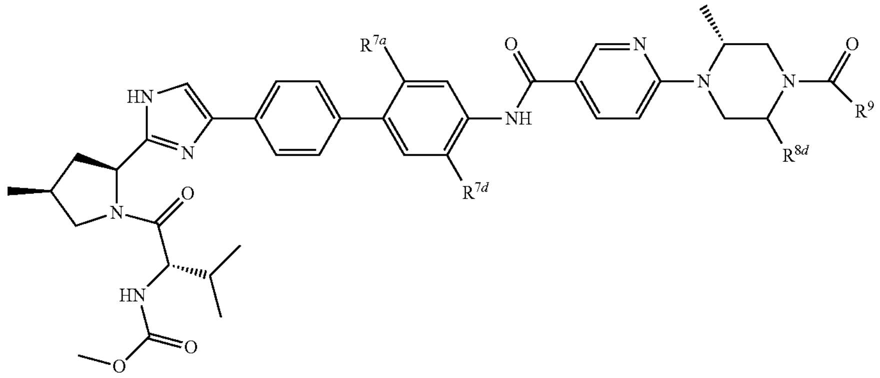
| Ex No. | $R^{7a}$ | $R^{7d}$ | $R^{8d(\#)}$ | $R^9$ | Formula | Calc [M + H]$^+$ | Found [M + H]$^+$ |
|---|---|---|---|---|---|---|---|
| 1-26 | $OCF_3$ | F | | 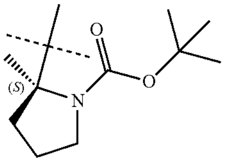 | $C_{50}H_{61}F_4N_9O_8$ | 992.46 | 993.0 |
| 1-27 | $OCF_3$ | F | | 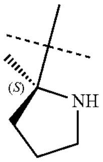 | $C_{45}H_{53}F_4N_9O_6$ | 892.41 | 892.8 |
| 1-28 | $OCF_3$ | F | | 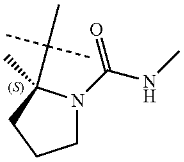 | $C_{47}H_{56}F_4N_{10}O_7$ | 949.43 | 949.6 |
| 1-29 | $CF_3$ | F | | 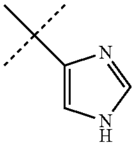 | $C_{43}H_{46}F_4N_{10}O_5$ | 859.36 | 858.8 |
| 1-30 | $CF_3$ | Cl | | $NHCH_3$ | $C_{41}H_{47}ClF_3N_9O_5$ | 838.33 | 838.8 |
| 1-31 | $CF_3$ | Cl | | 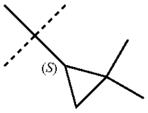 | $C_{45}H_{52}ClF_3N_8O_5$ | 877.37 | 877.8 |
| 1-32 | $CF_3$ | Cl | | 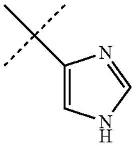 | $C_{43}H_{46}ClF_3N_{10}O_5$ | 875.33 | 875.8 |
| 1-33 | $OCF_3$ | Cl | | 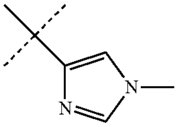 | $C_{44}H_{48}ClF_3N_{10}O_6$ | 905.34 | 905.8 |

TABLE 1-continued
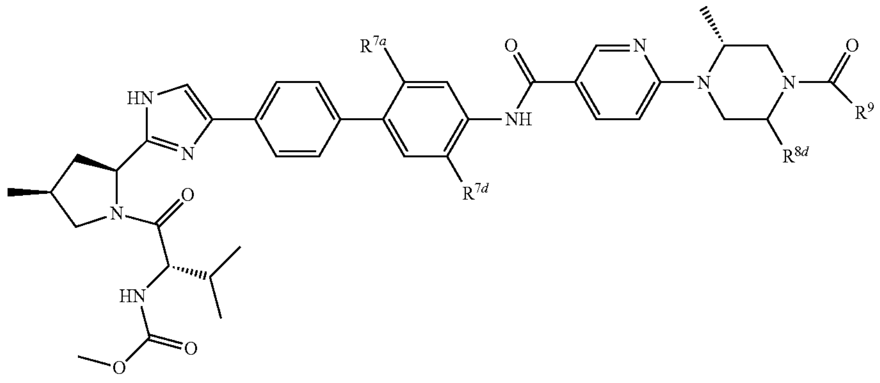
| Ex No. | $R^{7a}$ | $R^{7d}$ | $R^{8d(\#)}$ | $R^9$ | Formula | Calc $[M + H]^+$ | Found $[M + H]^+$ |
|---|---|---|---|---|---|---|---|
| 1-34 | $OCF_3$ | Cl | | 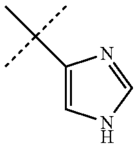 | $C_{44}H_{48}ClF_3N_{10}O_6$ | 905.34 | 905.8 |
| 1-35 | $OCF_3$ | Cl | | 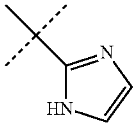 | $C_{43}H_{46}ClF_3N_{10}O_6$ | 891.32 | 891.8 |
| 1-36 | $OCF_3$ | Cl | | 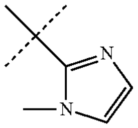 | $C_{44}H_{48}ClF_3N_{10}O_6$ | 905.34 | 905.8 |
| 1-37 | $OCF_3$ | Cl | | 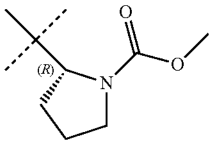 | $C_{46}H_{53}ClF_3N_9O_8$ | 952.37 | 952.8 |
| 1-38 | $OCF_3$ | Cl | | 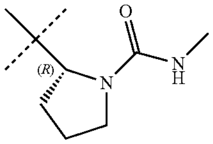 | $C_{46}H_{54}ClF_3N_{10}O_7$ | 951.38 | 952.0 |
| 1-39 | $OCF_3$ | Cl | | 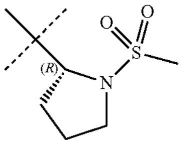 | $C_{45}H_{53}ClF_3N_9O_8S$ | 972.34 | 972.8 |
| 1-40 | $OCF_3$ | Cl | | 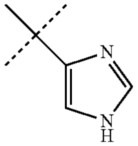 | $C_{44}H_{48}ClF_3N_{10}O_6$ | 905.34 | 905.8 |

TABLE 1-continued
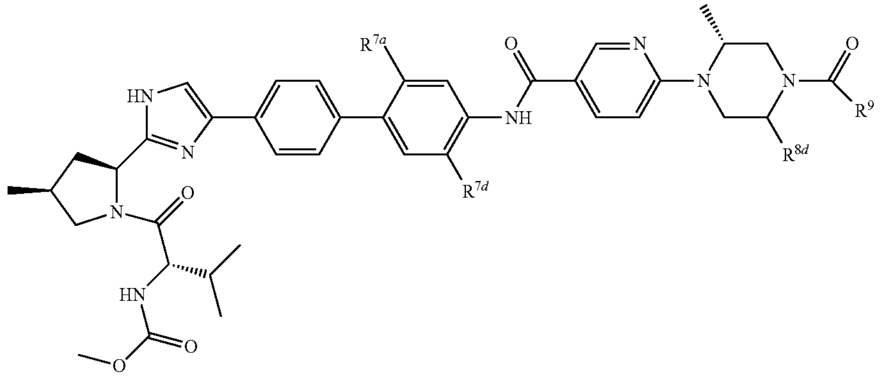
| Ex No. | $R^{7a}$ | $R^{7d}$ | $R^{8d(\#)}$ | $R^9$ | Formula | Calc [M + H]+ | Found [M + H]+ |
|---|---|---|---|---|---|---|---|
| 1-41 | $OCF_3$ | Cl | | 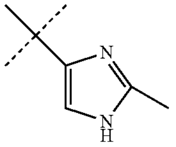 | $C_{45}H_{52}ClF_3N_8O_6$ | 893.37 | 893.8 |
| 1-42 | $OCF_3$ | Cl | | 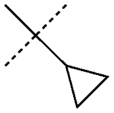 | $C_{43}H_{48}ClF_3N_8O_6$ | 865.33 | 865.8 |
| 1-43 | $OCF_3$ | Cl | $CH_3$ | 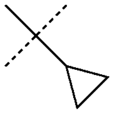 | $C_{44}H_{50}ClF_3N_8O_6$ | 879.35 | 879.8 |
| 1-44 | $OCF_3$ | Cl | $CH_3$ | 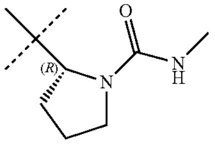 | $C_{47}H_{56}ClF_3N_{10}O_7$ | 965.40 | 966.0 |
| 1-45 | $OCF_3$ | Cl | $CH_3$ | 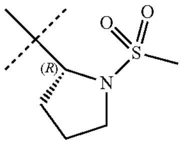 | $C_{46}H_{55}ClF_3N_9O_8S$ | 986.35 | 986.8 |
| 1-46 | $OCF_3$ | Cl | $CH_3$ | 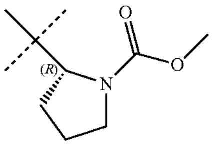 | $C_{47}H_{55}ClF_3N_9O_8$ | 966.38 | 966.8 |
| 1-47 | $OCF_3$ | Cl | | 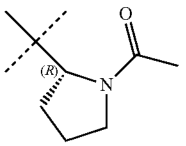 | $C_{46}H_{53}ClF_3N_9O_7$ | 936.37 | 936.8 |
| 1-48 | $OCF_3$ | Cl | | 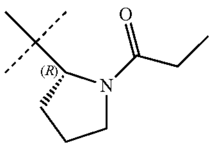 | $C_{47}H_{55}ClF_3N_9O_7$ | 950.39 | 950.8 |

TABLE 1-continued
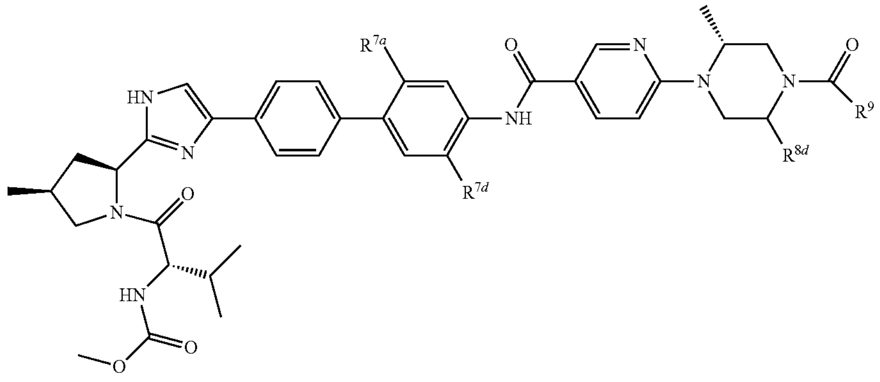
| Ex No. | $R^{7a}$ | $R^{7d}$ | $R^{8d(\#)}$ | $R^9$ | Formula | Calc $[M + H]^+$ | Found $[M + H]^+$ |
|---|---|---|---|---|---|---|---|
| 1-49 | $OCF_3$ | Cl | | 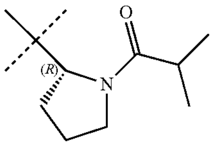 | $C_{48}H_{57}ClF_3N_9O_7$ | 964.40 | 965.0 |
| 1-50 | $OCF_3$ | Cl | | 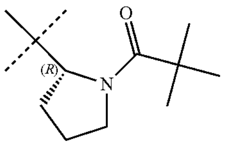 | $C_{49}H_{59}ClF_3N_9O_7$ | 978.42 | 979.0 |
| 1-51 | $OCF_3$ | Cl | | 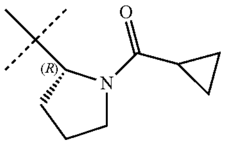 | $C_{48}H_{55}ClF_3N_9O_7$ | 962.39 | 963.0 |
| 1-52 | $CF_3$ | F | | 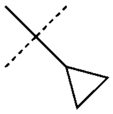 | $C_{43}H_{48}F_4N_8O_5$ | 833.37 | 833.8 |
| 1-53 | $CF_3$ | F | | 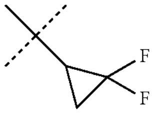 | $C_{43}H_{46}F_6N_8O_5$ | 869.35 | 869.8 |
| 1-54 | $CF_3$ | Cl | | 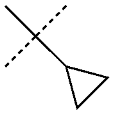 | $C_{43}H_{48}ClF_3N_8O_5$ | 849.34 | 849.8 |
| 1-55 | $CF_3$ | Cl | | 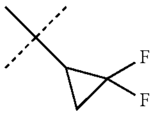 | $C_{43}H_{46}ClF_5N_8O_5$ | 885.32 | 885.8 |
| 1-56 | $OCF_3$ | Cl | | 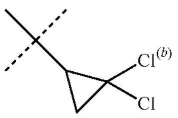 | $C_{43}H_{46}Cl_3F_3N_8O_6$ | 933.26 | 934.8 |

TABLE 1-continued
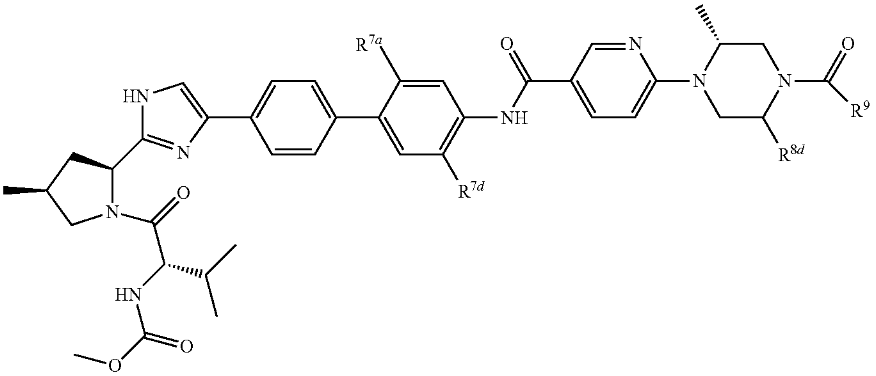
| Ex No. | $R^{7a}$ | $R^{7d}$ | $R^{8d(\#)}$ | $R^9$ | Formula | Calc $[M + H]^+$ | Found $[M + H]^+$ |
|---|---|---|---|---|---|---|---|
| 1-57 | $OCF_3$ | Cl | | 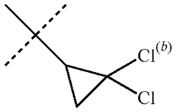 | $C_{43}H_{46}Cl_3F_3N_8O_6$ | 933.26 | 934.8 |
| 1-58 | $CF_3$ | F | | 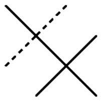 | $C_{44}H_{52}F_4N_8O_5$ | 849.40 | 849.8 |
| 1-59 | $OCF_3$ | Cl | | 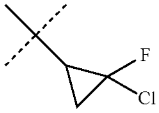 | $C_{43}H_{46}Cl_2F_4N_8O_6$ | 917.29 | 917.8 |
| 1-60 | $OCF_3$ | F | | 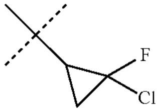 | $C_{43}H_{46}ClF_5N_8O_6$ | 901.32 | 901.8 |
| 1-61 | $CF_3$ | Cl | | 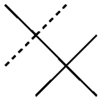 | $C_{44}H_{52}ClF_3N_8O_5$ | 865.37 | 865.8 |
| 1-62 | $CF_3$ | | | 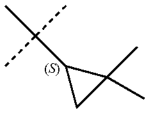 | $C_{44}H_{53}F_3N_8O_5$ | 843.41 | 843.8 |
| 1-63 | $CF_3$ | | | 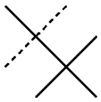 | $C_{44}H_{53}F_3N_8O_5$ | 831.41 | 831.8 |
| 1-64 | $CF_3$ | | | $N(CH_3)_2$ | $C_{42}H_{50}F_3N_9O_5$ | 818.39 | 818.8 |
| 1-65 | $CF_3$ | | | 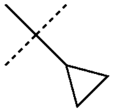 | $C_{43}H_{49}F_3N_8O_5$ | 815.38 | 815.8 |
| 1-66 | $OCF_3$ | Cl | | $CH_3$ | $C_{41}H_{46}ClF_3N_8O_6$ | 839.32 | 839.8 |
| 1-67 | $OCF_3$ | Cl | | 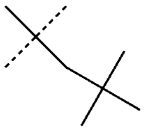 | $C_{45}H_{54}ClF_3N_8O_6$ | 895.38 | 895.8 |

TABLE 1-continued
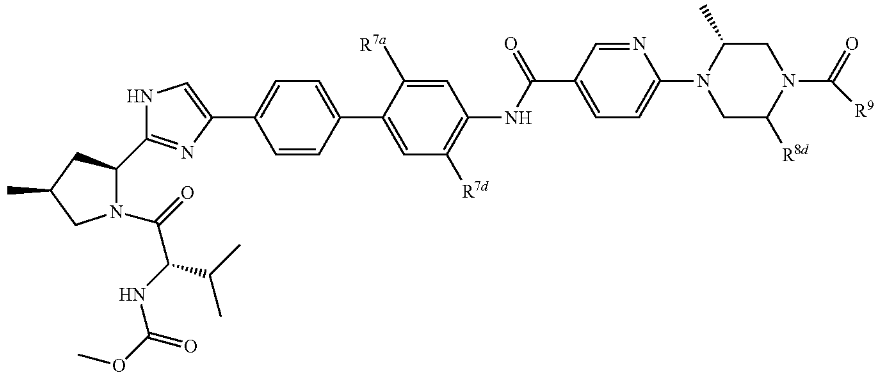
| Ex No. | $R^{7a}$ | $R^{7d}$ | $R^{8d(\#)}$ | $R^9$ | Formula | Calc $[M + H]^+$ | Found $[M + H]^+$ |
|---|---|---|---|---|---|---|---|
| 1-68 | $OCF_3$ | Cl | | 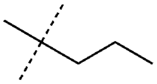 | $C_{43}H_{50}ClF_3N_8O_6$ | 867.35 | 867.8 |
| 1-69 | $OCF_3$ | Cl | | 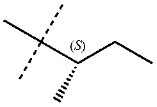 | $C_{44}H_{52}ClF_3N_8O_6$ | 881.37 | 881.8 |
| 1-70 | $OCF_3$ | Cl | | 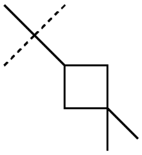 | $C_{44}H_{50}ClF_3N_8O_6$ | 879.35 | 879.8 |
| 1-71 | $OCF_3$ | Cl | | 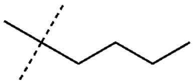 | $C_{44}H_{52}ClF_3N_8O_6$ | 881.37 | 881.8 |
| 1-72 | $OCF_3$ | Cl | | 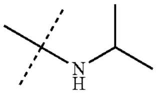 | $C_{43}H_{51}ClF_3N_9O_6$ | 882.36 | 882.8 |
| 1-73 | $OCF_3$ | Cl | | 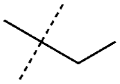 | $C_{42}H_{48}ClF_3N_8O_6$ | 853.33 | 853.8 |
| 1-74 | $OCF_3$ | | | 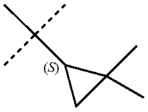 | $C_{45}H_{53}F_3N_8O_6$ | 859.40 | 859.6 |
| 1-75 | $OCF_3$ | | | 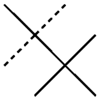 | $C_{44}H_{53}F_3N_8O_6$ | 847.40 | 847.5 |
| 1-76 | Cl | F | | 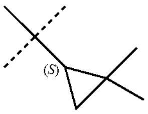 | $C_{44}H_{52}ClFN_8O_5$ | 827.37 | 827.8 |
| 1-77 | Cl | F | | 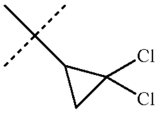 | $C_{42}H_{46}Cl_3FN_8O_5$ | 867.26 | 867.8 |

TABLE 1-continued
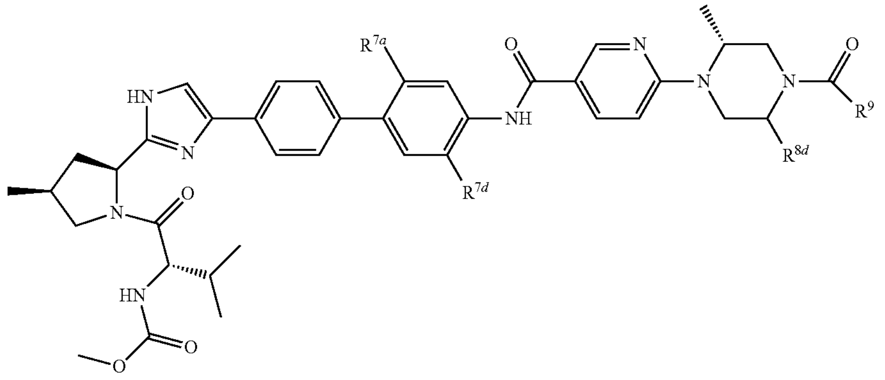
| Ex No. | $R^{7a}$ | $R^{7d}$ | $R^{8d(\#)}$ | $R^9$ | Formula | Calc $[M + H]^+$ | Found $[M + H]^+$ |
|---|---|---|---|---|---|---|---|
| 1-78 | Cl | F | | 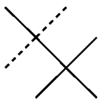 | $C_{43}H_{52}ClFN_8O_5$ | 815.37 | 815.8 |
| 1-79 | $OCF_3$ | F | | 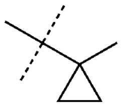 | $C_{44}H_{50}F_4N_8O_6$ | 863.38 | 863.8 |
| 1-80 | $OCF_3$ | Cl | | 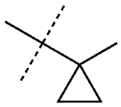 | $C_{44}H_{50}ClF_3N_8O_6$ | 879.35 | 879.8 |
| 1-81 | F | F | | 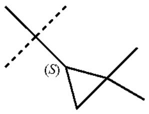 | $C_{44}H_{52}F_2N_8O_5$ | 811.40 | 811.8 |
| 1-82 | F | F | | 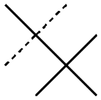 | $C_{43}H_{52}F_2N_8O_5$ | 799.40 | 799.8 |
| 1-83 | F | F | | 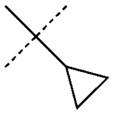 | $C_{42}H_{48}F_2N_8O_5$ | 783.37 | 783.8 |
| 1-84 | Cl | F | | 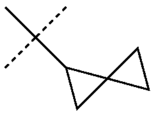 | $C_{44}H_{50}ClFN_8O_5$ | 825.36 | 825.8 |
| 1-85 | $OCF_3$ | Cl | | 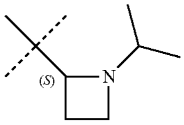 | $C_{46}H_{55}ClF_3N_9O_6$ | 922.39 | 922.8 |
| 1-86 | $OCF_3$ | Cl | | 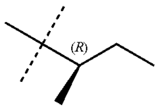 | $C_{44}H_{52}ClF_3N_8O_6$ | 881.37 | 881.8 |

TABLE 1-continued
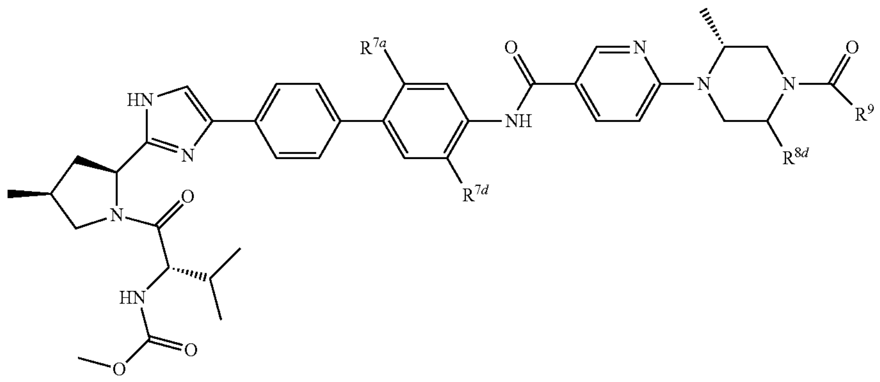
| Ex No. | $R^{7a}$ | $R^{7d}$ | $R^{8d(\#)}$ | $R^9$ | Formula | Calc [M + H]$^+$ | Found [M + H]$^+$ |
|---|---|---|---|---|---|---|---|
| 1-87 | $OCF_3$ | Cl | | 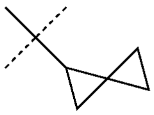 | $C_{45}H_{50}ClF_3N_8O_6$ | 891.35 | 891.8 |
| 1-88 | $OCF_3$ | F | | 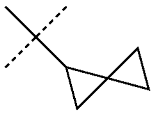 | $C_{45}H_{50}F_4N_8O_6$ | 875.38 | 875.8 |
| 1-89 | $CF_3$ | Cl | | 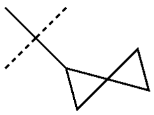 | $C_{45}H_{50}ClF_3N_8O_5$ | 875.35 | 875.8 |
| 1-90 | F | F | | 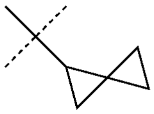 | $C_{44}H_{50}F_2N_8O_5$ | 809.39 | 809.8 |
| 1-91 | $OCF_3$ | Cl | | 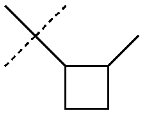 | $C_{45}H_{52}ClF_3N_8O_6$ | 893.37 | 893.8 |
| 1-92 | $OCF_3$ | F | | 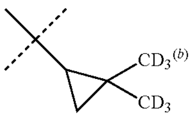 | $C_{45}H_{46}D_6F_4N_8O_6$ | 883.44 | 883.8 |
| 1-93 | $CF_3$ | | | 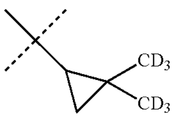 | $C_{45}H_{47}D_6F_3N_8O_6$ | 849.45 | 849.8 |
| 1-94 | $OCF_3$ | Cl | | 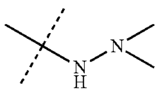 | $C_{42}H_{50}ClF_3N_{10}O_6$ | 883.36 | 883.8 |
| 1-95 | $OCF_3$ | F | | 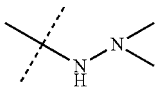 | $C_{42}H_{50}F_4N_{10}O_6$ | 867.39 | 867.8 |

TABLE 1-continued

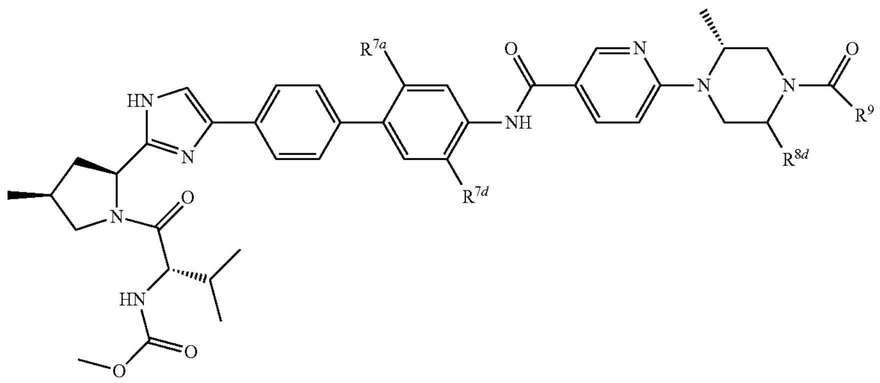

| Ex No. | $R^{7a}$ | $R^{7d}$ | $R^{8d(\#)}$ | $R^9$ | Formula | Calc [M + H]+ | Found [M + H]+ |
|---|---|---|---|---|---|---|---|
| 1-96 | $OCF_3$ | Cl | | 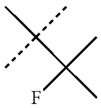 | $C_{43}H_{49}ClF_4N_8O_6$ | 885.34 | 885.8 |
| 1-97 | $OCF_3$ | Cl | | 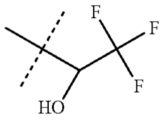 | $C_{42}H_{45}ClF_6N_8O_7$ | 923.30 | 923.8 |
| 1-98 | $OCF_3$ | Cl | | 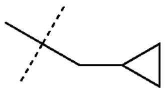 | $C_{44}H_{50}ClF_3N_8O_6$ | 879.35 | 879.8 |
| 1-99 | $OCF_3$ | Cl | | 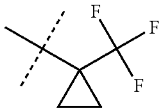 | $C_{44}H_{47}ClF_6N_8O_6$ | 933.32 | 933.8 |
| 1-100 | Cl | F | | 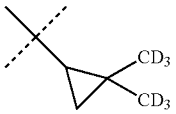 | $C_{44}H_{46}ClD_6FN_8O_5$ | 830.42 | 833.8 |
| 1-101 | $OCF_3$ | F | | 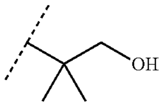 | $C_{44}H_{52}F_4N_8O_7$ | 881.39 | 881.8 |

(a)

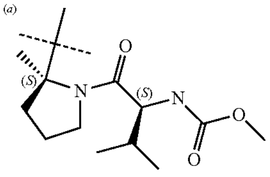

(b)Stereoisomers separated but unassigned (#)For all compounds, when the substituent $R^{8d}$ is present, the orientation of the chiral carbon atom bearing the substituent $R^{8d}$ is (S).

TABLE 2
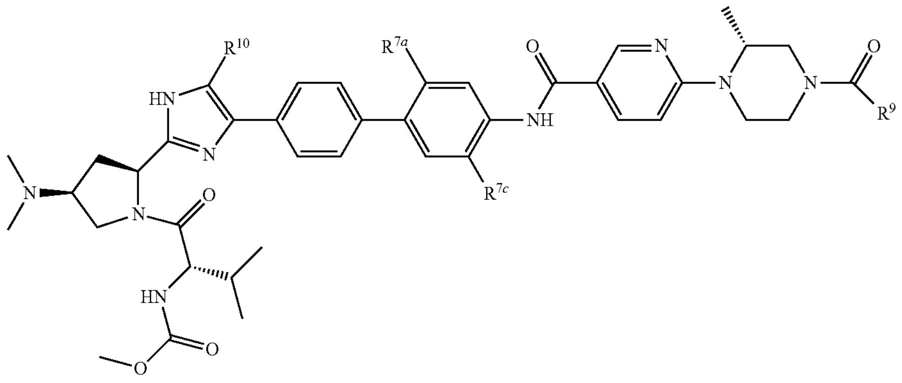
| Ex No. | $R^{7a}$ | $R^{7c}$ | $R^9$ | $R^{10}$ | Formula | Calc $[M + H]^+$ | Found $[M + H]^+$ |
|---|---|---|---|---|---|---|---|
| 2-1 | | | 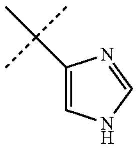 | | $C_{43}H_{51}N_{11}O_5$ | 802.41 | 802.4 |
| 2-2 | | | 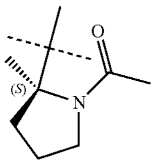 | | $C_{47}H_{60}N_{10}O_6$ | 861.47 | 861.4 |
| 2-3 | | | 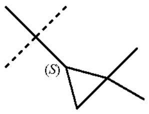 | | $C_{45}H_{57}N_9O_5$ | 804.45 | 805.4 |
| 2-4 | $CH_3$ | | 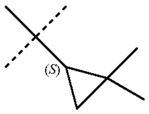 | | $C_{46}H_{59}N_9O_5$ | 818.46 | 818.4 |
| 2-5 | $CH_3$ | | $NHCH_3$ | | $C_{42}H_{54}N_{10}O_5$ | 779.43 | 779.4 |
| 2-6 | $OCF_3$ | Cl | 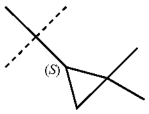 | | $C_{46}H_{55}ClF_3N_9O_6$ | 922.39 | 922.8 |
| 2-7 | $OCF_3$ | Cl | 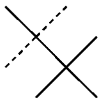 | | $C_{45}H_{55}ClF_3N_9O_6$ | 910.39 | 910.8 |
| 2-8 | $OCF_3$ | Cl | 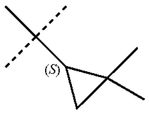 | | $C_{46}H_{54}Cl_2F_3N_9O_6$ | 956.35 | 957.8 |

TABLE 3
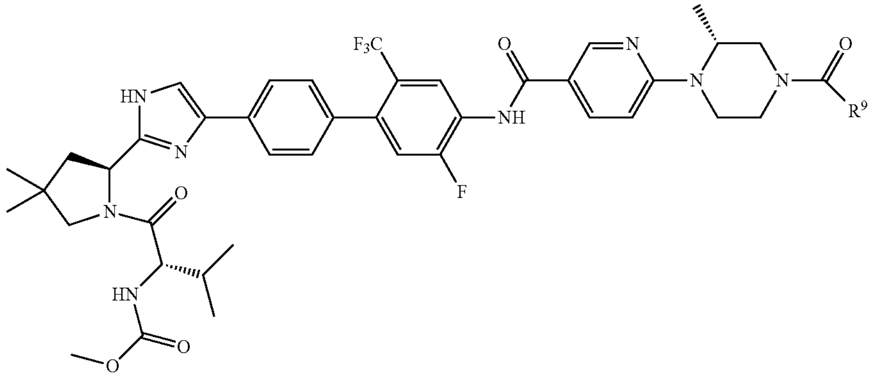
| Ex No. | $R^9$ | Formula | Calc $[M + H]^+$ | Found $[M + H]^+$ |
|---|---|---|---|---|
| 3-1 | 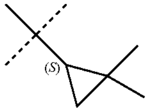 | $C_{46}H_{54}F_4N_8O_5$ | 875.42 | 874.6 |
| 3-2 | 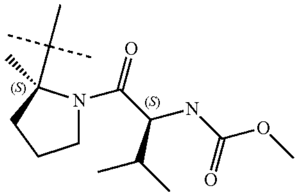 | $C_{53}H_{66}F_4N_{10}O_8$ | 1,047.50 | 1046.6 |
| 3-3 | 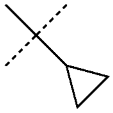 | $C_{44}H_{50}F_4N_8O_5$ | 847.38 | 846.8 |
| 3-4 | $NHCH_3$ | $C_{42}H_{49}F_4N_9O_5$ | 836.38 | 835.6 |
TABLE 4
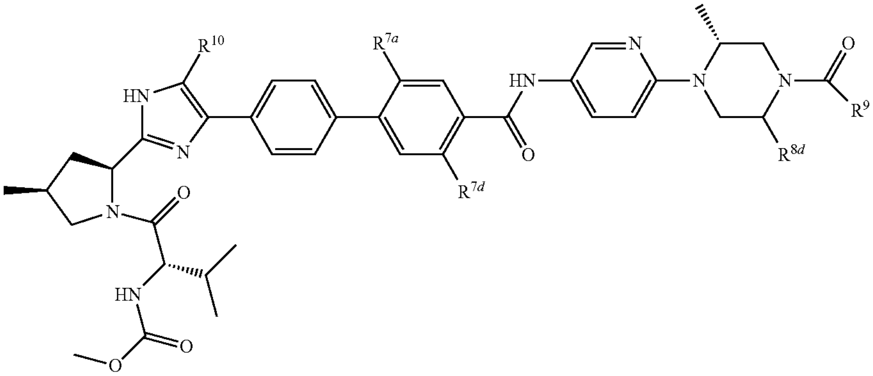
| Ex No. | $R^{7a}$ | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|---|
| 4-1 | | | | 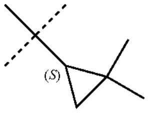 | | $C_{44}H_{54}N_8O_5$ | 775.42 | 775.4 |

TABLE 4-continued
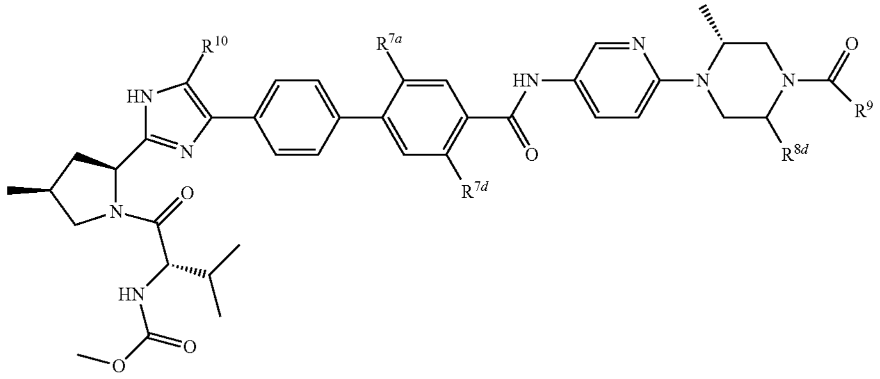
| Ex No. | $R^{7a}$ | $R^{7d}$ | $R^{8d(\#)}$ | $R^9$ | $R^{10}$ | Formula | Calc [M + H]+ | Found [M + H]+ |
|---|---|---|---|---|---|---|---|---|
| 4-2 | | | | 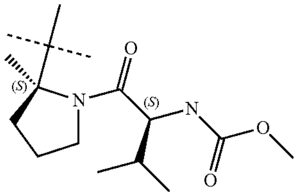 | | $C_{51}H_{66}N_{10}O_8$ | 947.51 | 947.6 |
| 4-3 | $OCF_3$ | | | 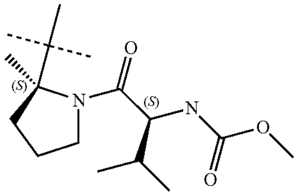 | | $C_{52}H_{65}F_3N_{10}O_9$ | 1031.49 | 1031.4 |
| 4-4 | $OCF_3$ | | | 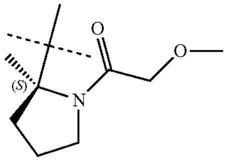 | | $C_{48}H_{58}F_3N_9O_8$ | 946.44 | 945.6 |
| 4-5 | $OCF_3$ | | | 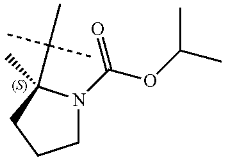 | | $C_{49}H_{60}F_3N_9O_8$ | 960.45 | 959.6 |
| 4-6 | $OCF_3$ | | | 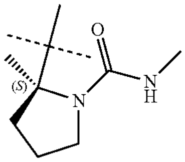 | | $C_{47}H_{57}F_3N_{10}O_7$ | 931.44 | 930.6 |
| 4-7 | $OCF_3$ | | | 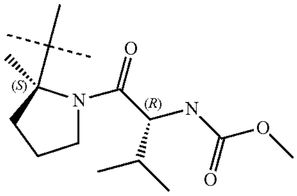 | | $C_{52}H_{65}F_3N_{10}O_9$ | 1031.49 | 1,030.6 |

TABLE 4-continued
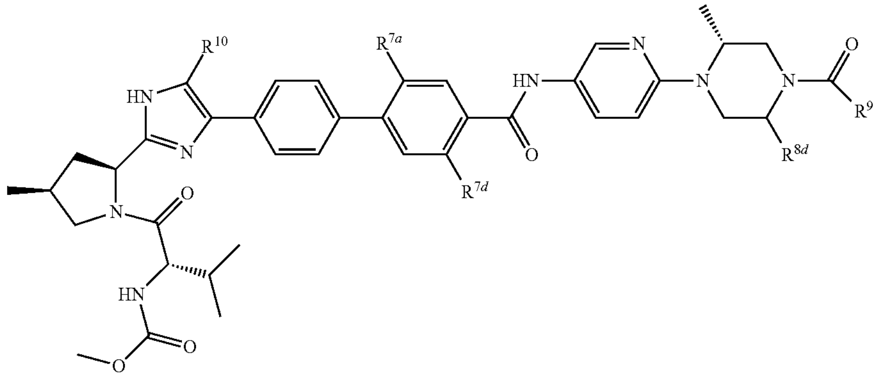
| Ex No. | $R^{7a}$ | $R^{7d}$ | $R^{8d(\#)}$ | $R^9$ | $R^{10}$ | Formula | Calc $[M+H]^+$ | Found $[M+H]^+$ |
|---|---|---|---|---|---|---|---|---|
| 4-8 | $OCF_3$ | | $CH_3$ | 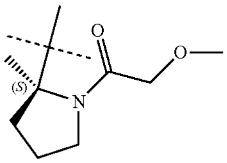 | | $C_{49}H_{60}F_3N_9O_8$ | 960.45 | 960.8 |
| 4-9 | $OCF_3$ | | $CH_3$ | 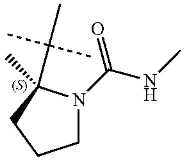 | | $C_{48}H_{59}F_3N_{10}O_7$ | 945.45 | 946.0 |
| 4-10 | $OCF_3$ | | $CH_3$ | 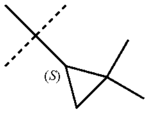 | Cl | $C_{46}H_{54}ClF_3N_8O_6$ | 907.38 | 907.8 |
| 4-11 | $OCF_3$ | | $CH_3$ | 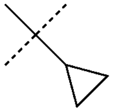 | Cl | $C_{44}H_{50}ClF_3N_8O_6$ | 879.35 | 879.8 |
| 4-12 | $OCF_3$ | | $CH_3$ | $NHCH_3$ | Cl | $C_{42}H_{49}ClF_3N_9O_6$ | 868.35 | 868.8 |
| 4-13 | $OCF_3$ | | $CH_3$ | 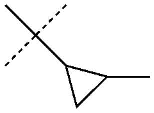 | Cl | $C_{45}H_{52}ClF_3N_8O_6$ | 893.37 | 893.8 |
| 4-14 | $OCF_3$ | | $CH_3$ | $NHCH_3$ | | $C_{42}H_{50}F_3N_9O_6$ | 834.38 | 834.8 |
| 4-15 | $OCF_3$ | | $CH_3$ | 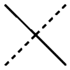 | | $C_{45}H_{55}F_3N_8O_6$ | 861.42 | 861.8 |
| 4-16 | $OCF_3$ | | $CH_3$ | 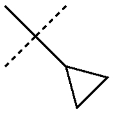 | | $C_{44}H_{51}F_3N_8O_6$ | 845.39 | 845.8 |
| 4-17 | $OCF_3$ | | $CH_3$ | 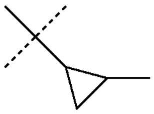 | | $C_{45}H_{53}F_3N_8O_6$ | 859.4 | 859.8 |

TABLE 4-continued
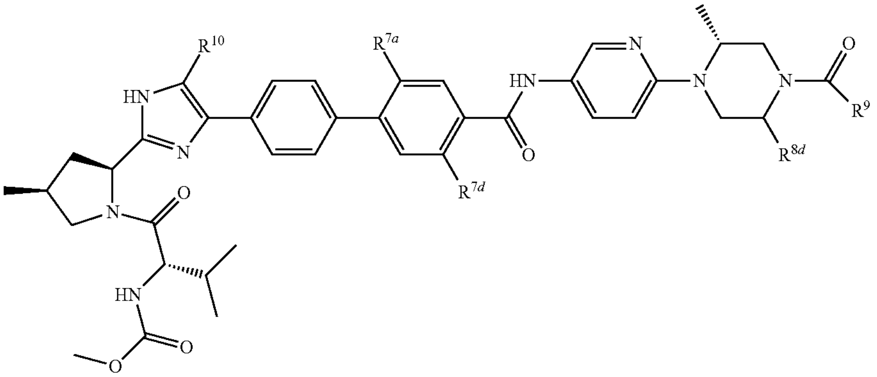
| Ex No. | $R^{7a}$ | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|---|
| 4-18 | $OCF_3$ | | $CH_3$ | 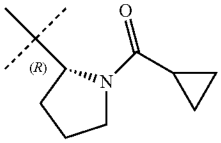 | | $C_{49}H_{58}F_3N_9O_7$ | 942.44 | 943.0 |
| 4-19 | $OCF_3$ | | $CH_3$ | 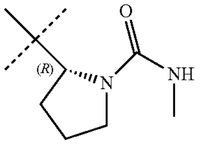 | | $C_{47}H_{57}F_3N_{10}O_7$ | 931.44 | 932.0 |
| 4-20 | $OCF_3$ | | $CH_3$ | 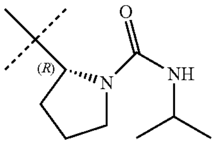 | | $C_{49}H_{61}F_3N_{10}O_7$ | 959.47 | 960.0 |
| 4-21 | $OCF_3$ | | $CH_3$ | 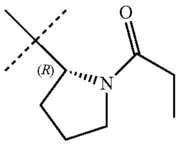 | | $C_{48}H_{58}F_3N_9O_7$ | 930.44 | 931.0 |
| 4-22 | $OCF_3$ | | $CH_3$ | 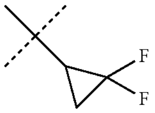 | | $C_{44}H_{49}F_5N_8O_6$ | 881.37 | 881.8 |
| 4-23 | $OCF_3$ | | $CH_3$ | 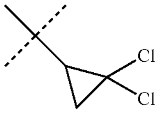 | | $C_{44}H_{49}Cl_2F_3N_8O_6$ | 913.31 | 913.8 |
| 4-24 | $OCF_3$ | | $CH_3$ | 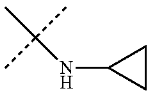 | | $C_{44}H_{52}F_3N_9O_6$ | 860.40 | 860.8 |
| 4-25 | $OCF_3$ | | $CH_3$ | 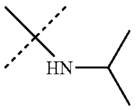 | | $C_{44}H_{54}F_3N_9O_6$ | 862.42 | 862.8 |
| 4-26 | $OCF_3$ | | $CH_3$ | 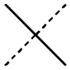 | Cl | $C_{45}H_{54}ClF_3N_8O_6$ | 895.38 | 895.8 |

TABLE 4-continued
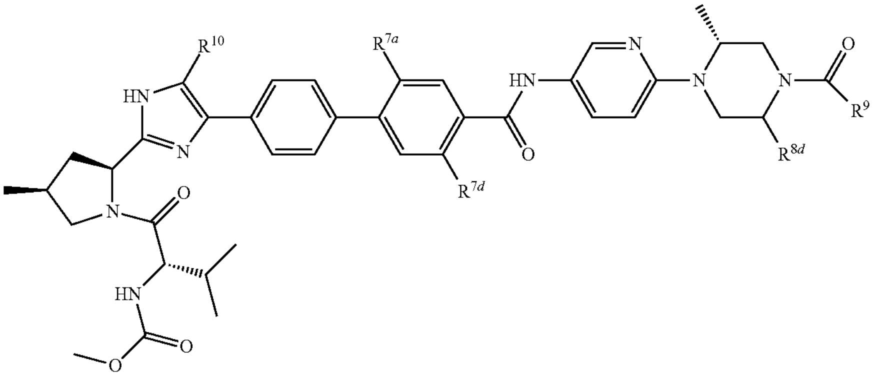
| Ex No. | $R^{7a}$ | $R^{7d}$ | $R^{8d(\#)}$ | $R^9$ | $R^{10}$ | Formula | Calc [M + H]+ | Found [M + H]+ |
|---|---|---|---|---|---|---|---|---|
| 4-27 | $OCF_3$ | | $CH_3$ | 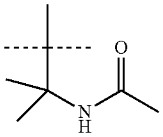 | | $C_{46}H_{56}F_3N_9O_7$ | 904.43 | 904.8 |
| 4-28 | $OCF_3$ | | $CH_3$ | 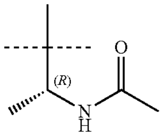 | | $C_{45}H_{54}F_3N_9O_7$ | 890.41 | 891.0 |
| 4-29 | $OCF_3$ | | | 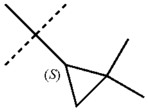 | Cl | $C_{45}H_{52}ClF_3N_8O_6$ | 893.37 | 893.8 |
| 4-30 | $OCF_3$ | | | 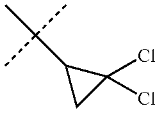 | Cl | $C_{43}H_{46}Cl_3F_3N_8O_6$ | 933.26 | 933.8 |
| 4-31 | $OCF_3$ | | | 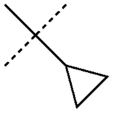 | Cl | $C_{43}H_{48}ClF_3N_8O_6$ | 865.33 | 865.8 |
| 4-32 | $OCF_3$ | | | 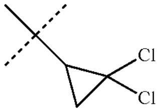 | | $C_{43}H_{47}Cl_2F_3N_8O_6$ | 899.30 | 899.8 |
| 4-33 | $OCF_3$ | | | $N(CH_3)_2$ | | $C_{42}H_{50}F_3N_9O_6$ | 834.38 | 834.8 |
| 4-34 | $OCF_3$ | | | $NHCH_3$ | | $C_{41}H_{48}F_3N_9O_6$ | 820.37 | 820.8 |
| 4-35 | $OCF_3$ | | | 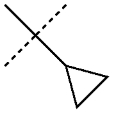 | | $C_{43}H_{49}F_3N_8O_6$ | 831.37 | 831.8 |
| 4-36 | $OCF_3$ | | | 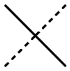 | | $C_{44}H_{53}F_3N_8O_6$ | 847.40 | 847.8 |

TABLE 4-continued
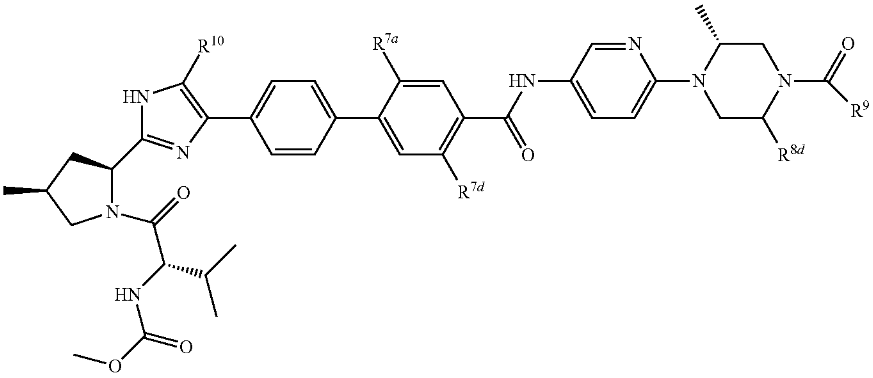
| Ex No. | $R^{7a}$ | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|---|
| 4-37 | $OCF_3$ | | $CH_3$ | 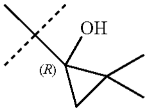 | Cl | $C_{46}H_{54}ClF_3N_8O_7$ | 923.38 | 923.8 |
| 4-38 | $OCF_3$ | | $CH_3$ | 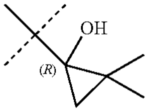 | | $C_{46}H_{55}F_3N_8O_7$ | 889.41 | 890.0 |
| 4-39 | $OCF_3$ | | $CH_3$ | 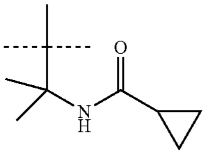 | | $C_{48}H_{58}F_3N_9O_7$ | 930.44 | 931.0 |
| 4-40 | $OCF_3$ | | $CH_3$ | 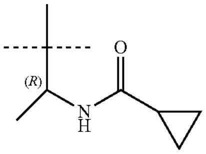 | | $C_{47}H_{56}F_3N_9O_7$ | 916.43 | 917.0 |
| 4-41 | $OCF_3$ | F | | 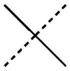 | | $C_{44}H_{52}F_4N_8O_6$ | 865.39 | 865.8 |
| 4-42 | $OCF_3$ | | | 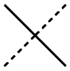 | F | $C_{44}H_{52}F_4N_8O_6$ | 865.39 | 865.8 |
| 4-43 | $OCF_3$ | F | | 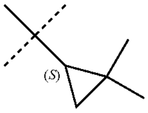 | | $C_{45}H_{52}F_4N_8O_6$ | 877.39 | 877.8 |
| 4-44 | $OCF_3$ | F | | 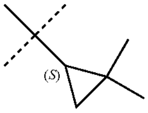 | Cl | $C_{45}H_{51}ClF_4N_8O_6$ | 911.36 | 911.8 |
| 4-45 | $OCF_3$ | F | | 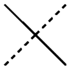 | Cl | $C_{44}H_{51}ClF_4N_8O_6$ | 899.36 | 899.8 |
| 4-46 | $OCF_3$ | Cl | | 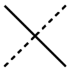 | | $C_{44}H_{52}ClF_3N_8O_6$ | 881.37 | 881.8 |

TABLE 4-continued
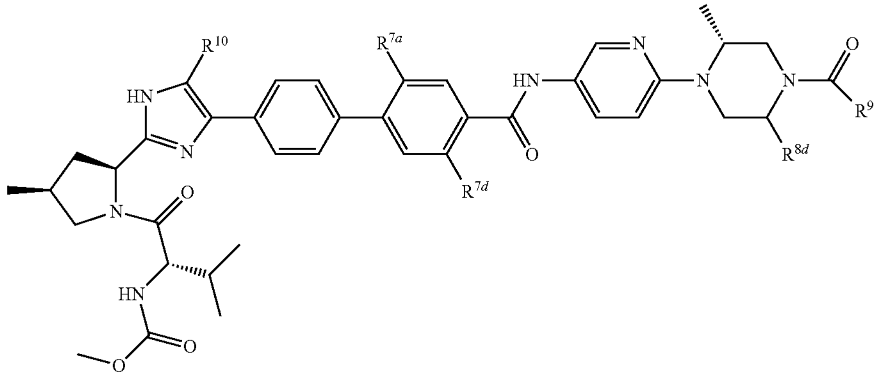
| Ex No. | $R^{7a}$ | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|---|
| 4-47 | $OCF_3$ | Cl | | 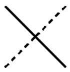 | Cl | $C_{44}H_{51}Cl_2F_3N_8O_6$ | 915.33 | 915.8 |
(#)For all compounds, when the substituent $R^{8d}$ is present, the orientation of the chiral carbon atom bearing the substituent $R^{8d}$ is (S).
TABLE 5
| Ex No. | | Formula | Calc $[M + H]^+$ | Found $[M + H]^+$ |
|---|---|---|---|---|
| 5-1 | 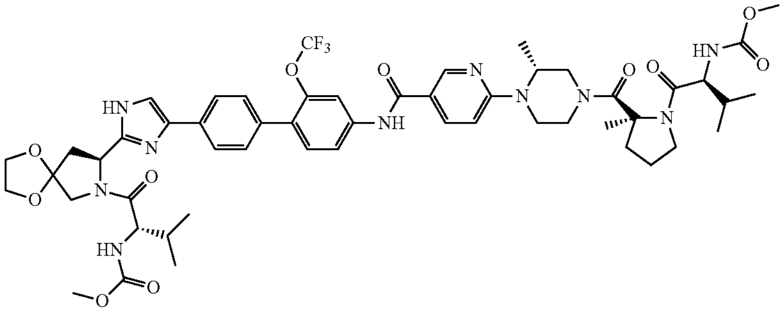 | $C_{53}H_{65}F_3N_{10}O_{11}$ | 1075.48 | 1076.2 |
| 5-2 | 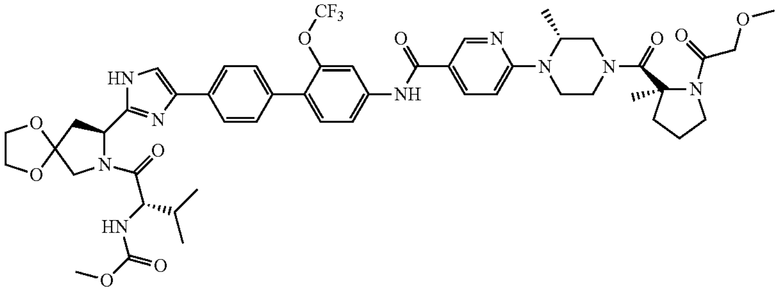 | $C_{49}H_{58}F_3N_9O_{10}$ | 990.43 | 989.6 |
| 5-3 | 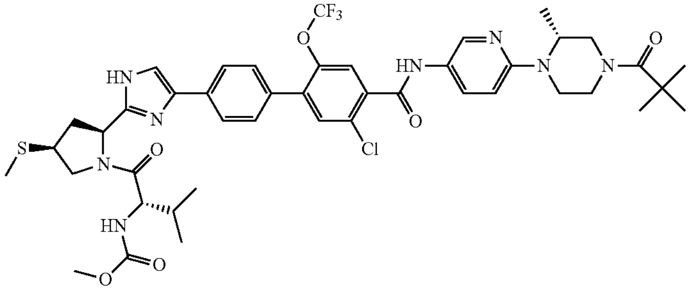 [SMILES: COC(=O)N[C@H](C(=O)N1C[C@@H](SC)C[C@H]1c1nc(-c2ccc(-c3cc(Cl)c(C(=O)Nc4ccc(N5CCN(C(=O)C(C)(C)C)C[C@H]5C)nc4)cc3OC(F)(F)F)cc2)c[nH]1)C(C)C] | $C_{44}H_{52}ClF_3N_8O_6S$ | 913.34 | 913.8 |

TABLE 5-continued
| Ex No. | | Formula | Calc [M + H]+ | Found [M + H]+ |
|---|---|---|---|---|
| 5-4 | 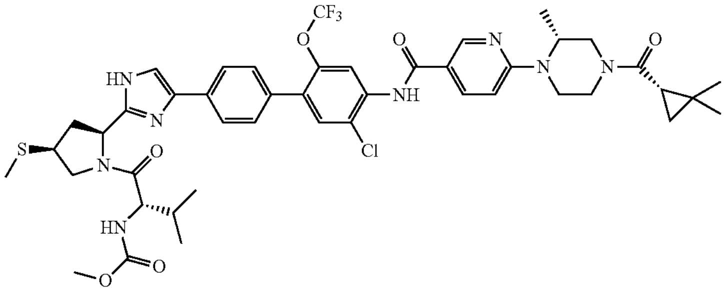 | $C_{45}H_{52}ClF_3N_8O_6S$ | 925.34 | 925.8 |
| 5-5 | 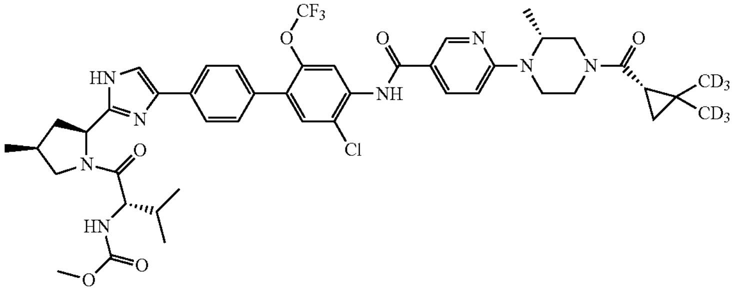 [SMILES: [2H]C([2H])([2H])C1(C([2H])([2H])[2H])C[C@@H]1C(=O)N1CCN(c2ccc(C(=O)Nc3cc(OC(F)(F)F)c(-c4ccc(-c5c[nH]c([C@@H]6C[C@H](C)CN6C(=O)[C@@H](NC(=O)OC)C(C)C)n5)cc4)cc3Cl)cn2)[C@H](C)C1] | $C_{44}H_{44}ClD_6F_3N_8O_6$ | 873.3 | 885.8 |
| 5-6 | 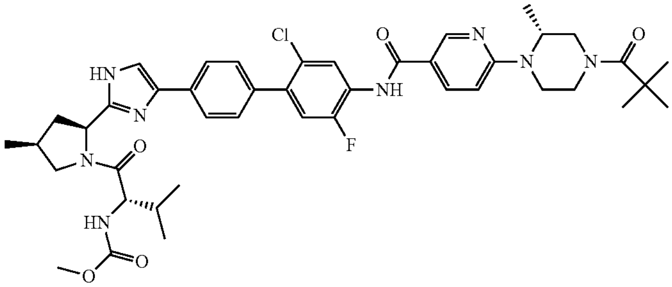 [SMILES: COC(=O)N[C@H](C(=O)N1C[C@@H](C)C[C@H]1c1nc(-c2ccc(-c3cc(F)c(NC(=O)c4ccc(N5CCN(C(=O)C(C)(C)C)C[C@H]5C)nc4)cc3Cl)cc2)c[nH]1)C(C)C] | $C_{43}H_{52}ClFN_8O_5$ | 815.37 | 815.8 |
| 5-7 | 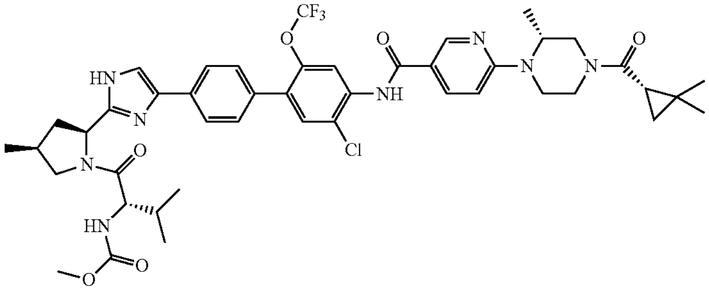 | $C_{44}H_{50}F_4N_8O_6$ | 863.38 | 863.8 |
| 5-8 | 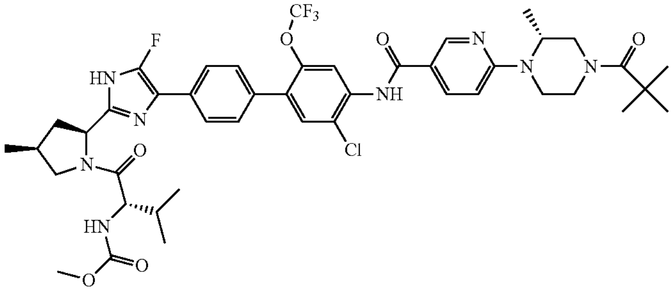 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c(F)[nH]1)C(C)C] | $C_{44}H_{51}ClF_4N_8O_6$ | 899.36 | 899.8 |

TABLE 5-continued
| Ex No. | | Formula | Calc [M + H]+ | Found [M + H]+ |
|---|---|---|---|---|
| 5-9 | 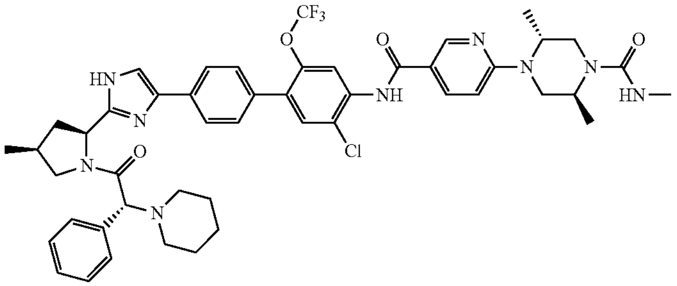 | $C_{48}H_{53}ClF_3N_9O_4$ | 912.39 | 912.8 |
| 5-10 | 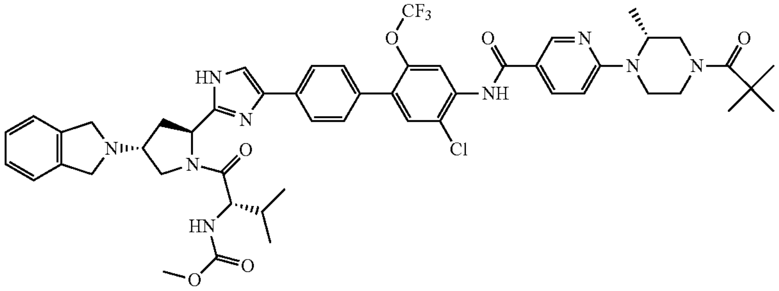 [SMILES: COC(=O)N[C@H](C(=O)N1C[C@H](N2Cc3ccccc3C2)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C] | $C_{51}H_{57}ClF_3N_9O_6$ | 984.41 | 984.8 |
| 5-11 | 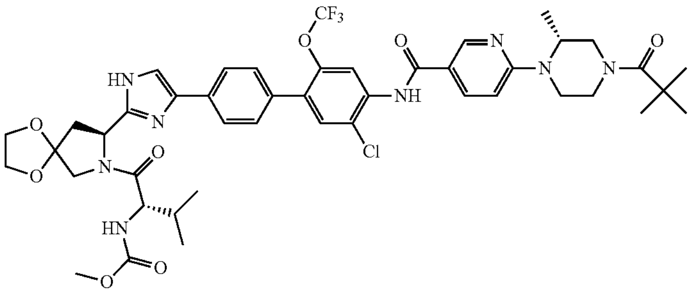 [SMILES: COC(=O)N[C@H](C(=O)N1CC2(C[C@H]1c1nc(-c3ccc(-c4cc(Cl)c(NC(=O)c5ccc(N6CCN(C(=O)C(C)(C)C)C[C@H]6C)nc5)cc4OC(F)(F)F)cc3)c[nH]1)OCCO2)C(C)C] | $C_{45}H_{52}ClF_3N_8O_8$ | 925.36 | 925.8 |
| 5-12 | 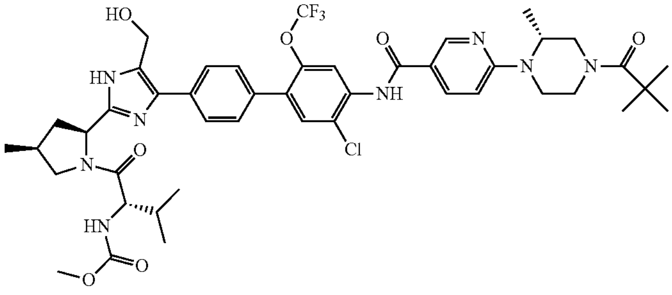 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c(CO)[nH]1)C(C)C] | $C_{45}H_{54}ClF_3N_8O_7$ | 911.38 | 911.6 |
| 5-13 | 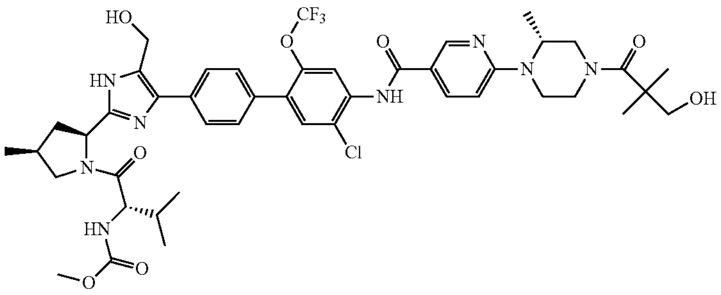 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)CO)C[C@H]5C)nc4)cc3OC(F)(F)F)cc2)c(CO)[nH]1)C(C)C] | $C_{45}H_{54}ClF_3N_8O_8$ | 927.37 | 927.6 |

TABLE 5-continued
| Ex No. | | Formula | Calc [M + H]+ | Found [M + H]+ |
|---|---|---|---|---|
| 5-14 | 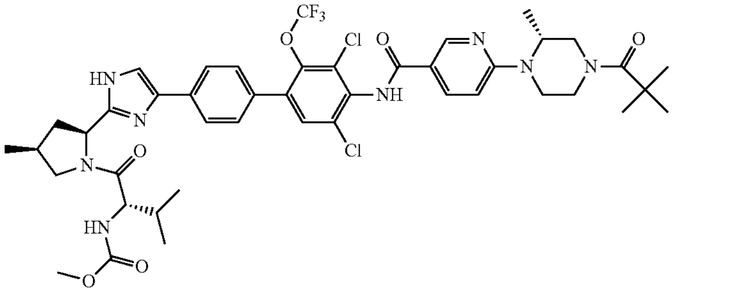 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)C)C[C@H]5C)nc4)c(Cl)c3OC(F)(F)F)cc2)c[nH]1)C(C)C] | $C_{44}H_{51}Cl_2F_3N_8O_6$ | 915.33 | 915.4 |
| 5-15 | 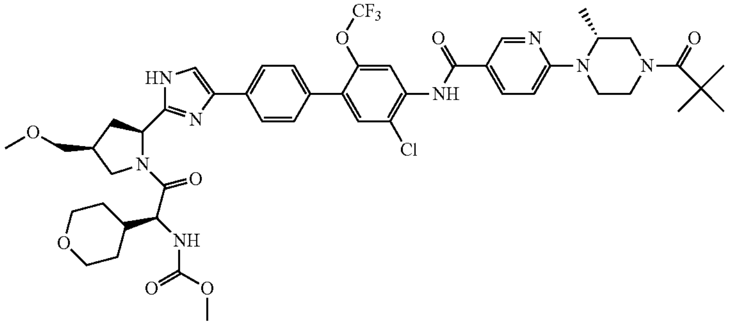 [SMILES: COC[C@H]1C[C@@H](c2nc(-c3ccc(-c4cc(Cl)c(NC(=O)c5ccc(N6CCN(C(=O)C(C)(C)C)C[C@H]6C)nc5)cc4OC(F)(F)F)cc3)c[nH]2)N(C(=O)[C@@H](NC(=O)OC)C2CCOCC2)C1] | $C_{47}H_{56}ClF_3N_8O_8$ | 953.39 | 953.6 |
| 5-16 | 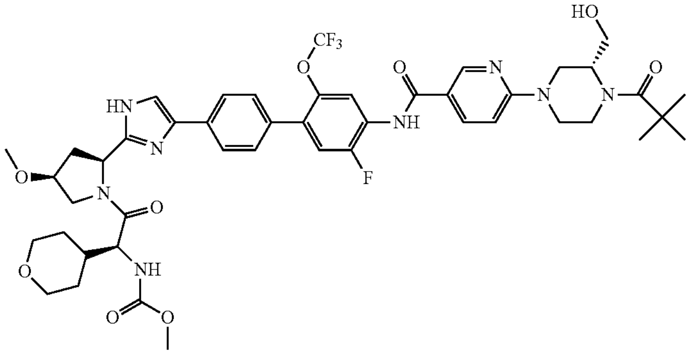 [SMILES: COC(=O)N[C@H](C(=O)N1C[C@@H](OC)C[C@H]1c1nc(-c2ccc(-c3cc(F)c(NC(=O)c4ccc(N5CCN(C(=O)C(C)(C)C)[C@@H](CO)C5)nc4)cc3OC(F)(F)F)cc2)c[nH]1)C1CCOCC1] | $C_{46}H_{54}F_4N_8O_9$ | 939.40 | 939.8 |
| 5-17 | 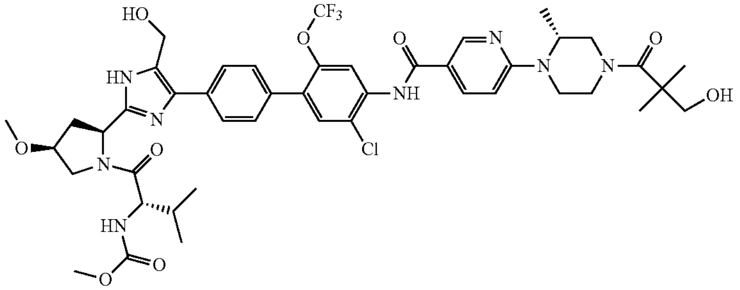 [SMILES: COC(=O)N[C@H](C(=O)N1C[C@@H](OC)C[C@H]1c1nc(-c2ccc(-c3cc(Cl)c(NC(=O)c4ccc(N5CCN(C(=O)C(C)(C)CO)C[C@H]5C)nc4)cc3OC(F)(F)F)cc2)c(CO)[nH]1)C(C)C] | $C_{45}H_{54}ClF_3N_8O_9$ | 943.37 | 943.6 |

TABLE 5-continued
| Ex No. | | Formula | Calc [M + H]+ | Found [M + H]+ |
|---|---|---|---|---|
| 5-18 | 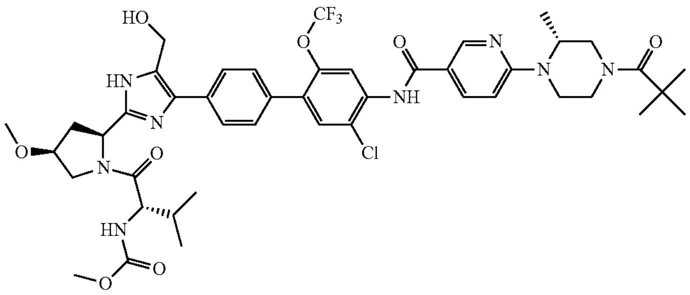 [SMILES: COC(=O)N[C@H](C(=O)N1C[C@@H](OC)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c(CO)[nH]1)C(C)C] | $C_{45}H_{54}ClF_3N_8O_8$ | 927.37 | 927.6 |
| 5-19 | 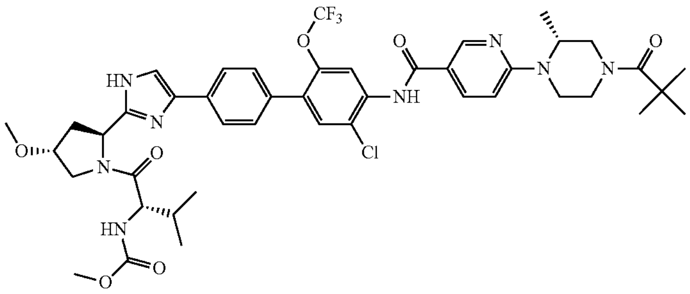 [SMILES: COC(=O)N[C@H](C(=O)N1C[C@H](OC)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C(C)C] | $C_{44}H_{52}ClF_3N_8O_7$ | 897.36 | 897.6 |
| 5-20 | 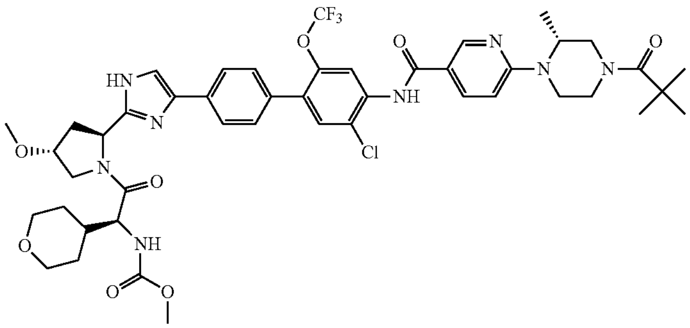 [SMILES: COC(=O)N[C@H](C(=O)N1C[C@H](OC)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C1CCOCC1] | $C_{46}H_{54}ClF_3N_8O_8$ | 939.37 | 939.6 |
TABLE 6
| Ex No. | | Formula | Calc [M + H]+ | Found [M + H]+ |
|---|---|---|---|---|
| 6-1 | 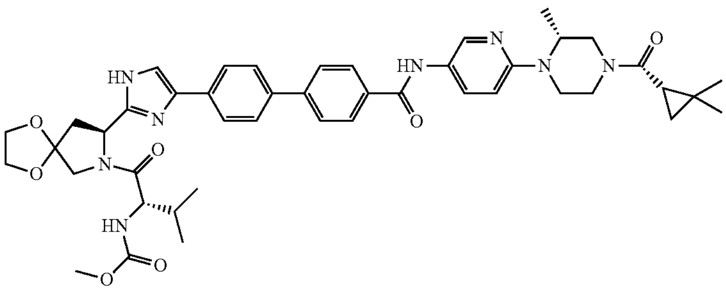 | $C_{45}H_{54}N_8O_7$ | 819.41 | 820.0 |

TABLE 6-continued
| Ex No. | | Formula | Calc [M + H]+ | Found [M + H]+ |
|---|---|---|---|---|
| 6-2 | 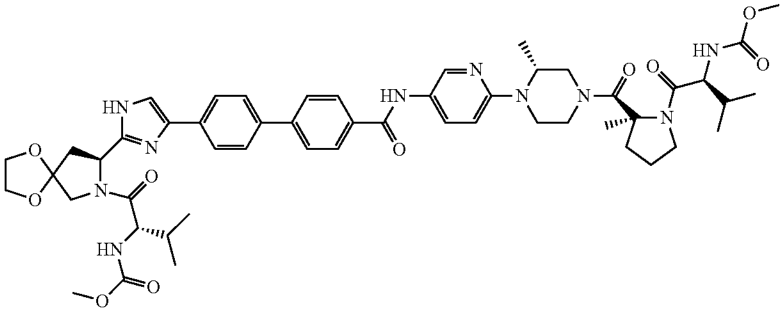 | $C_{41}H_{46}N_{10}O_6$ | 775.36 | 775.4 |
| 6-3 | 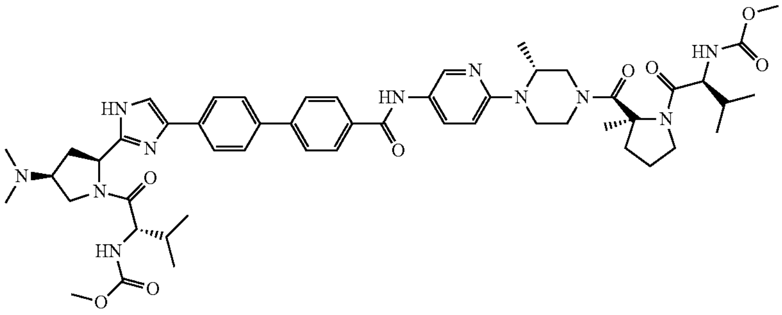 | $C_{52}H_{69}N_{11}O_8$ | 976.53 | 977.0 |
| 6-4 | 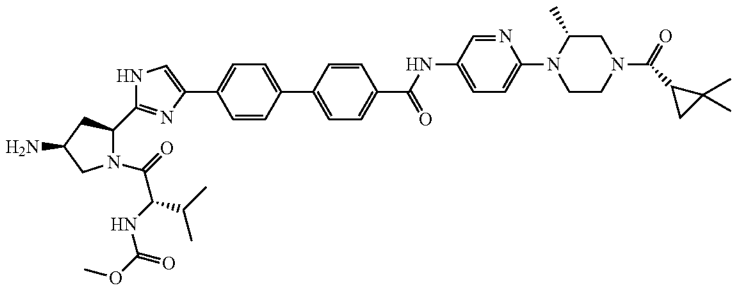 | $C_{43}H_{53}N_9O_5$ | 776.42 | 776.6 |
| 6-5 | 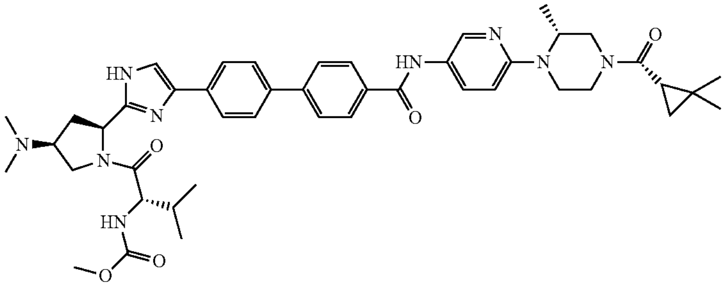 | $C_{45}H_{57}N_9O_5$ | 804.45 | 804.6 |
| 6-6 | 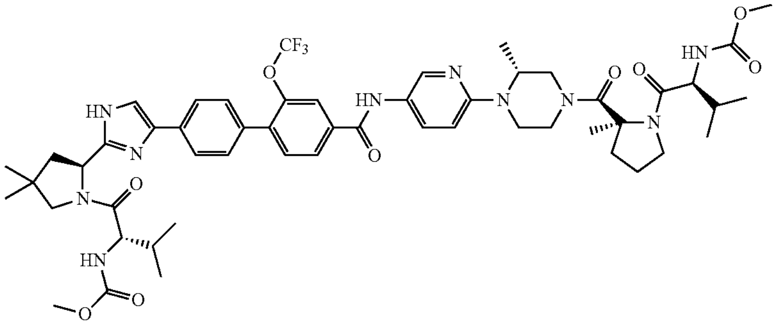 | $C_{53}H_{67}F_3N_{10}O_9$ | 1045.50 | 1044.6 |

TABLE 6-continued
| Ex No. | | Formula | Calc [M + H]+ | Found [M + H]+ |
|---|---|---|---|---|
| 6-7 | 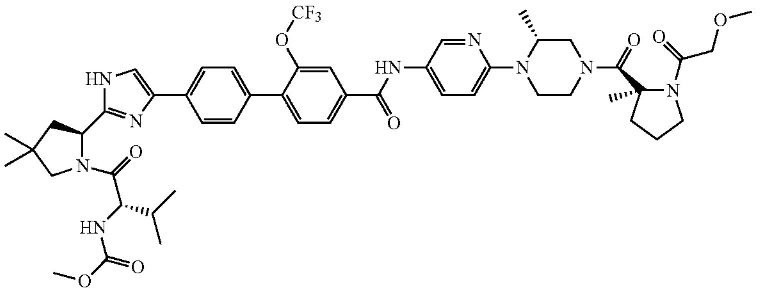 | $C_{49}H_{60}F_3N_9O_8$ | 960.45 | 959.6 |
| 6-8 | 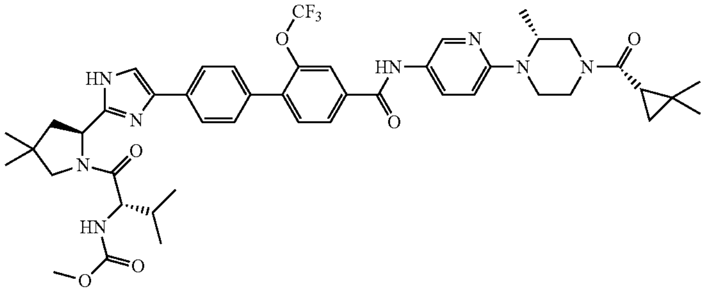 | $C_{46}H_{53}F_3N_8O_6$ | 873.42 | 872.8 |
| 6-9 | 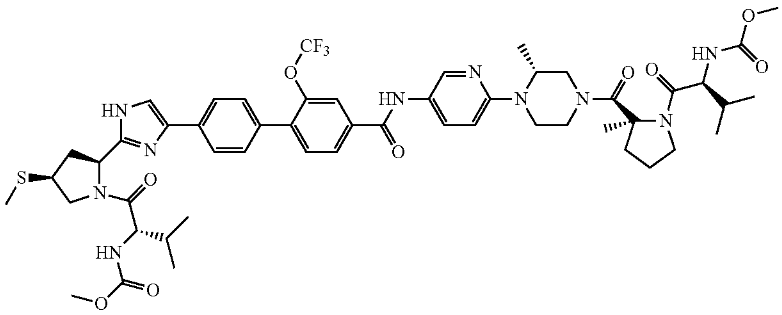 | $C_{52}H_{65}F_3N_{10}O_9S$ | 1063.46 | 1063.6 |
| 6-10 | 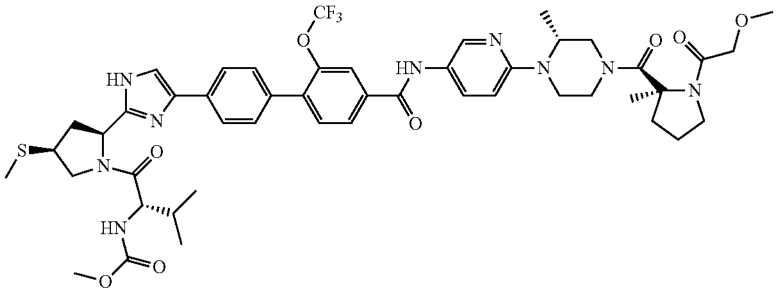 | $C_{48}H_{58}F_3N_9O_8S$ | 978.41 | 978.6 |
| 6-11 | 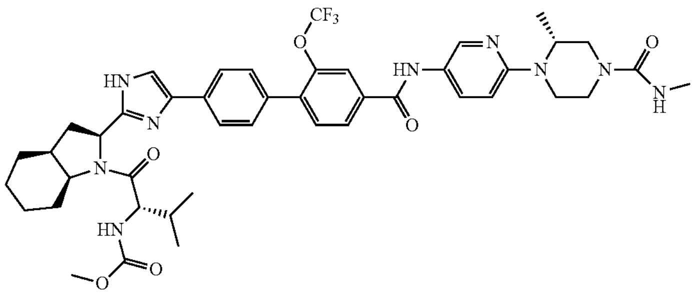 [SMILES: CNC(=O)N1CCN(c2ccc(NC(=O)c3ccc(-c4ccc(-c5c[nH]c([C@@H]6C[C@@H]7CCCC[C@@H]7N6C(=O)[C@@H](NC(=O)OC)C(C)C)n5)cc4)c(OC(F)(F)F)c3)cn2)[C@H](C)C1] | $C_{44}H_{52}F_3N_9O_6$ | 860.4 | 860.8 |

TABLE 6-continued
| Ex No. | | Formula | Calc [M + H]+ | Found [M + H]+ |
|---|---|---|---|---|
| 6-12 | 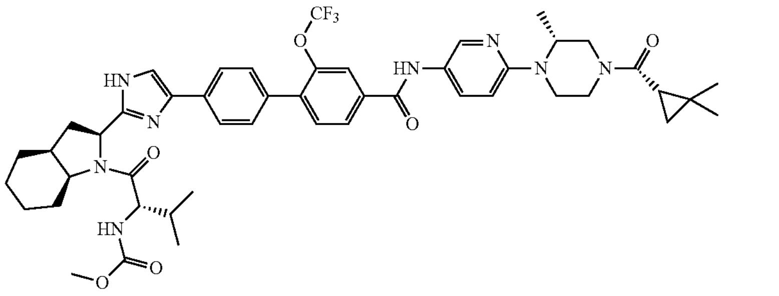 | $C_{48}H_{57}F_3N_8O_6$ | 899.44 | 900.0 |
| 6-13 | 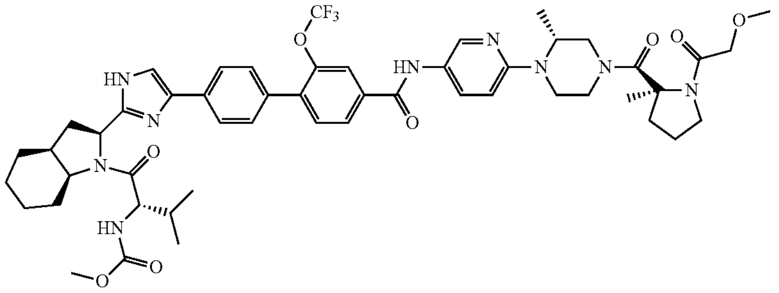 | $C_{51}H_{62}F_3N_9O_8$ | 986.47 | 987.0 |
| 6-14 | 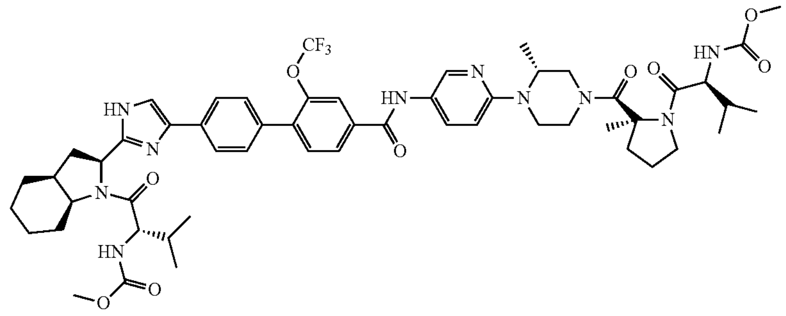 | $C_{55}H_{69}F_3N_{10}O_9$ | 1071.52 | 1072.0 |
| 6-15 | 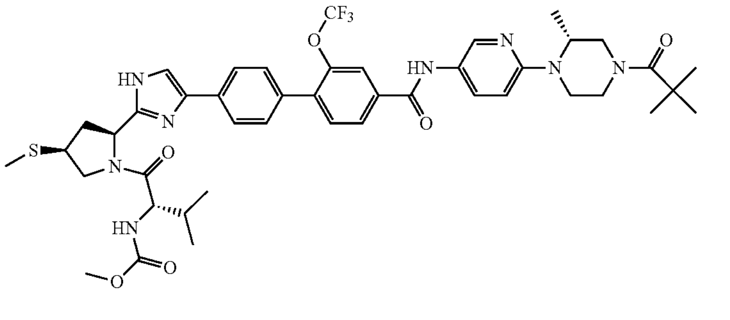 [SMILES: COC(=O)N[C@H](C(=O)N1C[C@@H](SC)C[C@H]1c1nc(-c2ccc(-c3ccc(C(=O)Nc4ccc(N5CCN(C(=O)C(C)(C)C)C[C@H]5C)nc4)cc3OC(F)(F)F)cc2)c[nH]1)C(C)C] | $C_{44}H_{53}F_3N_8O_6S$ | 879.38 | 879.8 |
| 6-16 | 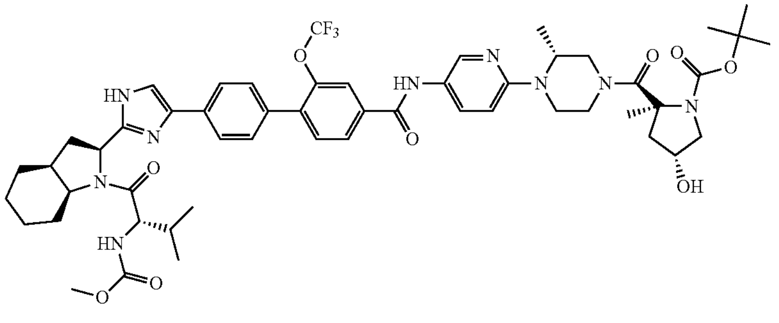 | $C_{53}H_{66}F_3N_9O_9$ | 1030.49 | 1031.2 |

TABLE 6-continued
| Ex No. | | Formula | Calc [M + H]+ | Found [M + H]+ |
|---|---|---|---|---|
| 6-17 | 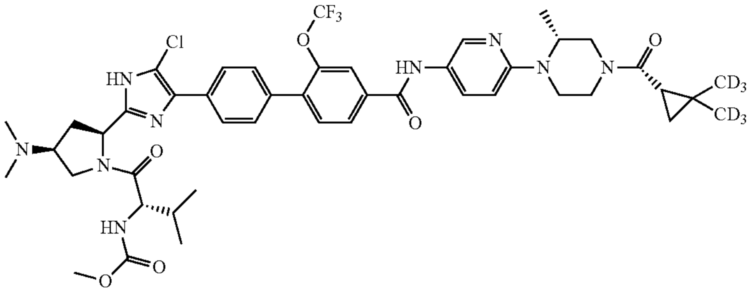 | $C_{46}H_{49}ClD_6F_3N_9O_6$ | 928.43 | 928.8 |
| 6-18 | 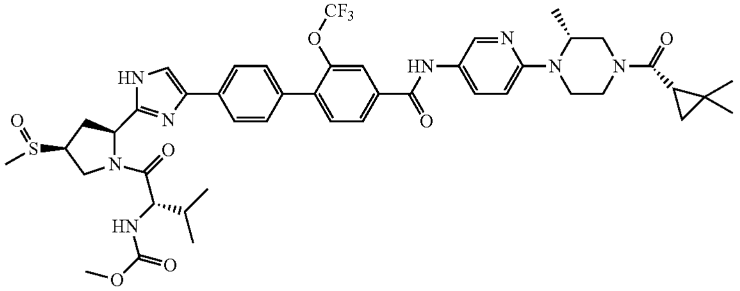 | $C_{45}H_{53}F_3N_8O_7S$ | 907.37 | 907.8 |
| 6-19 | 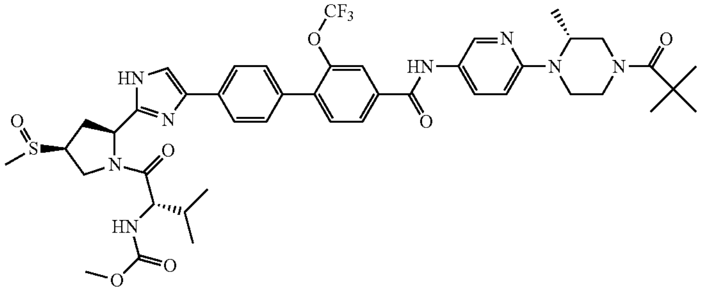 [SMILES: COC(=O)N[C@H](C(=O)N1C[C@@H](S(C)=O)C[C@H]1c1nc(-c2ccc(-c3ccc(C(=O)Nc4ccc(N5CCN(C(=O)C(C)(C)C)C[C@H]5C)nc4)cc3OC(F)(F)F)cc2)c[nH]1)C(C)C] | $C_{44}H_{53}F_3N_8O_7S$ | 895.37 | 895.8 |
| 6-20 | 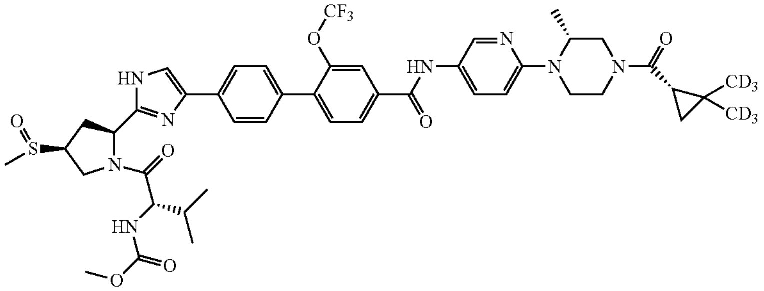 [SMILES: [2H]C([2H])([2H])C1(C([2H])([2H])[2H])C[C@@H]1C(=O)N1CCN(c2ccc(NC(=O)c3ccc(-c4ccc(-c5c[nH]c([C@@H]6C[C@H](S(C)=O)CN6C(=O)[C@@H](NC(=O)OC)C(C)C)n5)cc4)c(OC(F)(F)F)c3)cn2)[C@H](C)C1] | $C_{45}H_{47}D_6F_3N_8O_7S$ | 901.32 | 913.8 |
| 6-21 | 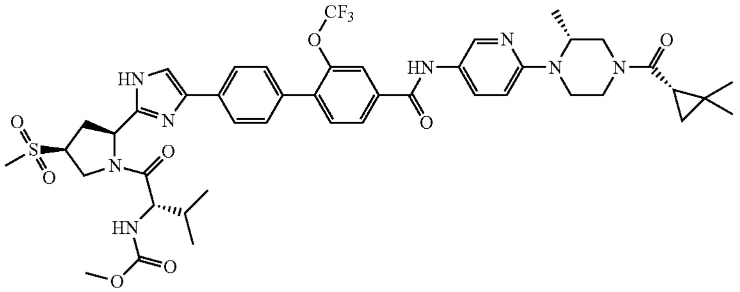 | $C_{45}H_{53}F_3N_8O_8S$ | 923.37 | 923.8 |

TABLE 6-continued
| Ex No. | | Formula | Calc [M + H]+ | Found [M + H]+ |
|---|---|---|---|---|
| 6-22 | 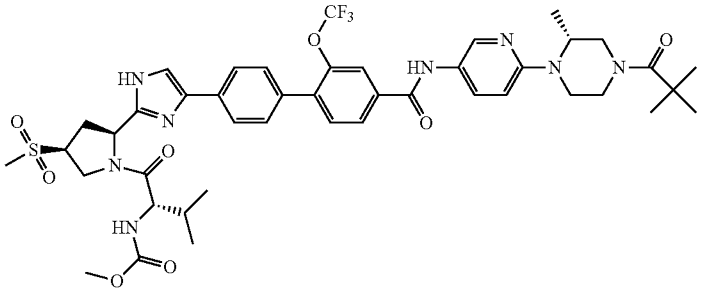 [SMILES: COC(=O)N[C@H](C(=O)N1C[C@@H](S(C)(=O)=O)C[C@H]1c1nc(-c2ccc(-c3ccc(C(=O)Nc4ccc(N5CCN(C(=O)C(C)(C)C)C[C@H]5C)nc4)cc3OC(F)(F)F)cc2)c[nH]1)C(C)C] | $C_{44}H_{53}F_3N_8O_8S$ | 911.37 | 911.8 |
| 6-23 | 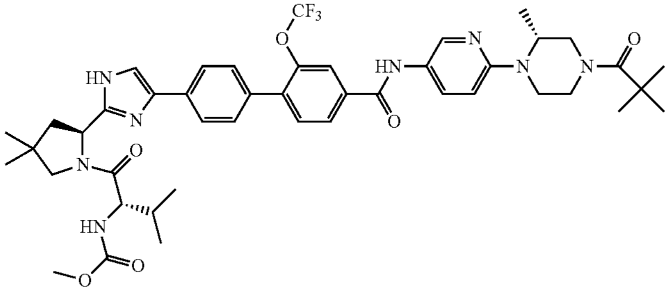 [SMILES: COC(=O)N[C@H](C(=O)N1CC(C)(C)C[C@H]1c1nc(-c2ccc(-c3ccc(C(=O)Nc4ccc(N5CCN(C(=O)C(C)(C)C)C[C@H]5C)nc4)cc3OC(F)(F)F)cc2)c[nH]1)C(C)C] | $C_{45}H_{55}F_3N_8O_6$ | 861.42 | 861.8 |
| 6-24 | 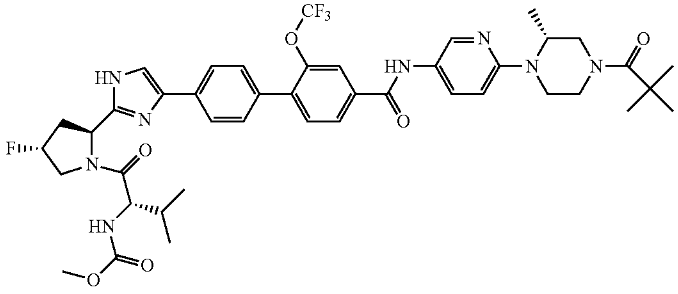 [SMILES: COC(=O)N[C@H](C(=O)N1C[C@H](F)C[C@H]1c1nc(-c2ccc(-c3ccc(C(=O)Nc4ccc(N5CCN(C(=O)C(C)(C)C)C[C@H]5C)nc4)cc3OC(F)(F)F)cc2)c[nH]1)C(C)C] | $C_{45}H_{52}F_4N_8O_7$ | 893.39 | 893.6 |
| 6-25 | 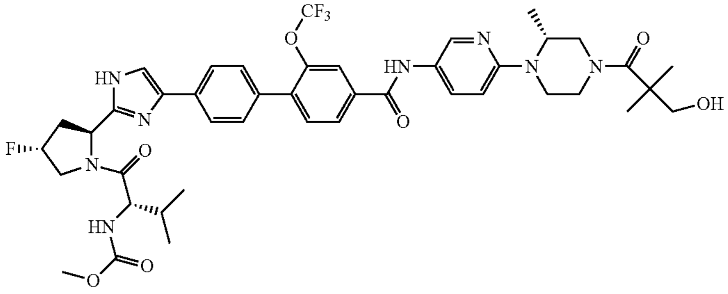 [SMILES: COC(=O)N[C@H](C(=O)N1C[C@H](F)C[C@H]1c1nc(-c2ccc(-c3ccc(C(=O)Nc4ccc(N5CCN(C(=O)C(C)(C)CO)C[C@H]5C)nc4)cc3OC(F)(F)F)cc2)c[nH]1)C(C)C] | $C_{45}H_{52}F_4N_8O_8$ | 909.38 | 909.6 |
| 6-26 | 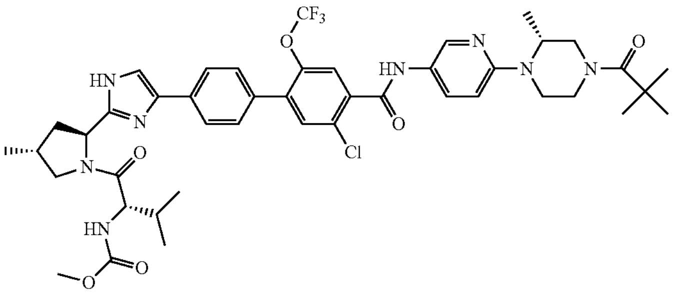 [SMILES: COC(=O)N[C@H](C(=O)N1C[C@H](C)C[C@H]1c1nc(-c2ccc(-c3cc(Cl)c(C(=O)Nc4ccc(N5CCN(C(=O)C(C)(C)C)C[C@H]5C)nc4)cc3OC(F)(F)F)cc2)c[nH]1)C(C)C] | $C_{44}H_{52}ClF_3N_8O_6$ | 881.37 | 881.4 |

TABLE 6-continued
| Ex No. | | Formula | Calc [M + H]+ | Found [M + H]+ |
|---|---|---|---|---|
| 6-27 | 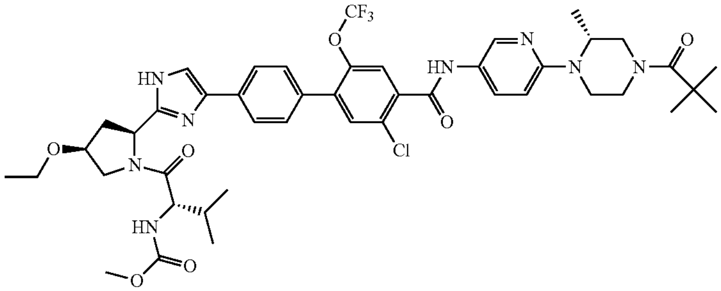 [SMILES: CCO[C@H]1C[C@@H](c2nc(-c3ccc(-c4cc(Cl)c(C(=O)Nc5ccc(N6CCN(C(=O)C(C)(C)C)C[C@H]6C)nc5)cc4OC(F)(F)F)cc3)c[nH]2)N(C(=O)[C@@H](NC(=O)OC)C(C)C)C1] | $C_{45}H_{54}ClF_3N_8O_7$ | 911.38 | 911.6 |
| 6-28 | 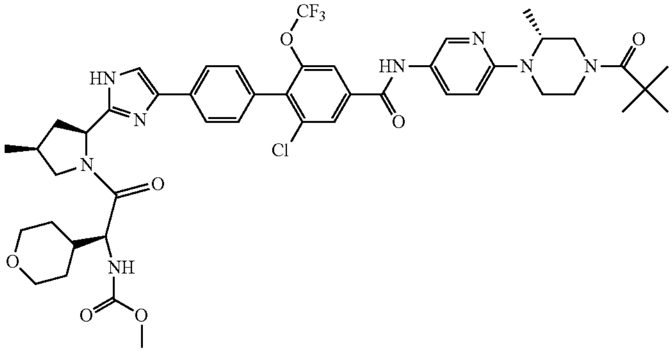 [SMILES: COC(=O)N[C@H](C(=O)N1C[C@@H](C)C[C@H]1c1nc(-c2ccc(-c3c(Cl)cc(C(=O)Nc4ccc(N5CCN(C(=O)C(C)(C)C)C[C@H]5C)nc4)cc3OC(F)(F)F)cc2)c[nH]1)C1CCOCC1] | $C_{46}H_{54}ClF_3N_8O_7$ | 923.38 | 923.6 |
| 6-29 | 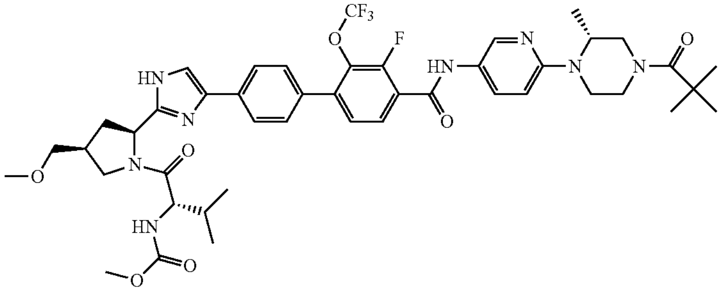 [SMILES: COC[C@H]1C[C@@H](c2nc(-c3ccc(-c4ccc(C(=O)Nc5ccc(N6CCN(C(=O)C(C)(C)C)C[C@H]6C)nc5)c(F)c4OC(F)(F)F)cc3)c[nH]2)N(C(=O)[C@@H](NC(=O)OC)C(C)C)C1] | $C_{47}H_{56}F_4N_8O_8$ | 937.42 | 937.6 |
TABLE 7
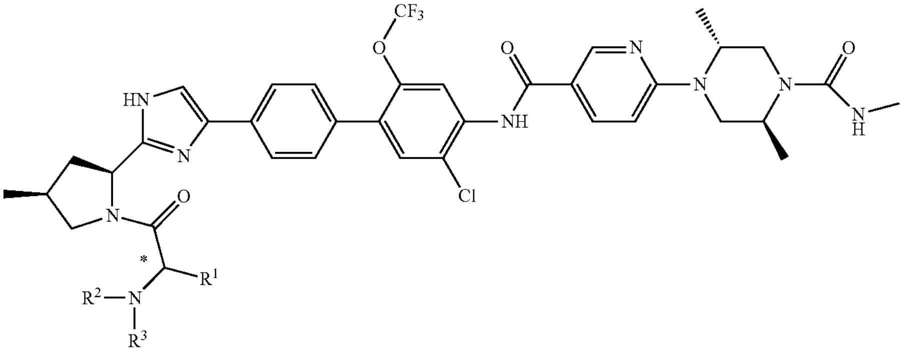
| Ex No. | $R^1$ | * | $R^2$ | $R^3$ | Formula | Calc [M + H]+ | Found [M + H]+ |
|---|---|---|---|---|---|---|---|
| 7-1 | 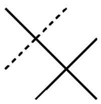 | (S) | | 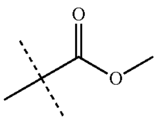 | $C_{43}H_{51}ClF_3N_9O_6$ | 882.36 | 882.8 |

TABLE 7-continued
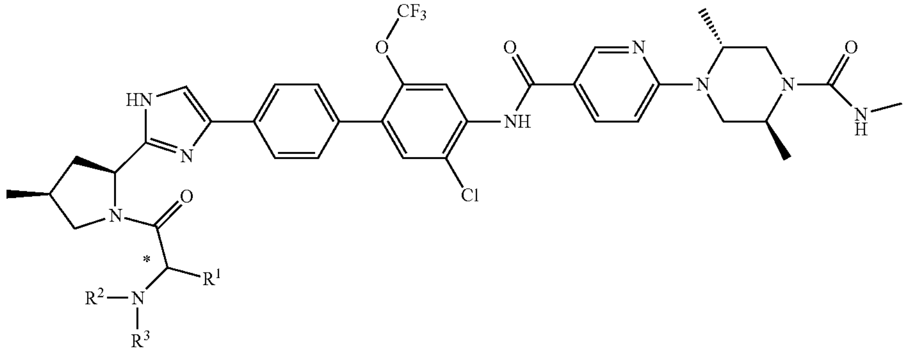
| Ex No. | $R^1$ | * | $R^2$ | $R^3$ | Formula | Calc $[M+H]^+$ | Found $[M+H]^+$ |
|---|---|---|---|---|---|---|---|
| 7-2 | 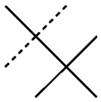 | (R) | | 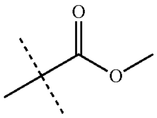 | $C_{43}H_{51}ClF_3N_9O_6$ | 882.36 | 882.8 |
| 7-3 | 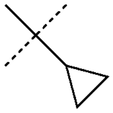 | (S) | | 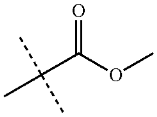 | $C_{42}H_{47}ClF_3N_9O_6$ | 866.33 | 866.8 |
| 7-4 | 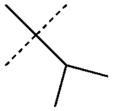 | (S) | | 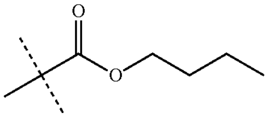 | $C_{45}H_{55}ClF_3N_9O_6$ | 910.39 | 910.8 |
| 7-5 | 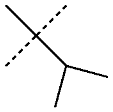 | (S) | | 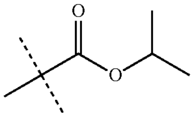 | $C_{44}H_{53}ClF_3N_9O_6$ | 896.38 | 896.8 |
| 7-6 | 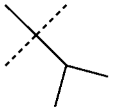 | (S) | | 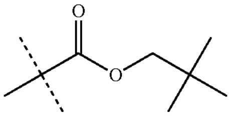 | $C_{46}H_{57}ClF_3N_9O_6$ | 924.41 | 924.8 |
| 7-7 | 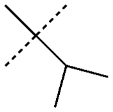 | (S) | | 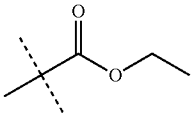 | $C_{43}H_{51}ClF_3N_9O_6$ | 882.36 | 882.8 |
| 7-8 | 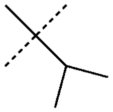 | (S) | | 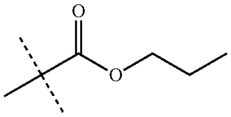 | $C_{44}H_{53}ClF_3N_9O_6$ | 896.38 | 896.8 |
| 7-9 | 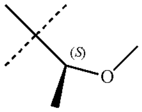 | (S) | | 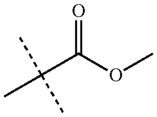 | $C_{42}H_{49}ClF_3N_9O_7$ | 884.34 | 884.8 |
| 7-10 | 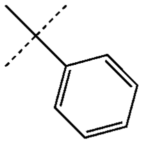 | (R) | | 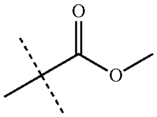 | $C_{43}H_{51}ClF_3N_9O_6$ | 882.36 | 882.8 |

TABLE 7-continued
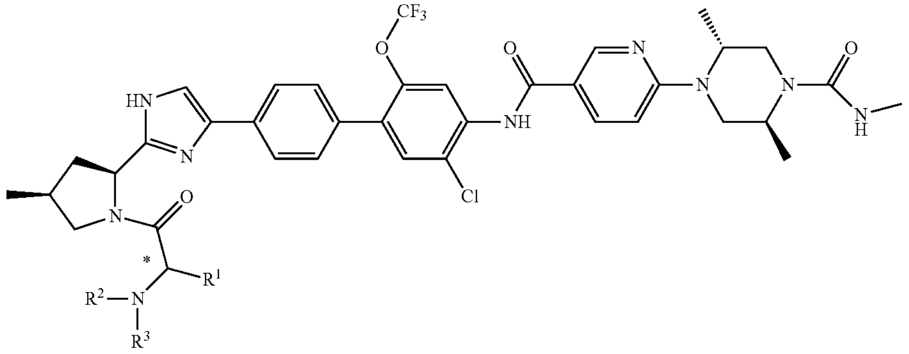
| Ex No. | $R^1$ | * | $R^2$ | $R^3$ | Formula | Calc $[M + H]^+$ | Found $[M + H]^+$ |
|---|---|---|---|---|---|---|---|
| 7-11 | 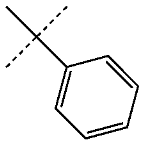 | (R) | $CH_3$ | $CH_3$ | $C_{45}H_{49}ClF_3N_9O_4$ | 872.36 | 872.8 |
| 7-12 | 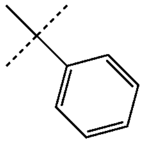 | (R) | $C_2H_5$ | $C_2H_5$ | $C_{47}H_{53}ClF_3N_9O_4$ | 900.39 | 900.8 |
| 7-13 | $C_2H_5$ | (S) | | 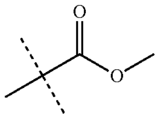 | $C_{41}H_{47}ClF_3N_9O_6$ | 854.33 | 854.8 |
| 7-14 | $CH_3$ | (S) | $CH_3$ | 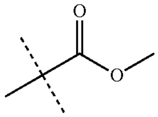 | $C_{41}H_{47}ClF_3N_9O_6$ | 854.33 | 854.8 |
| 7-15 | 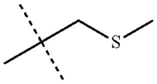 | (R) | | 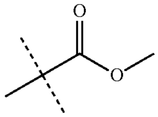 | $C_{41}H_{47}ClF_3N_9O_6S$ | 886.3 | 886.8 |
| 7-16 | 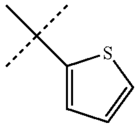 | (S) | | 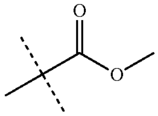 | $C_{43}H_{45}ClF_3N_9O_6S$ | 908.29 | 908.8 |
| 7-17 | 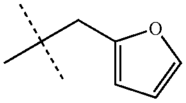 | (R) | | 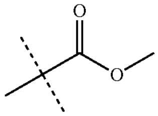 | $C_{44}H_{47}ClF_3N_9O_7$ | 906.32 | 906.8 |

TABLE 8
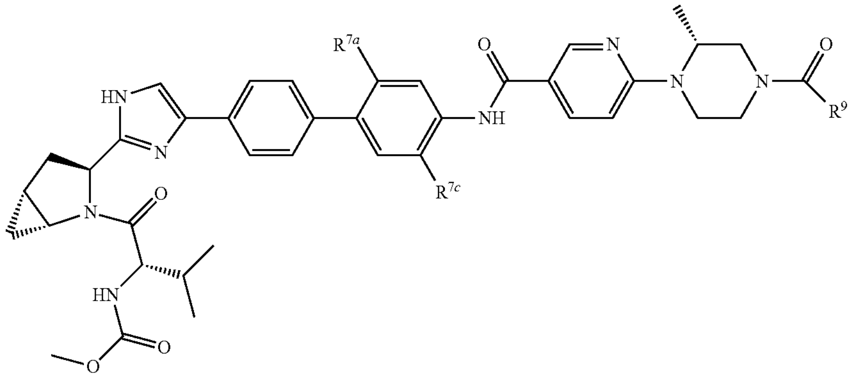
| Ex No. | $R^{7a}$ | $R^{7c}$ | $R^9$ | Formula | Calc [M + H]+ | Found [M + H]+ |
|---|---|---|---|---|---|---|
| 8-1 | $OCF_3$ | Cl | 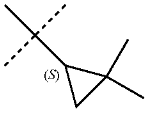 | $C_{45}H_{50}ClF_3N_8O_6$ | 891.35 | 891.8 |
| 8-2 | $OCF_3$ | Cl | 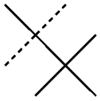 | $C_{44}H_{50}ClF_3N_8O_6$ | 879.35 | 879.8 |
| 8-3 | $CF_3$ | Cl | 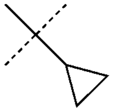 | $C_{43}H_{46}ClF_3N_8O_5$ | 847.32 | 847.8 |
| 8-4 | $CF_3$ | Cl | 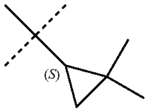 | $C_{45}H_{50}ClF_3N_8O_5$ | 875.35 | 875.8 |
| 8-5 | $CF_3$ | Cl | 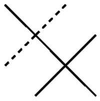 | $C_{44}H_{50}ClF_3N_8O_5$ | 863.35 | 863.8 |
| 8-6 | $CF_3$ | Cl | 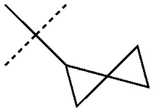 | $C_{45}H_{48}ClF_3N_8O_5$ | 873.34 | 873.8 |

TABLE 9
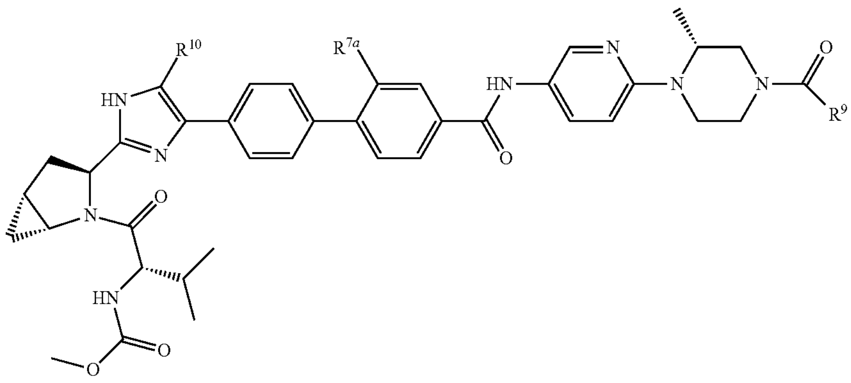
| Ex No. | $R^{7a}$ | $R^9$ | $R^{10}$ | Formula | Calc [M + H]$^+$ | Found [M + H]$^+$ |
|---|---|---|---|---|---|---|
| 9-1 | $OCF_3$ | 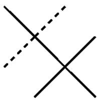 | Cl | $C_{44}H_{50}ClF_3N_8O_6$ | 879.35 | 879.8 |
| 9-2 | $OCF_3$ | 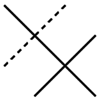 | | $C_{44}H_{51}F_3N_8O_6$ | 845.39 | 845.8 |
| 9-3 | $OCF_3$ | 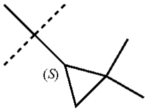 | | $C_{45}H_{51}F_3N_8O_6$ | 857.39 | 857.8 |
| 9-4 | $OCF_3$ | 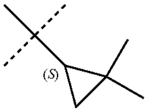 | Cl | $C_{45}H_{50}ClF_3N_8O_6$ | 891.35 | 891.8 |
| 9-5 | $OCF_3$ | 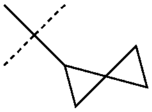 | | $C_{45}H_{49}F_3N_8O_6$ | 855.37 | 855.8 |

TABLE 10
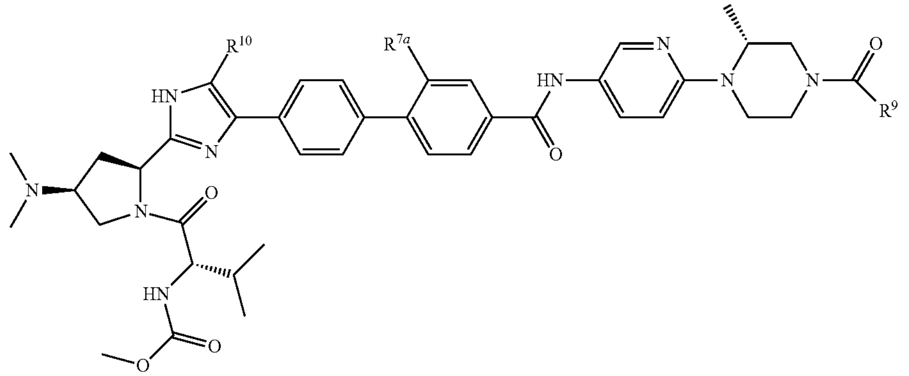
| Ex No. | $R^{7a}$ | $R^9$ | $R^{10}$ | Formula | Calc $[M + H]^+$ | Found $[M + H]^+$ |
|---|---|---|---|---|---|---|
| 10-1 | $OCF_3$ | 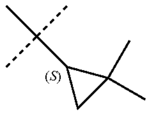 | | $C_{46}H_{56}F_3N_9O_6$ | 888.43 | 889.0 |
| 10-2 | $OCF_3$ | $NHCH_3$ | | $C_{42}H_{51}F_3N_{10}O_6$ | 849.39 | 849.8 |
| 10-3 | $OCF_3$ | 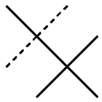 | Cl | $C_{45}H_{55}ClF_3N_9O_6$ | 910.39 | 910.8 |
| 10-4 | $OCF_3$ | $N(CH_3)_2$ | Cl | $C_{43}H_{52}ClF_3N_{10}O_6$ | 897.37 | 897.8 |
| 10-5 | $OCF_3$ | 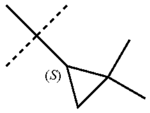 | Cl | $C_{46}H_{55}ClF_3N_9O_6$ | 922.39 | 922.8 |
TABLE 11
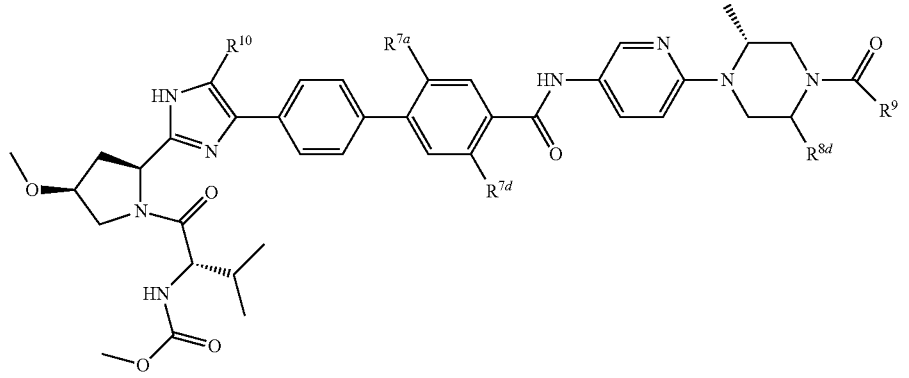
| Ex No. | $R^{7a}$ | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|---|
| 11-1 | $OCF_3$ | | $CH_3$ | 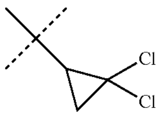 | | $C_{44}H_{49}Cl_2F_3N_8O_7$ | 929.31 | 929.8 |
| 11-2 | $OCF_3$ | | $CH_3$ | $NHCH_3$ | | $C_{42}H_{50}F_3N_9O_7$ | 850.38 | 850.8 |

TABLE 11-continued

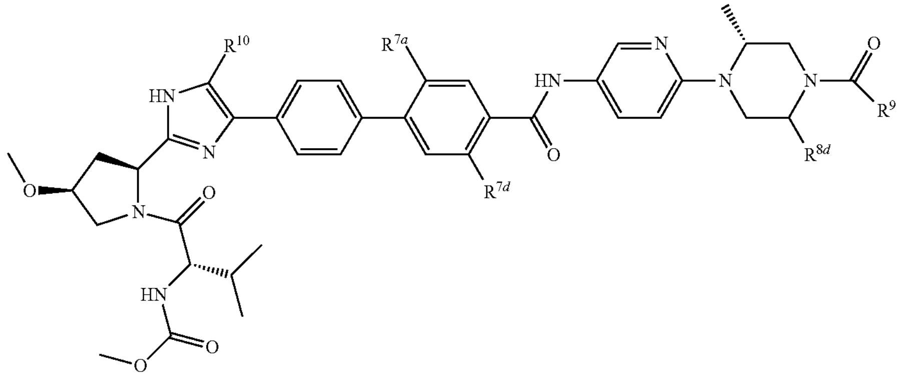

| Ex No. | $R^{7a}$ | $R^{7d}$ | $R^{8d(\#)}$ | $R^9$ | $R^{10}$ | Formula | Calc [M + H]$^+$ | Found [M + H]$^+$ |
|---|---|---|---|---|---|---|---|---|
| 11-3 | $OCF_3$ | | $CH_3$ | 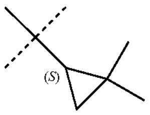 | Cl | $C_{46}H_{54}ClF_3N_8O_7$ | 923.38 | 923.8 |
| 11-4 | $OCF_3$ | | $CH_3$ | 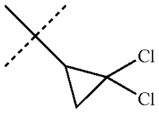 | Cl | $C_{44}H_{48}Cl_3F_3N_8O_7$ | 963.27 | 963.8 |
| 11-5 | $OCF_3$ | | $CH_3$ | 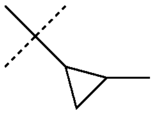 | Cl | $C_{45}H_{52}ClF_3N_8O_7$ | 909.36 | 909.8 |
| 11-6 | $OCF_3$ | | $CH_3$ | 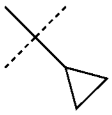 | Cl | $C_{44}H_{50}ClF_3N_8O_7$ | 895.34 | 895.8 |
| 11-7 | $OCF_3$ | | $CH_3$ | 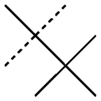 | Cl | $C_{45}H_{54}ClF_3N_8O_7$ | 911.38 | 911.8 |
| 11-8 | $OCF_3$ | | $CH_3$ | $NHCH_3$ | Cl | $C_{42}H_{49}ClF_3N_9O_7$ | 884.34 | 884.8 |
| 11-9 | $OCF_3$ | | $CH_3$ | $N(CH_3)_2$ | Cl | $C_{43}H_{51}ClF_3N_9O_7$ | 898.36 | 898.8 |
| 11-10 | $OCF_3$ | | | 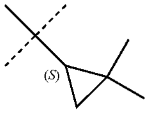 | Cl | $C_{45}H_{52}ClF_3N_8O_7$ | 909.36 | 909.8 |
| 11-11 | $OCF_3$ | | | 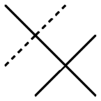 | Cl | $C_{44}H_{52}ClF_3N_8O_7$ | 897.36 | 897.8 |
| 11-12 | $OCF_3$ | | | 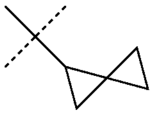 | Cl | $C_{45}H_{50}ClF_3N_8O_7$ | 907.34 | 907.8 |

(#)For all compounds, when the substituent $R^{8d}$ is present, the orientation of the chiral carbon atom bearing the substituent $R^{8d}$ is (S).

TABLE 12
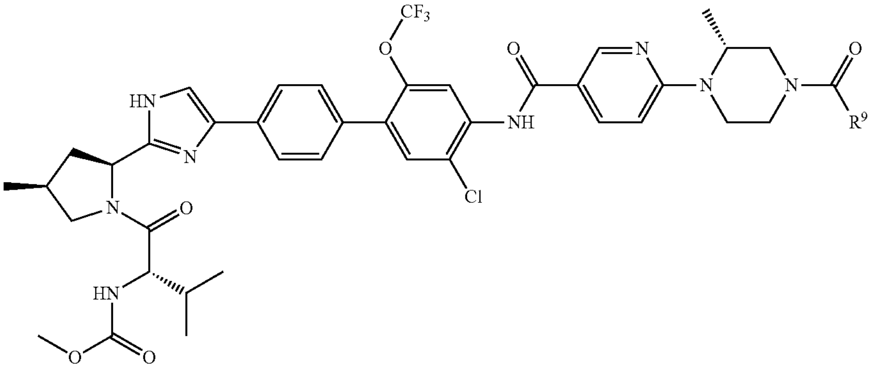
| Ex No. | $R^9$ | Formula | Calc $[M + H]^+$ | Found $[M + H]^+$ |
|---|---|---|---|---|
| 12-1 | 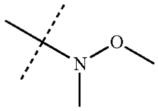 | $C_{42}H_{49}ClF_3N_9O_7$ | 884.34 | 884.8 |
| 12-2 | 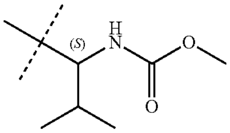 | $C_{46}H_{55}ClF_3N_9O_8$ | 954.38 | 954.8 |
| 12-3 | 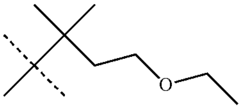 | $C_{47}H_{58}ClF_3N_8O_7$ | 939.41 | 939.8 |
| 12-4 | 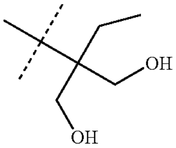 | $C_{45}H_{54}ClF_3N_8O_8$ | 927.37 | 927.8 |
| 12-5 | 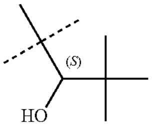 | $C_{45}H_{54}ClF_3N_8O_7$ | 911.38 | 911.8 |
| 12-6 | 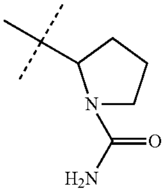 | $C_{45}H_{52}ClF_3N_{10}O_7$ | 937.37 | 937.8 |
| 12-7 | 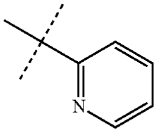 | $C_{45}H_{47}ClF_3N_9O_6$ | 902.33 | 902.8 |
| 12-8 | 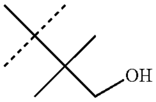 | $C_{44}H_{52}ClF_3N_8O_7$ | 897.36 | 897.8 |

TABLE 12-continued
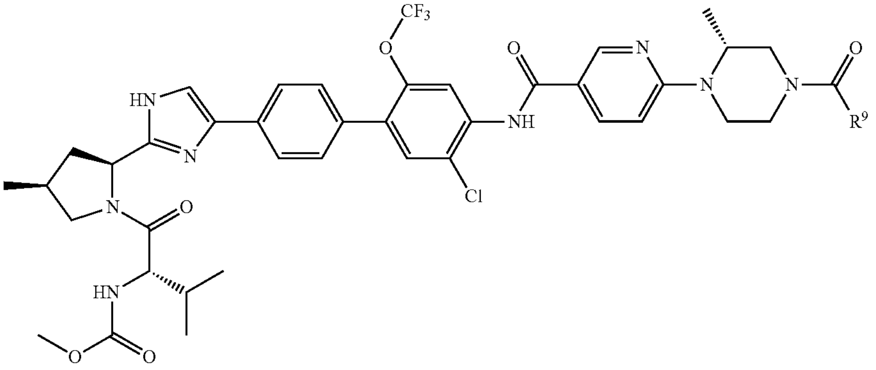
| Ex No. | $R^9$ | Formula | Calc $[M + H]^+$ | Found $[M + H]^+$ |
|---|---|---|---|---|
| 12-9 | 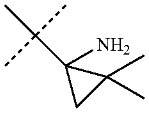 | $C_{45}H_{53}ClF_3N_9O_6$ | 908.38 | 908.8 |
| 12-10 | 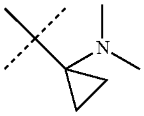 | $C_{45}H_{53}ClF_3N_9O_6$ | 908.38 | 908.8 |
| 12-11 | 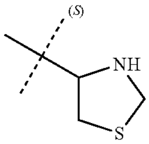 | $C_{43}H_{49}ClF_3N_9O_6S$ | 912.32 | 912.8 |
| 12-12 | 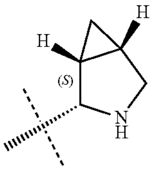 | $C_{45}H_{51}ClF_3N_9O_6$ | 906.36 | 906.8 |
| 12-13 | 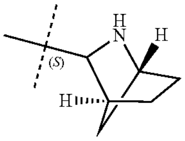 | $C_{46}H_{53}ClF_3N_9O_6$ | 920.38 | 920.8 |
| 12-14 | 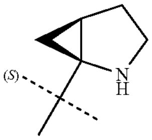 | $C_{45}H_{51}ClF_3N_9O_6$ | 906.36 | 906.8 |
| 12-15 | 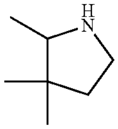 | $C_{46}H_{55}ClF_3N_9O_6$ | 922.39 | 922.8 |
| 12-16 | 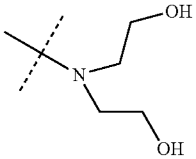 | $C_{44}H_{53}ClF_3N_9O_8$ | 928.37 | 928.8 |

TABLE 12-continued
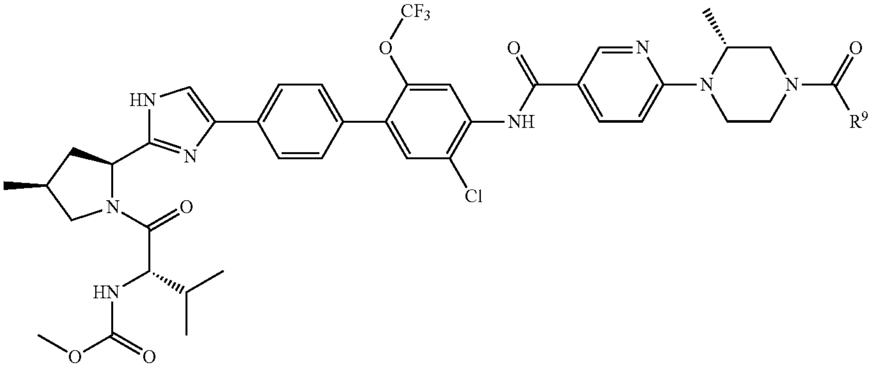
| Ex No. | $R^9$ | Formula | Calc [M + H]$^+$ | Found [M + H]$^+$ |
|---|---|---|---|---|
| 12-17 | 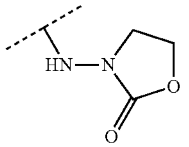 | $C_{43}H_{48}ClF_3N_{10}O_8$ | 925.33 | 925.8 |
| 12-18 | 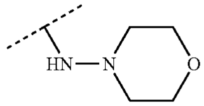 | $C_{44}H_{52}ClF_3N_{10}O_7$ | 925.37 | 925.8 |
| 12-19 | 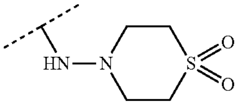 | $C_{44}H_{52}ClF_3N_{10}O_8S$ | 973.33 | 973.8 |
| 12-20 | 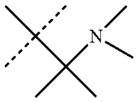 | $C_{45}H_{55}ClF_3N_9O_6$ | 910.39 | 910.8 |
| 12-21 | 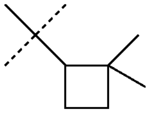 | $C_{46}H_{54}ClF_3N_8O_6$ | 907.38 | 907.8 |
| 12-22 | 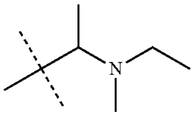 | $C_{45}H_{55}ClF_3N_9O_6$ | 910.39 | 910.8 |
| 12-23 | 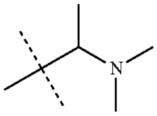 | $C_{44}H_{53}ClF_3N_9O_6$ | 896.38 | 896.8 |
| 12-24 | 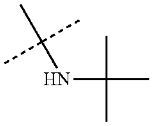 | $C_{44}H_{53}ClF_3N_9O_6$ | 896.38 | 896.8 |
| 12-25 | 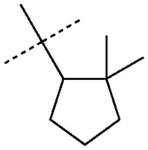 | $C_{47}H_{56}ClF_3N_8O_6$ | 921.4 | 921.8 |

TABLE 12-continued
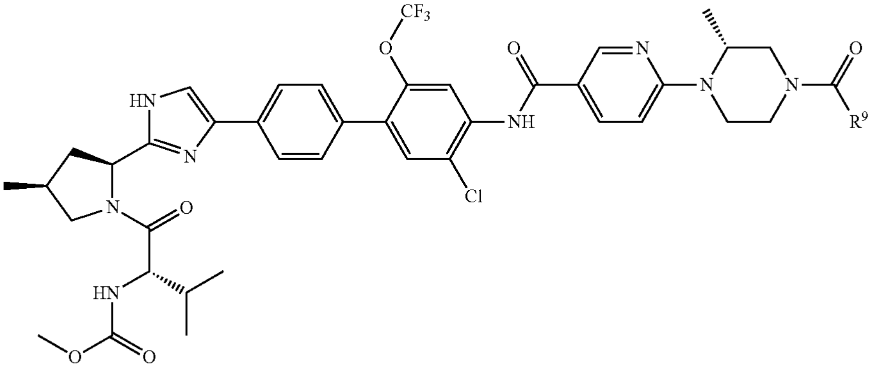
| Ex No. | $R^9$ | Formula | Calc $[M + H]^+$ | Found $[M + H]^+$ |
|---|---|---|---|---|
| 12-26 | 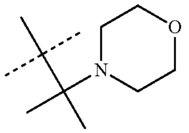 | $C_{47}H_{57}ClF_3N_9O_7$ | 952.40 | 952.8 |
| 12-27 | 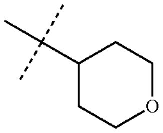 | $C_{45}H_{52}ClF_3N_8O_7$ | 909.36 | 909.8 |
| 12-28 | 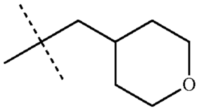 | $C_{46}H_{54}ClF_3N_8O_7$ | 923.38 | 923.8 |
| 12-29 | 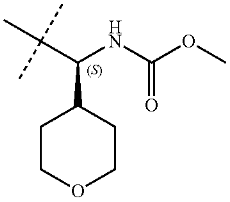 | $C_{48}H_{57}ClF_3N_9O_9$ | 996.39 | 996.8 |
| 12-30 | 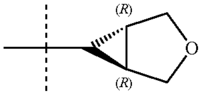 | $C_{45}H_{50}ClF_3N_8O_7$ | 907.34 | 908.8 |
| 12-31 | 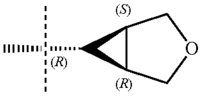 | $C_{45}H_{50}ClF_3N_8O_7$ | 907.34 | 907.6 |
| 12-32 | 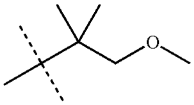 | $C_{45}H_{54}ClF_3N_8O_7$ | 911.38 | 911.8 |
| 12-33 | 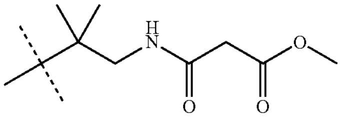 | $C_{48}H_{57}ClF_3N_9O_9$ | 996.39 | 996.6 |

TABLE 12-continued
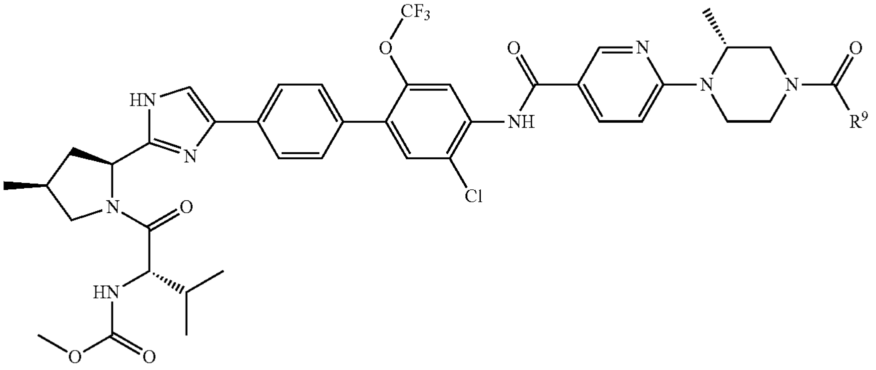
| Ex No. | $R^9$ | Formula | Calc $[M + H]^+$ | Found $[M + H]^+$ |
|---|---|---|---|---|
| 12-34 | 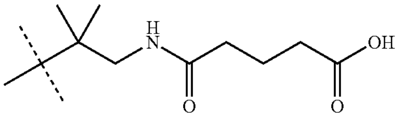 | $C_{49}H_{59}ClF_3N_9O_9$ | 1010.41 | 1010.8 |
| 12-25 | 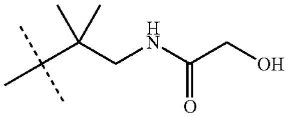 | $C_{46}H_{55}ClF_3N_9O_8$ | 954.38 | 954.6 |
| 12-36 | 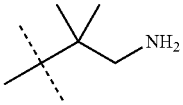 | $C_{44}H_{53}ClF_3N_9O_6$ | 896.38 | 896.6 |
| 12-37 | 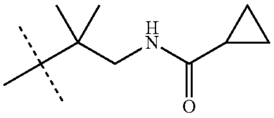 | $C_{48}H_{57}ClF_3N_9O_7$ | 964.40 | 964.6 |
| 12-38 | 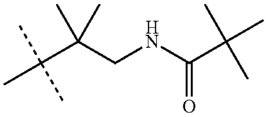 | $C_{49}H_{61}ClF_3N_9O_7$ | 980.43 | 980.6 |
| 12-39 | 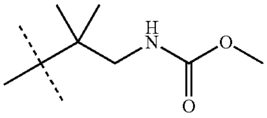 | $C_{46}H_{55}ClF_3N_9O_8$ | 954.38 | 954.6 |
| 12-40 | 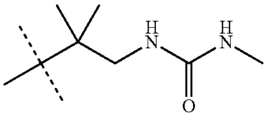 | $C_{46}H_{56}ClF_3N_{10}O_7$ | 953.40 | 953.4 |
| 12-41 | 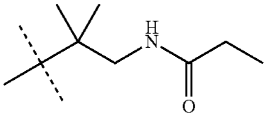 | $C_{47}H_{57}ClF_3N_9O_7$ | 952.40 | 952.6 |
| 12-42 | 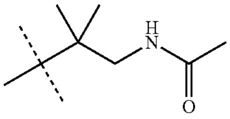 | $C_{46}H_{55}ClF_3N_9O_7$ | 938.39 | 938.6 |

TABLE 12-continued
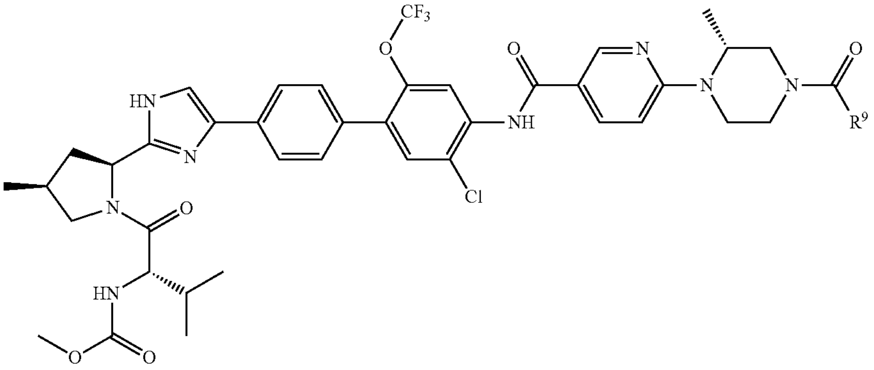
| Ex No. | R⁹ | Formula | Calc [M + H]⁺ | Found [M + H]⁺ |
|---|---|---|---|---|
| 12-43 | 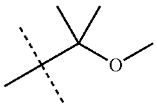 | $C_{44}H_{52}ClF_3N_8O_7$ | 897.36 | 897.6 |
| 12-44 | 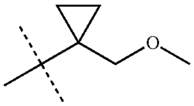 | $C_{45}H_{52}ClF_3N_8O_7$ | 909.36 | 909.6 |
| 12-45 | 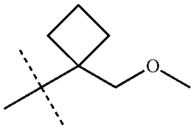 | $C_{46}H_{54}ClF_3N_8O_7$ | 923.38 | 923.6 |
| 12-46 | 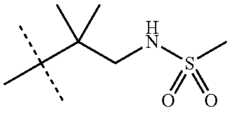 | $C_{45}H_{55}ClF_3N_9O_8S$ | 974.35 | 974.6 |
| 12-47 | 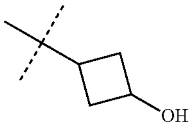 | $C_{44}H_{50}ClF_3N_8O_7$ | 895.34 | 895.6 |
| 12-48 | 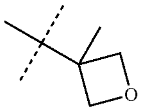 | $C_{44}H_{50}ClF_3N_8O_7$ | 895.34 | 895.6 |
| 12-49 | 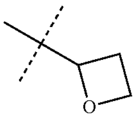 | $C_{43}H_{48}ClF_3N_8O_7$ | 881.33 | 881.6 |
| 12-50 | 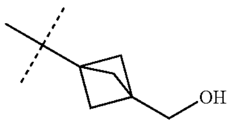 | $C_{46}H_{52}ClF_3N_8O_7$ | 921.36 | 921.6 |
| 12-51 | 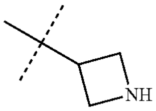 | $C_{43}H_{49}ClF_3N_9O_6$ | 880.35 | 880.6 |

TABLE 12-continued
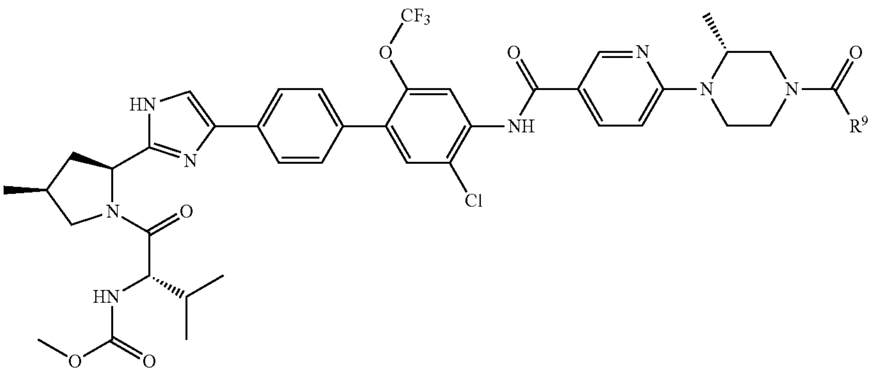
| Ex No. | $R^9$ | Formula | Calc $[M + H]^+$ | Found $[M + H]^+$ |
|---|---|---|---|---|
| 12-52 | 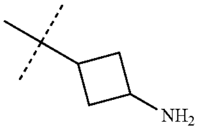 | $C_{44}H_{51}ClF_3N_9O_6$ | 894.36 | 894.6 |
| 12-53 | 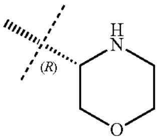 | $C_{44}H_{51}ClF_3N_9O_7$ | 910.36 | 910.6 |
| 12-54 | 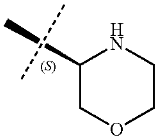 | $C_{44}H_{51}ClF_3N_9O_7$ | 910.36 | 910.6 |
| 12-55 | 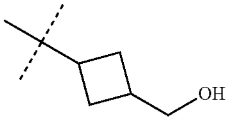 | $C_{45}H_{52}ClF_3N_8O_7$ | 909.36 | 909.6 |
| 12-56 | 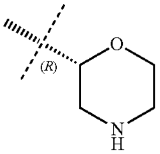 | $C_{44}H_{51}ClF_3N_9O_7$ | 910.36 | 910.6 |
| 12-57 | 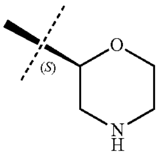 | $C_{44}H_{51}ClF_3N_9O_7$ | 910.36 | 910.6 |
| 12-58 | 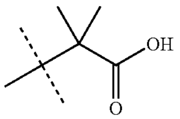 | $C_{44}H_{50}ClF_3N_8O_8$ | 911.34 | 912.6 |

TABLE 13
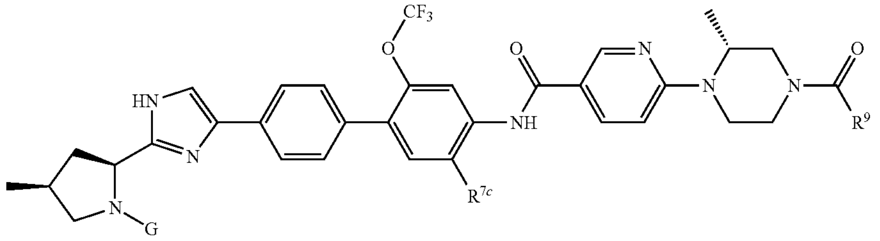
| Ex No. | G | $R^{7c}$ | $R^9$ | Formula | Calc $[M + H]^+$ | Found $[M + H]^+$ |
|---|---|---|---|---|---|---|
| 13-1 | 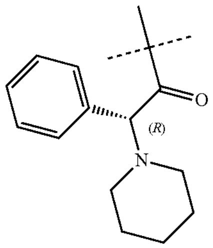 | Cl | 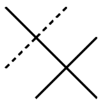 | $C_{50}H_{56}ClF_3N_8O_4$ | 925.41 | 925.8 |
| 13-2 | 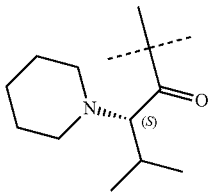 | Cl | 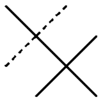 | $C_{47}H_{58}ClF_3N_8O_4$ | 891.42 | 891.8 |
| 13-3 | 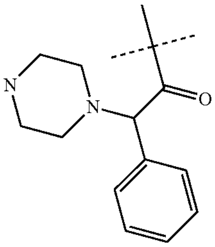 | Cl | 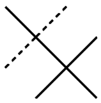 | $C_{49}H_{55}ClF_3N_9O_4$ | 926.4 | 926.8 |
| 13-4 | 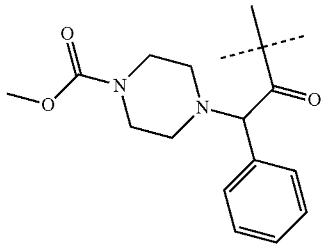 | Cl | 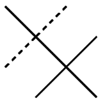 | $C_{51}H_{57}ClF_3N_9O_6$ | 984.41 | 984.8 |
| 13-5 | 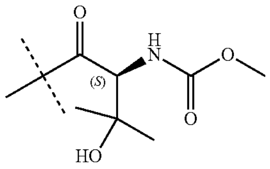 | Cl | 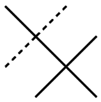 | $C_{44}H_{52}ClF_3N_8O_7$ | 897.36 | 897.8 |
| 13-6 | 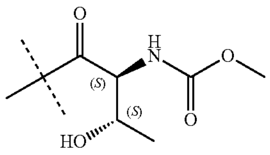 | Cl | 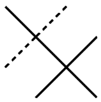 | $C_{43}H_{50}ClF_3N_8O_7$ | 883.34 | 883.8 |

TABLE 13-continued
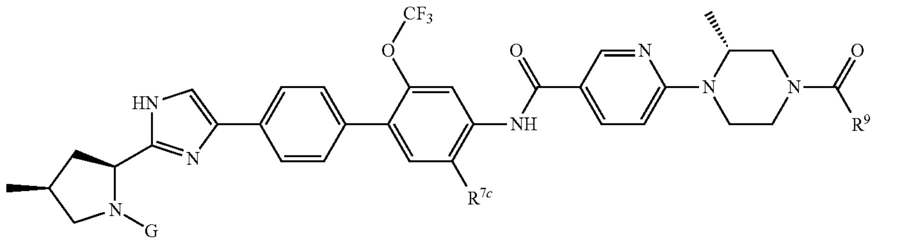
| Ex No. | G | $R^{7c}$ | $R^9$ | Formula | Calc $[M + H]^+$ | Found $[M + H]^+$ |
|---|---|---|---|---|---|---|
| 13-7 | 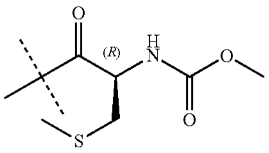 | Cl | 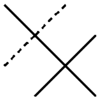 | $C_{43}H_{50}ClF_3N_8O_6S$ | 899.32 | 899.8 |
| 13-8 | 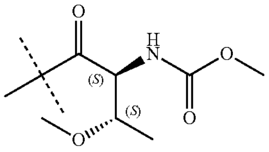 | Cl | 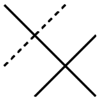 | $C_{44}H_{52}ClF_3N_8O_7$ | 897.36 | 879.8 |
| 13-9 | 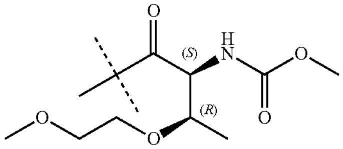 | Cl | 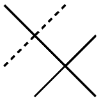 | $C_{46}H_{56}ClF_3N_8O_8$ | 941.39 | 941.4 |
| 13-10 | 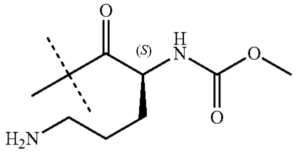 | Cl | 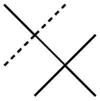 | $C_{43}H_{51}ClF_3N_9O_6$ | 882.36 | 882.8 |
| 13-11 | 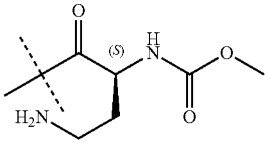 | Cl | 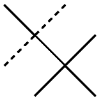 | $C_{42}H_{49}ClF_3N_9O_6$ | 868.35 | 868.8 |
| 13-12 | 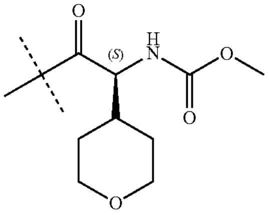 | | 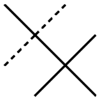 | $C_{46}H_{55}F_3N_8O_7$ | 889.41 | 889.8 |
| 13-13 | 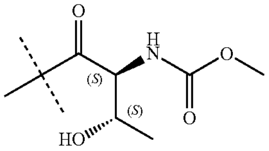 | | 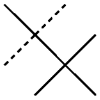 | $C_{43}H_{51}F_3N_8O_7$ | 849.38 | 849.8 |

TABLE 13-continued
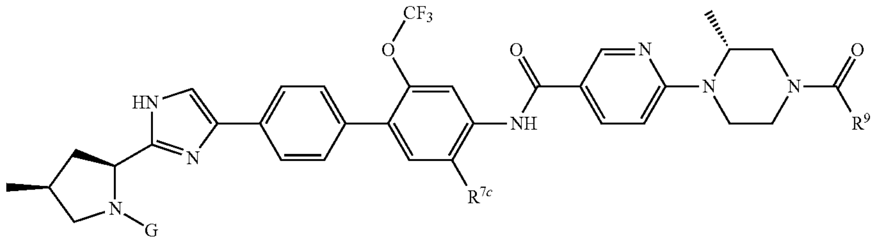
| Ex No. | G | $R^{7c}$ | $R^9$ | Formula | Calc $[M + H]^+$ | Found $[M + H]^+$ |
|---|---|---|---|---|---|---|
| 13-14 | 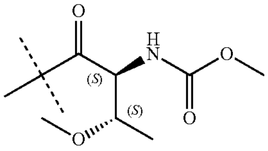 | | 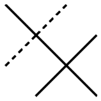 | $C_{44}H_{53}F_3N_8O_7$ | 863.4 | 863.8 |
| 13-15 | 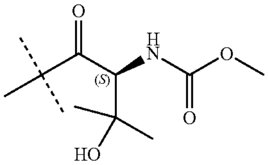 | | 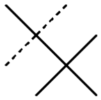 | $C_{44}H_{53}F_3N_8O_7$ | 863.4 | 863.8 |
| 13-16 | 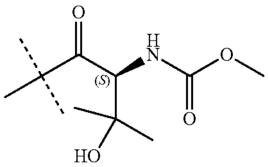 | Cl | 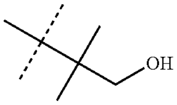 | $C_{44}H_{52}ClF_3N_8O_8$ | 913.36 | 913.8 |
| 13-17 | 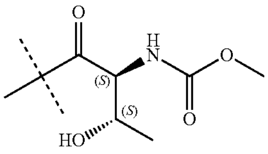 | Cl | 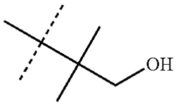 | $C_{43}H_{50}ClF_3N_8O_8$ | 899.34 | 899.8 |
| 13-18 | 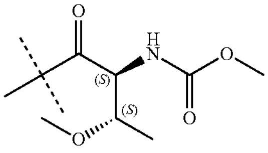 | Cl | 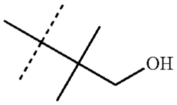 | $C_{44}H_{52}ClF_3N_8O_8$ | 913.36 | 913.8 |
| 13-19 | 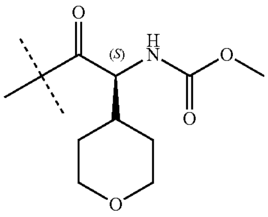 | Cl | 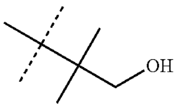 | $C_{46}H_{54}ClF_3N_8O_8$ | 939.37 | 939.8 |
| 13-20 | 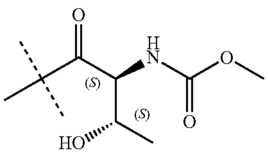 | F | 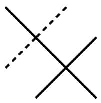 | $C_{43}H_{50}F_4N_8O_7$ | 867.37 | 867.8 |

TABLE 13-continued
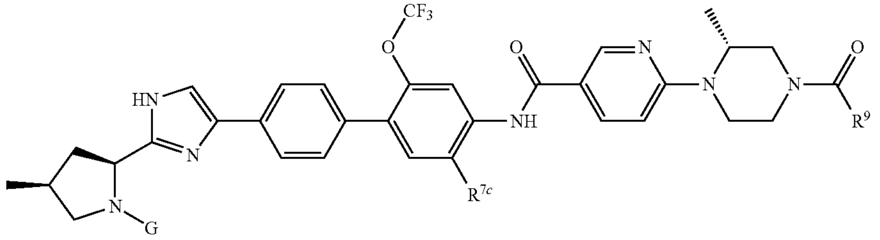
| Ex No. | G | $R^{7c}$ | $R^9$ | Formula | Calc $[M + H]^+$ | Found $[M + H]^+$ |
|---|---|---|---|---|---|---|
| 13-21 | 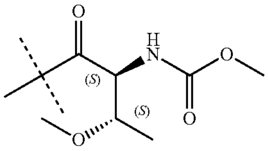 | F | 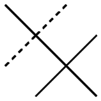 | $C_{44}H_{52}F_4N_8O_7$ | 881.39 | 881.8 |
| 13-22 | 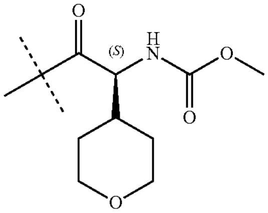 | F | 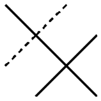 | $C_{46}H_{54}F_4N_8O_7$ | 907.41 | 907.8 |
| 13-23 | 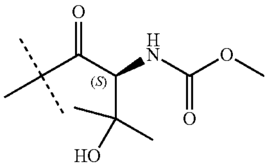 | F | 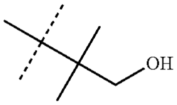 | $C_{44}H_{52}F_4N_8O_8$ | 897.38 | 897.8 |
| 13-24 | 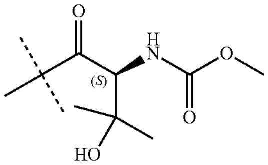 | F | 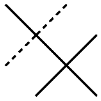 | $C_{44}H_{52}F_4N_8O_7$ | 881.39 | 881.8 |
| 13-25 | 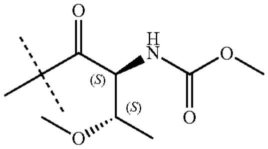 | F | 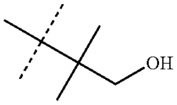 | $C_{44}H_{52}F_4N_8O_8$ | 897.38 | 897.8 |
| 13-26 | 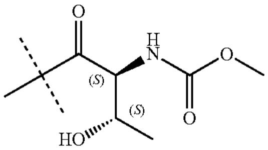 | F | 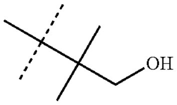 | $C_{43}H_{50}F_4N_8O_8$ | 883.37 | 883.8 |
| 13-27 | 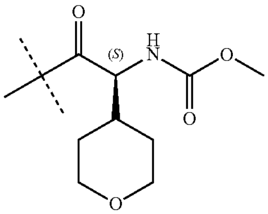 | F | 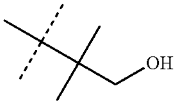 | $C_{46}H_{54}F_4N_8O_8$ | 923.4 | 923.8 |

TABLE 13-continued
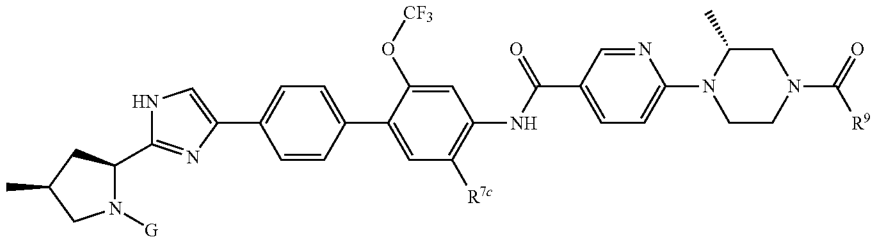
| Ex No. | G | $R^{7c}$ | $R^9$ | Formula | Calc $[M + H]^+$ | Found $[M + H]^+$ |
|---|---|---|---|---|---|---|
| 13-28 | 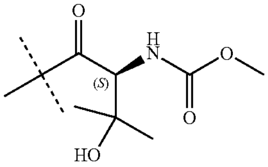 | | 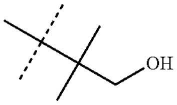 | $C_{44}H_{53}F_3N_8O_8$ | 879.39 | 879.8 |
| 13-29 | 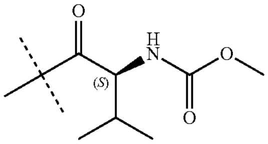 | | 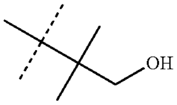 | $C_{44}H_{53}F_3N_8O_7$ | 863.40 | 863.8 |
| 13-30 | 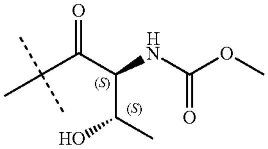 | | 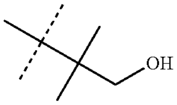 | $C_{43}H_{51}F_3N_8O_8$ | 865.38 | 865.8 |
| 13-31 | 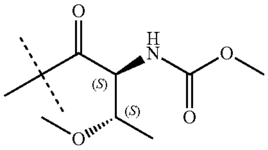 | | 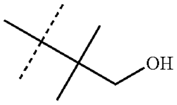 | $C_{44}H_{53}F_3N_8O_8$ | 879.39 | 879.8 |
| 13-32 | 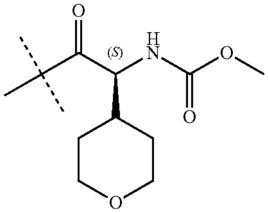 | | 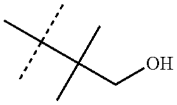 | $C_{46}H_{55}F_3N_8O_8$ | 905.41 | 905.8 |
| 13-33 | 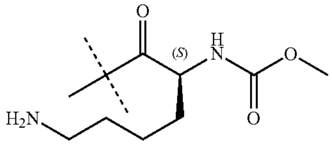 | Cl | 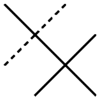 | $C_{45}H_{55}ClF_3N_9O_6$ | 910.39 | 910.8 |
| 13-34 | 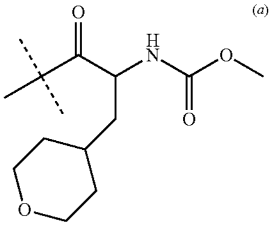 (a) | Cl | 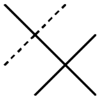 | $C_{47}H_{56}ClF_3N_8O_7$ | 937.39 | 937.8 |

TABLE 13-continued
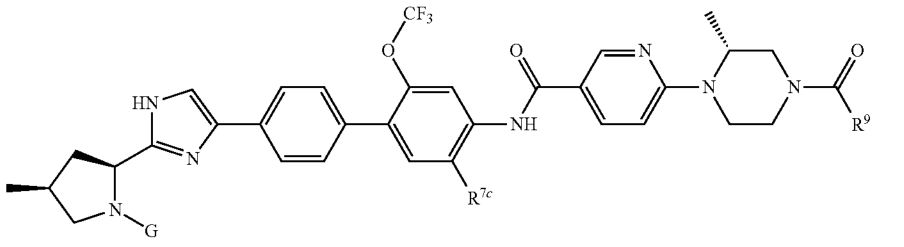
| Ex No. | G | $R^{7c}$ | $R^9$ | Formula | Calc $[M + H]^+$ | Found $[M + H]^+$ |
|---|---|---|---|---|---|---|
| 13-35 | 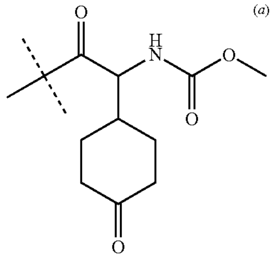 (a) | Cl | 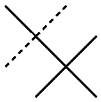 | $C_{47}H_{54}ClF_3N_8O_7$ | 935.38 | 935.8 |
| 13-36 | 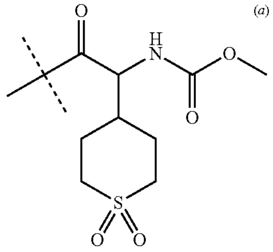 (a) | Cl | 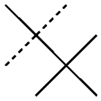 | $C_{46}H_{54}ClF_3N_8O_8S$ | 971.34 | 971.4 |
| 13-37 | 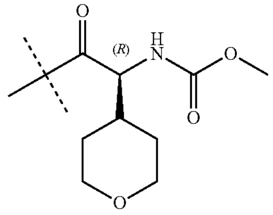 | Cl | 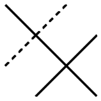 | $C_{46}H_{54}ClF_3N_8O_7$ | 923.38 | 923.8 |
| 13-38 | 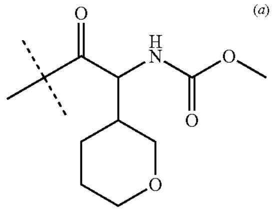 (a) | Cl | 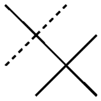 | $C_{46}H_{54}ClF_3N_8O_7$ | 923.38 | 924.3 |
| 13-39 | 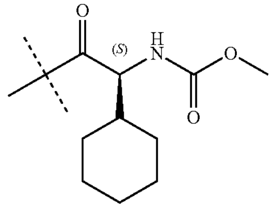 | Cl | 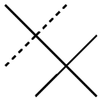 | $C_{47}H_{56}ClF_3N_8O_6$ | 921.40 | 921.6 |

TABLE 13-continued
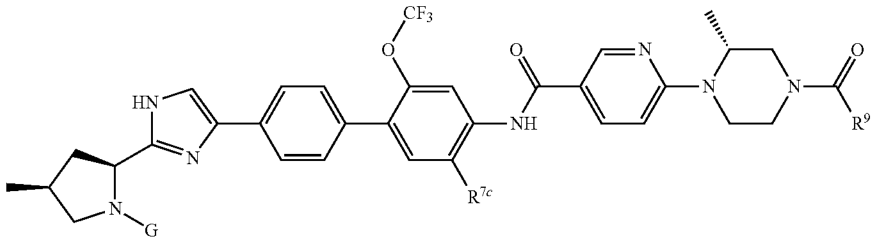
| Ex No. | G | $R^{7c}$ | $R^9$ | Formula | Calc $[M + H]^+$ | Found $[M + H]^+$ |
|---|---|---|---|---|---|---|
| 13-40 | 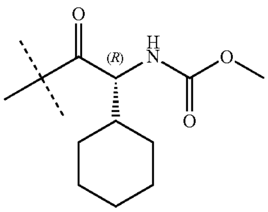 | Cl | 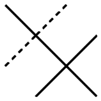 | $C_{47}H_{56}ClF_3N_8O_6$ | 921.40 | 921.6 |
| 13-41 | 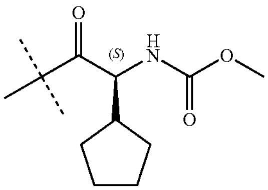 | Cl | 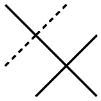 | $C_{46}H_{54}ClF_3N_8O_6$ | 907.38 | 907.6 |
| 13-42 | 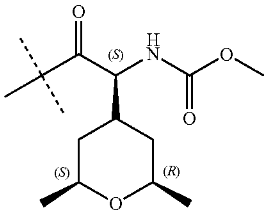 | Cl | 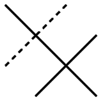 | $C_{48}H_{58}ClF_3N_8O_7$ | 951.41 | 951.6 |
| 13-43 | 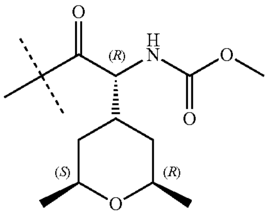 | Cl | 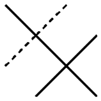 | $C_{48}H_{58}ClF_3N_8O_7$ | 951.41 | 951.6 |
| 13-44 | 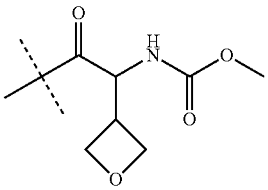 | Cl | 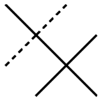 | $C_{44}H_{50}ClF_3N_8O_7$ | 895.34 | 895.4 |
| 13-45 | 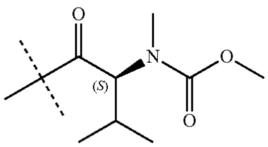 | Cl | 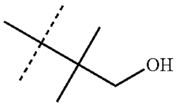 | $C_{44}H_{50}ClF_3N_8O_8$ | 911.34 | 912.6 |
[a]Stereoisomers separated but unassigned TABLE 14
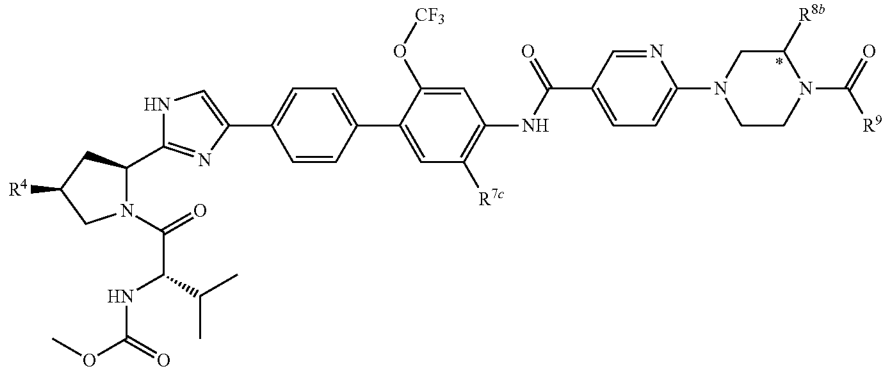
| Ex No. | $R^4$ | $R^{7c}$ | * | $R^{8b}$ | $R^9$ | Formula | Calc [M + H]$^+$ | Found [M + H]$^+$ |
|---|---|---|---|---|---|---|---|---|
| 14-1 | $CH_3$ | Cl | (R) | $CH_2OH$ | 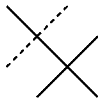 | $C_{44}H_{52}ClF_3N_8O_7$ | 897.36 | 897.8 |
| 14-2 | $CH_3$ | Cl | (S) | $CH_2OH$ | 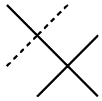 | $C_{44}H_{52}ClF_3N_8O_7$ | 897.36 | 897.8 |
| 14-3 | $CH_3$ | Cl | (R) | $CH_2OH$ | 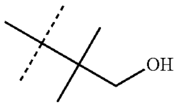 | $C_{44}H_{52}ClF_3N_8O_8$ | 913.36 | 913.8 |
| 14-4 | $CH_3$ | Cl | (S) | $CH_2OH$ | 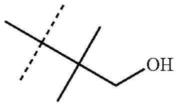 | $C_{44}H_{52}ClF_3N_8O_8$ | 913.36 | 913.8 |
| 14-5 | $OCH_3$ | F | (S) | $CH_2OH$ | 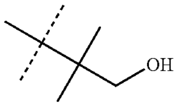 | $C_{44}H_{52}F_4N_8O_9$ | 913.38 | 913.8 |
| 14-6 | $OCH_3$ | F | (S) | $CH_2OH$ | 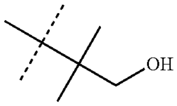 | $C_{44}H_{52}F_4N_8O_9$ | 913.38 | 913.8 |

TABLE 15
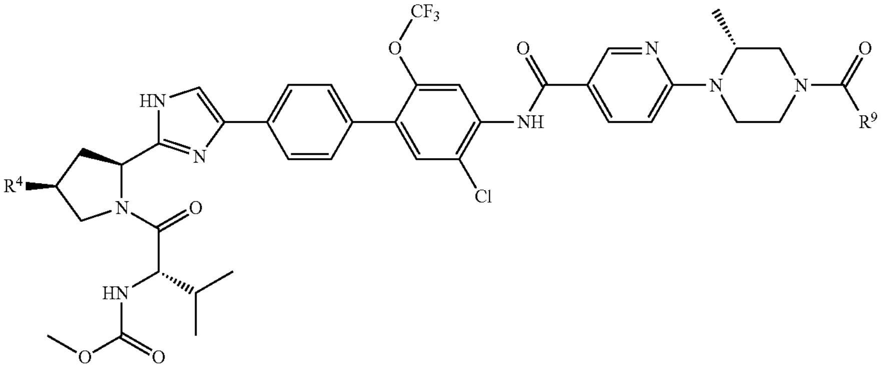
| Ex No. | $R^4$ | $R^9$ | Formula | Calc $[M + H]^+$ | Found $[M + H]^+$ |
|---|---|---|---|---|---|
| 15-1 | 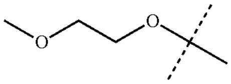 | 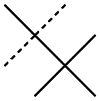 | $C_{46}H_{56}ClF_3N_8O_8$ | 941.39 | 941.8 |
| 15-2 | 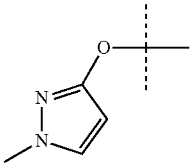 | 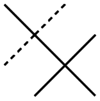 | $C_{47}H_{54}ClF_3N_{10}O_7$ | 963.38 | 963.8 |
| 15-3 | 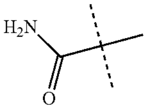 | 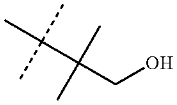 | $C_{44}H_{51}ClF_3N_9O_8$ | 926.35 | 926.8 |
| 15-4 | 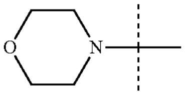 | 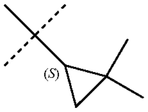 | $C_{48}H_{57}ClF_3N_9O_7$ | 964.40 | 964.8 |
| 15-5 | 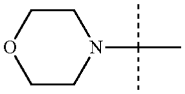 | 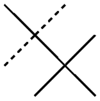 | $C_{47}H_{57}ClF_3N_9O_7$ | 952.40 | 952.8 |
| 15-6 | 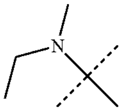 | 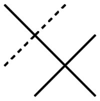 | $C_{46}H_{57}ClF_3N_9O_6$ | 924.41 | 924.8 |
| 15-7 | 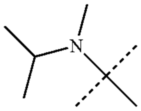 | 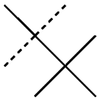 | $C_{47}H_{59}ClF_3N_9O_6$ | 938.42 | 938.8 |
| 15-8 | 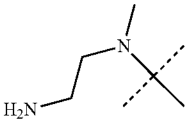 | 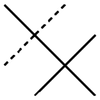 | $C_{46}H_{58}ClF_3N_{10}O_6$ | 939.42 | 939.8 |
| 15-9 | 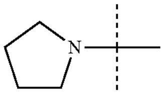 | 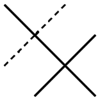 | $C_{47}H_{57}ClF_3N_9O_6$ | 936.41 | 936.8 |

TABLE 15-continued
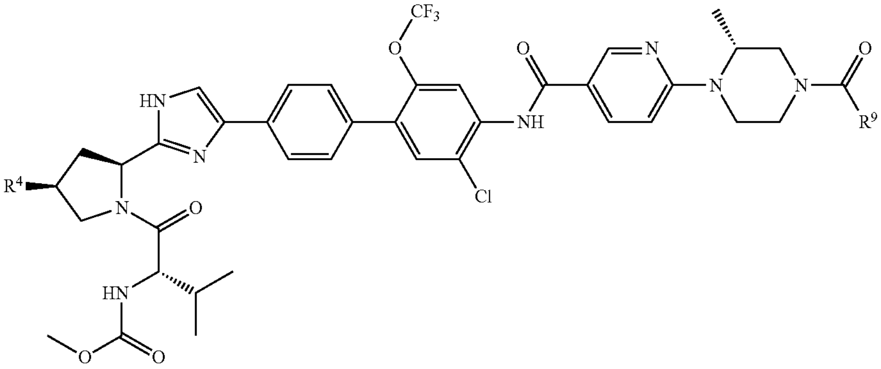
| Ex No. | $R^4$ | $R^9$ | Formula | Calc [M + H]$^+$ | Found [M + H]$^+$ |
|---|---|---|---|---|---|
| 15-10 | 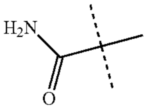 | 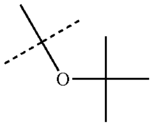 | $C_{44}H_{51}ClF_3N_9O_8$ | 926.35 | 926.8 |
| 15-11 | 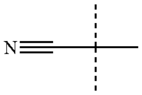 | 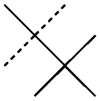 | $C_{44}H_{49}ClF_3N_9O_6$ | 892.35 | 892.8 |
| 15-12 | 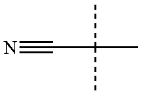 | 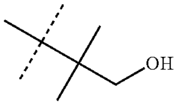 | $C_{44}H_{49}ClF_3N_9O_7$ | 908.34 | 908.8 |
| 15-13 | 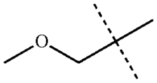 | 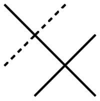 | $C_{45}H_{54}ClF_3N_8O_7$ | 911.38 | 911.6 |
TABLE 16
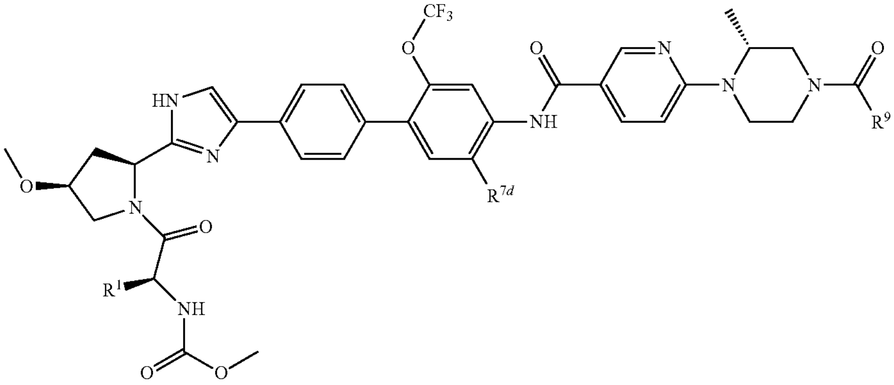
| Ex No. | $R^{1(\#)}$ | $R^{7d}$ | $R^9$ | Formula | Calc [M + H]$^+$ | Found [M + H]$^+$ |
|---|---|---|---|---|---|---|
| 16-1 | 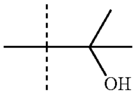 | Cl | 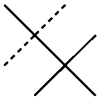 | $C_{44}H_{52}ClF_3N_8O_8$ | 913.36 | 913.8 |

TABLE 16-continued
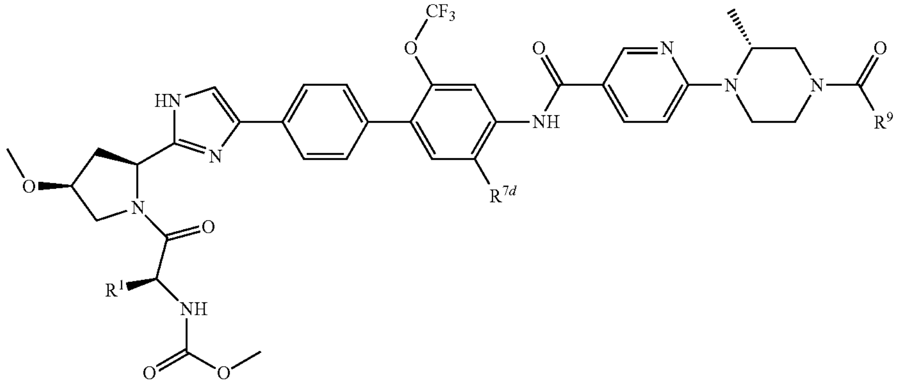
| Ex No. | $R^{1(\#)}$ | $R^{7d}$ | $R^9$ | Formula | Calc [M + H]$^+$ | Found [M + H]$^+$ |
|---|---|---|---|---|---|---|
| 16-2 | 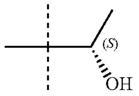 | Cl | 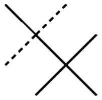 | $C_{43}H_{50}ClF_3N_8O_8$ | 899.34 | 899.8 |
| 16-3 | 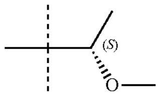 | Cl | 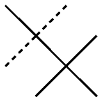 | $C_{44}H_{52}ClF_3N_8O_8$ | 913.36 | 913.8 |
| 16-4 | 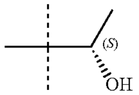 | F | 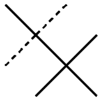 | $C_{43}H_{50}F_4N_8O_8$ | 883.37 | 883.8 |
| 16-5 | 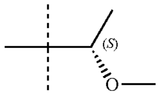 | F | 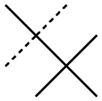 | $C_{44}H_{52}F_4N_8O_8$ | 897.38 | 897.8 |
| 16-6 | 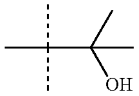 | F | 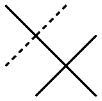 | $C_{44}H_{52}F_4N_8O_8$ | 897.38 | 897.8 |
| 16-7 | 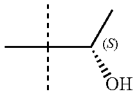 | Cl | 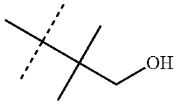 | $C_{43}H_{50}ClF_3N_8O_9$ | 915.33 | 915.8 |
| 16-8 | 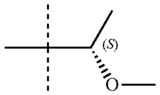 | Cl | 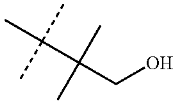 | $C_{44}H_{52}ClF_3N_8O_9$ | 929.35 | 929.8 |
| 16-9 | 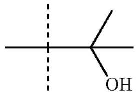 | Cl | 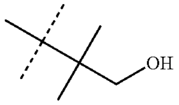 | $C_{44}H_{52}ClF_3N_8O_9$ | 929.35 | 929.8 |
| 16-10 | 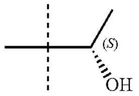 | | 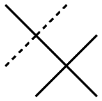 | $C_{43}H_{51}F_3N_8O_8$ | 865.38 | 865.8 |
| 16-11 | 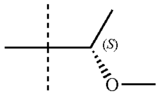 | | 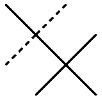 | $C_{44}H_{53}F_3N_8O_8$ | 879.39 | 879.8 |

TABLE 16-continued
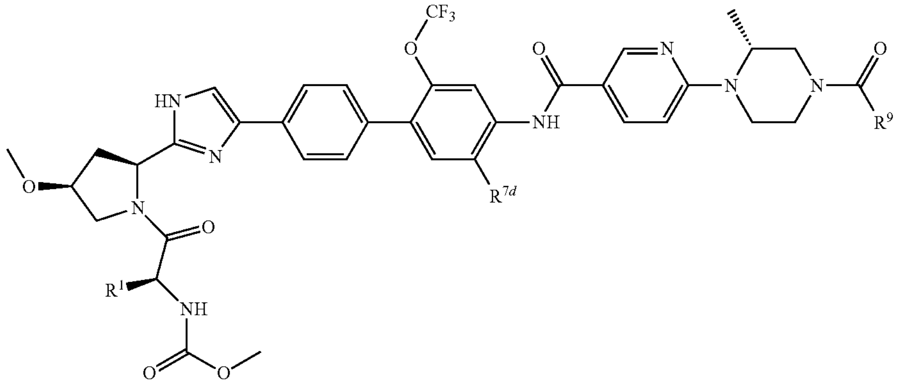
| Ex No. | $R^{1(\#)}$ | $R^{7d}$ | $R^9$ | Formula | Calc $[M + H]^+$ | Found $[M + H]^+$ |
|---|---|---|---|---|---|---|
| 16-12 | 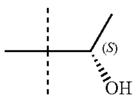 | F | 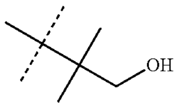 | $C_{43}H_{50}F_4N_8O_9$ | 899.36 | 899.8 |
| 16-13 | 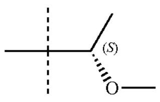 | F | 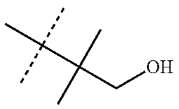 | $C_{44}H_{52}F_4N_8O_9$ | 913.38 | 913.8 |
| 16-14 | 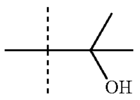 | F | 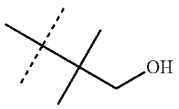 | $C_{44}H_{52}F_4N_8O_9$ | 913.38 | 913.8 |
| 16-15 | 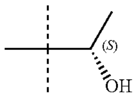 | | 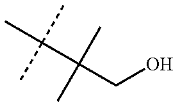 | $C_{43}H_{51}F_3N_8O_9$ | 881.37 | 881.8 |
| 16-16 | 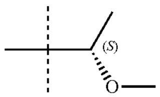 | | 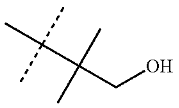 | $C_{44}H_{53}F_3N_8O_9$ | 895.39 | 895.8 |
| 16-17 | 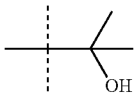 | | 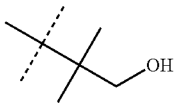 | $C_{44}H_{53}F_3N_8O_9$ | 895.39 | 895.8 |
| 16-18 | 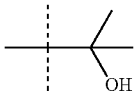 | | 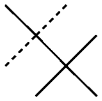 | $C_{44}H_{53}F_3N_8O_8$ | 879.39 | 879.8 |
(#)For all compounds, the orientation of the chiral carbon bearing the substituent $R^1$ is (S)

TABLE 17
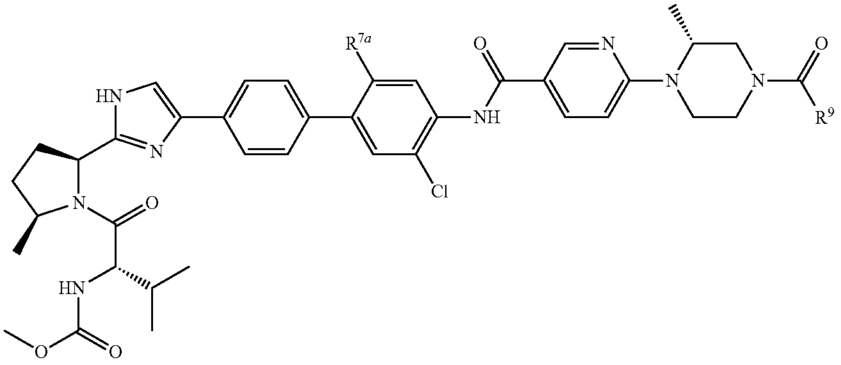
| Ex No. | $R^{7a}$ | $R^9$ | Formula | Calc $[M + H]^+$ | Found $[M + H]^+$ |
|---|---|---|---|---|---|
| 17-1 | $CF_3$ | 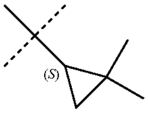 | $C_{45}H_{52}ClF_3N_8O_5$ | 877.37 | 877.8 |
| 17-2 | $CF_3$ | 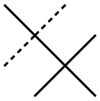 | $C_{44}H_{52}ClF_3N_8O_5$ | 865.37 | 865.8 |
| 17-3 | $OCF_3$ | 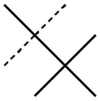 | $C_{44}H_{52}ClF_3N_8O_6$ | 881.37 | 881.8 |
| 17-4 | $OCF_3$ | 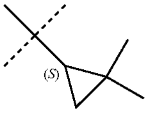 | $C_{45}H_{52}ClF_3N_8O_6$ | 893.37 | 893.8 |
TABLE 18
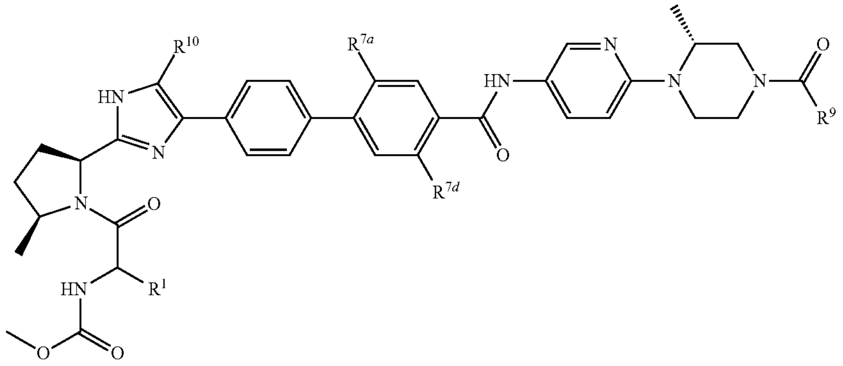
| Ex No. | $R^{1(\#)}$ | $R^{7a}$ | $R^{7d}$ | $R^9$ | $R^{10}$ | Formula | Calc $[M + H]^+$ | Found $[M + H]^+$ |
|---|---|---|---|---|---|---|---|---|
| 18-1 | 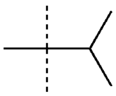 | $OCF_3$ | | 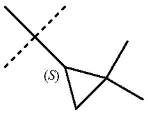 | Cl | $C_{45}H_{52}ClF_3N_8O_6$ | 893.37 | 893.8 |

TABLE 18-continued
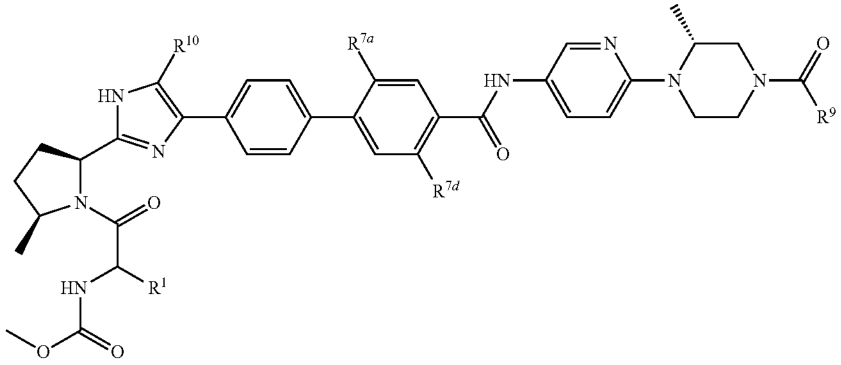
| Ex No. | $R^{1(\#)}$ | $R^{7a}$ | $R^{7d}$ | $R^9$ | $R^{10}$ | Formula | Calc $[M + H]^+$ | Found $[M + H]^+$ |
|---|---|---|---|---|---|---|---|---|
| 18-2 | 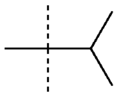 | $OCF_3$ | | 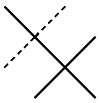 | Cl | $C_{44}H_{52}ClF_3N_8O_6$ | 881.37 | 881.8 |
| 18-3 | 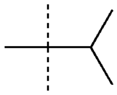 | $OCF_3$ | | 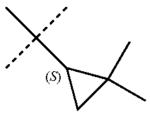 | | $C_{45}H_{53}F_3N_8O_6$ | 859.40 | 859.8 |
| 18-4 | 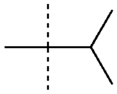 | $OCF_3$ | | 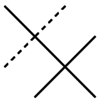 | | $C_{44}H_{53}F_3N_8O_6$ | 847.40 | 847.8 |
| 18-5 | 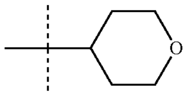 | $OCF_3$ | Cl | 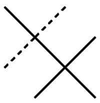 | | $C_{46}H_{54}ClF_3N_8O_7$ | 923.38 | 923.6 |
| 18-6 | 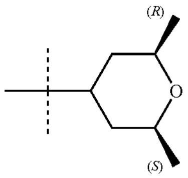 | $OCF_3$ | Cl | 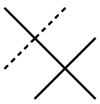 | | $C_{48}H_{58}ClF_3N_8O_7$ | 951.41 | 951.6 |
(#)For all compounds, the orientation of the chiral carbon bearing the substituent $R^1$ is (S)

TABLE 19
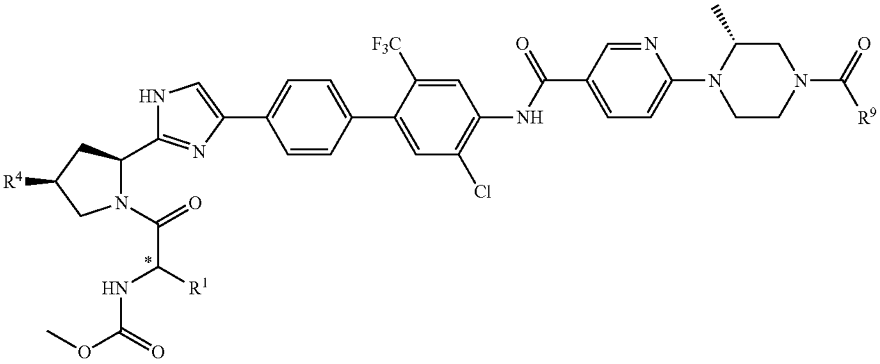
| Ex No. | $R^1$ | * | $R^4$ | $R^9$ | Formula | Calc $[M + H]^+$ | Found $[M + H]^+$ |
|---|---|---|---|---|---|---|---|
| 19-1 | 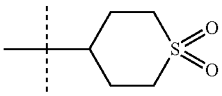 | (a) | $CH_3$ | 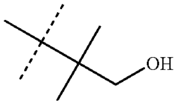 | $C_{46}H_{54}ClF_3N_8O_8S$ | 971.34 | 971.4 |
| 19-2 | 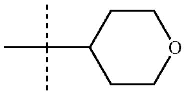 | (S) | $CH_3$ | 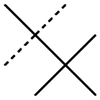 | $C_{46}H_{54}ClF_3N_8O_6$ | 907.38 | 906.6 |
| 19-3 | 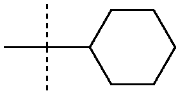 | (R) | $CH_3$ | 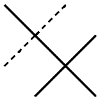 | $C_{47}H_{56}ClF_3N_8O_5$ | 905.40 | 904.6 |
| 19-4 | 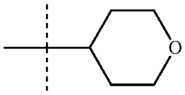 | (S) | $CH_3$ | 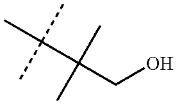 | $C_{46}H_{54}ClF_3N_8O_7$ | 923.38 | 922.6 |
| 19-5 | 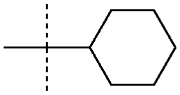 | (R) | $CH_3$ | 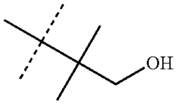 | $C_{47}H_{56}ClF_3N_8O_6$ | 921.40 | 920.6 |
| 19-6 | 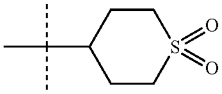 | (a) | $CH_3$ | 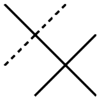 | $C_{46}H_{54}ClF_3N_8O_7S$ | 955.35 | 955.5 |
| 19-7 | 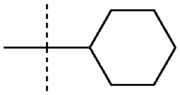 | (S) | $CH_3$ | 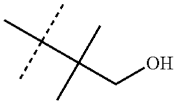 | $C_{47}H_{56}ClF_3N_8O_6$ | 921.40 | 921.6 |
| 19-8 | 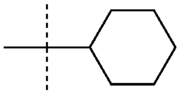 | (S) | $CH_3$ | 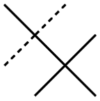 | $C_{47}H_{56}ClF_3N_8O_5$ | 905.40 | 905.6 |
| 19-9 | 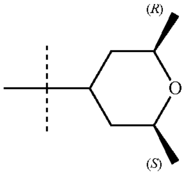 | (S) | $CH_3$ | 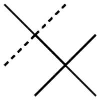 | $C_{48}H_{58}ClF_3N_8O_6$ | 935.41 | 935.6 |

TABLE 19-continued
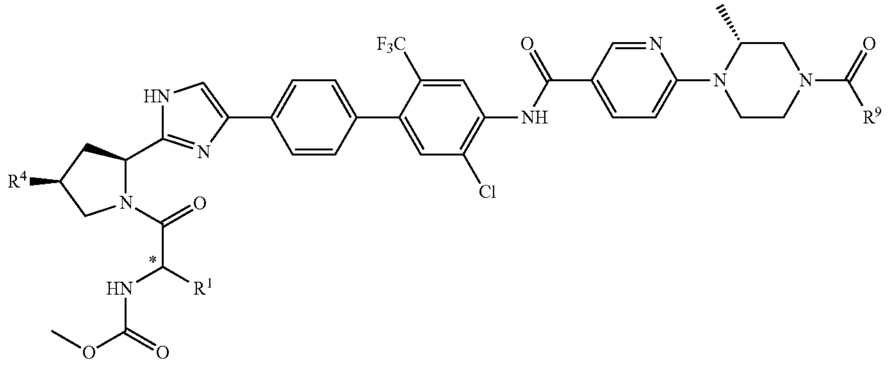
| Ex No. | $R^1$ | * | $R^4$ | $R^9$ | Formula | Calc $[M + H]^+$ | Found $[M + H]^+$ |
|---|---|---|---|---|---|---|---|
| 19-10 | 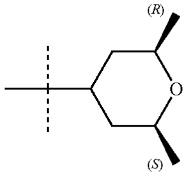 | (R) | $CH_3$ | 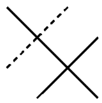 | $C_{48}H_{58}ClF_3N_8O_6$ | 935.41 | 935.6 |
| 19-11 | 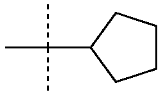 | (S) | $CH_3$ | 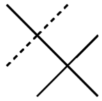 | $C_{46}H_{54}ClF_3N_8O_5$ | 891.39 | 891.6 |
| 19-12 | 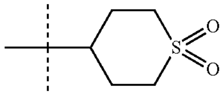 | [(a)] | $OCH_3$ | 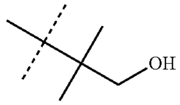 | $C_{46}H_{54}ClF_3N_8O_9S$ | 987.34 | 987.2 |
| 19-13 | 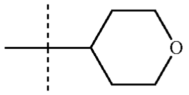 | (S) | $OCH_3$ | 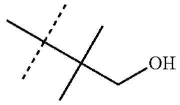 | $C_{46}H_{54}ClF_3N_8O_8$ | 939.37 | 939.6 |
| 19-14 | 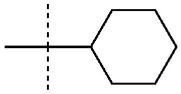 | (R) | $OCH_3$ | 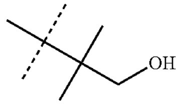 | $C_{47}H_{56}ClF_3N_8O_7$ | 937.39 | 937.6 |
| 19-15 | 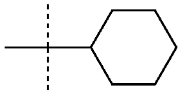 | (S) | $OCH_3$ | 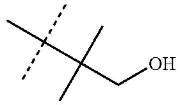 | $C_{47}H_{56}ClF_3N_8O_7$ | 937.39 | 937.6 |
| 19-16 | 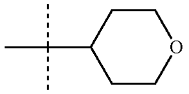 | (S) | $OCH_3$ | 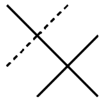 | $C_{46}H_{54}ClF_3N_8O_7$ | 923.38 | 923.6 |
| 19-17 | 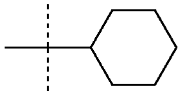 | (S) | $OCH_3$ | 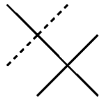 | $C_{47}H_{56}ClF_3N_8O_6$ | 921.40 | 921.6 |
| 19-18 | 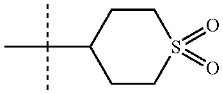 | [(a)] | $OCH_3$ | 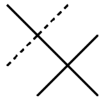 | $C_{46}H_{54}ClF_3N_8O_8S$ | 971.34 | 971.5 |
[(a)]Stereoisomers separated but unassigned TABLE 20
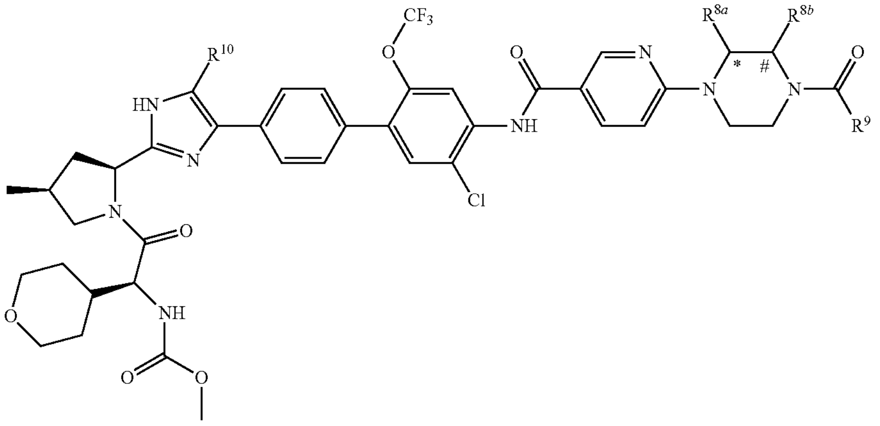
| Ex No. | $R^{8a}$ | * | $R^{8b}$ | # | $R^9$ | $R^{10}$ | Formula | Calc $[M + H]^+$ | Found $[M + H]^+$ |
|---|---|---|---|---|---|---|---|---|---|
| 20-1 | $CH_3$ | (R) | | | 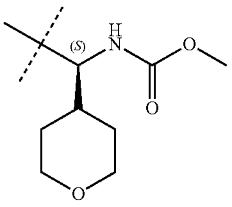 | | $C_{50}H_{59}ClF_3N_9O_{10}$ | 1038.40 | 1038.8 |
| 20-2 | $CH_3$ | (R) | | | 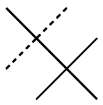 | $CH_2OH$ | $C_{47}H_{56}ClF_3N_8O_8$ | 953.39 | 953.8 |
| 20-3 | $CH_3$ | (R) | | | 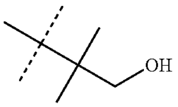 | $CH_2OH$ | $C_{47}H_{56}ClF_3N_8O_9$ | 969.38 | 969.4 |
| 20-4 | $CH_3$ | (S) | | | 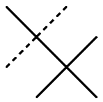 | | $C_{46}H_{54}ClF_3N_8O_7$ | 923.38 | 923.6 |
| 20-5 | | | $CH_3$ | (S) | 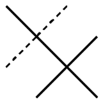 | | $C_{46}H_{54}ClF_3N_8O_2$ | 923.38 | 923.6 |
| 20-6 | | | $CH_3$ | (R) | 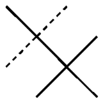 | | $C_{46}H_{54}ClF_3N_8O_7$ | 923.38 | 923.6 |
| 20-7 | | | $CH_2OCH_3$ | (R) | 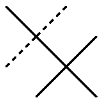 | | $C_{47}H_{56}ClF_3N_8O_8$ | 953.39 | 953.6 |

TABLE 21
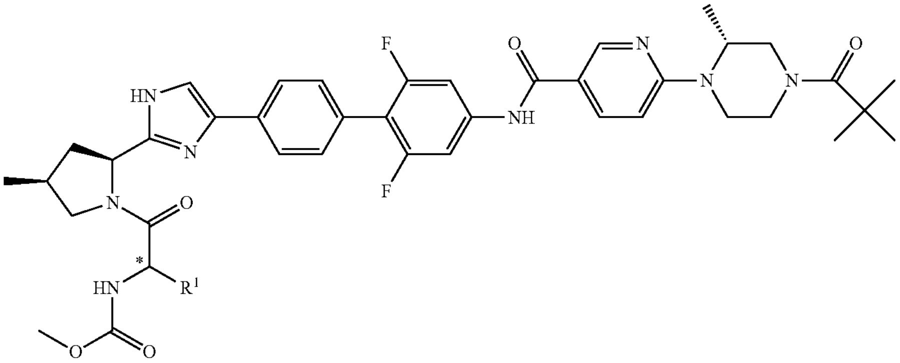
| Ex No. | $R^1$ | * | Formula | Calc $[M + H]^+$ | Found $[M + H]^+$ |
|---|---|---|---|---|---|
| 21-1 | 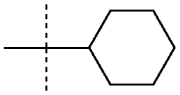 | (R) | $C_{46}H_{56}F_2N_8O_5$ | 839.43 | 838.8 |
| 21-2 | 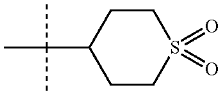 | | $C_{45}H_{54}F_2N_8O_7S$ | 889.38 | 888.6 |
| 21-3 | 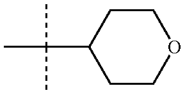 | (S) | $C_{45}H_{54}F_2N_8O_6$ | 841.41 | 840.6 |
| 21-4 | 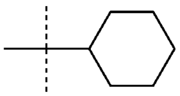 | (S) | $C_{46}H_{56}F_2N_8O_5$ | 839.43 | 839.6 |
TABLE 22
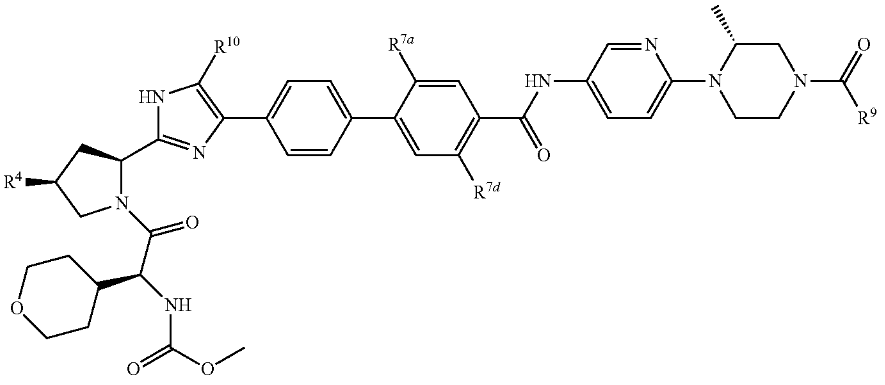
| Ex No. | $R^4$ | $R^{7a}$ | $R^{7d}$ | $R^9$ | $R^{10}$ | Formula | Calc $[M + H]^+$ | Found $[M + H]^+$ |
|---|---|---|---|---|---|---|---|---|
| 22-1 | $CH_3$ | | | 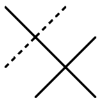 | | $C_{45}H_{56}N_8O_6$ | 805.43 | 805.8 |

TABLE 22-continued
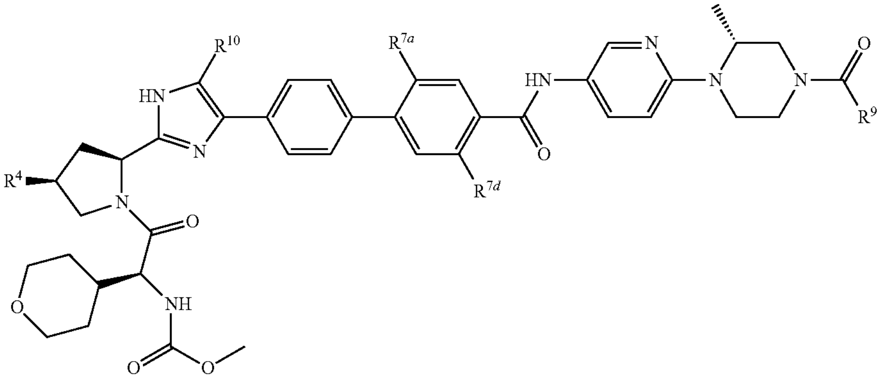
| Ex No. | $R^4$ | $R^{7a}$ | $R^{7d}$ | $R^9$ | $R^{10}$ | Formula | Calc $[M + H]^+$ | Found $[M + H]^+$ |
|---|---|---|---|---|---|---|---|---|
| 22-2 | $CH_3$ | | | 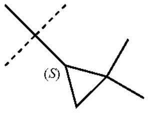 | | $C_{46}H_{56}N_8O_6$ | 817.43 | 817.8 |
| 22-3 | $CH_3$ | $OCF_3$ | | 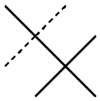 | | $C_{46}H_{55}F_3N_8O_7$ | 889.41 | 889.8 |
| 22-4 | $CH_3$ | $OCF_3$ | | 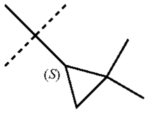 | | $C_{47}H_{55}F_3N_8O_7$ | 901.41 | 901.8 |
| 22-5 | $CH_3$ | $OCF_3$ | Cl | 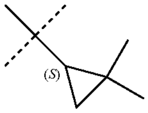 | | $C_{47}H_{54}ClF_3N_8O_7$ | 935.38 | 935.8 |
| 22-6 | $CH_3$ | $OCF_3$ | | 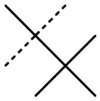 | Cl | $C_{46}H_{54}ClF_3N_8O_7$ | 923.38 | 923.8 |
| 22-7 | $CH_3$ | $OCF_3$ | Cl | 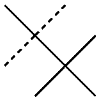 | Cl | $C_{46}H_{53}Cl_2F_3N_8O_7$ | 957.34 | 957.8 |
| 22-8 | $CH_3$ | $OCF_3$ | | 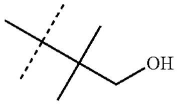 | Cl | $C_{46}H_{54}ClF_3N_8O_8$ | 939.37 | 939.8 |
| 22-9 | $CH_3$ | $OCF_3$ | Cl | 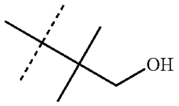 | Cl | $C_{46}H_{53}Cl_2F_3N_8O_8$ | 973.33 | 973.8 |
| 22-10 | $CH_3$ | | | 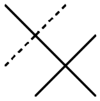 | Cl | $C_{45}H_{55}ClN_8O_6$ | 839.39 | 838.6 |

TABLE 22-continued
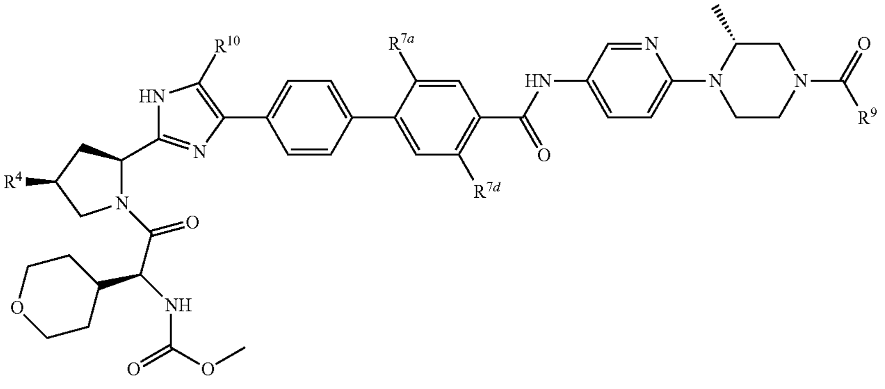
| Ex No. | $R^4$ | $R^{7a}$ | $R^{7d}$ | $R^9$ | $R^{10}$ | Formula | Calc $[M + H]^+$ | Found $[M + H]^+$ |
|---|---|---|---|---|---|---|---|---|
| 22-11 | $CH_3$ | | | 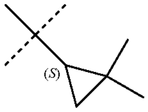 | Cl | $C_{46}H_{55}ClN_8O_6$ | 851.39 | 850.6 |
| 22-12 | $OCH_3$ | $OCF_3$ | | 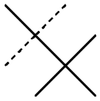 | | $C_{46}H_{55}F_3N_8O_8$ | 905.41 | 905.8 |
| 22-13 | $OCH_3$ | | | 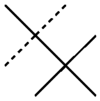 | | $C_{45}H_{56}N_8O_7$ | 821.43 | 821.8 |
| 22-14 | $OCH_3$ | $OCF_3$ | | 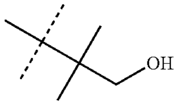 | | $C_{46}H_{55}F_3N_8O_9$ | 921.40 | 921.6 |
| 22-15 | $OCH_3$ | | | 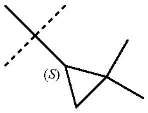 | | $C_{46}H_{56}N_8O_7$ | 833.43 | 833.6 |
| 22-16 | $OCH_3$ | $OCF_3$ | Cl | 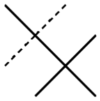 | | $C_{46}H_{54}ClF_3N_8O_8$ | 939.37 | 939.6 |
| 22-17 | $OCH_3$ | $OCF_3$ | Cl | 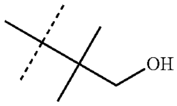 | | $C_{46}H_{54}ClF_3N_8O_9$ | 955.37 | 955.6 |

TABLE 23
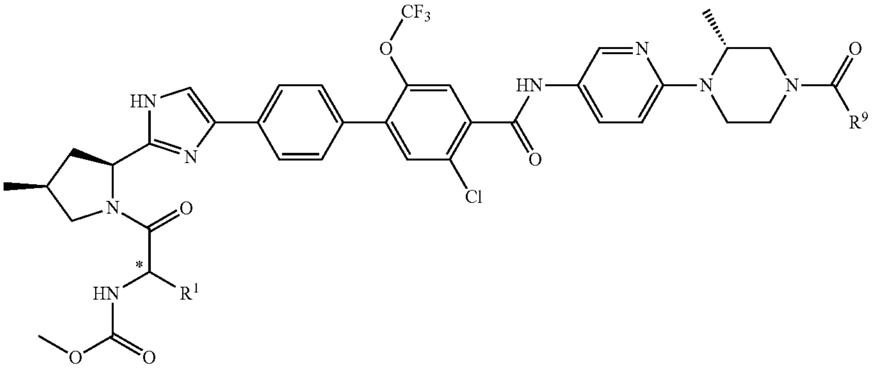
| Ex No. | $R^1$ | * | $R^9$ | Formula | Calc $[M + H]^+$ | Found $[M + H]^+$ |
|---|---|---|---|---|---|---|
| 23-1 | 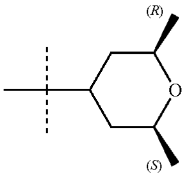 | (R) | 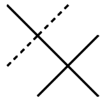 | $C_{48}H_{58}ClF_3N_8O_7$ | 951.41 | 951.6 |
| 23-2 | 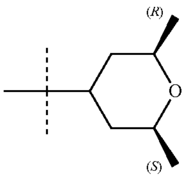 | (S) | 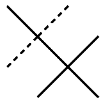 | $C_{48}H_{58}ClF_3N_8O_7$ | 951.41 | 951.6 |
| 23-3 | 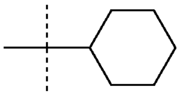 | (S) | 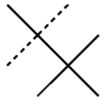 | $C_{47}H_{56}ClF_3N_8O_6$ | 921.40 | 921.6 |
TABLE 24
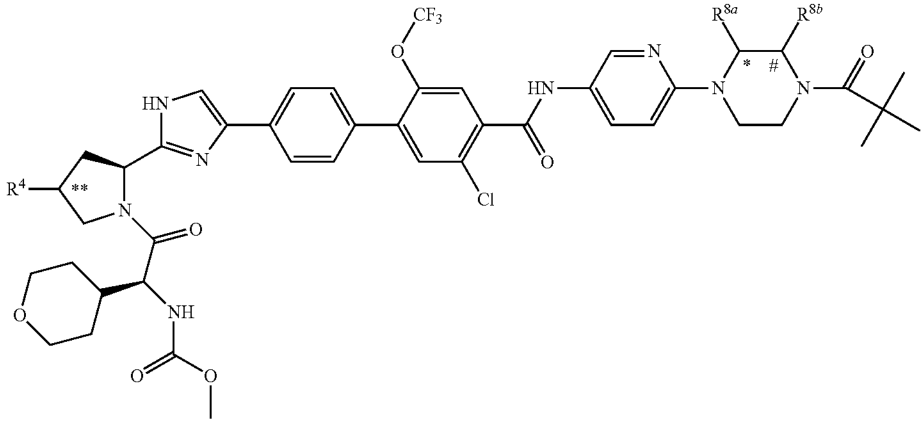
| Ex No. | $R^4$ | ** | $R^{8a}$ | * | $R^{8b}$ | # | Formula | Calc $[M + H]^+$ | Found $[M + H]^+$ |
|---|---|---|---|---|---|---|---|---|---|
| 24-1 | $CH_3$ | (S) | $CH_3$ | (S) | | | $C_{46}H_{54}ClF_3N_8O_7$ | 923.38 | 923.6 |
| 24-2 | $CH_3$ | (S) | $CH_3$ | (S) | | | $C_{46}H_{54}ClF_3N_8O_7$ | 923.38 | 923.6 |
| 24-3 | $CH_3$ | (S) | | | $CH_3$ | (R) | $C_{46}H_{54}ClF_3N_8O_7$ | 923.38 | 923.6 |
| 24-4 | $CH_3$ | (S) | | | $CH_2OCH_3$ | (R) | $C_{47}H_{56}ClF_3N_8O_8$ | 953.39 | 953.6 |
| 24-5 | $CH_3$ | (R) | $CH_3$ | (R) | | | $C_{46}H_{54}ClF_3N_8O_7$ | 923.38 | 923.6 |
| 24-6 | $CH_2OCH_3$ | (S) | $CH_3$ | (R) | | | $C_{47}H_{56}ClF_3N_8O_8$ | 953.39 | 953.6 |

TABLE 25
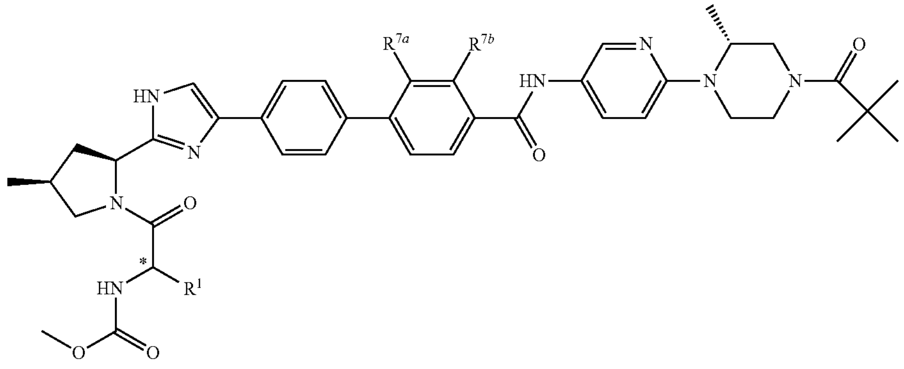
| Ex No. | $R^1$ | * | $R^4$ | $R^{7a}$ | $R^{7b}$ | Formula | Calc $[M+H]^+$ | Found $[M+H]^+$ |
|---|---|---|---|---|---|---|---|---|
| 25-1 | 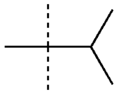 | (S) | $CH_3$ | $OCF_3$ | F | $C_{44}H_{52}F_4N_8O_6$ | 865.39 | 865.6 |
| 25-2 | 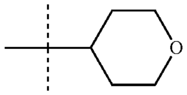 | (S) | $CH_3$ | $OCF_3$ | F | $C_{46}H_{54}F_4N_8O_7$ | 907.41 | 907.6 |
| 25-3 | 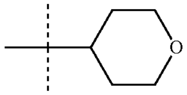 | (S) | $CH_3$ | $OCF_3$ | Cl | $C_{46}H_{54}ClF_3N_8O_7$ | 923.38 | 923.6 |
| 25-4 | 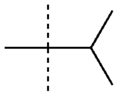 | (S) | $CH_3$ | $OCF_3$ | Cl | $C_{44}H_{52}ClF_3N_8O_6$ | 881.37 | 881.4 |
| 25-5 | 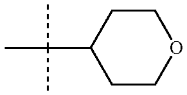 | (S) | $CH_3$ | $OCHF_2$ | | $C_{46}H_{56}F_2N_8O_7$ | 871.42 | 871.6 |
| 25-6 | 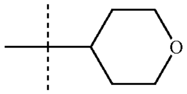 | (S) | $CH_3OCH_2$ | $OCF_3$ | Cl | $C_{47}H_{56}ClF_3N_8O_8$ | 953.39 | 953.6 |
| 25-7 | 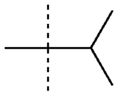 | (S) | $CH_3OCH_2$ | $OCF_3$ | Cl | $C_{45}H_{54}ClF_3N_8O_7$ | 911.38 | 911.6 |

TABLE 26
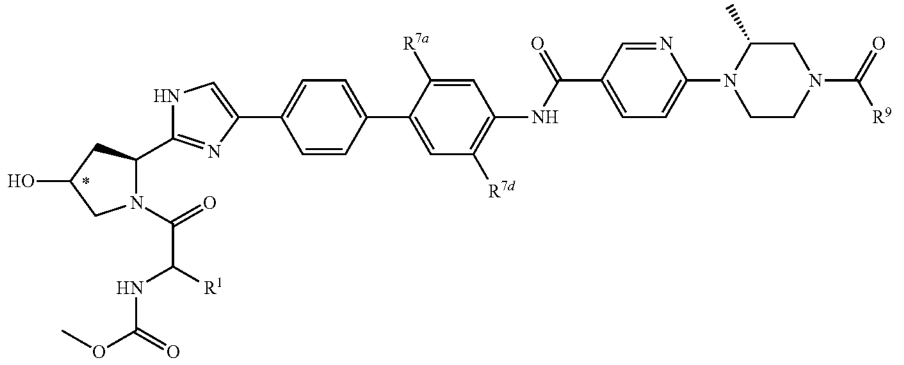
| Ex No. | $R^{1(\#)}$ | * | $R^{7a}$ | $R^{7d}$ | $R^9$ | Formula | Calc [M + H]$^+$ | Found [M + H]$^+$ |
|---|---|---|---|---|---|---|---|---|
| 26-1 | 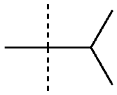 | (R) | | | 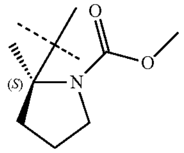 | $C_{45}H_{55}N_9O_8$ | 850.42 | 850.4 |
| 26-2 | 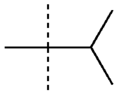 | (S) | | | 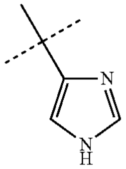 | $C_{41}H_{46}N_{10}O_6$ | 775.36 | 775.4 |
| 26-3 | 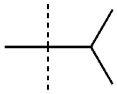 | (S) | | | $NHCH_3$ | $C_{39}H_{47}N_9O_6$ | 738.37 | 738.2 |
| 26-4 | 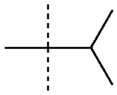 | (S) | | | 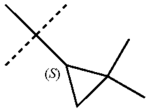 | $C_{43}H_{52}N_8O_6$ | 777.40 | 777.4 |
| 26-5 | 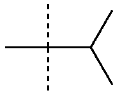 | (R) | | | 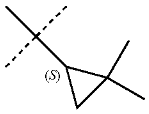 | $C_{41}H_{46}N_{10}O_6$ | 775.36 | 775.2 |
| 26-6 | 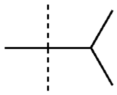 | (S) | $OCF_3$ | F | 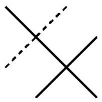 | $C_{43}H_{50}F_4N_8O_7$ | 867.37 | 867.8 |
| 26-7 | 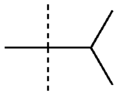 | (S) | $OCF_3$ | F | 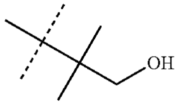 | $C_{43}H_{50}F_4N_8O_8$ | 883.37 | 883.8 |
| 26-8 | 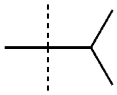 | (S) | $OCF_3$ | Cl | 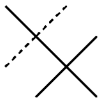 | $C_{43}H_{50}ClF_3N_8O_7$ | 883.34 | 883.8 |
| 26-9 | 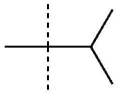 | (S) | $OCF_3$ | Cl | 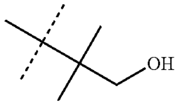 | $C_{43}H_{50}ClF_3N_8O_8$ | 899.34 | 899.8 |

TABLE 26-continued
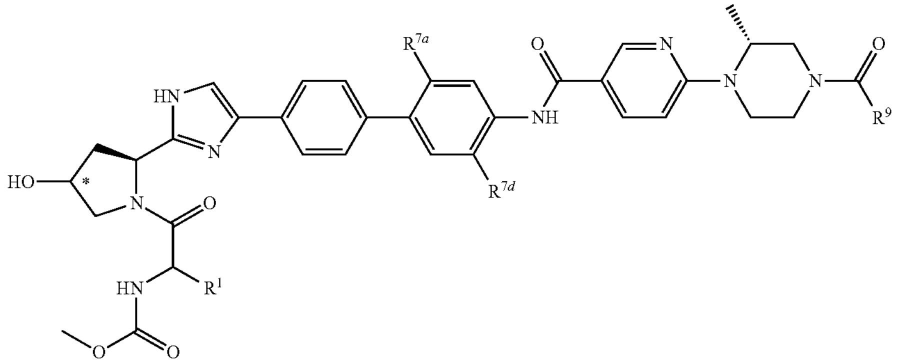
| Ex No. | $R^{1(\#)}$ | * | $R^{7a}$ | $R^{7d}$ | $R^9$ | Formula | Calc $[M + H]^+$ | Found $[M + H]^+$ |
|---|---|---|---|---|---|---|---|---|
| 26-10 | 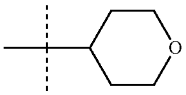 | (S) | $OCF_3$ | Cl | 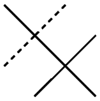 | $C_{45}H_{52}ClF_3N_8O_8$ | 925.36 | 925.8 |
| 26-11 | 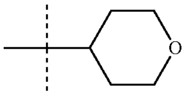 | (S) | $OCF_3$ | Cl | 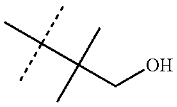 | $C_{45}H_{52}ClF_3N_8O_9$ | 941.35 | 941.8 |
(#)For all compounds, the orientation of the chiral carbon bearing the substituent $R^1$ is (S)
TABLE 27
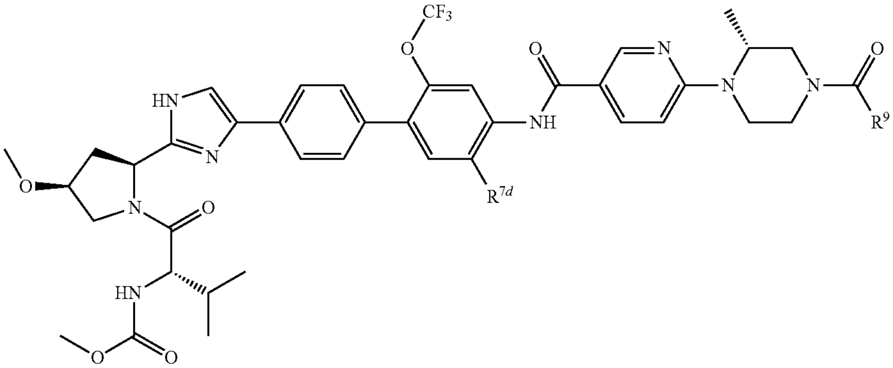
| Ex No. | $R^{7d}$ | $R^9$ | Formula | Calc $[M + H]^+$ | Found $[M + H]^+$ |
|---|---|---|---|---|---|
| 27-1 | Cl | 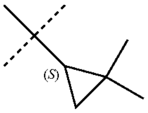 | $C_{45}H_{52}ClF_3N_8O_7$ | 909.36 | 909.8 |
| 27-2 | Cl | 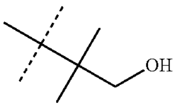 | $C_{44}H_{52}ClF_3N_8O_8$ | 913.36 | 913.8 |
| 27-3 | F | 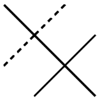 | $C_{44}H_{52}F_4N_8O_7$ | 881.39 | 881.8 |

TABLE 27-continued
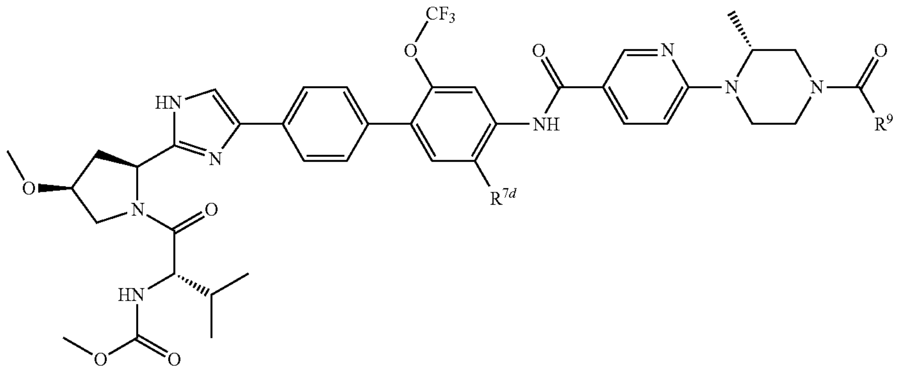
| Ex No. | $R^{7d}$ | $R^9$ | Formula | Calc $[M + H]^+$ | Found $[M + H]^+$ |
|---|---|---|---|---|---|
| 27-4 | F | 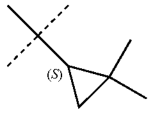 | $C_{45}H_{52}F_4N_8O_7$ | 893.39 | 893.8 |
| 27-5 | Cl | 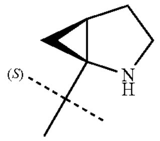 | $C_{45}H_{51}ClF_3N_9O_7$ | 922.36 | 922.8 |
| 27-6 | F | 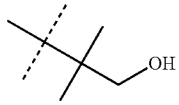 | $C_{44}H_{52}F_4N_8O_8$ | 897.38 | 897.8 |
| 27-7 | | 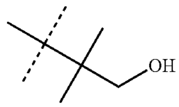 | $C_{44}H_{53}F_3N_8O_8$ | 879.39 | 879.8 |
| 27-8 | | 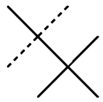 | $C_{44}H_{53}F_3N_8O_7$ | 863.40 | 863.8 |

TABLE 28
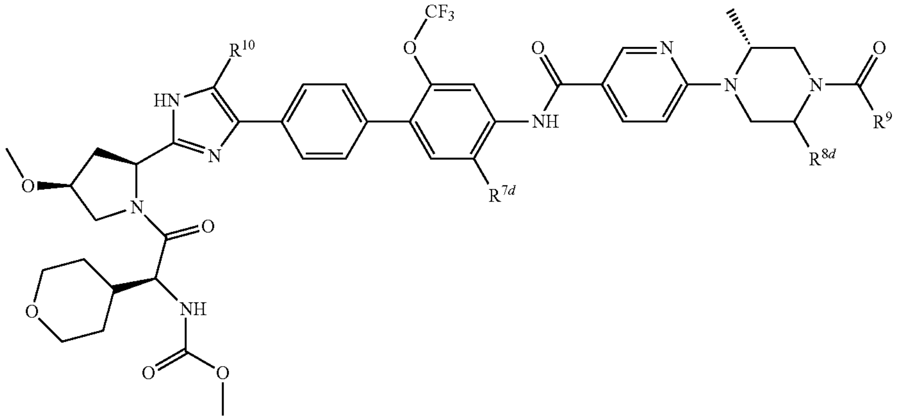
| Ex No. | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|
| 28-1 | F | | 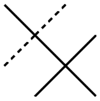 | | $C_{46}H_{54}F_4N_8O_8$ | 923.40 | 923.8 |
| 28-2 | | | 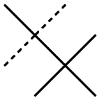 | | $C_{46}H_{55}F_3N_8O_8$ | 905.41 | 905.8 |
| 28-3 | F | | 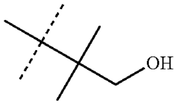 | | $C_{46}H_{54}F_4N_8O_9$ | 939.40 | 939.8 |
| 28-4 | | | 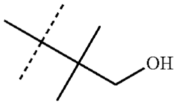 | | $C_{46}H_{55}F_3N_8O_9$ | 921.40 | 921.8 |
| 28-5 | Cl | $CH_3$ | 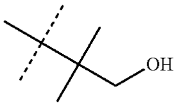 | | $C_{47}H_{56}ClF_3N_8O_9$ | 969.38 | 969.8 |
| 28-6 | Cl | $CH_3$ | 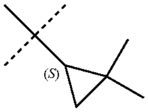 | | $C_{48}H_{56}ClF_3N_8O_8$ | 965.39 | 965.8 |
| 28-7 | Cl | $CH_3$ | 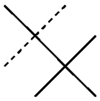 | | $C_{47}H_{56}ClF_3N_8O_8$ | 953.39 | 953.8 |
| 28-8 | Cl | $CH_3$ | $NHCH_3$ | | $C_{44}H_{51}ClF_3N_9O_8$ | 926.35 | 926.8 |
| 28-9 | Cl | $CH_3$ | 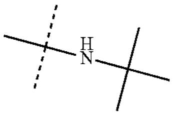 | | $C_{47}H_{57}ClF_3N_9O_8$ | 968.40 | 968.8 |
| 28-10 | Cl | $CH_3$ | 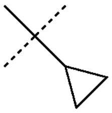 | | $C_{46}H_{52}ClF_3N_8O_8$ | 937.36 | 937.8 |

TABLE 28-continued
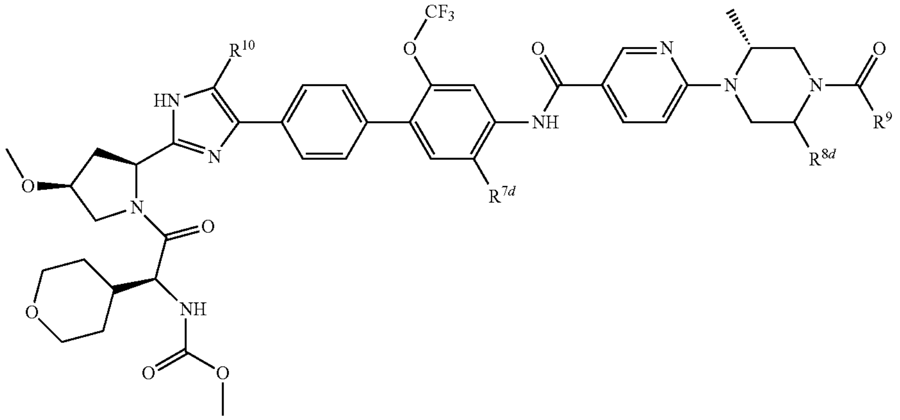
| Ex No. | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|
| 28-11 | Cl | | 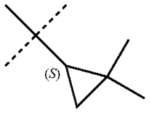 | | $C_{47}H_{54}ClF_3N_8O_8$ | 951.37 | 951.8 |
| 28-12 | Cl | | 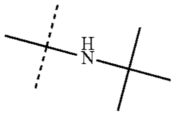 | | $C_{46}H_{55}ClF_3N_9O_8$ | 954.38 | 954.8 |
| 28-13 | Cl | | $NHCH_3$ | | $C_{43}H_{49}ClF_3N_9O_8$ | 912.33 | 912.8 |
| 28-14 | Cl | | 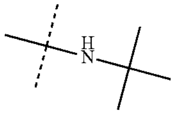 | | $C_{45}H_{50}ClF_3N_8O_8$ | 923.34 | 923.8 |
| 28-15 | Cl | | 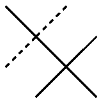 | $CH_2OH$ | $C_{47}H_{56}ClF_3N_8O_9$ | 969.38 | 969.8 |
| 28-16 | Cl | | 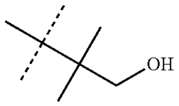 | $CH_2OH$ | $C_{47}H_{56}ClF_3N_8O_{10}$ | 985.38 | 985.8 |
| 28-17 | Cl | $CH_3$ | 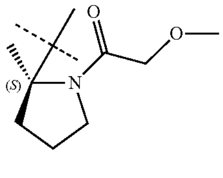 | | $C_{51}H_{61}ClF_3N_9O_{10}$ | 1,052.42 | 1053.0 |

TABLE 28-continued
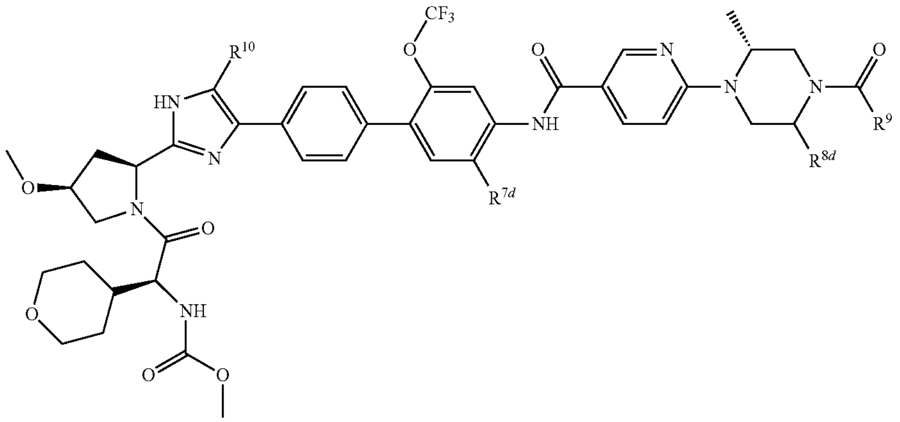
| Ex No. | $R^{7d}$ | $R^{8d(\#)}$ | $R^9$ | $R^{10}$ | Formula | Calc $[M + H]^+$ | Found $[M + H]^+$ |
|---|---|---|---|---|---|---|---|
| 28-18 | Cl | $CH_3$ | 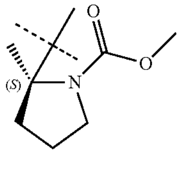 | | $C_{50}H_{59}ClF_3N_9O_{10}$ | 1,038.40 | 1039.0 |
| 28-19 | Cl | $CH_3$ | 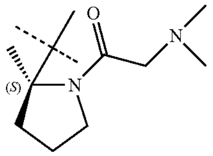 | | $C_{52}H_{64}ClF_3N_{10}O_9$ | 1,065.45 | 1066.0 |
| 28-20 | Cl | | 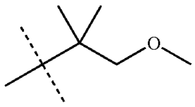 | | $C_{46}H_{54}ClF_3N_8O_9$ | 955.37 | 955.6 |
| 28-21 | Cl | | 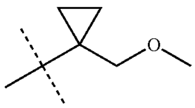 | | $C_{47}H_{54}ClF_3N_8O_9$ | 967.37 | 967.6 |
| 28-22 | Cl | | 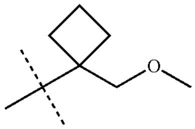 | | $C_{48}H_{56}ClF_3N_8O_9$ | 981.38 | 981.5 |
| 28-23 | Cl | | 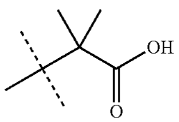 | | $C_{46}H_{52}ClF_3N_8O_{10}$ | 969.35 | 969.6 |
(#)When the substituent $R^{8d}$ is other than hydrogen, the orientation of the chiral carbon bearing the substituent $R^{8d}$ is (S)

TABLE 29

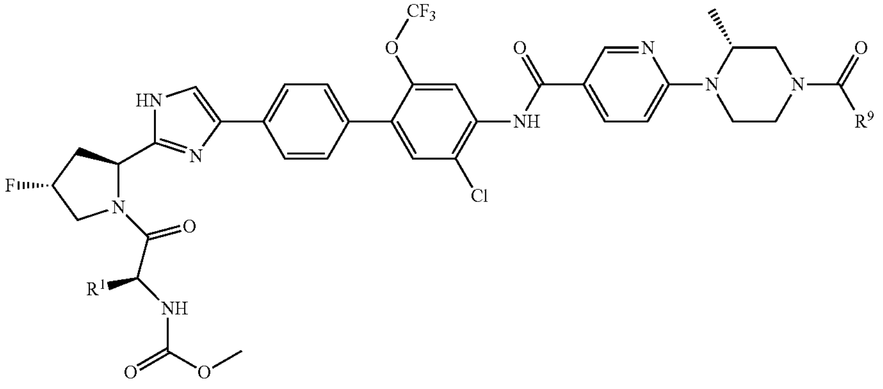

| Ex No. | $R^1$ | $R^9$ | Formula | Calc $[M + H]^+$ | Found $[M + H]^+$ |
|---|---|---|---|---|---|
| 29-1 | 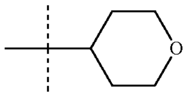 | 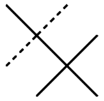 | $C_{45}H_{51}ClF_4N_8O_7$ | 927.35 | 927.6 |
| 29-2 | 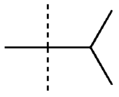 | 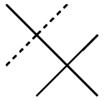 | $C_{43}H_{49}ClF_4N_8O_6$ | 885.34 | 885.4 |
| 29-3 | 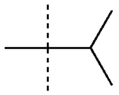 | 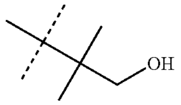 | $C_{43}H_{49}ClF_4N_8O_7$ | 901.34 | 901.6 |
| 29-4 | 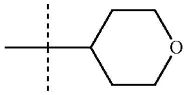 | 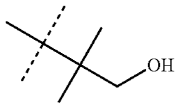 | $C_{45}H_{51}ClF_4N_8O_8$ | 943.35 | 943.6 |

Biological Assays

The hepatitis C virus has been classified into six major different genotypes on the basis of nucleotide sequence, and further divided into subtypes within genotypes. Compounds of the invention demonstrated inhibition of HCV replication in one or more of the following HCV replicon assays.

Assay 1: HCV Genotype 1b Replicon Assay

The HCV genotype 1b replicon cell line was obtained from Apath LLC (Brooklyn, N.Y.) (APC144; Huh7 cell background). This subgenomic replicon contains the N-terminus of the HCV core protein fused to the neomycin-resistance selectable marker. The EMCV IRES lies downstream and drives expression of humanized Renilla luciferase fused to the non-structural proteins NS3-NS5B. This cell line was used to determine compound potency using the luciferase activity readout as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 500 μg/mL G418 (Invitrogen). On day 1 of the assay, cells were plated at 10,000 cells/well in white 96-well tissue culture plates (Costar) in 200 μL media lacking G418. Four hours later, once the cells have adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 hours. At the end of the incubation period, media and compound were removed from the plates and the luciferase activity was determined using Promega Renilla-Glo reagents.

To analyze the data, the luciferase activity was plotted vs. the compound concentration, and $EC_{50}$ values were determined from a 4-parameter robust fit model with the GraphPad Prism software package (GraphPad Software, Inc., San Diego, Calif.). Results are expressed as the negative decadic logarithm of the $EC_{50}$ value, $pEC_{50}$.

Test compounds having a higher $pEC_{50}$ value in this assay show greater inhibition of HCV genotype 1b replication. Compounds of the invention tested in this assay typically exhibited $pEC_{50}$ values between about 7 and about 12.

Assay 2: HCV Genotype 1a Replicon Assay

The HCV genotype 1a replicon cell line was obtained from Apath LLC (APC89; Huh7.5 cell background). This subgenomic replicon contains the N-terminus of the HCV core protein fused to the neomycin-resistance selectable marker. The EMCV IRES lies downstream and drives expression of the non-structural proteins NS3-NS5B. Compound potencies were determined using the NS3-specific protease activity in lysates as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 850 μg/mL G418 (Invitrogen). On day 1 of the assay, cells were plated at 15,000 cells/well in black 96-well tissue culture plates (Costar) in 200 μL media lacking G418. Four hours later, once the cells had adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 or 72 hours. At the end of the incubation period, media and compound were removed from the plates.

To determine the NS3-specific protease activity in lysates, the cells were lysed at room temperature in 50 μL/well of 50 mM Hepes pH 7.5, 150 mM NaCl, 15% Glycerol, 0.15% Triton X-100, 10 mM DTT for 20 minutes with shaking. 50 μL of an NS3/4a protease-specific FRET substrate (Anaspec RET S1 Cat#22991) was then added to the wells at a final concentration of 15 μM. The plates were incubated at 37° C. for 20 minutes, which corresponds to a timepoint at which the protease activity is still in the linear phase. Protease activity was determined by measuring fluorescence (Excitation: 340 nm; Emission: 509 nm).

To analyze the data, the fluorescence was plotted vs. the compound concentration, and EC50 values were determined from a 4-parameter robust fit model using GraphPad Prism software. Compounds of the invention tested in this assay typically exhibited $pEC_{50}$ values between about 6 and about 11.5.

Assay 3: Replicon Assays Against Resistant Mutants

To create replicon cells with resistant mutations of interest, the mutation was first introduced into the parental plasmid by site-directed mutagenesis. Mutations in genotype 1b included L31V, Y93H, and the L31V/Y93H double mutant. Mutations in genotype 1a included Q30R and L31V. The replicon plasmid was then linearized and in vitro transcribed to RNA. The RNA was used to stably transfect Huh7 cells by electroporation, and new cell lines were selected with 500 μg/mL G418. Potencies of test compounds against these mutant cell lines were determined as previously described above for the HCV Genotype 1b and 1a replicon assays.

Potencies of test compounds against additional mutations of interest were determined using transient transfection assays. These mutants included genotype 1a Y93C, Y93H, M28T, Q30E, Q30K, L31M, and Y93N. The mutation was first introduced into the parental plasmid by site-directed mutagenesis. The replicon plasmid was then linearized and in vitro transcribed to RNA. The RNA was used to transiently transfect Huh-LUNET cells (obtained from ReBLikon GmbH, Schriesheim, Germany) by electroporation, and the potencies of test compounds against the mutants were determined as previously described.

Assay 4: Replicon Assays Against NS5A Sequences of Other Genotypes

Potencies of test compounds against NS5A sequences of other genotypes were determined by creating intergenotypic chimeras. The entire NS5A gene from genotypes 2a, 2b, 3a, 4a, 5a, and 6a, or the nucleotide sequence encoding amino acids 11-118 of NS5A, was subcloned into a genotype 1b replicon. For genotype 2a, intergenotypic chimeras with both the JFH and the J6 strain were created. In general, NS5A inhibitors have been shown to exhibit significantly weaker potency against the J6 strain due to the presence of a naturally occurring L31M sequence variant. Since the majority of genotype 2a sequences in public databases contain the L31M sequence variant, the use of the J6 genotype 2a sequence may better reflect the antiviral potency of NS5A inhibitors.

These chimeric replicon plasmids were then linearized and in vitro transcribed to RNA. The RNA was used to transiently or stably transfect Huh-LUNET cells by electroporation, and the potencies of test compounds against the chimeras were determined as previously described.

Assay 5: Colony Formation Assays

Colony formation assays were used to compare test compounds with respect to their overall genetic barrier to resistance. Genotype 1b and genotype 1a replicon cells were grown in the presence of various concentrations of test compounds and 500 μg/mL or 850 μg/mL geneticin selection, respectively. Media, including test compound, was replaced twice per week. After 3-4 weeks, most cells had been killed and resistant colonies were visualized by staining with crystal violet. Compounds with enhanced potency against the key resistant mutants showed significantly fewer colonies, consistent with an improved overall genetic barrier to resistance.

Assay Results

All of the compounds of Examples 1 to 21 and Tables 1 to 29 were tested in one or more of the assays described above. Representative results for the compounds of Examples 1 to 21 in the HCV genotype 1a, 1b, 2a (J6 strain), 3a, and the resistant mutant 1aY93H replicon assays, as well as results for the HCV genotype 1a and 1b replicon assays for the compounds of Tables 1 to 29 are given below. In the following tables, A represents a $pEC_{50}$ value between 6 and 8 ($EC_{50}$ between 1 μM and 10 nM), B represents $pEC_{50}$ between 8 and 9 ($EC_{50}$ between 1 and 10 nM), C represents $pEC_{50}$ between and 9 and about 10, ($EC_{50}$ between 1 nM and 0.1 nM), and D represents $pEC_{50}$>10 ($EC_{50}$<0.1 nM).

| Example No. | Genotype 1a | Genotype 1b | Genotype 1a Y93H | Genotype 2a (J6) | Genotype 3a |
|---|---|---|---|---|---|
| 1 | D | D | A | A | A |
| 2 | D | D | | B | B |
| 3 | D | D | | | |
| 4 | D | D | C | B | B |
| 5 | C | D | | | |
| 6 | C | D | | | |
| 7 | D | D | | A | A |
| 8 | D | D | A | A | A |
| 9 | D | D | | A | A |
| 10 | D | D | B | B | B |
| 11 | D | D | A | B | B |
| 12 | D | D | B | B | B |
| 13 | D | D | B | C | C |
| 14 | D | D | B | C | C |
| 15 | D | D | B | C | C |
| 16 | D | D | B | B | B |
| 17 | C | | A | A | A |
| 18 | D | D | B | C | B |
| 19 | D | D | A | B | B |
| 20 | D | D | B | B | B |
| 21 | D | D | C | C | C |

TABLE 1

| Example No. | Genotype 1a | Genotype 1b |
|---|---|---|
| 1-1 | D | D |
| 1-2 | D | |
| 1-3 | D | D |
| 1-4 | D | |
| 1-5 | D | D |
| 1-6 | D | |
| 1-7 | D | D |
| 1-8 | D | D |
| 1-9 | D | D |
| 1-10 | D | D |
| 1-11 | D | D |

TABLE 1-continued

| Example No. | Genotype 1a | Genotype 1b |
|---|---|---|
| 1-12 | D | D |
| 1-13 | D | D |
| 1-14 | D | D |
| 1-15 | D | D |
| 1-16 | D | D |
| 1-17 | D | D |
| 1-18 | D | D |
| 1-19 | D | D |
| 1-20 | D | D |
| 1-21 | D | |
| 1-22 | D | |
| 1-23 | D | |
| 1-24 | D | |
| 1-25 | D | |
| 1-26 | D | |
| 1-27 | C | |
| 1-28 | D | |
| 1-29 | D | |
| 1-30 | D | D |
| 1-31 | D | |
| 1-32 | D | |
| 1-33 | C | |
| 1-34 | D | D |
| 1-35 | D | D |
| 1-36 | D | D |
| 1-37 | D | |
| 1-38 | D | |
| 1-39 | D | |
| 1-40 | D | D |
| 1-41 | | |
| 1-42 | D | |
| 1-43 | D | D |
| 1-44 | D | |
| 1-45 | D | |
| 1-46 | D | |
| 1-47 | D | |
| 1-48 | D | |
| 1-49 | D | |
| 1-50 | D | |
| 1-51 | D | |
| 1-52 | C | |
| 1-53 | D | D |
| 1-54 | D | |
| 1-55 | D | D |
| 1-56 | D | |
| 1-57 | D | |
| 1-58 | D | |
| 1-59 | D | |
| 1-60 | D | |
| 1-61 | D | D |
| 1-62 | D | D |
| 1-63 | D | |
| 1-64 | C | |
| 1-65 | C | |
| 1-66 | C | |
| 1-67 | D | |
| 1-68 | C | |
| 1-69 | D | |
| 1-70 | D | |
| 1-71 | C | |
| 1-72 | D | |
| 1-73 | D | |
| 1-74 | D | |
| 1-75 | D | D |
| 1-76 | D | |
| 1-77 | D | |
| 1-78 | C | D |
| 1-79 | C | |
| 1-80 | C | |
| 1-81 | D | D |
| 1-82 | C | D |
| 1-83 | C | |
| 1-84 | C | |
| 1-85 | B | |
| 1-86 | D | |
| 1-87 | D | |
| 1-88 | D | |
| 1-89 | D | |
| 1-90 | C | |
| 1-91 | D | |
| 1-92 | D | D |
| 1-93 | D | D |
| 1-94 | D | |
| 1-95 | C | |
| 1-96 | D | D |
| 1-97 | C | |
| 1-98 | C | |
| 1-99 | D | |
| 1-100 | D | |
| 1-101 | D | D |

TABLE 2

| Example No. | Genotype 1a | Genotype 1b |
|---|---|---|
| 2-1 | C | D |
| 2-2 | C | C |
| 2-3 | D | D |
| 2-4 | D | |
| 2-5 | C | D |
| 2-6 | D | |
| 2-7 | C | |
| 2-8 | D | |

TABLE 3

| Example No. | Genotype 1a | Genotype 1b |
|---|---|---|
| 3-1 | D | D |
| 3-2 | D | |
| 3-3 | C | |
| 3-4 | C | |

TABLE 4

| Example No. | Genotype 1a | Genotype 1b |
|---|---|---|
| 4-1 | D | D |
| 4-2 | D | D |
| 4-3 | D | |
| 4-4 | D | D |
| 4-5 | D | D |
| 4-6 | D | D |
| 4-7 | D | D |
| 4-8 | D | D |
| 4-9 | D | |
| 4-10 | D | D |
| 4-11 | D | D |
| 4-12 | D | D |
| 4-13 | C | |
| 4-14 | C | D |
| 4-15 | D | |
| 4-16 | C | D |
| 4-17 | C | D |
| 4-18 | D | D |
| 4-19 | D | D |
| 4-20 | C | D |
| 4-21 | D | D |
| 4-22 | C | |
| 4-23 | C | |
| 4-24 | C | |
| 4-25 | C | |
| 4-26 | D | |
| 4-27 | C | |
| 4-28 | D | |
| 4-29 | D | |
| 4-30 | C | |
| 4-31 | C | |
| 4-32 | C | |

TABLE 4-continued

| Example No. | Genotype 1a | Genotype 1b |
|---|---|---|
| 4-33 | C | |
| 4-34 | C | |
| 4-35 | C | |
| 4-36 | C | |
| 4-37 | D | D |
| 4-38 | C | |
| 4-39 | C | |
| 4-40 | D | |
| 4-41 | C | |
| 4-42 | D | D |
| 4-43 | C | |
| 4-44 | D | |
| 4-45 | C | |
| 4-46 | D | D |
| 4-47 | C | |

TABLE 5

| Example No. | Genotype 1a | Genotype 1b |
|---|---|---|
| 5-1 | D | |
| 5-2 | D | |
| 5-3 | D | D |
| 5-4 | D | D |
| 5-5 | D | D |
| 5-6 | C | D |
| 5-7 | D | D |
| 5-8 | D | D |
| 5-9 | D | D |
| 5-10 | A | |
| 5-11 | D | |
| 5-12 | D | |
| 5-13 | D | |
| 5-14 | C | |
| 5-15 | D | |
| 5-16 | D | |
| 5-17 | D | |
| 5-18 | D | D |
| 5-19 | D | |
| 5-20 | D | |

TABLE 6

| Example No. | Genotype 1a | Genotype 1b |
|---|---|---|
| 6-1 | C | D |
| 6-2 | C | |
| 6-3 | C | |
| 6-4 | A | |
| 6-5 | C | D |
| 6-6 | C | |
| 6-7 | D | |
| 6-8 | C | |
| 6-9 | D | D |
| 6-10 | D | D |
| 6-11 | C | D |
| 6-12 | C | D |
| 6-13 | D | |
| 6-14 | D | |
| 6-15 | C | |
| 6-16 | B | |
| 6-17 | D | |
| 6-18 | C | |
| 6-19 | C | |
| 6-20 | B | |
| 6-21 | C | |
| 6-22 | B | |
| 6-23 | B | |
| 6-24 | B | |
| 6-25 | B | |
| 6-26 | B | |
| 6-27 | C | |

TABLE 6-continued

| Example No. | Genotype 1a | Genotype 1b |
|---|---|---|
| 6-28 | D | D |
| 6-29 | D | |

TABLE 7

| Example No. | Genotype 1a | Genotype 1b |
|---|---|---|
| 7-1 | D | |
| 7-2 | A | |
| 7-3 | D | |
| 7-4 | B | |
| 7-5 | B | |
| 7-6 | A | |
| 7-7 | D | |
| 7-8 | B | |
| 7-9 | D | |
| 7-10 | D | |
| 7-11 | D | |
| 7-12 | D | |
| 7-13 | D | |
| 7-14 | D | |
| 7-15 | D | D |
| 7-16 | D | |
| 7-17 | B | |

TABLE 8

| Example No. | Genotype 1a | Genotype 1b |
|---|---|---|
| 8-1 | D | D |
| 8-2 | D | D |
| 8-3 | C | |
| 8-4 | D | D |
| 8-5 | C | |
| 8-6 | C | |

TABLE 9

| Example No. | Genotype 1a | Genotype 1b |
|---|---|---|
| 9-1 | C | |
| 9-2 | C | |
| 9-3 | C | |
| 9-4 | D | D |
| 9-5 | C | |

TABLE 10

| Example No. | Genotype 1a | Genotype 1b |
|---|---|---|
| 10-1 | D | D |
| 10-2 | C | |
| 10-3 | D | |
| 10-4 | C | |
| 10-5 | D | |

TABLE 11

| Example No. | Genotype 1a | Genotype 1b |
|---|---|---|
| 11-1 | C | |
| 11-2 | C | |
| 11-3 | D | |
| 11-4 | D | |
| 11-5 | D | |
| 11-6 | D | |
| 11-7 | D | |

TABLE 11-continued

| Example No. | Genotype 1a | Genotype 1b |
|---|---|---|
| 11-8 | D | |
| 11-9 | C | |
| 11-10 | D | |
| 11-11 | D | |
| 11-12 | D | |

TABLE 12

| Example No. | Genotype 1a | Genotype 1b |
|---|---|---|
| 12-1 | D | D |
| 12-2 | C | |
| 12-3 | D | |
| 12-4 | D | |
| 12-5 | D | |
| 12-6 | D | |
| 12-7 | C | |
| 12-8 | D | D |
| 12-9 | D | |
| 12-10 | D | |
| 12-11 | D | |
| 12-12 | D | |
| 12-13 | B | |
| 12-14 | D | |
| 12-15 | D | |
| 12-16 | C | |
| 12-17 | D | D |
| 12-18 | D | |
| 12-19 | D | |
| 12-20 | D | |
| 12-21 | D | |
| 12-22 | C | |
| 12-23 | D | |
| 12-24 | D | D |
| 12-25 | D | |
| 12-26 | D | |
| 12-27 | C | |
| 12-28 | D | |
| 12-29 | D | |
| 12-30 | C | |
| 12-31 | D | |
| 12-32 | D | D |
| 12-33 | C | |
| 12-34 | C | |
| 12-35 | D | |
| 12-36 | A | |
| 12-37 | C | |
| 12-38 | C | |
| 12-39 | D | |
| 12-40 | D | |
| 12-41 | C | |
| 12-42 | D | |
| 12-43 | D | |
| 12-44 | D | |
| 12-45 | D | |
| 12-46 | D | |
| 12-47 | D | D |
| 12-48 | D | |
| 12-49 | D | |
| 12-50 | D | D |
| 12-51 | C | |
| 12-52 | C | |
| 12-53 | D | |
| 12-54 | C | |
| 12-55 | D | |
| 12-56 | D | |
| 12-57 | D | |
| 12-58 | C | |

TABLE 13

| Example No. | Genotype 1a | Genotype 1b |
|---|---|---|
| 13-1 | D | D |
| 13-2 | A | |
| 13-3 | C | |
| 13-4 | C | |
| 13-5 | D | D |
| 13-6 | D | |
| 13-7 | D | |
| 13-8 | D | |
| 13-9 | D | |
| 13-10 | D | |
| 13-11 | D | D |
| 13-12 | D | D |
| 13-13 | D | |
| 13-14 | D | |
| 13-15 | D | |
| 13-16 | D | D |
| 13-17 | D | D |
| 13-18 | D | D |
| 13-19 | D | D |
| 13-20 | D | D |
| 13-21 | D | D |
| 13-22 | D | D |
| 13-23 | D | |
| 13-24 | D | D |
| 13-25 | C | |
| 13-26 | D | |
| 13-27 | D | D |
| 13-28 | D | D |
| 13-29 | D | D |
| 13-30 | D | D |
| 13-31 | D | D |
| 13-32 | D | |
| 13-33 | D | |
| 13-34 | D | D |
| 13-35 | D | D |
| 13-36 | B | |
| 13-37 | B | |
| 13-38 | D | D |
| 13-39 | B | |
| 13-40 | A | |
| 13-41 | D | |
| 13-42 | D | D |
| 13-43 | B | |
| 13-44 | C | |
| 13-45 | C | |

TABLE 14

| Example No. | Genotype 1a | Genotype 1b |
|---|---|---|
| 14-1 | C | |
| 14-2 | C | |
| 14-3 | C | |
| 14-4 | B | |
| 14-5 | | |
| 14-6 | | |

TABLE 15

| Example No. | Genotype 1a | Genotype 1b |
|---|---|---|
| 15-1 | C | |
| 15-2 | C | |
| 15-3 | D | D |
| 15-4 | D | |
| 15-5 | D | |
| 15-6 | | |
| 15-7 | D | |
| 15-8 | C | |
| 15-9 | D | |
| 15-10 | B | |

TABLE 15-continued

| Example No. | Genotype 1a | Genotype 1b |
|---|---|---|
| 15-11 | D | D |
| 15-12 | D | D |
| 15-13 | D | |

TABLE 16

| Example No. | Genotype 1a | Genotype 1b |
|---|---|---|
| 16-1 | D | D |
| 16-2 | D | D |
| 16-3 | D | D |
| 16-4 | D | D |
| 16-5 | D | D |
| 16-6 | D | |
| 16-7 | D | D |
| 16-8 | D | |
| 16-9 | D | |
| 16-10 | C | |
| 16-11 | D | |
| 16-12 | C | |
| 16-13 | D | D |
| 16-14 | D | D |
| 16-15 | C | D |
| 16-16 | D | |
| 16-17 | D | |
| 16-18 | D | |

TABLE 17

| Example No. | Genotype 1a | Genotype 1b |
|---|---|---|
| 17-1 | D | D |
| 17-2 | D | D |
| 17-3 | D | D |
| 17-4 | D | D |

TABLE 18

| Example No. | Genotype 1a | Genotype 1b |
|---|---|---|
| 18-1 | C | |
| 18-2 | C | |
| 18-3 | C | |
| 18-4 | C | |
| 18-5 | D | D |
| 18-6 | D | D |

TABLE 19

| Example No. | Genotype 1a | Genotype 1b |
|---|---|---|
| 19-1 | D | |
| 19-2 | D | D |
| 19-3 | A | |
| 19-4 | D | |
| 19-5 | A | |
| 19-6 | D | D |
| 19-7 | B | |
| 19-8 | B | |
| 19-9 | D | D |
| 19-10 | A | |
| 19-11 | D | |
| 19-12 | D | |
| 19-13 | D | |
| 19-14 | A | |
| 19-15 | D | |

TABLE 19-continued

| Example No. | Genotype 1a | Genotype 1b |
|---|---|---|
| 19-16 | D | |
| 19-17 | C | |
| 19-18 | C | |

TABLE 20

| Example No. | Genotype 1a | Genotype 1b |
|---|---|---|
| 20-1 | D | D |
| 20-2 | D | D |
| 20-3 | D | D |
| 20-4 | D | D |
| 20-5 | D | D |
| 20-6 | D | D |
| 20-7 | D | D |

TABLE 21

| Example No. | Genotype 1a | Genotype 1b |
|---|---|---|
| 21-1 | A | |
| 21-2 | A | |
| 21-3 | D | D |
| 21-4 | C | |

TABLE 22

| Example No. | Genotype 1a | Genotype 1b |
|---|---|---|
| 22-1 | D | D |
| 22-2 | D | |
| 22-3 | D | D |
| 22-4 | D | D |
| 22-5 | D | D |
| 22-6 | D | D |
| 22-7 | D | D |
| 22-8 | D | D |
| 22-9 | D | D |
| 22-10 | D | D |
| 22-11 | D | D |
| 22-12 | D | D |
| 22-13 | D | D |
| 22-14 | D | |
| 22-15 | D | |
| 22-16 | D | D |
| 22-17 | D | |

TABLE 23

| Example No. | Genotype 1a | Genotype 1b |
|---|---|---|
| 23-1 | A | |
| 23-2 | D | |
| 23-3 | C | |

TABLE 24

| Example No. | Genotype 1a | Genotype 1b |
|---|---|---|
| 24-1 | C | D |
| 24-2 | C | D |
| 24-3 | C | D |
| 24-4 | C | D |
| 24-5 | C | |
| 24-6 | D | D |

TABLE 25

| Example No. | Genotype 1a | Genotype 1b |
|---|---|---|
| 25-1 | C | |
| 25-2 | D | D |
| 25-3 | C | |
| 25-4 | C | |
| 25-5 | D | |
| 25-6 | C | |
| 25-7 | B | |

TABLE 26

| Example No. | Genotype 1a | Genotype 1b |
|---|---|---|
| 26-1 | A | |
| 26-2 | B | |
| 26-3 | B | |
| 26-4 | C | D |
| 26-5 | A | |
| 26-6 | C | |
| 26-7 | C | D |
| 26-8 | C | |
| 26-9 | C | |
| 26-10 | A | |
| 26-11 | A | |

TABLE 27

| Example No. | Genotype 1a | Genotype 1b |
|---|---|---|
| 27-1 | D | D |
| 27-2 | D | |
| 27-3 | D | D |
| 27-4 | D | |
| 27-5 | D | D |
| 27-6 | D | D |
| 27-7 | D | |
| 27-8 | D | D |

TABLE 28

| Example No. | Genotype 1a | Genotype 1b |
|---|---|---|
| 28-1 | D | D |
| 28-2 | D | D |
| 28-3 | D | D |
| 28-4 | D | |
| 28-5 | D | |
| 28-6 | D | D |
| 28-7 | D | D |
| 28-8 | D | |
| 28-9 | D | |
| 28-10 | D | |
| 28-11 | D | D |
| 28-12 | D | |
| 28-13 | D | |
| 28-14 | D | |
| 28-15 | D | D |
| 28-16 | D | D |
| 28-17 | D | D |
| 28-18 | D | D |
| 28-19 | C | D |
| 28-20 | D | D |
| 28-21 | D | D |
| 28-22 | D | D |
| 28-23 | C | |

TABLE 29

| Example No. | Genotype 1a | Genotype 1b |
|---|---|---|
| 29-1 | D | |
| 29-2 | C | |
| 29-3 | C | |
| 29-4 | D | |

While the present invention has been described with reference to specific aspects or embodiments thereof, it will be understood by those of ordinary skill in the art that various changes can be made or equivalents can be substituted without departing from the true spirit and scope of the invention. Additionally, to the extent permitted by applicable patent statutes and regulations, all publications, patents, and patent applications cited herein are hereby incorporated by reference in their entirety as though individually incorporated by reference.

What is claimed is:

1. A compound of formula (IV):

(IV)

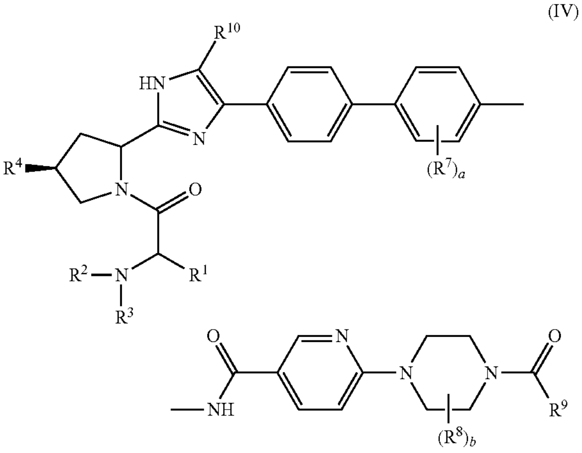

or a compound of formula (V):

(V)

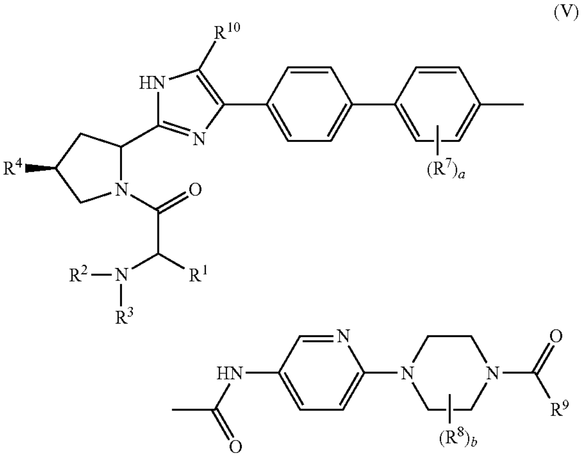

wherein:

$R^1$ is tetrahydropyran;

$R^2$ is hydrogen;

$R^3$ is —$C(O)OC_{1-6}$alkyl;

$R^4$ is methyl, methoxy, or —$CH_2OCH_3$;

$R^7$ is selected from fluoro, chloro, —$CF_3$, and —$OCF_3$;

$R^8$ is independently methyl or hydroxymethyl;

$R^9$ is selected from —$NHCH_3$, cyclopropyl, 2,2-dimethylcyclopropyl, tert-butyl, 3-hydroxy-2,2-dimethylpropyl, and imidazolyl;

$R^{10}$ is hydrogen or hydroxymethyl;

a is 1 or 2; and b is 1;

or a pharmaceutically-acceptable salt thereof.

2. The compound of claim 1 wherein the compound is selected from

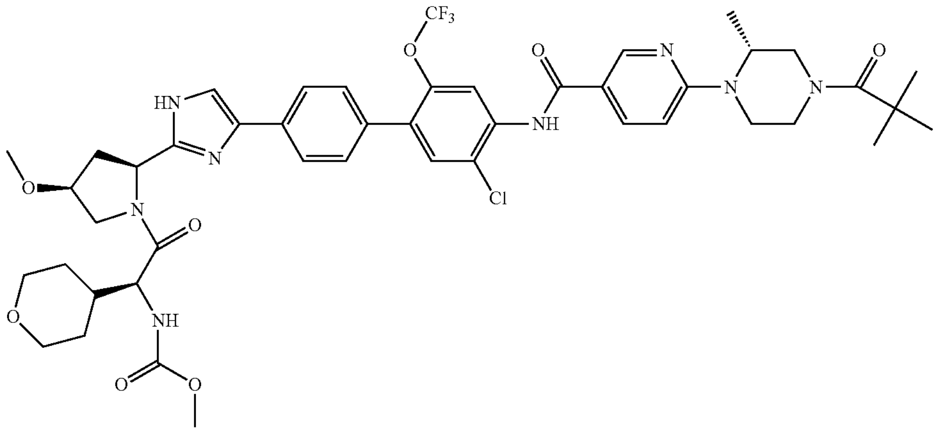

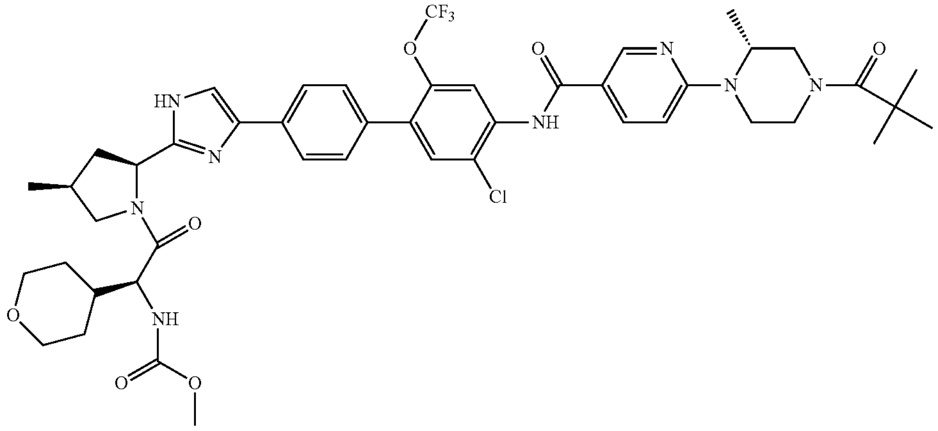 [SMILES: COC(=O)N[C@H](C(=O)N1C[C@@H](C)C[C@H]1c1nc(-c2ccc(-c3cc(Cl)c(NC(=O)c4ccc(N5CCN(C(=O)C(C)(C)C)C[C@H]5C)nc4)cc3OC(F)(F)F)cc2)c[nH]1)C1CCOCC1]

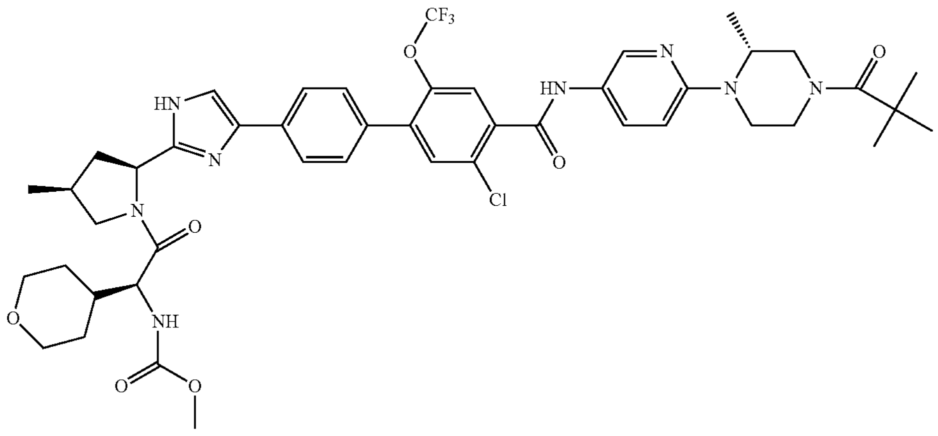

-continued

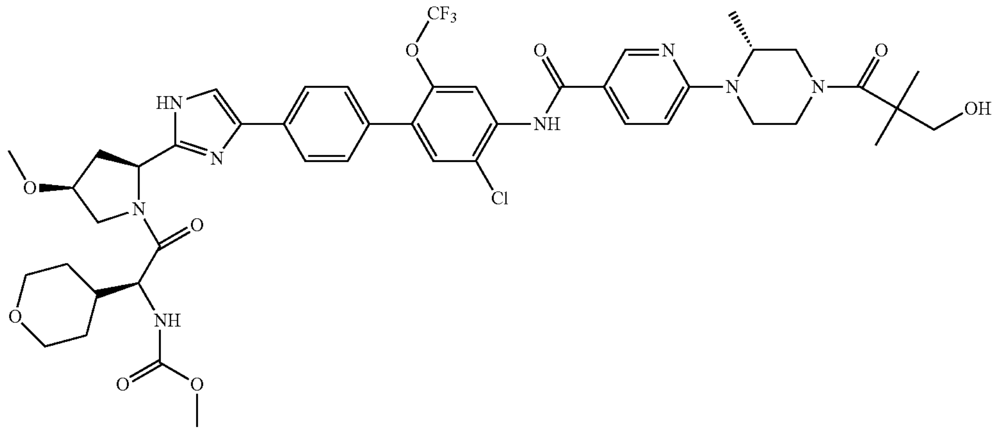

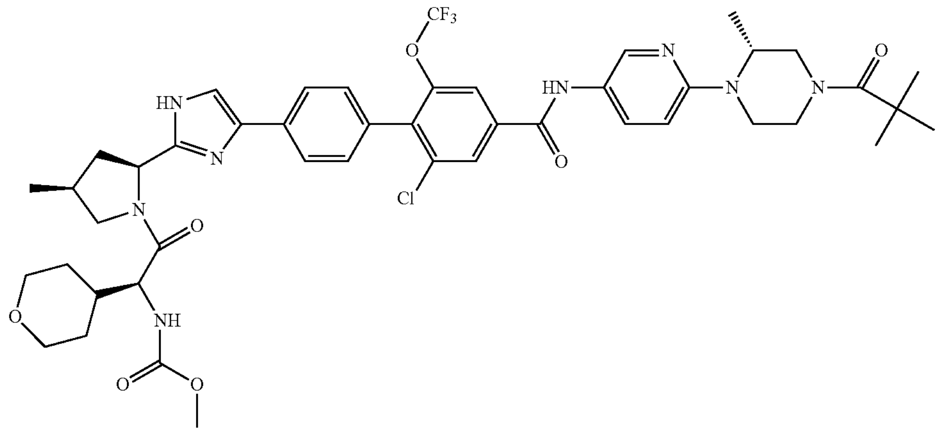

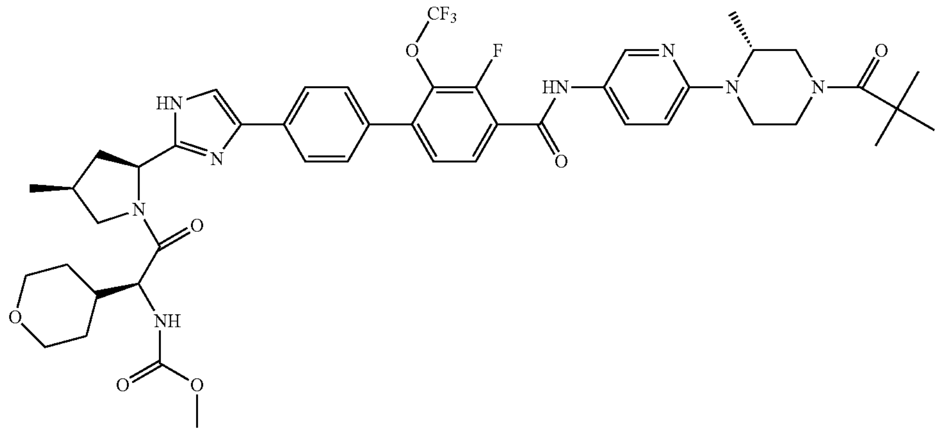

and pharmaceutically-acceptable salts thereof.

3. A pharmaceutical composition comprising a compound of claim 1 and a pharmaceutically-acceptable carrier.

4. The pharmaceutical composition of claim 3 further comprising one or more other therapeutic agents useful for treating hepatitis C viral infections.

5. The pharmaceutical composition of claim 4 wherein the one or more other therapeutic agents is selected from HCV NS3 protease inhibitors, and HCV NS5B nucleoside and non-nucleoside polymerase inhibitors.

6. The compound of claim 1 wherein the compound is a compound of formula (IV).

7. The compound of claim 1 wherein the compound is a compound of formula (V).
8. The compound of claim 2 wherein the compound is:
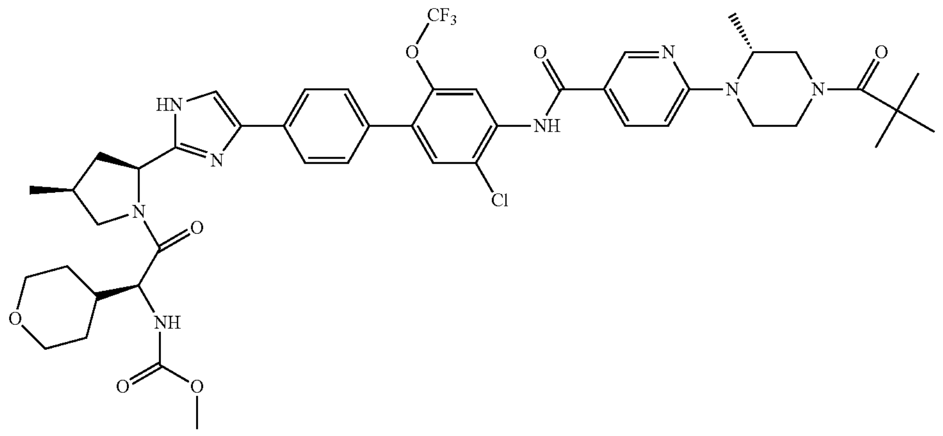
or a pharmaceutically-acceptable salt thereof.
* * * * *